(12) United States Patent
Bessler et al.

(10) Patent No.: US 9,394,528 B2
(45) Date of Patent: Jul. 19, 2016

(54) **GENE PRODUCTS OF *BACILLUS LICHENIFORMIS* WHICH FORM ODOROUS SUBSTANCES AND IMPROVED BIOTECHNOLOGICAL PRODUCTION METHODS BASED THEREON**

(75) Inventors: Cornelius Bessler, Düsseldorf (DE); Jörg Feesche, Erkrath (DE); Stefan Evers, Mettmann (DE); Karl-Heinz Maurer, Erkrath (DE); Armin Ehrenreich, Göttingen (DE); Birgit Veith, Göttingen (DE); Heiko Liesegang, Höxter (DE); Anke Henne, Solingen (DE); Christina Herzberg, Bilshausen (DE); Gerhard Gottschalk, Nörten-Hardenberg (DE)

(73) Assignee: BASF SE, Ludwigshafen (DE)

( * ) Notice: Subject to any disclaimer, the term of this patent is extended or adjusted under 35 U.S.C. 154(b) by 529 days.

(21) Appl. No.: 11/616,319

(22) Filed: Dec. 27, 2006

(65) Prior Publication Data

US 2007/0190605 A1  Aug. 16, 2007

Related U.S. Application Data

(63) Continuation of application No. PCT/EP2005/006540, filed on Jun. 17, 2005.

(30) Foreign Application Priority Data

Jun. 29, 2004 (DE) .......................... 10 2004 031 177

(51) Int. Cl.
| | |
|---|---|
| *C12N 15/74* | (2006.01) |
| *C12N 1/20* | (2006.01) |
| *C12P 21/06* | (2006.01) |
| *C12N 9/06* | (2006.01) |
| *C12N 9/04* | (2006.01) |
| *C12N 9/02* | (2006.01) |
| *C12N 9/10* | (2006.01) |
| *C12N 9/12* | (2006.01) |
| *C12N 9/16* | (2006.01) |
| *C12N 9/78* | (2006.01) |
| *C12N 9/80* | (2006.01) |
| *C12N 9/88* | (2006.01) |
| *C12N 9/00* | (2006.01) |
| *C12N 15/52* | (2006.01) |
| *C12P 7/16* | (2006.01) |
| *C12P 7/40* | (2006.01) |

(Continued)

(52) U.S. Cl.
CPC .............. *C12N 9/0016* (2013.01); *C12N 9/001* (2013.01); *C12N 9/0006* (2013.01); *C12N 9/0008* (2013.01); *C12N 9/1029* (2013.01); *C12N 9/1096* (2013.01); *C12N 9/1217* (2013.01); *C12N 9/16* (2013.01); *C12N 9/78* (2013.01); *C12N 9/80* (2013.01); *C12N 9/88* (2013.01); *C12N 9/93* (2013.01); *C12N 15/52* (2013.01); *C12P 7/16* (2013.01); *C12P 7/40* (2013.01); *C12P 7/52* (2013.01); *C12P 13/001* (2013.01); *C12Y 305/01001* (2013.01); *C12Y 401/01018* (2013.01); *C12Y 401/01019* (2013.01); *C12Y 602/01001* (2013.01); *Y02E 50/10* (2013.01); *Y02P 20/52* (2015.11)

(58) Field of Classification Search
None
See application file for complete search history.

(56) References Cited

U.S. PATENT DOCUMENTS 5,583,015 A * 12/1996 Hafner et al. ................... 435/76
5,807,522 A    9/1998 Brown et al.

(Continued)

FOREIGN PATENT DOCUMENTS

DE  WO2006/000343 A2  1/2006
JP      2000224982 A    8/2000

(Continued)

OTHER PUBLICATIONS

Willecke et al. Fatty Acid-requiring Mutant of Bacillus subtillus Defective in Branched Chain α-Keto Acid Dehydrogenase, J. Biol. Chem. vol. 246, No. 17, Sep. 10, 1971, pp. 5264-5272.*

(Continued)

*Primary Examiner* — Catherine S Hibbert
*Assistant Examiner* — Channing S Mahatan
(74) *Attorney, Agent, or Firm* — Marshall, Gerstein & Borun LLP

(57) ABSTRACT

The present invention relates to 25 hitherto undescribed genes of *B. licheniformis* and gene products derived therefrom and all sufficiently homologous nucleic acids and proteins thereof. They occur in five different metabolic pathways for the formation of odorous substances. The metabolic pathways in question are for the synthesis of: 1) isovalerian acid (as part of the catabolism of leucine), 2) 2-methylbutyric acid and/or isobutyric acid (as part of the catabolism of valine and/or isoleucine), 3) butanol and/or butyric acid (as part of the metabolism of butyric acid), 4) propyl acid (as part of the metabolism of propionate) and/or 5) cadaverine and/or putrescine (as parts of the catabolism of lysine and/or arginine). The identification of these genes allows biotechnological production methods to be developed that are improved to the extent that, to assist these nucleic acids, the formation of the odorous substances synthesized via these metabolic pathways can be reduced by deactivating the corresponding genes in the micro-organism used for the biotechnological production. In addition, these gene products are thus available for preparing reactions or for methods according to their respective biochemical properties.

13 Claims, 7 Drawing Sheets

(51) Int. Cl.
C12P 7/52 (2006.01)
C12P 13/00 (2006.01)

(56) References Cited

U.S. PATENT DOCUMENTS

| | | | |
|---|---|---|---|
| 7,018,794 B2 | 3/2006 | Berka et al. | |
| 7,220,572 B2 * | 5/2007 | Cusyatiner et al. | 435/252.33 |
| 7,494,798 B2 * | 2/2009 | Berka et al. | 435/209 |
| 2008/0050774 A1 * | 2/2008 | Berka et al. | 435/69.1 |

FOREIGN PATENT DOCUMENTS

| | | | |
|---|---|---|---|
| WO | 9950422 A2 | | 10/1999 |
| WO | WO 01/16329 | * | 3/2001 |
| WO | WO02/29113 A2 | | 4/2002 |

OTHER PUBLICATIONS

Lessie et al. Unusual Mutations Affecting Branched-Chain Amino Acid Biosynthesis in Bacillus licheniformis. Microbiology. 1976. pp. 91-100.*
Supek et al. Enhancement of Bacitracin Biosynthesis by Branched-Chain Amino Acids in a Regulatory Mutant of Bacillus licheniformis. Folia Microbiol. 1985. vol. 30, pp. 342-348.*
Reddick et al. The mmgA gene from Bacillus subtilis encodes a degradative acetoacetyl-CoA thiolase. 2008. Biotechnol. Lett. vol. 30, pp. 1045-1050.*
Neumuller et al. The two-component regulatory system BacRS is associated with bacitracin 'self-resistance' of Bacillus licheniformis ATCC 10716. 2001. Eur. J. Biochem. vol. 268, p. 3180-3189.*
Sequence Alignment Search for SEQ ID No. 9. Apr. 13, 2012, 2 pages.*
Sequence Alignment Search for SEQ ID No. 10. Jun. 5, 2013, 2 pages.*
Sequence Alignment Search for SEQ ID No. 12. Feb. 5, 2014, 1 page.*
Sequence Alignment Search for SEQ ID No. 28. Feb. 5, 2014, 1 page.*
Short-Chain Acyl-CoA dehydrogenase. BRENDA—The Comprehensive Enzyme Information System. Accessed on Feb. 25, 2015. 2 pages.*
Butyryl-CoA Dehydrogenase. NCBI MeSH. Accessed on Feb. 25, 2015. 2 pages.*
Chang & Cohen "High Frequency Transformation of Bacillus subtilis Protoplasts by Plasmid DNA", Molec. Gen. Genet, vol. 168, pp. 111-115 (1979).
D. Hannahan "Studies on transformation on *Escherichia coli*", J. Mol. Microbiol., vol. 166, pp. 557-850 (1983).
J. Vehmaanpera, et al. "Genetic manipulation of Bacillus amyloliquefaciens", J. Biotechnol., vol. 19, pp. 221-240 (1991).
T. J. Gryczan, et al. "Replication and incompatibility properties of plasmid p. E194 in Bacillus cubtilis" J. Bacteriol, vol. 152, pp. 722-735 (1982).
Takemura, et al. "Breeding of Branched Short-Chain Fatty Acids Non-Producing Natto Bacteria and its Application to Production of Natto with Light Smells." Journal of Japanese Society of Food Sciense and Technology, vol. 47, 2000, pp. 773-779.

Pronk, et al. "Propionate metabolism in *Saccharomyces cerevisiae*: implications for the metabolon hypothesis." Microbiology, 1994, pp. 717-722.
"Bacillus subtilis homologues of motA and motB genes acetoin utilization operon genes acuA, acuB and acuC, and acetyl-coA synthase (acsA) genes, complete cds." Nov. 27, 1993, XP2600270A.
Kretzschmar, et al. "The Pseudomonas aeruginosa acsA gene, encoding an acetyl-CoA synthetase, is essential for growth on ethanol." Microbiology, 2001, pp. 271-2677.
Berger, Bradley et al. "Methionine Regeneration and Aminotransferases in Bacillus subtilis, Bacillus cereus, and Bacillus anthracia." Journal of Bacteriology, vol. 185, No. 8, Apr. 2003, pp. 2418-2431.
Cary, J.W. et al. "Cloning and expression of Clostridium acetobutylicum phosphotransbutyrylase and butyrate kinase genes in *Escherichia coli*." Journal of Bacteriology, American Society for Microbiology, vol. 170, No. 10, Oct. 1988, pp. 4613-4618.
Vazquez, G. J. et al. "Phosphotransbutyrylase Expression in Bacillus megaterium," Current Microbiology, Springer-Verlag, vol. 42, No. 5, 2001, pp. 345-349.
Veith, B. et al. "RecName: Full=Probable butyrate kinase," Retrieved from http://www.uniprot.org/uniprot/Q65HK6 on Oct. 25, 2004, XP-002658530.
Harris, L.M. et al. "Characterization of Recombinant Strains of the Clostridium acetobutylicum Butyrate Kinase Inactivation Mutant: Need for New Phenomenological Models for Solventogenesis and Butanol Inhibition?" Biotechnology and Bioengineering, John Wiley & Sons, Inc., vol. 67, Issue 1, Jan. 2000, pp. 1-11.
Mizuno, Motoki et al. "RecName: Full=Probably butyrate kinase," Retrieved from http://www.uniprot.org/uniprot/P54532 on Oct. 25, 2004, XP-002658532.
Veith, B. et al. "RecName: Full=Phosphate butyryltransferase," Retrieved from http://www.uniprot/org/uniprot/Q65HK4 on Oct. 25, 2004,XP002658650.
Mizuno, Motoki et al. "RecName: Full=Probably phosphate butyryltransferase," Retrieved from http://www.uniprot.org/uniprot/P54530 on Oct. 1, 2004, XP002658653.
Nagata, S. et al. "Gene cloning, purification, and characterization of thermostable and halophilic leucine dehydrogenase from a halophilic thermophile, Bacillus licheniformis TSN9," Applied Microbiology and Biotechnology, Springer-Verlag, vol. 44, Dec. 1995, pp. 432-438.
Kanda, M. et al. "Purification and properties of branched chain amino acid aminotransferase from gramicidin S-producing Bacillus brevis," J. Nutr. Sci. Vitaminol., vol. 41, No. 1, Feb. 1995, pp. 51-60.
Rey, M. et al. "D-alanine aminotransferase [Bacillus licheniformis ATCC 14580]," Retrieved from http://www.uniprot.org/uniprot/Q65LW6 on Nov. 14, 2011.
Julie D. Thompson et al.; "LEON: multiple aLignment Evaluation of Neighbours; Nucleic Acids Research", 2004, vol. 32, No. 4; pp. 1298-1307.
NCBI; "Short chain acyl-CoA dehydrogenases and eukaryotic short/branched chain acyl-CoA dehydrogenases", 2 pages.
"Q65DT5 (Q65DT5_BACLD)"; Last modified Apr. 3, 2013. Version 72; 2002-2013 UniProt Consortium, 4 pages.
"Protein existence"; Last modified Oct. 24, 2012. 2002-2013 UniProt Consortium, 1 page.
NCBI. "Conserved domains on . . . SEQ-010", 2 pages.
NCBI. "CaiA, with user query added . . . Acyl-CoA dehydrogenases", 2 pages.

* cited by examiner

GENE PRODUCTS OF *BACILLUS LICHENIFORMIS* WHICH FORM ODOROUS SUBSTANCES AND IMPROVED BIOTECHNOLOGICAL PRODUCTION METHODS BASED THEREON

CROSS REFERENCE TO RELATED APPLICATIONS

The present application is a Section 365(c) continuation of International Application No. PCT/EP2005/006540 filed 17 Jun. 2005, which in turn claims the priority of DE Application 10 2004 031 177.3 filed Jun. 29, 2004, each of which is incorporated herein by reference.

FIELD OF THE INVENTION

The present invention relates to 25 not previously described genes of *B. licheniformis* and gene products derived therefrom which are involved in the formation of odorous substances in five different metabolic pathways, and to biotechnological production methods which are improved inasmuch as, on the basis of the identification of these genes, the formation of these odorous substances can be reduced.

The present invention is in the area of biotechnology, in particular the preparation of valuable products by fermentation of microorganisms able to form the valuable products of interest. This includes for example the preparation of low molecular weight compounds, for instance of dietary supplements or pharmaceutically relevant compounds, or of proteins for which, because of their diversity, there is in turn a large area of industrial use. In the first case, the metabolic properties of the relevant microorganisms are utilized and/or modified to prepare the valuable products; in the second case, cells which express the genes of the proteins of interest are employed. In both cases, genetically modified organisms (GMO) are mostly involved.

There is an extensive prior art on the fermentation of microorganisms, especially on the industrial scale; it extends from the optimization of the relevant strains in relation to the formation rate and the nutrient utilization via the technical design of the fermenters and up to the isolation of the valuable products from the relevant cells themselves and/or the fermentation medium. Both genetic and microbiological, and process engineering and biochemical approaches are applied thereto. The aim of the present invention is to improve this process in relation to a common property of the microorganisms employed, which impairs the actual fermentation step, specifically at the level of the genetic properties of the strains employed.

For industrial biotechnological production, the relevant microorganisms are cultured in fermenters which are designed appropriate for their metabolic properties. During the culturing, they metabolize the provided substrate and normally form, besides the actual product, a large number of other substances in which there is usually no interest and/or which may lead to unwanted side effects.

These include odorous and/or poisonous substances which are a nuisance and/or harmful and are discharged even during the fermentation via the exit air and/or are only incompletely removed during the subsequent working up of the valuable product and thus impair the quality of the product. The concomitant odorous and/or poisonous substances are thus deleterious firstly for the production process, meaning the staff involved and the surroundings of the plant. Secondly, failure to reach a desired quality (specification) of the product may lead to it being unavailable for the intended area of use (for example food production), which means a considerable economic disadvantage. Conversely, reducing the formation of odorous and/or poisonous substances could increase occupational and environmental safety and open up additional areas of use and markets for sales of the product.

Odors frequently found during fermentation of microorganisms are caused by small organic molecules from the classes of volatile, branched and unbranched fatty acids, alcohols and diamines. These include isovaleric acid, 2-methylbutyric acid, isobutyric acid from the class of branched fatty acids, butyric acid, propionic acid (unbranched fatty acids), butanol (alcohol), cadaverine and putrescine (diamines).

Some of these volatile substances are additionally toxic for humans and animals, for example cadaverine and putrescine, which are also known as ptomaines. They can therefore be defined not only as odorous substances but also, depending on the concentration and the exposure time for the relevant organism, as poisonous substances.

Efforts are being made even at present to remove such compounds subsequently from fermentation products. For this purpose, usual working up of the valuable products formed comprises, besides steps to remove cell detritus and high molecular weight compounds, also additional process steps which are referred to as deodorizing. To these are ordinarily added filtrations, precipitation steps and/or chromatography steps, each of which also contribute to a certain extent to the deodorizing. Nevertheless, all these steps carried out for removal lead to a purity which is only inadequate according to the above-mentioned criteria.

The exit air from the fermenter is likewise checked in order to minimize the pollution during the production process.

It would nevertheless be desirable to combat odors causally where possible, i.e. to prevent the relevant substances being produced at all. It would thus be possible firstly to keep the number of subsequent purification and working-up steps small, which appears to be advantageous because they represent in each case a physicochemical stress on the desired product, and reduce the yield. Overall, therefore, a better product quality would be obtained. Secondly, the production conditions would be improved per se, and the systems for filtering the fermenter exit air could be kept simpler. Such a combating of odors causally would, if the properties of the microorganism itself were to be changed thereby, also increase its tolerability for further operations on this microorganism.

SUMMARY OF THE INVENTION

The object was thus to reduce the formation of unpleasant odors and/or poisonous compounds which occurs during the fermentation of microorganisms, especially Gram-positive bacteria of the species *Bacillus*, and is attributable to the same. It was intended preferably that this take place at the genetic level in order to obtain odorous and/or poisonous substance-depleted microorganisms. In partial problems, this means identifying metabolic pathways relevant thereto, finding genes which code for proteins and/or enzymes which catalyze reactions lying on these pathways and are suitable as possible starting points for solving the problem, and, via identification of the relevant nucleotide sequences, acquiring tools for the desired genetic modification and providing corresponding applications.

To solve this problem, the following five metabolic pathways have been identified:
(1) the metabolic pathway for synthesizing isovaleric acid (as part of leucine catabolism), (2) the metabolic pathway for synthesizing 2-methylbutyric acid and/or isobutyric acid (as part of valine and/or isoleucine catabolism),
(3) the metabolic pathway for synthesizing butanol and/or butyric acid (as part of butyric acid metabolism),
(4) the metabolic pathway for synthesizing propionic acid (as part of propionate metabolism) and
(5) the metabolic pathway for synthesizing cadaverine and/or putrescine (as parts of lysine and/or arginine catabolism).

The following genes which code for proteins and/or enzymes which catalyze reactions lying on these pathways and are suitable as starting points for biotechnological production processes of the invention were then found; the non-consecutive numbering in some cases is based in each case on the complete description hereinafter of the respective metabolic pathways; in addition, some of them are involved in more than one of these pathways:

on the metabolic pathway for synthesizing isovaleric acid and as part of leucine catabolism:
(1) L-leucine dehydrogenase (E.C. 1.4.1.9),
(2) 3-methyl-2-oxobutanoate dehydrogenase or 2-oxoglutarate dehydrogenase E1 (E.C. 1.2.4.2),
(3) enzyme for hydrolyzing isovaleryl-CoA to isovaleric acid and coenzyme A,
(4) acyl-CoA dehydrogenase (E.C. 1.3.99.-),
(5) methylcrotonyl carboxylase,
(6) 3-methylglutaconyl-CoA hydratase and
(7) enoyl-CoA hydratase (E.C. 4.2.1.17);
on the metabolic pathway for synthesizing 2-methylbutyric acid and/or isobutyric acid and as part of valine and/or isoleucine catabolism:
(1) branched-chain amino acid aminotransferase (E.C. 2.6.1.42),
(2) 3-methyl-2-oxobutanoate dehydrogenase or 2-oxoglutarate dehydrogenase E1 (E.C. 1.2.4.2),
(3) enzyme for hydrolyzing 2-methylbutyryl-CoA to 2-methylbutyric acid or isobutyryl-CoA to isobutyric acid and coenzyme A,
(4) acyl-CoA dehydrogenase (E.C. 1.3.99.-),
(5) enoyl-CoA hydratase (protein) (E.C. 4.2.1.17),
(6) 3-hydroxy-acyl-CoA dehydrogenase (E.C. 1.1.1.35),
(7) acetyl-CoA acyltransferase,
(8) enoyl-(3-hydroxyisobutyryl)-CoA hydrolase protein and
(9) 3-hydroxyisobutyrate dehydrogenase (E.C. 1.1.1.31) or oxidoreductase
(E.C. 1.1.-.-);
on the metabolic pathway for synthesizing butanol and/or butyric acid and as part of butyric acid metabolism:
(1) 3-hydroxybutyryl-CoA dehydrogenase (E.C. 1.1.1.157),
(2) 3-hydroxybutyryl-CoA dehydratase (E.C. 4.2.1.55),
(3) butyryl-CoA dehydrogenase (E.C. 1.3.99.25),
(4) phosphate butyryltransferase (E.C. 2.3.1.19),
(5) butyrate kinase (E.C. 2.7.2.7),
(6) butyraldehyde dehydrogenase and
(8) NADH-dependent butanol dehydrogenase A (E.C. 1.1.1.-);
on the metabolic pathway for synthesizing propionic acid and as part of propionate metabolism:
(1) succinate-propionate CoA-transferase,
(2) acetate-CoA ligase or synthetase or propionate-CoA ligase or synthetase (E.C. 6.2.1.1) and
(3) acetate-CoA ligase or synthetase or propionate-CoA ligase or synthetase (E.C. 6.2.1.1); and
on the metabolic pathway for synthesizing cadaverine and/or putrescine and as parts of lysine and/or arginine catabolism:
(1) lysine decarboxylase (E.C. 4.1.1.18) and/or arginine decarboxylase (E.C. 4.1.1.19),
(2) agmatinase (E.C. 3.5.1.11) and
(3) ornithine decarboxylase (E.C. 4.1.1.17).

Finally, nucleotide and amino acid sequences coding for these proteins/enzymes were completely determined by sequencing relevant genes in *B. licheniformis* DSM 13, and thus made available for the desired modification of the microorganisms of interest. They are compiled in the sequence listing for the present application. These involve the following nucleic acids (odd numbers) and amino acid sequences derived therefrom for enzymes or proteins as parts of those enzymes which consist of a plurality of subunits (even numbers below in each case):

putative branched-chain amino acid aminotransferase (E.C. 2.6.1.42), defined by SEQ ID NO. 1 and 2,
putative branched-chain amino acid aminotransferase (E.C. 2.6.1.42) defined by SEQ ID NO. 3 and 4,
lysine and/or arginine decarboxylase (protein SpeA; E.C. 4.1.1.18 or E.C. 4.1.1.19) defined by SEQ ID NO. 5 (speA gene) and 6,
NADH-dependent butanol dehydrogenase A (protein YugJ; E.C. 1.1.1.-) defined by SEQ ID NO. 7 (yugJ gene) and 8,
butyryl-CoA dehydrogenase (E.C. 1.3.99.25) or acyl-CoA dehydrogenase (E.C. 1.3.99.-) defined by SEQ ID NO. 9 and 10,
butyryl-CoA dehydrogenase (E.C. 1.3.99.25) or acyl-CoA dehydrogenase (E.C. 1.3.99.-) defined by SEQ ID NO. 11 and 12,
3-hydroxybutyryl-CoA dehydrogenase (E.C. 1.1.1.157) defined by SEQ ID NO. 13 and 14,
putative enoyl-CoA hydratase protein (E.C. 4.2.1.17) defined by SEQ ID NO. 15 and 16,
probable enoyl-(3-hydroxyisobutyryl)-CoA hydrolase protein defined by SEQ ID NO. 17 and 18,
probable enoyl-CoA hydratase (protein EchA8; E.C. 4.2.1.17) defined by SEQ ID NO. 19 (echA8 gene) and 20,
acyl-CoA dehydrogenase (E.C. 1.3.99.-) defined by SEQ ID NO. 21 and 22,
acetate-CoA ligase or propionate-CoA ligase (or synthetase; protein AcsA; E.C. 6.2.1.1) defined by SEQ ID NO. 23 (acsA gene) and 24,
3-hydroxybutyryl-CoA dehydratase (protein YngF; E.C. 4.2.1.55) defined by SEQ ID No. 25 (yngF gene) and 26,
butyryl-CoA dehydrogenase (protein YusJ; E.C. 1.3.99.25) or acyl-CoA dehydrogenase (E.C. 1.3.99.-) defined by SEQ ID NO. 27 (yusJ gene) and 28,
3-hydroxyisobutyrate dehydrogenase (protein YkwC; E.C. 1.1.1.31) or oxidoreductase (E.C. 1.1.-.-) defined by SEQ ID NO. 29 (ykwC gene) and 30,
probable phosphate butyryltransferase (E.C. 2.3.1.19) defined by SEQ ID NO. 31 and 32,
probable butyrate kinase (E.C. 2.7.2.7) defined by SEQ ID NO. 33 and 34,
acetate-CoA ligase or synthetase or propionate-CoA ligase or synthetase (protein AcsA; E.C. 6.2.1.1) defined by SEQ ID NO. 35 (acsA gene) and 36,
acetate-CoA ligase or propionate-CoA ligase (protein Ytcl; E.C. 6.2.1.1) defined by SEQ ID NO. 37 (ytcl gene) and 38,
lysine and/or arginine decarboxylase (protein speA; E.C. 4.1.1.18 or E.C. 4.1.1.19) defined by SEQ ID NO. 39 (speA gene) and 40,
probable enoyl-CoA hydratase (E.C. 4.2.1.17) defined by SEQ ID NO. 41 (ysiB gene) and 42, similar to 3-hydroxy-acyl-CoA dehydrogenase (E.C. 1.1.1.35) defined by SEQ ID NO. 43 and 44, 3-methyl-2-oxobutanoate dehydrogenase or 2-oxoglutarate dehydrogenase E1 (E.C. 1.2.4.2) defined by SEQ ID NO. 45 and 46, probable acetate-CoA ligase or propionate-CoA ligase (protein YhfL; E.C. 6.2.1.1) or acid-CoA ligase (E.C. 6.2.1.-) defined by SEQ ID NO. 47 (yhfL gene) and 48 or agmatinase (E.C. 3.5.1.11) defined by SEQ ID NO. 49 (ywhG gene) and 50.

All of them are made available by the present application.

The stated problem is thus solved in the same way in principle by all 25 nucleic acids of SEQ ID NO. 1, 3, 5, 7, 9, 11, 13, 15, 17, 19, 21, 23, 25, 27, 29, 31, 33, 35, 37, 39, 41, 43, 45, 47 and 49 which are indicated in the sequence listing and are obtainable from B. licheniformis DSM 13, including an in each case corresponding homology region which is defined hereinafter and which effects a delimitation from the sequences described in the prior art. It is likewise solved by the gene products derived therefrom of SEQ ID NO. 2, 4, 6, 8, 10, 12, 14, 16, 18, 20, 22, 24, 26, 28, 30, 32, 34, 36, 38, 40, 42, 44, 46, 48 and 50, once again including a corresponding homology region defined hereinafter. The respective most similar nucleic acid and amino acid sequences described in the prior art are compiled in Example 2 (Table 1) with reference to the relevant database entries. The homology regions claimed in each case have been defined on the basis of this information. Solutions according to the invention of the stated problem are preferably in each case those nucleic acids and proteins which actually originate from microorganisms.

Which of these genes is preferred must be ascertained experimentally taking account of the individual strain to be cultured (and possibly different gene activities) and the respective metabolic situation (for example (over)supply of certain C or N sources) in the individual case. For this it is necessary for a series of several mutants, which are to be produced in the same way in principle, of the various relevant genes to be generated in parallel and cultured under conditions which are otherwise identical.

Further solutions are represented by fermentation processes in which one or more of the metabolic pathways for synthesizing (1) isovaleric acid (as part of leucine catabolism), (2) 2-methylbutyric acid and/or isobutyric acid (as part of valine and/or isoleucine catabolism), (3) butanol and/or butyric acid (as part of butyric acid metabolism), (4) propionic acid (as part of propionate metabolism) and/or (5) cadaverine and/or putrescine (as parts of lysine and/or arginine catabolism) are functionally inactivated, preferably via the abovementioned enzymes/proteins which are active on these pathways, and particularly preferably via the nucleotide sequences provided according to the invention. The latter can be used in a manner known per se and established in the prior art, for example for producing knock-out constructs and for introducing them via vectors in the host cells so that gene disruption takes place.

Further solutions are represented by appropriately modified microorganisms in particular relevant to industrial production, all fermentation processes in which these are employed, and among these especially those used to produce valuable products.

In addition, these gene products are available on the basis of the present invention for reaction mixtures or processes according to their respective biochemical properties, by which is meant in particular the synthesis of (1) isovaleric acid, (2) 2-methylbutyric acid and/or isobutyric acid, (3) butanol and/or butyric acid, (4) propionic acid and/or (5) cadaverine and/or putrescine.

The present invention enables, at least as far as these important metabolic pathways are concerned, causal combating of odors. This is because it is possible by switching off the identified metabolic pathways via the proteins involved with the aid of the nucleic acids coding for these proteins to substantially prevent the relevant substances being produced at all. It is thus possible firstly to keep the number of subsequent purification and working-up steps small, which is advantageous because they represent in each case a physicochemical stress on the desired product and reduce the yield; the product quality is thus overall improved. Secondly, the production conditions are improved per se, and the systems for filtration of the fermenter exit air can be kept simpler. This causal combating of odors acts, because it operates at the genetic level, on the properties of the respective microorganism itself, thus increasing its tolerability of further operations on this microorganism.

In particular, industrial fermentation is improved thereby, which ought also to lead to a reduction of the costs of the fermentation products.

In addition, the identified genes and gene products are thus available for diverse applications, for example for chemical and/or at least partly biocatalyzed synthesis of the relevant compounds.

As described in the examples of the present application, it was possible by sequencing the genomic DNA of the B. licheniformis DSM 13, the reference strain obtainable from the Deutschen Sammlung von Mikroorganismen and Zellkulturen GmbH, Mascheroder Weg 1b, 38124 Brunswick, to identify said 25 novel genes for this species. These are ones which code for enzymes or enzyme subunits which are involved in the reactions described herein for synthesizing odorous substances.

The most similar genes and relevant proteins in each case which are known in this connection in the prior art show the sequence homologies indicated in Example 2 (Table 1) of the present application. The range of protection covered in each case by the present application is defined thereby. Accordingly, all the following nucleic acids and proteins represent in principle equivalent embodiments of the present invention:

nucleic acid coding for a gene product (putative branched-chain amino acid aminotransferase; E.C. 2.6.1.42) involved in the synthesis of 2-methylbutyric acid and/or isobutyric acid and having a nucleotide sequence which shows at least 67% identity and with increasing preference at least 70%, 75%, 80%, 85%, 90%, 92%, 94%, 96%, 97%, 98%, 99% and particularly preferably 100% identity to the nucleotide sequence indicated in SEQ ID NO. 1, gene product (putative branched-chain amino acid aminotransferase; E.C. 2.6.1.42) involved in the synthesis of 2-methylbutyric acid and/or isobutyric acid and having an amino acid sequence which shows at least 73% identity and with increasing preference at least 75%, 80%, 85%, 90%, 92%, 94%, 96%, 97%, 98%, 99% and particularly preferably 100% identity to the amino acid sequence indicated in SEQ ID NO. 2;

nucleic acid coding for a gene product (putative branched-chain amino acid aminotransferase; E.C. 2.6.1.42) involved in the synthesis of 2-methylbutyric acid and/or isobutyric acid and having a nucleotide sequence which shows at least 78% identity and with increasing preference at least 80%, 85%, 90%, 92%, 94%, 95%, 96%, 97%, 98%, 99% and particularly preferably 100% identity to the nucleotide sequence indicated in SEQ ID NO. 3;

gene product (putative branched-chain amino acid aminotransferase; E.C. 2.6.1.42) involved in the synthesis of 2-methylbutyric acid and/or isobutyric acid and having an amino acid sequence which shows at least 83% identity and with increasing preference at least 85%, 87.5% 90%, 92%, 94%, 96%, 97%, 98%, 99% and particularly preferably 100% identity to the amino acid sequence indicated in SEQ ID NO. 4;

nucleic acid speA coding for a gene product (lysine and/or arginine decarboxylase; E.C. 4.1.1.18 or 4.1.1.19) involved in the synthesis of cadaverine and/or putrescine and having a nucleotide sequence which shows at least 78% identity and with increasing preference at least 80%, 85%, 90%, 92%, 94%, 95%, 96%, 97%, 98%, 99% and particularly preferably 100% identity to the nucleotide sequence indicated in SEQ ID NO. 5;

gene product SpeA (lysine and/or arginine decarboxylase; E.C. 4.1.1.18 or E.C. 4.1.1.19) involved in the synthesis of cadaverine and/or putrescine and having an amino acid sequence which shows at least 89% identity and with increasing preference at least 90%, 92%, 94%, 95%, 96%, 97%, 98%, 99% and particularly preferably 100% identity to the amino acid sequence indicated in SEQ ID NO. 6;

nucleic acid yugJ coding for a gene product (NADH-dependent butanol dehydrogenase A; E.C. 1.1.1.-) involved in the synthesis of butanol and/or butyric acid and having a nucleotide sequence which shows at least 81% identity and with increasing preference at least 85%, 90%, 92%, 93%, 94%, 95%, 96%, 97%, 98%, 99% and particularly preferably 100% identity to the nucleotide sequence indicated in SEQ ID NO. 7;

gene product YugJ (NADH-dependent butanol dehydrogenase A; E.C. 1.1.1.-) involved in the synthesis of butanol and/or butyric acid and having an amino acid sequence which shows at least 93% identity and with increasing preference at least 94%, 95%, 96%, 97%, 98%, 98.5%, 99%, 99.5% and particularly preferably 100% identity to the amino acid sequence indicated in SEQ ID NO. 8;

nucleic acid coding for a gene product (acyl-CoA dehydrogenase; E.C. 1.3.99.-) involved in the synthesis of isovaleric acid, 2-methylbutyric acid, isobutyric acid, butanol and/or butyric acid and having a nucleotide sequence which shows at least 79% identity and with increasing preference at least 75%, 80%, 85%, 90%, 92%, 94%, 96%, 97%, 98%, 99% and particularly preferably 100% identity to the nucleotide sequence indicated in SEQ ID NO. 9;

gene product (acyl-CoA dehydrogenase; E.C. 1.3.99.-) involved in the synthesis of isovaleric acid, 2-methylbutyric acid, isobutyric acid or butanol and/or butyric acid and having an amino acid sequence which shows at least 86% identity and with increasing preference at least 87.5%, 90%, 92%, 93%, 94%, 95%, 96%, 97%, 98%, 99% and particularly preferably 100% identity to the amino acid sequence indicated in SEQ ID NO. 10;

nucleic acid coding for a gene product (acyl-CoA dehydrogenase; E.C. 1.3.99.-) involved in the synthesis of isovaleric acid, 2-methylbutyric acid, isobutyric acid, butanol and/or butyric acid and having a nucleotide sequence which shows at least 64% identity and with increasing preference at least 65%, 70%, 75%, 80%, 85%, 90%, 92%, 94%, 96%, 97%, 98%, 99% and particularly preferably 100% identity to the nucleotide sequence indicated in SEQ ID NO. 11;

gene product (acyl-CoA dehydrogenase; E.C. 1.3.99.-) involved in the synthesis of isovaleric acid, 2-methylbutyric acid, isobutyric acid, butanol and/or butyric acid and having an amino acid sequence which shows at least 67% identity and with increasing preference at least 70%, 75%, 80%, 85%, 87.5%, 90%, 92%, 94%, 95%, 96%, 97%, 98%, 99% and particularly preferably 100% identity to the amino acid sequence indicated in SEQ ID NO. 12;

nucleic acid coding for a gene product (3-hydroxybutyryl-CoA dehydrogenase; E.C. 1.1.1.157) involved in the synthesis of butanol and/or butyric acid and having a nucleotide sequence which shows at least 67% identity and with increasing preference at least 70%, 75%, 80%, 85%, 90%, 92%, 94%, 96%, 97%, 98%, 99% and particularly preferably 100% identity to the nucleotide sequence indicated in SEQ ID NO. 13;

gene product (3-hydroxybutyryl-CoA dehydrogenase; E.C. 1.1.1.157) involved in the synthesis of butanol and/or butyric acid and having an amino acid sequence which shows at least 69% identity and with increasing preference at least 70%, 75%, 80%, 85%, 90%, 92%, 94%, 96%, 97%, 98%, 99% and particularly preferably 100% identity to the amino acid sequence indicated in SEQ ID NO. 14;

nucleic acid coding for a gene product (putative enoyl-CoA hydratase protein; E.C. 4.2.1.17) involved in the synthesis of isovaleric acid, 2-methylbutyric acid and/or isobutyric acid and having a nucleotide sequence which shows at least 65% identity and with increasing preference at least 70%, 75%, 80%, 85%, 90%, 92%, 94%, 96%, 97%, 98%, 99% and particularly preferably 100% identity to the nucleotide sequence indicated in SEQ ID NO. 15;

gene product (putative enoyl-CoA hydratase protein; E.C. 4.2.1.17) involved in the synthesis of isovaleric acid, 2-methylbutyric acid and/or isobutyric acid and having an amino acid sequence which shows at least 62% identity and with increasing preference at least 65%, 70%, 75%, 80%, 85%, 90%, 92%, 94%, 96%, 97%, 98%, 99% and particularly preferably 100% identity to the amino acid sequence indicated in SEQ ID NO. 16;

nucleic acid coding for a gene product (probable enoyl-(3-hydroxyisobutyryl)-coenzyme A hydrolase protein) involved in the synthesis of isovaleric acid, 2-methylbutyric acid and/or isobutyric acid and having a nucleotide sequence which shows at least 66% identity and with increasing preference at least 70%, 75%, 80%, 85%, 90%, 92%, 94%, 96%, 97%, 98%, 99% and particularly preferably 100% identity to the nucleotide sequence indicated in SEQ ID NO. 17;

gene product (probable enoyl-(3-hydroxyisobutyryl)-coenzyme A hydrolase protein) involved in the synthesis of isovaleric acid, 2-methylbutyric acid and/or isobutyric acid and having an amino acid sequence which shows at least 66% identity and with increasing preference at least 70%, 75%, 80%, 85%, 87.5%, 90%, 92%, 94%, 96%, 97%, 98%, 99% and particularly preferably 100% identity to the amino acid sequence indicated in SEQ ID NO. 18;

nucleic acid echA8 coding for a gene product (probable enoyl-CoA hydratase; E.C. 4.2.1.17) involved in the synthesis of isovaleric acid, 2-methylbutyric acid and/or isobutyric acid and having a nucleotide sequence which shows at least 48% identity and with increasing preference at least 50%, 55%, 60%, 65%, 70%, 75%, 80%, 85%, 90%, 92%, 94%, 96%, 97%, 98%, 99% and particularly preferably 100% identity to the nucleotide sequence indicated in SEQ ID NO. 19;

gene product EchA8 (probable enoyl-CoA hydratase; E.C. 4.2.1.17) involved in the sythesis of isovaleric acid, 2-methylbutyric acid and/or isobutyric acid and having an amino acid sequence which shows at least 52% identity and with increasing preference at least 55%, 60%, 70%, 75%, 80%, 85%, 90%, 92%, 94%, 96%, 97%, 98%, 99% and particularly preferably 100% identity to the amino acid sequence indicated in SEQ ID NO. 20;

nucleic acid coding for a gene product (acyl-CoA dehydrogenase; E.C. 1.3.99.-) involved in the synthesis of isovaleric acid, 2-methylbutyric acid and/or isobutyric acid and having a nucleotide sequence which shows at least 54% identity and with increasing preference at least 55%, 60%, 65%, 70%, 75%, 80%, 85%, 90%, 92%, 94%, 96%, 97%, 98%, 99% and particularly preferably 100% identity to the nucleotide sequence indicated in SEQ ID NO. 21;

gene product (acyl-CoA dehydrogenase) involved in the synthesis of isovaleric acid, 2-methylbutyric acid and/or isobutyric acid and having an amino acid sequence which shows at least 65% identity and with increasing preference at least 70%, 75%, 80%, 85%, 87.5%, 90%, 92%, 94%, 96%, 97%, 98%, 99% and particularly preferably 100% identity to the amino acid sequence indicated in SEQ ID NO. 22;

nucleic acid acsA coding for a gene product (acetyl-coenzyme A synthetase; E.C. 6.2.1.1) involved in the synthesis of propionic acid and having a nucleotide sequence which shows at least 67% identity and with increasing preference at least 70%, 75%, 80%, 85%, 90%, 92%, 94%, 96%, 97%, 98%, 99% and particularly preferably 100% identity to the nucleotide sequence indicated in SEQ ID NO. 23;

gene product AscA (acetyl-coenzyme A synthetase; E.C. 6.2.1.1) involved in the synthesis of propionic acid and having an amino acid sequence which shows at least 65% identity and with increasing preference at least 70%, 75%, 80%, 85%, 87.5%, 90%, 92%, 94%, 96%, 97%, 98%, 99% and particularly preferably 100% identity to the amino acid sequence indicated in SEQ ID NO. 24;

nucleic acid yngF coding for a gene product (3-hydroxybutyryl-CoA dehydratase; E.C. 4.2.1.55) involved in the synthesis of butanol and/or butyric acid and having a nucleotide sequence which shows at least 68% identity and with increasing preference at least 70%, 75%, 80%, 85%, 90%, 92%, 94%, 96%, 97%, 98%, 99% and particularly preferably 100% identity to the nucleotide sequence indicated in SEQ ID NO. 25;

gene product YngF (3-hydroxybutyryl-CoA dehydratase; E.C. 4.2.1.55) involved in the synthesis of butanol and/or butyric acid and having an amino acid sequence which shows at least 69% identity and with increasing preference at least 70%, 75%, 80%, 85%, 87.5%, 90%, 92%, 94%, 96%, 97%, 98%, 99% and particularly preferably 100% identity to the amino acid sequence indicated in SEQ ID NO. 26;

nucleic acid yusJ coding for a gene product (acyl-CoA dehydrogenase; E.C. 1.3.99.-) involved in the synthesis of isovaleric acid, 2-methylbutyric acid, isobutyric acid, butanol and/or butyric acid and having a nucleotide sequence which shows at least 77% identity and with increasing preference at least 80%, 85%, 90%, 92%, 94%, 95%, 96%, 97%, 98%, 99% and particularly preferably 100% identity to the nucleotide sequence indicated in SEQ ID NO. 27;

gene product YusJ (acyl-CoA dehydrogenase; E.C. 1.3.99.-) involved in the synthesis of isovaleric acid, 2-methylbutyric acid, isobutyric acid, butanol and/or butyric acid and having an amino acid sequence which shows at least 86% identity and with increasing preference at least 87.5%, 90%, 91%, 92%, 93%, 94%, 95%, 96%, 97%, 98%, 99% and particularly preferably 100% identity to the amino acid sequence indicated in SEQ ID NO. 28;

nucleic acid ykwC coding for a gene product (hypothetical oxidoreductase; E.C. 1.1.-.-) involved in the synthesis of 2-methylbutyric acid and/or isobutyric acid and having a nucleotide sequence which shows at least 77% identity and with increasing preference at least 80%, 85%, 90%, 92%, 94%, 95%, 96%, 97%, 98%, 99% and particularly preferably 100% identity to the nucleotide sequence indicated in SEQ ID NO. 29;

gene product YkwC (hypothetical oxidoreductase; E.C. 1.1.-.-) involved in the synthesis of 2-methylbutyric acid and/or isobutyric acid and having an amino acid sequence which shows at least 85% identity and with increasing preference at least 87.5%, 90%, 91%, 92%, 93%, 94%, 95%, 96%, 97%, 98%, 99% and particularly preferably 100% identity to the amino acid sequence indicated in SEQ ID NO. 30;

nucleic acid coding for a gene product (probable phosphate butyryltransferase; E.C. 2.3.1.19) involved in the synthesis of butanol and/or butyric acid and having a nucleotide sequence which shows at least 51% identity and with increasing preference at least 55%, 60%, 65%, 70%, 75%, 80%, 85%, 90%, 92%, 94%, 96%, 97%, 98%, 99% and particularly preferably 100% identity to the nucleotide sequence indicated in SEQ ID NO. 31;

gene product (probable phosphate butyryltransferase; E.C. 2.3.1.19) involved in the synthesis of butanol and/or butyric acid and having an amino acid sequence which shows at least 69% identity and with increasing preference at least 70%, 75%, 80%, 85%, 90%, 92%, 94%, 96%, 97%, 98%, 99% and particularly preferably 100% identity to the amino acid sequence indicated in SEQ ID NO. 32;

nucleic acid coding for a gene product (probable butyrate kinase; E.C. 2.7.2.7) involved in the synthesis of butanol and/or butyric acid and having a nucleotide sequence which shows at least 77% identity and with increasing preference at least 80%, 85%, 90%, 92%, 94%, 95%, 96%, 97%, 98%, 99% and particularly preferably 100% identity to the nucleotide sequence indicated in SEQ ID NO. 33;

gene product (probable butyrate kinase; E.C. 2.7.2.7) involved in the synthesis of butanol and/or butyric acid and having an amino acid sequence which shows at least 84% identity and with increasing preference at least 85%, 87.5%, 90%, 92%, 93%, 94%, 95%, 96%, 97%, 98%, 99% and particularly preferably 100% identity to the amino acid sequence indicated in SEQ ID NO. 34;

nucleic acid acsA coding for a gene product (acetyl-coenzyme A synthetase; E.C. 6.2.1.1) involved in the synthesis of propionic acid and having a nucleotide sequence which shows at least 79% identity and with increasing preference at least 80%, 85%, 90%, 92%, 94%, 95%, 96%, 97%, 98%, 99% and particularly preferably 100% identity to the nucleotide sequence indicated in SEQ ID NO. 35;

gene product AcsA (acetyl-coenzyme A synthetase: E.C. 6.2.1.1) involved in the synthesis of propionic acid and having an amino acid sequence which shows at least 85% identity and with increasing preference at least 87.5%, 90%, 91%, 92%, 93%, 94%, 95%, 96%, 97%, 98%, 99% and particularly preferably 100% identity to the amino acid sequence indicated in SEQ ID NO. 36;

nucleic acid ytcl coding for a gene product (acetate-CoA ligase; E.C. 6.2.1.1) involved in the synthesis of propionic acid and having a nucleotide sequence which shows at least 74% identity and with increasing preference at least 75%, 80%, 85%, 90%, 92%, 94%, 96%, 97%, 98%, 99% and particularly preferably 100% identity to the nucleotide sequence indicated in SEQ ID NO. 37;

gene product Ytcl (acetate-CoA ligase; E.C. 6.2.1.1) involved in the synthesis of propionic acid and having an amino acid sequence which shows at least 77% identity and with increasing preference at least 80%, 85%, 87.5%, 90%, 92%, 94%, 96%, 97%, 98%, 99% and particularly preferably 100% identity to the amino acid sequence indicated in SEQ ID NO. 38;

nucleic acid speA coding for a gene product (lysine and/or arginine decarboxylase; E.C. 4.1.1.18 or E.C. 4.1.1.19) involved in the synthesis of cadaverine and/or putrescine and having a nucleotide sequence which shows at least 68% identity and with increasing preference at least 75%, 80%, 85%, 90%, 92%, 94%, 96%, 97%, 98%, 99% and particularly preferably 100% identity to the nucleotide sequence indicated in SEQ ID NO. 39;

gene product SpeA (lysine and/or arginine decarboxylase; E.C. 4.1.1.18 or E.C. 4.1.1.19) involved in the synthesis of cadaverine and/or putrescine and having an amino acid sequence which shows at least 66% identity and with increasing preference at least 70%, 75%, 80%, 85%, 87.5%, 90%, 92%, 94%, 96%, 97%, 98%, 99% and particularly preferably 100% identity to the amino acid sequence indicated in SEQ ID NO. 40;

nucleic acid ysiB coding for a gene product (probable enoyl-CoA hydratrase; E.C. 4.2.1.17) involved in the synthesis of isovaleric acid, 2-methylbutyric acid and/or isobutyric acid and having a nucleotide sequence which shows at least 75% identity and with increasing preference at least 80%, 85%, 90%, 92%, 94%, 95%, 96%, 97%, 98%, 99% and particularly preferably 100% identity to the nucleotide sequence indicated in SEQ ID NO. 41;

gene product YsiB (probable enoyl-CoA hydratrase; E.C. 4.2.1.17) involved in the synthesis of isovaleric acid, 2-methylbutyric acid and/or isobutyric acid and having an amino acid sequence which shows at least 77% identity and with increasing preference at least 80%, 85%, 87.5%, 90%, 92%, 94%, 96%, 97%, 98%, 99% and particularly preferably 100% identity to the amino acid sequence indicated in SEQ ID NO. 42;

nucleic acid coding for a gene product (similar to 3-hydroxyacyl-CoA dehydrogenase; E.C. 1.1.1.35) involved in the synthesis of 2-methylbutyric acid and having a nucleotide sequence which shows at least 76% identity and with increasing preference at least 80%, 85%, 90%, 92%, 94%, 95%, 96%, 97%, 98%, 99% and particularly preferably 100% identity to the nucleotide sequence indicated in SEQ ID NO. 43;

gene product (similar to 3-hydroxyacyl-CoA dehydrogenase) involved in the synthesis of 2-methylbutyric acid and having an amino acid sequence which shows at least 80% identity and with increasing preference at least 85%, 87.5%, 90%, 92%, 94%, 95%, 96%, 97%, 98%, 99% and particularly preferably 100% identity to the amino acid sequence indicated in SEQ ID NO. 44;

nucleic acid coding for a gene product (2-oxoglutarate dehydrogenase E1 component; E.C. 1.2.4.2) involved in the synthesis of isovaleric acid, 2-methylbutyric acid and/or isobutyric acid and having a nucleotide sequence which shows at least 80% identity and with increasing preference at least 80%, 85%, 90%, 92%, 94%, 95%, 96%, 97%, 98%, 99% and particularly preferably 100% identity to the nucleotide sequence indicated in SEQ ID NO. 45;

gene product (2-oxoglutarate dehydrogenase E1 component; E.C. 1.2.4.2) involved in the synthesis of isovaleric acid, 2-methylbutyric acid and/or isobutyric acid and having an amino acid sequence which shows at least 82% identity and with increasing preference at least 85%, 87.5%, 90%, 92%, 94%, 95%, 96%, 97%, 98%, 99% and particularly preferably 100% identity to the amino acid sequence indicated in SEQ ID NO. 46;

nucleic acid yhfL coding for a gene product (probable acid-CoA ligase; E.C. 6.2.1.-) involved in the synthesis of propionic acid and having a nucleotide sequence which shows at least 67% identity and with increasing preference at least 70%, 75%, 80%, 85%, 90%, 92%, 94%, 96%, 97%, 98%, 99% and particularly preferably 100% identity to the nucleotide sequence indicated in SEQ ID NO. 47;

gene product YhfL (probable acid-CoA ligase; E.C. 6.2.1.-) involved in the synthesis of propionic acid and having an amino acid sequence which shows at least 76% identity and with increasing preference at least 80%, 85%, 90%, 92%, 94%, 95%, 96%, 97%, 98%, 99% and particularly preferably 100% identity to the amino acid sequence indicated in SEQ ID NO. 48;

nucleic acid ywhG coding for a gene product (agmatinase; E.C. 3.5.1.11) involved in the synthesis of cadaverine and/or putrescine and having a nucleotide sequence which shows at least 85% identity and with increasing preference at least 90%, 91%, 92%, 93%, 94%, 95%, 96%, 97%, 98%, 99% and particularly preferably 100% identity to the nucleotide sequence indicated in SEQ ID NO. 49;

gene product YwhG (agmatinase; E.C. 3.5.1.11) involved in the synthesis of cadaverine and/or putrescine and having an amino acid sequence which shows at least 97% identity and with increasing preference at least 97.5%, 98%, 98.5%, 99%, 99.5% and particularly preferably 100% identity to the amino acid sequence indicated in SEQ ID NO. 50.

In connection with the present application, an expression of the form "at least X %" means "X % to 100%, including the extreme values X and 100 and all integral and non-integral percentages in between".

DETAILED DESCRIPTION

Figure 1:
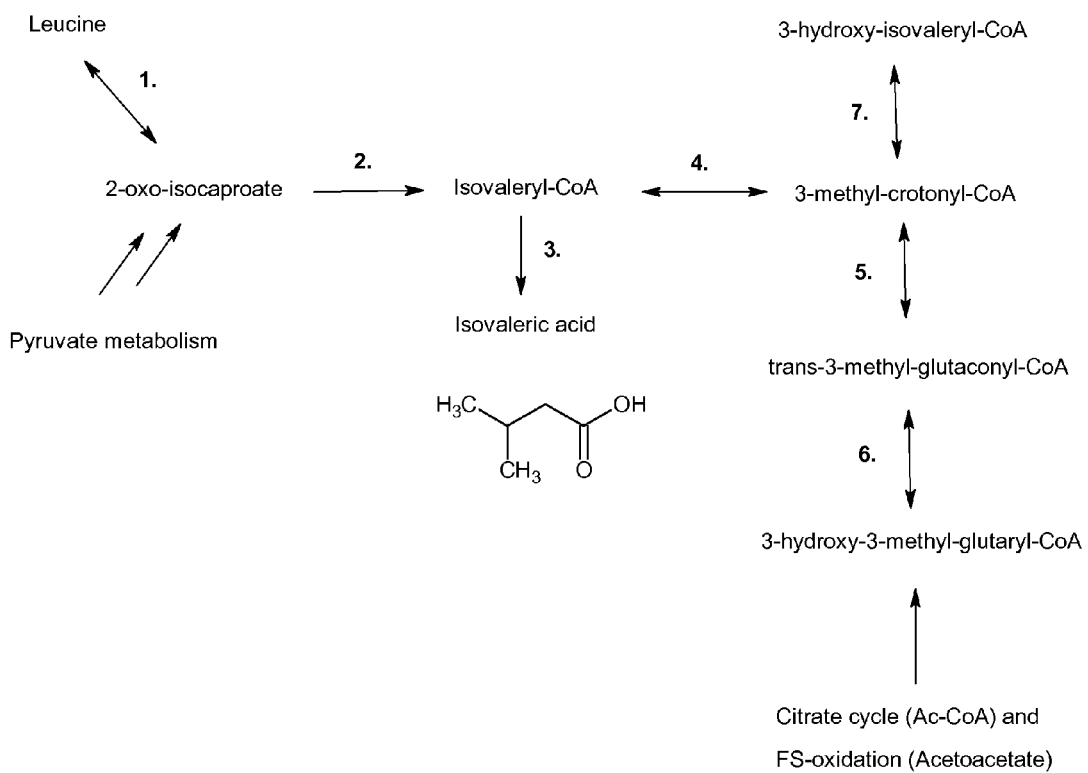
FIG. 1: Metabolic pathway for the formation of isovaleric acid. Explanations: see text

The designations of the respective enzymes are governed by the specific reactions catalyzed by them, as are depicted for example in FIGS. 1 to 7. (Detailed explanations of the figures and of the relevant metabolic pathways following hereinafter.) Thus, it is also possible for a single enzyme to be able to catalyze two reactions which are chemically virtually identical but are assigned to different pathways on the basis of the respective substrate. This may also be associated with a different enzyme classification (E.C. numbers) according to IUBMB. The enzyme designation is governed according to the invention according to the respective specific reaction. This is because the specific function which is implemented in the course of the present invention or is to be switched off where appropriate is also associated therewith.

For illustration, reference may be made by way of example to the enzyme which is indicated in SEQ ID NO. 18 and with which such a deviation is in fact located on the same metabolic pathway defined according to the invention. According to the relevant statement in SEQ ID NO. 17, this is a "probable enoyl-(3-hydroxyisobutyryl)-coenzyme A hydrolase protein". At the time of the application, the IUBMB has not yet allocated an E.C. number for this reaction, which is why reference can be made for definition of the relevant enzymic activity only to reaction (6.) in FIG. 3. On the same metabolic pathway for synthesizing 2-methylbutyric acid and/or isobutyric acid (as part of valine and/or isoleucine catabolism) there is also a reaction which is catalyzed by an enoyl-CoA hydratase, reaction (3.) in FIG. 3; the situation is likewise for reaction (7.) in FIG. 1. A plurality of enzymes with E.C. class 4.2.1.17 are in each case suitable for this, for example those shown in SEQ ID NO. 16, 20 and 42 (see below), but also the enzyme according to SEQ ID NO. 18. In the course of this specific reaction, the enzyme according to SEQ ID NO. 18 is thus to be regarded as enoyl-CoA hydratase and assigned to E.C. class 4.2.1.17.

These genes and gene products can now be synthesized artificially by methods known per se, and without the need to reproduce the sequencing described in Example 1, in a targeted manner on the basis of these sequences.

As a further alternative thereto, it is possible to obtain the relevant genes from a *Bacillus* strain, in particular the strain *B. licheniformis* DSM 13 which is obtainable from the DSMZ, via PCR, it being possible to use the respective border sequences listed in the sequence listing for synthesizing primers. On use of other strains, the genes homologous thereto are obtained in each case, and the success of the PCR should increase with the closeness of the relationship of the selected strains to *B. licheniformis* DSM 13, because an increasing agreement in sequence also within the primer binding regions should be associated therewith.

As an alternative thereto, the nucleic acids indicated in the sequence listing can also be employed as DNA probes in order to detect the respective homologous genes in preparations of genomic DNA from other species. The procedure for this is known per se; as is the isolation of the genes obtained in this way, their cloning, their expression and obtaining of the relevant proteins. Consideration is given in this connection in particular to operating steps like those described for *B. licheniformis* itself in Example 1.

The existence of the relevant proteins in a strain of interest is detected in the first place by a chemical detection of whether the relevant odorous substances are formed. It is then possible for the enzymic activities presumed therefor to be ascertained in suitable detection reactions. This takes place for example by the starting compound relevant to the reaction in question being incubated with a cell extract. When the relevant enzymic activity is present, the products following in the relevant metabolic pathway should accumulate and, if all the subsequent enzymes are present, result in the odorous substance.

As detection at the level of molecular biology it is possible to synthesize proteins on the basis of the amino acid sequences shown in the present sequence listing, and to form antibodies against them. These can then be used for example in Western blots for detecting the homologous protein in cell extracts of the host cells of interest.

Among the nucleic acids mentioned herein and coding for a gene product of the invention involved in the synthesis of isovaleric acid, 2-methylbutyric acid, isobutyric acid, butanol, butyric acid, propionic acid, cadaverine and/or putrescine and defined as above on the basis of SEQ ID NO. 1, 3, 5, 7, 9, 11, 13, 15, 17, 19, 21, 23, 25, 27, 29, 31, 33, 35, 37, 39, 41, 43, 45, 47 or 49, preference is given in each case to that present naturally in a microorganism, preferably a bacterium, particularly preferably a Gram-positive bacterium, among these preferably one of the genus *Bacillus*, among these particularly preferably one of the species *B. licheniformis* and among these very particularly preferably *B. licheniformis* DSM13.

It is thus possible as just described comparatively easy in relation to neosynthesis for the relevant nucleic acids to be obtained from natural species, especially microorganisms. Among these, increasing preference is given in view of the stated problem to those which can be fermented and which can in fact be employed in industrial fermentations. These include in particular representatives of the genera *Staphylococcus*, *Corynebacterium* and *Bacillus*. Mention should be made among these for example of *S. carnosus* and *C. glutamicum*, and *B. subtilis*, *B. licheniformis*, *B. amyloliquefaciens*, *B. agaradherens*, *B. lentus*, *B. globigii* and *B. alkalophilus*. Most preference is given to *B. licheniformis* DSM 13 because it was possible to obtain therefrom exactly the sequences listed in the sequence listing.

These explanations apply in the same way to the relevant proteins.

Thus, among the gene products mentioned herein and involved in the synthesis of isovaleric acid, 2-methylbutyric acid, isobutyric acid, butanol, butyric acid, propionic acid, cadaverine and/or putrescine and defined on the basis of SEQ ID NO. 2, 4, 6, 8, 10, 12, 14, 16, 18, 20, 22, 24, 26, 28, 30, 32, 34, 36, 38, 40, 42, 44, 46, 48 or 50, preference is given in each case to those naturally formed by a microorganism, preferably by a bacterium, particularly preferably by a Gram-positive bacterium, among these preferably by one of the genus *Bacillus*, among these particularly preferably by one of the species *B. licheniforms* and among these very particularly preferably by *B. licheniforms* DSM 13.

The metabolic pathway utilized in Gram-positive bacteria of the genus *Bacillus* for synthesizing isovaleric acid as part of leucine catabolism is depicted in FIG. 1. It ultimately represents an interface between the citrate cycle and/or fatty acid metabolism and pyruvate metabolism as far as the synthesis of leucine.

The enzymes involved in the reactions shown in FIG. 1 are, as mentioned above, the following, where the relevant number designates the respective reaction step indicated in the figure:
(1.) L-leucine dehydrogenase (E.C. 1.4.1.9),
(2.) 3-methyl-2-oxobutanoate dehydrogenase or 2-oxoglutarate dehydrogenase E1 (E.C. 1.2.4.2),
(3.) enzyme for hydrolyzing isovaleryl-CoA to isovaleric acid and coenzyme A (where non-enzymatic hydrolysis is also possible),
(4.) acyl-CoA dehydrogenase (E.C. 1.3.99.-),
(5.) methylcrotonyl carboxylase,
(6.) 3-methylglutaconyl-CoA hydratase and
(7.) enoyl-CoA hydratase (E.C. 4.2.1.17).

Solutions of the stated problem and thus independent embodiments of the present invention are thus represented by all processes for fermenting a microorganism in which at least one of the genes on a metabolic pathway for synthesizing isovaleric acid (as part of leucine catabolism) is functionally inactivated.

The advantages previously explained are associated with this solution.

Preference is given in this connection to any process of this type in which the microorganism now forms only 50% of the amount naturally formed under the same conditions, preferably now only 10%, particularly preferably no isovaleric acid.

These percentages (and all subsequent corresponding data for the further metabolic pathways) mean, in analogy to the statement made above for the sequence homology, once again all intermediate integral or fractional percentages in correspondingly preferred gradation. To determine these values, cells of an untreated strain and of a treated strain are fermented under conditions which are otherwise identical and, during the fermentation, the rate of formation of the unwanted odorous substance is suitably ascertained in a manner known per se. Since the strains are otherwise identical, the differences in the formation of this substance are attributable to the different gene activities. In this connection, any reduction in the formation of the odorous substance is desired according to the invention. Values comparable in percentage terms are obtained by taking samples (for instance from the exit air) from both fermentations and determining the content of the respective substance by analytical methods known per se. It is preferred to determine this value at the transition to the stationary phase of growth, because this time can usually be identified unambiguously and, at the same time, is normally associated with the highest metabolic rate.

Account is taken thereby of the generally high flexibility of microorganisms in relation to their metabolism. Thus, it is conceivable for inactivation of one gene to be partly compensated by enhancement of the activity of another gene and/or protein which is possibly not quite as effective in vivo. However, increasing preference is given to inactivation of the said pathway as extensively as possible. It is possible for this to test in the individual case the inactivation of various genes for the effectiveness according to the invention thereof and to select those with the strongest effect. It is additionally possible to combine a plurality of inactivations together.

Preference is given to a process according to the invention in which at least one of the following enzymes is functionally inactivated:
(1.) L-leucine dehydrogenase (E.C. 1.4.1.9),
(2.) 3-methyl-2-oxobutanoate dehydrogenase or 2-oxoglutarate dehydrogenase E1 (E.C. 1.2.4.2),
(3.) enzyme for hydrolyzing isovaleryl-CoA to isovaleric acid and coenzyme A,
(4.) acyl-CoA dehydrogenase (E.C. 1.3.99.-),
(5.) methylcrotonyl carboxylase,
(6.) 3-methylglutaconyl-CoA hydratase and
(7.) enoyl-CoA hydratase (protein) (E.C. 4.2.1.17).

This is because, as depicted in FIG. 1, these activities may be connected with the metabolic pathway under consideration here.

As already stated above and described in the examples of the present application, it was possible by sequencing the genomic DNA of *B. licheniformis* DSM 13 to identify several of the genes coding for enzymes located on this pathway, or for subunits thereof. The genes involved are the following (the preceding number designates in each case the reaction in which the relevant enzyme is involved):
(2.) 3-methyl-2-oxobutanoate dehydrogenase or 2-oxoglutarate dehydrogenase E1 (E.C. 1.2.4.2) defined by SEQ ID NO. 45,
(4.) a subunit of acyl-CoA dehydrogenase (E.C. 1.3.99.-) defined by SEQ ID NO. 9, 11, 21 or 27 (yusJ gene), and
(7.) enoyl-CoA hydratase (protein) (E.C. 4.2.1.17) defined by SEQ ID NO. 15, 17, 19 (echA8 gene) or 41 (ysiB gene).

The amino acid sequences derived therefrom are indicated in SEQ ID NO. 46, 10, 12, 22, 28, 16, 18, 20 and 42, respectively. It was thus possible to identify these specific gene products in the course of the present invention as involved in this metabolic pathway for synthesizing isovaleric acid (as part of leucine catabolism).

A process of the invention which is therefore preferred is one where the functionally inactivated enzyme is the homolog, which is naturally active in the relevant microorganism, to one of the following proteins from *B. licheniformis* DSM13:
(2.) 3-methyl-2-oxobutanoate dehydrogenase or 2-oxoglutarate dehydrogenase E1 (E.C. 1.2.4.2) defined by SEQ ID NO. 46,
(4.) a subunit of acyl-CoA dehydrogenase (E.C. 1.3.99.-) defined by SEQ ID NO. 10, 12, 22 or 28, and
(7.) enoyl-CoA hydratase (protein) (E.C. 4.2.1.17) defined by SEQ ID NO. 16, 18, 20 or 42.

A preferred process of the invention is one where the enzyme is functionally inactivated at the genetic level, preferably by inactivation of a gene which corresponds to the nucleic acid which codes for one of the following proteins from *B. licheniformis* DSM 13:
(2.) 3-methyl-2-oxobutanoate dehydrogenase or 2-oxoglutarate dehydrogenase E1 (E.C. 1.2.4.2) defined by SEQ ID NO. 45,
(4.) a subunit of acyl-CoA dehydrogenase (E.C. 1.3.99.-) defined by SEQ ID NO. 9, 11, 21 or 27 (yusJ gene), and
(7.) enoyl-CoA hydratase (protein) (E.C. 4.2.1.17) defined by SEQ ID NO. 15, 17, 19 (echA8 gene) or 41 (ysiB gene).

This is because, in accordance with the stated problem, it was preferably intended to find a causal solution, meaning one applying at the level of molecular biology. This is available with the stated nucleotide sequences. Example 3 explains how corresponding deletions can be undertaken; further statements concerning this are given hereinafter because they apply in principle to all described metabolic pathways.

A preferred process of the invention is thus one where, for inactivation at the genetic level, one of the nucleic acids of the invention within the region designated above homologous to
(2.) SEQ ID NO. 45,
(4.) 9, 11, 21 or 27 and
(7.) 15, 17, 19 or 41
has been used, preferably one, particularly preferably two parts in each case one of these sequences which in each case comprise at least 70 connected positions.

This can be detected for example by a molecular biological investigation (such as, for example, restriction, sequencing) of the gene region modified by the mutagenesis.

A further embodiment of the present invention is represented by the use of a gene which corresponds to the nucleic acid which codes for one of the following proteins of *B. licheniformis* DSM 13 for functional inactivation of a metabolic pathway for synthesizing isovaleric acid (as part of leucine catabolism) at the genetic level in a microorganism:

(2.) 3-methyl-2-oxobutanoate dehydrogenase or 2-oxoglutarate dehydrogenase E1 (E.C. 1.2.4.2) defined by SEQ ID NO. 45,
(4.) a subunit of acyl-CoA dehydrogenase (E.C. 1.3.99.-) defined by SEQ ID NO. 9, 11, 21 or 27 (yusJ gene), and
(7.) enoyl-CoA hydratase (protein) (E.C. 4.2.1.17) defined by SEQ ID NO. 15, 17, 19 (echA8 gene) or 41 (ysiB gene).

The same statements as previously made about the corresponding processes apply in principle to such uses.

Accordingly, a preferred use according to the invention of nucleic acids of the invention is within the region of homology designated above to (2.) SEQ ID NO. 45,
(4.) 9, 11, 21 or 27 and
(7.) 15, 17, 19 or 41 for functional inactivation, preferably of one, particularly preferably of two parts in each case of one of these sequences, where these parts in each case comprise at least 70 connected positions.

Further embodiments based on these fermentation processes and uses are detailed hereinafter because they can be applied in principle to all the metabolic pathways described within the scope of the present invention.

Figure 2:
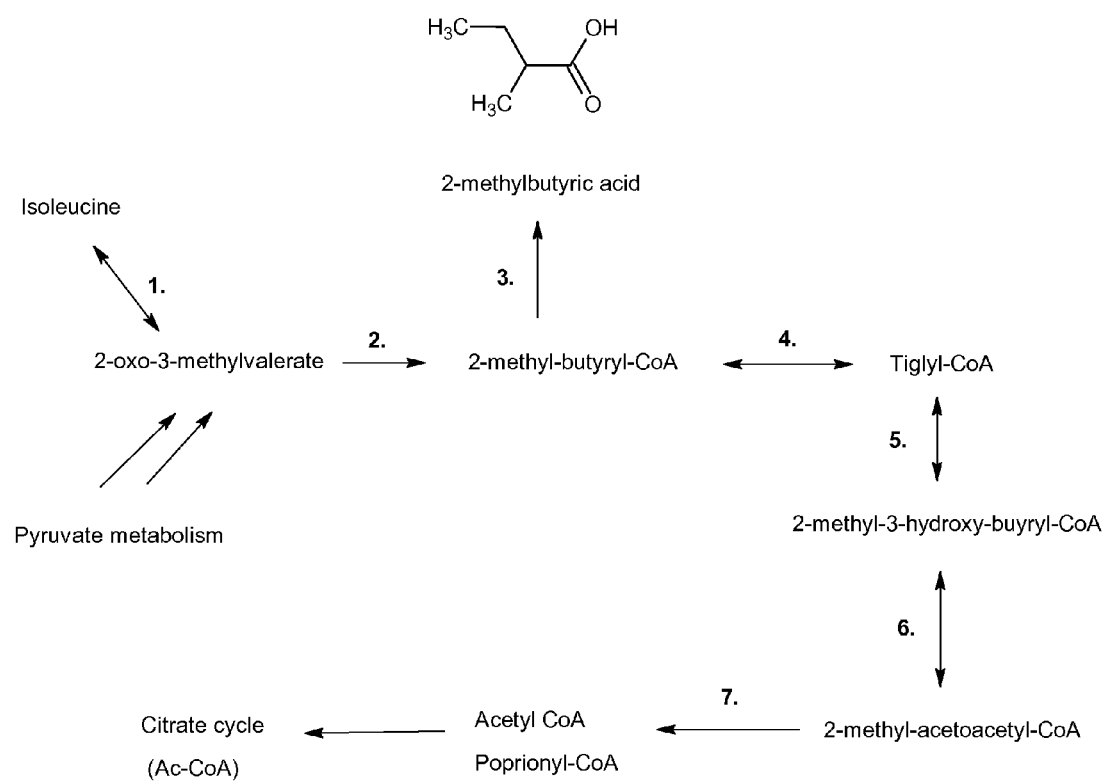
FIG. 2: Metabolic pathway for the formation of 2-methylbutyric acid and/or isobutyric acid; aspect of the formation of 2-methylbutyric acid. Explanations: see text
Figure 3:
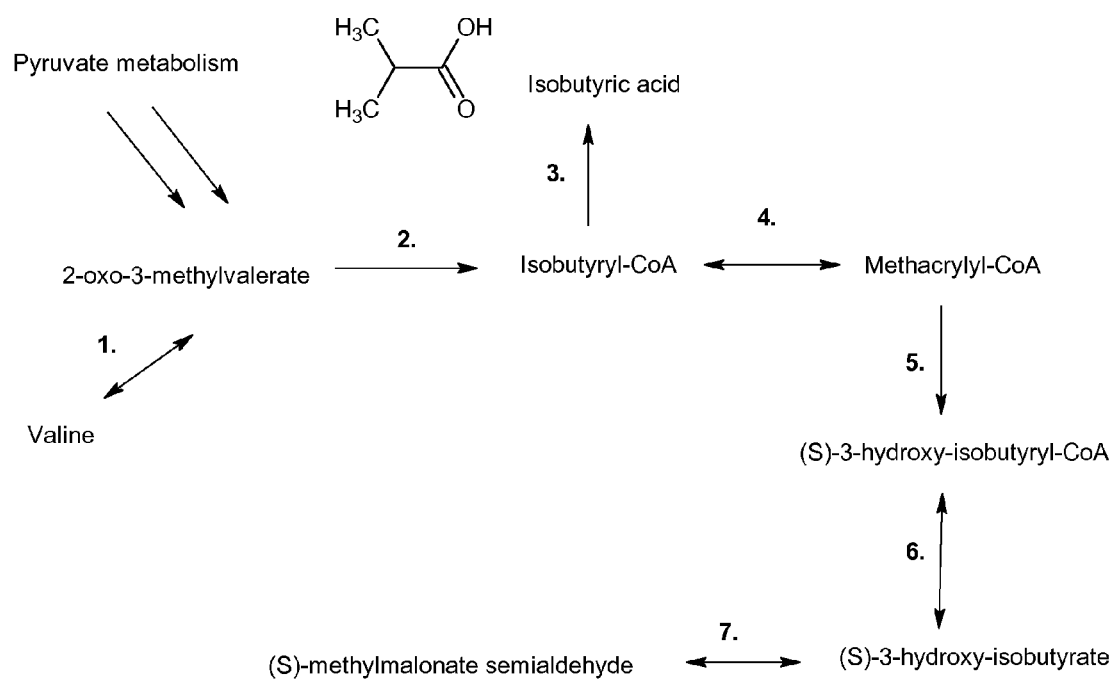
FIG. 3: Metabolic pathway for the formation of 2-methylbutyric acid and/or isobutyric acid; aspect of the formation of isobutyric acid. Explanations: see text

The metabolic pathway utilized in Gram-positive bacteria of the genus *Bacillus* for synthesizing 2-methylbutyric acid as part of isoleucine catabolism is depicted in FIG. 2; the corresponding pathway proceeding via the same enzymes in principle for synthesizing isobutyric acid as part of valine catabolism is evident from FIG. 3. This aspect, which is regarded in connection with the present application as a single pathway, of bacterial metabolism ultimately represents, like the pathway considered previously too, an interface between the citrate cycle and/or fatty acid metabolism and pyruvate metabolism as far as the synthesis of the two amino acids isoleucine and valine.

As already mentioned, the following enzymes are involved in the reactions shown in FIGS. 2 and 3, in each case the relevant numbers of the reaction steps indicated in the figures being indicated:

(1.) branched-chain amino acid aminotransferase (E.C. 2.6.1.42; reaction 1 in FIGS. 2 and 3),
(2.) 3-methyl-2-oxobutanoate dehydrogenase or 2-oxoglutarate dehydrogenase E1 (E.C. 1.2.4.2; reaction 2 in FIGS. 2 and 3),
(3.) enzyme for hydrolyzing 2-methylbutyryl-CoA to 2-methylbutyric acid (reaction 3 in FIG. 2) or isobutyryl-CoA to isobutyric acid and coenzyme A (reaction 3 in FIG. 3; a non-enzymatic hydrolysis also being possible in both cases),
(4.) acyl-CoA dehydrogenase (E.C. 1.3.99.-; reaction 4 in FIGS. 2 and 3),
(5.) enoyl-CoA hydratase (protein) (E.C. 4.2.1.17; reaction 5 in FIGS. 2 and 3),
(6.) 3-hydroxy-acyl-CoA dehydrogenase (E.C. 1.1.1.35) (reaction 6 in FIG. 2),
(7.) acetyl-CoA acyltransferase (reaction step 7 in FIG. 2),
(8.) enoyl-(3-hydroxyisobutyryl)-CoA hydrolase protein (step 6 in FIG. 3) and
(9.) 3-hydroxyisobutyrate dehydrogenase (E.C. 1.1.1.31) or oxidoreductase
(E.C. 1.1.-.-; step 7 in FIG. 3).

Solutions of the stated problem and thus independent embodiments of the present invention are thus represented by all processes for fermenting a microorganism in which at least one of the genes on a metabolic pathway for synthesizing 2-methylbutyric acid and/or isobutyric acid (as part of valine and/or isoleucine catabolism) is functionally inactivated.

The advantages already explained are associated with this solution.

Preference is given in this connection to any process of this type in which the microorganism now forms only 50% of the amount formed naturally under the same conditions, preferably now only 10%, particularly preferably no 2-methylbutyric acid and/or isobutyric acid.

Account is thereby taken, as explained above for the first metabolic pathway described, of the generally high flexibility of microorganisms in relation to their metabolism.

A preferred process of the invention is one in which at least one of the following enzymes is functionally inactivated:

(1.) branched-chain amino acid aminotransferase (E.C. 2.6.1.42),
(2.) 3-methyl-2-oxobutanoate dehydrogenase or 2-oxoglutarate dehydrogenase E1 (E.C. 1.2.4.2),
(3.) enzyme for hydrolyzing 2-methylbutyryl-CoA to 2-methylbutyric acid or isobutyryl-CoA to isobutyric acid and coenzyme A,
(4.) acyl-CoA dehydrogenase (E.C. 1.3.99.-),
(5.) enoyl-CoA hydratase (protein) (E.C. 4.2.1.17),
(6.) 3-hydroxy-acyl-CoA dehydrogenase (E.C. 1.1.1.35),
(7.) acetyl-CoA acyltransferase,
(8.) enoyl-(3-hydroxyisobutyryl)-CoA hydrolase protein and
(9.) 3-hydroxyisobutyrate dehydrogenase (E.C. 1.1.1.31) or oxidoreductase (E.C. 1.1.-.-).

This is because, as depicted in FIGS. 2 and 3, these activities may be associated with the metabolic pathway considered.

As stated previously and described in the examples of the present application, it was possible by sequencing the genomic DNA of *B. licheniformis* DSM 13 to identify several of the genes which code for enzymes located on this pathway, or for subunits thereof. These involve the following genes (the preceding number designates in each case the reaction in which the relevant enzyme is involved):

(1.) branched-chain amino acid aminotransferase (E.C. 2.6.1.42) defined by SEQ ID NO. 1 or 3,
(2.) 3-methyl-2-oxobutanoate dehydrogenase or 2-oxoglutarate dehydrogenase E1 (E.C. 1.2.4.2) defined by SEQ ID NO. 45,
(4.) acyl-CoA dehydrogenase (E.C. 1.3.99.-) defined by SEQ ID NO. 9, 11, 21 or 27 (yusJ gene),
(5.) enoyl-CoA hydratase (protein) (E.C. 4.2.1.17) defined by SEQ ID NO. 15, 17, 19 (echA8 gene) or 41 (ysiB gene),
(6.) 3-hydroxy-acyl-CoA dehydrogenase (E.C. 1.1.1.35) defined by SEQ ID NO. 43,
(8.) enoyl-(3-hydroxyisobutyryl)-CoA hydrolase protein defined by SEQ ID NO. 17 and
(9.) 3-hydroxyisobutyrate dehydrogenase (E.C. 1.1.1.31) or oxidoreductase
(E.C. 1.1.-.-) defined by SEQ ID NO. 29 (ykwC gene).

The amino acid sequences derived therefrom are indicated in SEQ ID NO. 2, 4, 46, 10, 12, 22, 28, 16, 18, 20, 42, 44, 18 and 30. It was thus possible in the course of the present invention to identify the specific gene products as involved in this metabolic pathway for synthesizing 2-methylbutyric acid and/or isobutyric acid (as part of valine and/or isoleucine catabolism).

A preferred process of the invention is therefore one where the functionally inactivated enzyme is the homolog, naturally active in the relevant microorganism, to one of the following proteins from *B. licheniformis* DSM 13:
(1.) branched-chain amino acid aminotransferase (E.C. 2.6.1.42) defined by SEQ ID NO. 2 or 4,
(2.) 3-methyl-2-oxobutanoate dehydrogenase or 2-oxoglutarate dehydrogenase E1 (E.C. 1.2.4.2) defined by SEQ ID NO. 46,
(4.) acyl-CoA dehydrogenase (E.C. 1.3.99.-) defined by SEQ ID NO. 10, 12, 22 or 28,
(5.) enoyl-CoA hydratase (protein) (E.C. 4.2.1.17) defined by SEQ ID NO. 16, 18, 20 or 42,
(6.) 3-hydroxy-acyl-CoA dehydrogenase (E.C. 1.1.1.35) defined by SEQ ID NO. 44,
(8.) enoyl-(3-hydroxyisobutyryl)-CoA hydrolase protein defined by SEQ ID NO. 18 and
(9.) 3-hydroxyisobutyrate dehydrogenase (E.C. 1.1.1.31) or oxidoreductase (E.C. 1.1.-.-) defined by SEQ ID NO. 30.

A preferred process of the invention is one where the enzyme is functionally inactivated at the genetic level, preferably by inactivation of a gene which corresponds to the nucleic acid which codes for one of the following proteins of *B. licheniformis* DSM 13:
(1.) branched-chain amino acid aminotransferase (E.C. 2.6.1.42) defined by SEQ ID NO. 1 or 3,
(2.) 3-methyl-2-oxobutanoate dehydrogenase or 2-oxoglutarate dehydrogenase E1 (E.C. 1.2.4.2) defined by SEQ ID NO. 45,
(4.) acyl-CoA dehydrogenase (E.C. 1.3.99.-) defined by SEQ ID NO. 9, 11, 21 or 27 (yusJ gene),
(5.) enoyl-CoA hydratase (protein) (E.C. 4.2.1.17) defined by SEQ ID NO. 15, 17, 19 (echA8 gene) or 41 (ysiB gene),
(6.) 3-hydroxy-acyl-CoA dehydrogenase (E.C. 1.1.1.35) defined by SEQ ID NO. 43,
(8.) enoyl-(3-hydroxyisobutyryl)-CoA hydrolase protein defined by SEQ ID NO. 17 and
(9.) 3-hydroxyisobutyrate dehydrogenase (E.C. 1.1.1.31) or oxidoreductase (E.C. 1.1.-.-) defined by SEQ ID NO. 29 (ykwC gene).

This is because, in accordance with the stated problem, the intention was preferably to find a causal solution, meaning one applying at the level of molecular biology. Example 3 explains how corresponding deletions can be undertaken; further statements concerning this are given hereinafter.

A preferred process of the invention is thus one where, for inactivation at the genetic level, one of the nucleic acids of the invention within the region designated above and homologous to
(1.) SEQ ID NO. 1 or 3,
(2.) 45,
(4.) 9, 11, 21 or 27,
(5.) 15, 17, 19 or 41,
(6.) 43,
(8.) 17 and
(9.) 29
has been used, preferably one, particularly preferably two parts in each case of one of these sequences which in each case comprise at least 70 connected positions.

A further embodiment of the present invention is represented by the use of a gene which corresponds to the nucleic acid which codes for one of the following proteins of *B. licheniformis* DSM 13 for functional inactivation of a metabolic pathway for synthesizing isovaleric acid (as part of leucine catabolism) at the genetic level in a microorganism:
(1.) branched-chain amino acid aminotransferase (E.C. 2.6.1.42) defined by SEQ ID NO. 1 or 3,
(2.) 3-methyl-2-oxobutanoate dehydrogenase or 2-oxoglutarate dehydrogenase E1 (E.C. 1.2.4.2) defined by SEQ ID NO. 45,
(4.) acyl-CoA dehydrogenase (E.C. 1.3.99.-) defined by SEQ ID NO. 9, 11, 21 or 27 (yusJ gene),
(5.) enoyl-CoA hydratase (protein) (E.C. 4.2.1.17) defined by SEQ ID NO. 15, 17, 19 (echA8 gene) or 41 (ysiB gene),
(6.) 3-hydroxy-acyl-CoA dehydrogenase (E.C. 1.1.1.35) defined by SEQ ID NO. 43,
(8.) enoyl-(3-hydroxyisobutyryl)-CoA hydrolase protein defined by SEQ ID NO. 17 and
(9.) 3-hydroxyisobutyrate dehydrogenase (E.C. 1.1.1.31) or oxidoreductase (E.C. 1.1.-.-) defined by SEQ ID NO. 29 (ykwC gene).

The same as previously stated concerning the corresponding processes applies in principle to such uses.

Accordingly, a preferred use according to the invention is of nucleic acids of the invention within the regions designated above and homologous to
(1.) SEQ ID NO. 1 or 3,
(2.) 45,
(4.) 9, 11, 21 or 27,
(5.) 15, 17, 19 r 41,
(6.) 43,
(8.) 17 and
(9.) 29
for functional inactivation, preferably of one, particularly preferably of two parts in each case of one of these sequences, where these parts comprise in each case at least 70 connected positions.

Further embodiments based on these fermentation processes and uses are detailed hereinafter.

Figure 4:
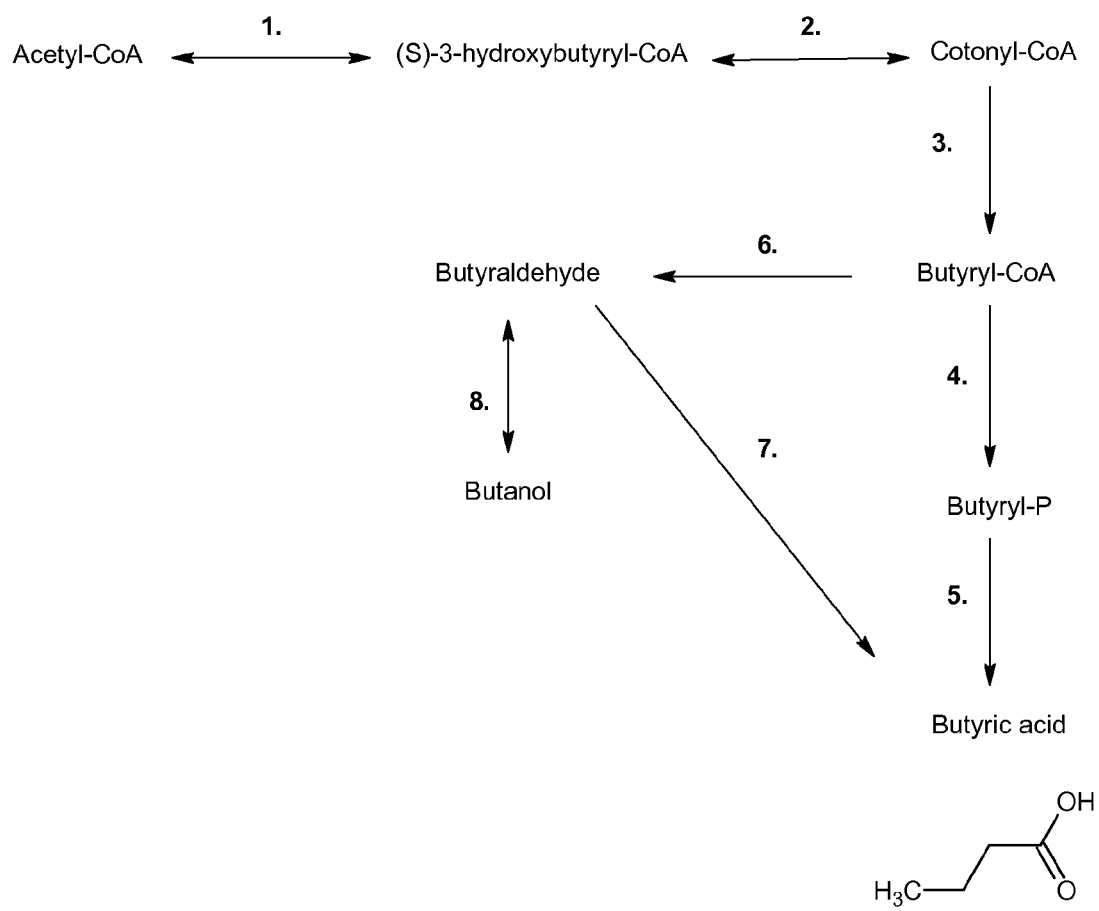
FIG. 4: Metabolic pathway for the formation of butanol and/or butyric acid. Explanations: see text

The metabolic pathway utilized in Gram-positive bacteria of the genus *Bacillus* for synthesizing butanol and/or butyric acid as part of butyric acid metabolism is depicted in FIG. 4. This metabolic pathway is ultimately derived from fatty acid metabolism.

As previously mentioned, the following enzymes are involved in the reactions shown in FIG. 4, the relevant number designating the respective reaction step indicated in the figure:
(1.) 3-hydroxybutyryl-CoA dehydrogenase (E.C. 1.1.1.157),
(2.) 3-hydroxybutyryl-CoA dehydrogenase (E.C. 4.2.1.55),
(3.) butyryl-CoA dehydrogenase (E.C. 1.3.99.25),
(4.) phosphate butyryltransferase (E.C. 2.3.1.19),
(5.) butyrate kinase (E.C. 2.7.2.7),
(6.) butyraldehyde dehydrogenase and
(8.) NADH-dependent butanol dehydrogenase A (E.C. 1.1.1.-).

Reaction (7.) normally takes place by non-enzymatic oxidation by atmospheric oxygen.

Solutions of the stated problem and thus independent embodiments of the present invention are thus represented by all processes for fermenting a microorganism in which at least one of the genes on a metabolic pathway for synthesizing butanol and/or butyric acid (as part of butyric acid metabolism) is functionally inactivated.

The advantages already explained are associated with this solution.

Preference is given in this connection to any process of this type in which the microorganism now forms only 50% of the amount naturally formed under the same conditions, preferably now only 10%, particularly preferably no butanol or no butyric acid.

This takes account, as explained above for the first metabolic pathway described, of the generally high flexibility of microorganisms in relation to their metabolism.

A preferred process of the invention is one in which at least one of the following enzymes is functionally inactivated:
(1.) 3-hydroxybutyryl-CoA dehydrogenase (E.C. 1.1.1.157),
(2.) 3-hydroxybutyryl-CoA dehydratase (E.C. 4.2.1.55),
(3.) butyryl-CoA dehydrogenase (E.C. 1.3.99.25),
(4.) phosphate butyryltransferase (E.C. 2.3.1.19),
(5.) butyrate kinase (E.C. 2.7.2.7),
(6.) butyraldehyde dehydrogenase and
(8.) NADH-dependent butanol dehydrogenase A (E.C. 1.1.1.-).

This is because, as depicted in FIG. 4, these activities can be associated with the metabolic pathway under consideration here.

As stated above and described in the examples of the present application, it was possible by sequencing the genomic DNA of *B. licheniformis* DSM 13 to identify several of the genes which code for enzymes located on this pathway, or for subunits thereof. These are the following genes (the preceding number designates in each case the reaction in which the relevant enzyme is involved):
(1.) 3-hydroxybutyryl-CoA dehydrogenase (E.C. 1.1.1.157) defined by SEQ ID NO. 13,
(2.) 3-hydroxybutyryl-CoA dehydratase (E.C. 4.2.1.55) defined by SEQ ID NO. 25 (yngF gene),
(3.) butyryl-CoA dehydrogenase (E.C. 1.3.99.25) defined by SEQ ID NO. 9, 11 or 27 (yusJ gene),
(4.) phosphate butyryltransferase (E.C. 2.3.1.19) defined by SEQ ID NO. 31,
(5.) butyrate kinase (E.C. 2.7.2.7) defined by SEQ ID NO. 33 and
(8.) NADH-dependent butanol dehydrogenase A (E.C. 1.1.1.-) defined by SEQ ID NO. 7 (yugJ gene).

The amino acid sequences derived therefrom are indicated in SEQ ID NO. 14, 26, 10, 12, 28, 32, 34 and 8. It was thus possible in the course of the present invention to identify these specific gene products as involved in this metabolic pathway for synthesizing butanol and/or butyric acid (as part of butyric acid metabolism).

A preferred process of the invention is therefore one where the functionally inactivated enzyme is the homolog, which is naturally active in the relevant microorganism, to one of the following proteins from *B. licheniformis* DSM 13:
(1.) 3-hydroxybutyryl-CoA dehydrogenase (E.C. 1.1.1.157) defined by SEQ ID NO. 14,
(2.) 3-hydroxybutyryl-CoA dehydratase (E.C. 4.2.1.55) defined by SEQ ID NO. 26,
(3.) butyryl-CoA dehydrogenase (E.C. 1.3.99.25) defined by SEQ ID NO. 10, 12 or 28,
(4.) phosphate butyryltransferase (E.C. 2.3.1.19) defined by SEQ ID NO. 32,
(5.) butyrate kinase (E.C. 2.7.2.7) defined by SEQ ID NO. 34 and
(8.) NADH-dependent butanol dehydrogenase A (E.C. 1.1.1.-) defined by SEQ ID NO. 8.

The preferred process according to the invention is one where the enzyme is functionally inactivated at the genetic level, preferably by inactivation of a gene which corresponds to the nucleic acid which codes for one of the following proteins of *B. licheniformis* DSM 13:
(1.) 3-hydroxybutyryl-CoA dehydrogenase (E.C. 1.1.1.157) defined by SEQ ID NO. 13,
(2.) 3-hydroxybutyryl-CoA dehydratase (E.C. 4.2.1.55) defined by SEQ ID NO. 25 (yngF gene),
(3.) butyryl-CoA dehydrogenase (E.C. 1.3.99.25) defined by SEQ ID NO. 9, 11 or 27 (yusJ gene),
(4.) phosphate butyryltransferase (E.C. 2.3.1.19) defined by SEQ ID NO. 31,
(5.) butyrate kinase (E.C. 2.7.2.7) defined by SEQ ID NO. 33 and
(8.) NADH-dependent butanol dehydrogenase A (E.C. 1.1.1.-) defined by SEQ ID NO. 7 (yugJ gene).

This is because, in accordance with the stated problem, it was intended preferably to find a causal solution, meaning one applying at the level of molecular biology. Example 3 explains how corresponding deletions can be undertaken; further statements concerning this are given hereinafter.

Thus, a preferred process of the invention is one where, for inactivation at the genetic level, one of the nucleic acids of the invention within the region designated above and homologous to
(1.) SEQ ID NO. 13,
(2.) 25,
(3.) 9, 11 or 27,
(4.) 31,
(5.) 33 and
(6.) 7
has been used, preferably one, particularly preferably two parts in each case of one of these sequences, which in each case comprise at least 70 connected positions.

A further embodiment of the present invention is represented by the use of a gene which corresponds to the nucleic acid which codes for one of the following proteins of *B. licheniformis* DSM 13 for functional inactivation of a metabolic pathway for synthesizing butanol and/or butyric acid (as part of butyric acid metabolism) at the genetic level in a microorganism:
(1.) 3-hydroxybutyryl-CoA dehydrogenase (E.C. 1.1.1.157) defined by SEQ ID NO. 13,
(2.) 3-hydroxybutyryl-CoA dehydratase (E.C. 4.2.1.55) defined by SEQ ID NO. 25 (yngF gene),
(3.) butyryl-CoA dehydrogenase (E.C. 1.3.99.25) defined by SEQ ID NO. 9, 11 or 27 (yusJ gene),
(4.) phosphate butyryltransferase (E.C. 2.3.1.19) defined by SEQ ID NO. 31,
(5.) butyrate kinase (E.C. 2.7.2.7) defined by SEQ ID NO. 33 and
(8.) NADH-dependent butanol dehydrogenase A (E.C. 1.1.1.-) defined by SEQ ID NO. 7 (yugJ gene).

The same as has previously been stated concerning the corresponding processes applies in principle to such uses.

Accordingly, a preferred use according to the invention is of nucleic acids of the invention within the region designated above and homologous to
(1.) SEQ ID NO. 13,
(2.) 25,
(3.) 9, 11 or 27,
(4.) 31,
(5.) 33 and
(8.) 7
for functional inactivation, preferably of one, particularly preferably of two parts in each case of one of these sequences, where these parts comprise in each case at least 70 connected positions.

Further embodiments based on these fermentation processes and uses are detailed hereinafter.

Figure 5:
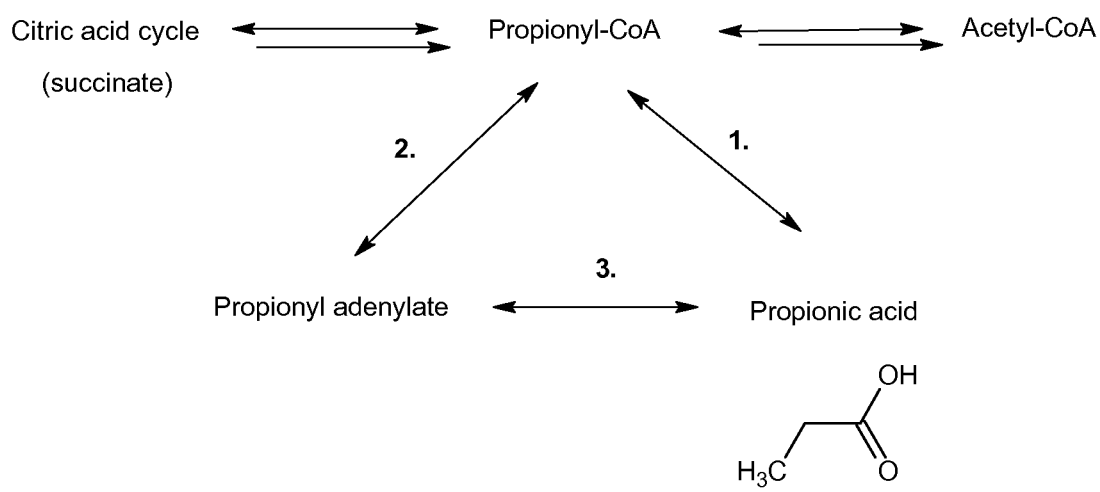
FIG. 5: Metabolic pathway for the formation of propionic acid. Explanations: see text

The metabolic pathway utilized in Gram-positive bacteria of the genus *Bacillus* for synthesizing propionic acid (as part of propionate metabolism) is depicted in FIG. 5. This metabolic pathway ultimately represents an interface between the citrate cycle and fatty acid metabolism.

As already mentioned, the following enzymes are involved in the reactions shown in FIG. 5, where the relevant number designates the respective reaction step indicated in the figure:
(1.) succinate-propionate CoA-transferase,
(2.) acetate-CoA ligase or synthetase or propionate-CoA ligase or synthetase (E.C. 6.2.1.1) and
(3.) acetate-CoA ligase or synthetase or propionate-CoA ligase or synthetase (E.C. 6.2.1.1).

Solutions of the stated problem and thus independent embodiments of the present invention are thus represented by all processes for fermenting a microorganism in which at least one of the genes on a metabolic pathway for synthesizing propionic acids (as part of propionate metabolism) is functionally inactivated.

The previously explained advantages are associated with this solution.

Preference is given in this connection to any process of this type in which the microorganism now forms only 50% of the amount naturally formed under the same conditions, preferably now only 10%, particularly preferably no propionic acid.

This takes account, as explained above for the first metabolic pathway described, of the generally high flexibility of microorganisms in relation to their metabolism.

A preferred process of the invention is one in which at least one of the following enzymes is functionally inactivated:
(1.) succinate-propionate CoA-transferase,
(2.) acetate-CoA ligase or synthetase or propionate-CoA ligase or synthetase (E.C. 6.2.1.1) and
(3.) acetate-CoA ligase or synthetase or propionate-CoA ligase or synthetase (E.C. 6.2.1.1).

This is because, as depicted in FIG. 5, these activities can be connected with the metabolic pathway under consideration herein.

As already stated above and described in the examples in the present application, it was possible to identify by sequencing the genomic DNA of B. licheniformis DSM 13 several of the genes which code for enzymes located on this pathway, or for subunits thereof. These are the following genes (the preceding number designates in each case the reaction in which the relevant enzyme is involved):
acetate-CoA ligase or synthetase or propionate-CoA ligase or synthetase (E.C. 6.2.1.1) defined by SEQ ID NO. 35 (acsA gene), 37 (ytcl gene), 47 (yhfL gene) or 23 (acsA gene).

The amino acid sequences derived therefrom are indicated in SEQ ID NO. 36, 38, 48 and 24. It was thus possible to identify the specific gene products in the course of the present invention as involved in this metabolic pathway for synthesizing propionic acid (as part of propionate metabolism).

A preferred process of the invention is therefore one where the functionally inactivated enzyme is the homolog, which is naturally active in the relevant microorganism, to one of the following proteins from B. licheniformis DSM 13: acetate-CoA ligase or synthetase or propionate-CoA ligase or synthetase (E.C. 6.2.1.1) defined by SEQ ID NO. 36, 38, 48 or 24.

A preferred process of the invention is one where the enzyme is functionally inactivated at the genetic level, preferably by inactivation of a gene which corresponds to the nucleic acid which codes for one of the following proteins of B. licheniformis DSM 13: acetate-CoA ligase or synthetase or propionate-CoA ligase or synthetase (E.C. 6.2.1.1) defined by SEQ ID NO. 35 (acsA gene), 37 (ytcl gene), 47 (yhfL gene) or 23 (acsA gene).

This is because, in accordance with the stated problem, the intention was preferably to find a causal solution, meaning one applying at the level of molecular biology. Example 3 explains how corresponding deletions can be undertaken; further statements concerning this are given hereinafter.

A preferred process of the invention is thus one where, for the inactivation at the genetic level, one of the nucleic acids of the invention has been used within the region designated above and homologous to SEQ ID NO. 35, 37, 47 or 23, preferably one, particularly preferably two parts in each case of one of these sequences which comprise in each case at least 70 connected positions.

A further embodiment of the present invention is represented by the use of a gene which corresponds to the nucleic acid which codes for one of the following proteins of B. licheniformis DSM 13 for the functional inactivation of a metabolic pathway for synthesizing propionic acid (as part of propionate metabolism) at the genetic level in a microorganism: acetate-CoA ligase or synthetase or propionate-CoA ligase or synthetase (E.C. 6.2.1.1) defined by SEQ ID NO. 35 (acsA gene), 37 (ytcl gene), 47 (yhfL gene) or 23 (acsA gene).

The same as previously stated concerning the corresponding processes applies in principle to uses of this type.

Accordingly, preference is given to such a use according to the invention of nucleic acids of the invention within the region designated above and homologous to SEQ ID NO. 35, 37, 47 or 23 for functional inactivation, preferably of one, particularly preferably of two parts in each case of one of these sequences, where these parts comprise in each case at least 70 connected positions.

Further embodiments based on these fermentation processes and uses are detailed hereinafter.

Figure 6:
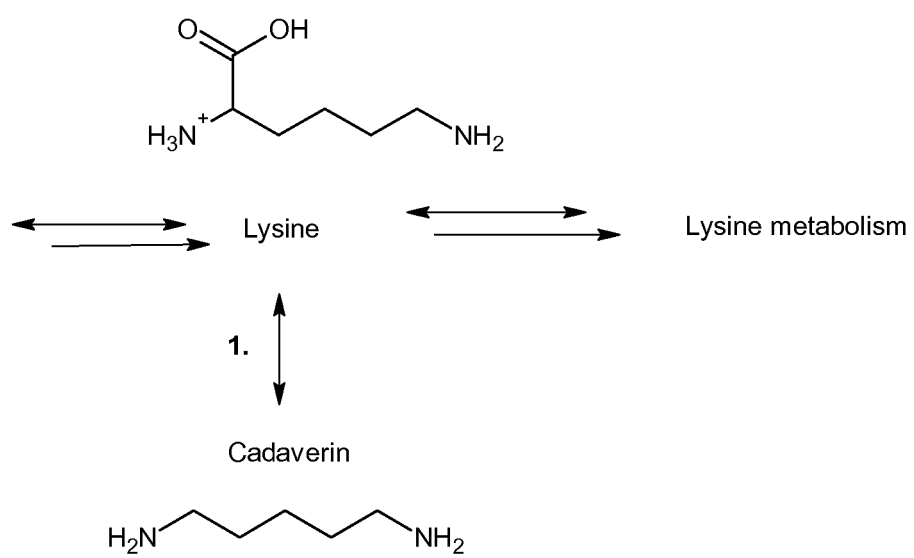
FIG. 6: Metabolic pathway for the formation of cadaverine and/or putrescine; aspect of the formation of cadaverine. Explanations: see text

The metabolic pathway utilized in Gram-positive bacteria of the genus *Bacillus* for synthesizing cadaverine and/or putrescine (as parts of lysine and/or arginine catabolism) is depicted in FIGS. 6 (for lysine and the cadaverine derived therefrom) and 7 (for arginine and the putrescine derived therefrom). This aspect, which is designated as a single pathway in the present application, of the bacterial metabolism is ultimately derived as side pathway from amino acid metabolism and in the second case additionally from the urea cycle.

Figure 7:
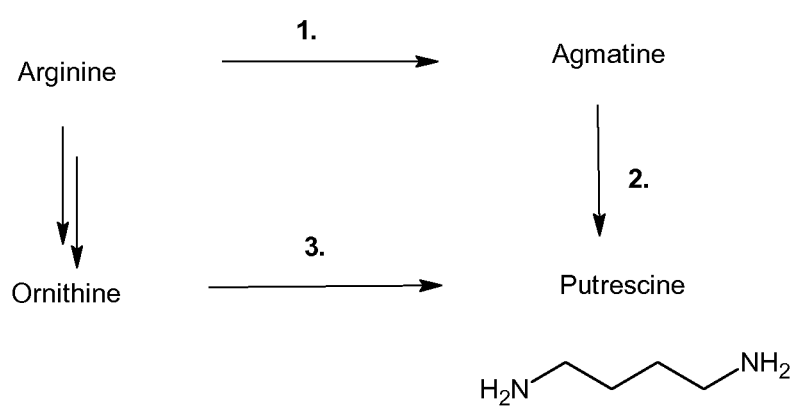
FIG. 7: Metabolic pathway for the formation of cadaverine and/or putrescine; aspect of the formation of putrescine. Explanations: see text

As already mentioned, the following enzymes are involved in the reactions shown in FIGS. 6 and 7, where the relevant number designates the respective reaction step indicated in the figures:
(1.) lysine decarboxylase (E.C. 4.1.1.18) and/or arginine decarboxylase (E.C. 4.1.1.19) (single demonstrated reaction in FIG. 6; step 1 in FIG. 7; the case where the same enzyme is able to catalyze both reactions also applies here),
(2.) agmatinase (E.C. 3.5.1.11); step 2 in FIG. 7) and
(3.) ornithine decarboxylase (E.C. 4.1.1.17; step 3 in FIG. 7).

Solutions of the stated problem and thus independent embodiments of the present invention are thus represented by all processes for fermenting a microorganism in which at least one of the genes on a metabolic pathway for synthesizing cadaverine and/or putrescine (as parts of lysine and/or arginine catabolism) is functionally inactivated.

The previously explained advantages are associated with this solution.

Preference is given in this connection to any process of this type in which the microorganism now forms only 50% of the amount naturally formed under the same conditions, preferably now only 10%, particularly preferably no cadaverine and/or no putrescine.

This takes account, as explained above for the first metabolic pathway described, of the generally high flexibility of microorganisms in relation to their metabolism.

A preferred process of the invention is one where at least one of the following enzymes is functionally inactivated:

(1.) lysine decarboxylase (E.C. 4.1.1.18) and/or arginine decarboxylase (E.C. 4.1.1.19),
(2.) agmatinase (E.C. 3.5.1.11) and
(3.) ornithine decarboxylase (E.C. 4.1.1.17).

This is because, as depicted in FIGS. 6 and 7, these activities can be associated with the metabolic pathway under consideration here.

As stated above and described in the examples of the present application, it was possible by sequencing the genomic DNA of *B. licheniformis* DSM 13 to identify several of the genes coding for enzymes located on this pathway, or for subunits thereof. These are the following genes (the preceding number designates in each case the reaction in which the relevant enzyme is involved):
(1.) lysine and/or arginine decarboxylase (E.C. 4.1.1.18 or E.C. 4.1.1.19) defined by SEQ ID NO. 5 (speA gene) or 39 (speA gene) and
(2.) agmatinase (E.C. 3.5.1.11) defined by SEQ ID NO. 49 (ywhG gene).

The amino acid sequences derived therefrom are indicated in SEQ ID NO. 6, 40 and 50. It was thus possible in the course of the present invention to identify these specific gene products as involved in this metabolic pathway for synthesizing cadaverine and/or putrescine (as parts of lysine and/or arginine catabolism).

A preferred process of the invention is therefore one where the functionally inactivated enzyme is the homolog, which is naturally active in the relevant microorganism, to one of the following proteins from *licheniformis* DSM 13:
(1.) lysine and/or arginine decarboxylase (E.C. 4.1.1.18 or E.C. 4.1.1.19) defined by SEQ ID NO. 6 or 40 and
(2.) agmatinase (E.C. 3.5.1.11) defined by SEQ ID NO. 50.

A preferred process of the invention is one where the enzyme is functionally inactivated at the genetic level, preferably by inactivation of a gene which corresponds to the nucleic acid which codes for one of the following proteins of *B. licheniformis* DSM 13:
(1.) lysine and/or arginine decarboxylase (E.C. 4.1.1.18 or E.C. 4.1.1.19) defined by SEQ ID NO. 5 (speA gene) or 39 (speA gene) and
(2.) agmatinase (E.C. 3.5.1.11) defined by SEQ ID NO. 49 (ywhG gene).

This is because, in accordance with the stated problem, the intention was preferably to find a causal solution, meaning one applying at the level of molecular biology. Example 3 explains how corresponding deletions can be undertaken; further statements concerning this are given hereinafter.

Thus, preference is given to a process of the invention where for the inactivation at the genetic level one of the nucleic acids of the invention within the region designated above and homologous to
(1.) SEQ ID NO. 5 or 39 and
(2.) 49
has been used, preferably one, particularly preferably two parts in each case of one of these sequences which in each case comprise at least 70 connected positions.

A further embodiment of the present invention is represented by the use of a gene which corresponds to the nucleic acid which codes for one of the following proteins of *B. licheniformis* DSM 13 for functional inactivation of a metabolic pathway for synthesizing cadaverine and/or putrescine (as parts of lysine and/or arginine catabolism) at the genetic level in a microorganism:
(1.) lysine and/or arginine decarboxylase (E.C. 4.1.1.18 or E.C. 4.1.1.19) defined by SEQ ID NO. 5 (speA gene) or 39 (speA gene) and
(2.) agmatinase (E.C. 3.5.1.11) defined by SEQ ID NO. 49 (ywhG gene).

The same as has previously been stated concerning corresponding processes applies in principle to such uses.

Accordingly, preference is given to a use according to the invention of nucleic acids of the invention within the region designated above and homologous to
(1.) SEQ ID NO. 5 or 39 and
(2.) 49
for functional inactivation, preferably of one, particularly preferably of two parts in each case of one of these sequences, where these parts comprise in each case at least 70 connected positions.

Further embodiments based on these fermentation processes and uses are detailed hereinafter.

Embodiments which are preferred in each case of the uses described above according to the invention of the genes and/or nucleic acids on each of the described five metabolic pathways are those where the functional inactivation takes place during the fermentation of the microorganism.

This is because in accordance with the stated problem the intention was to improve the fermentation at the genetic level. On fermentation of microorganisms which have been correspondingly modified via these genes and/or nucleic acids is to be expected that the amount of the odorous and/or poisonous substances is less than with unmodified strains. This advantage, which emerges during the fermentation, is preferred according to the invention because it has advantageous effects both on the production process, meaning the fermentation process, and on the subsequent working up.

Among these, preference is given to any use of this type where (if present) with increasing preference 2, 3 or 4 of the genes mentioned for each metabolic pathway ((1.) for synthesizing isovaleric acid, (2.) for synthesizing 2-methylbutyric acid and/or isobutyric acid, (3.) for synthesizing butanol and/or butyric acid, (4) for synthesizing propionic acid and/or (5.) for synthesizing cadaverine and/or putrescine) are inactivated.

This is because, as already explained, microorganisms may in individual cases escape inactivation by activating an alternative pathway or at least enzymes with comparable reactions and thus continuing to form the relevant odorous and/or poisonous substance. This problem can be solved in particular by blocking a plurality of single reactions.

Preference is further given to any use of this type where (if present in the relevant microorganism) with increasing preference 2, 3, 4 or 5 of the metabolic pathways (1.) for synthesizing isovaleric acid, (2.) for synthesizing 2-methylbutyric acid and/or isobutyric acid, (3.) for synthesizing butanol and/or butyric acid, (4.) for synthesizing propionic acid and/or (5.) for synthesizing cadaverine and/or putrescine are blocked at least in part.

This is because firstly the inactivation of a single reaction may block a plurality of said pathways. This applies for example to butyryl-CoA dehydrogenase (E.C. 1.3.99.25) defined by SEQ ID NO. 9, 11 or 27 (yusJ gene) which occurs on the first three metabolic pathways mentioned; or to the three following enzymes or groups of enzymes which are equally involved in the two pathways mentioned first: 3-methyl-2-oxobutanoate dehydrogenase or 2-oxoglutarate dehydrogenase E1 (E.C. 1.2.4.2) defined by SEQ ID NO. 46, a subunit of acyl-CoA dehydrogenase (E.C. 1.3.99.-) defined by SEQ ID NO. 10, 12, 22 or 28, and enoyl-CoA hydratase (protein) (E.C. 4.2.1.17) defined by SEQ ID NO. 16, 18, 20 or 42. In these cases too, the enzymic activities are defined with reference to the reactions described above and indicated in the figures.

Secondly, it is possible by generally known methods of molecular biology to inactivate a plurality of genes in parallel, so that in principle all these pathways can be switched off and thus correspondingly favorable fermentation processes can be obtained.

In one alternative, all these uses of genes and/or of the described nucleic acids of the invention are ones where in each case a nucleic acid coding for an inactive protein and having a point mutation is employed.

Nucleic acids of this type can be generated by methods of point mutagenesis known per se. Such methods are described for example in relevant handbooks such as that of Fritsch, Sambrook and Maniatis "Molecular cloning: a laboratory manual", Cold Spring Harbour Laboratory Press, New York, 1989. In addition, numerous commercial construction kits are now available therefor, for instance the QuickChange® kit from Stratagene, La Jolla, USA. The principle thereof is for oligonucleotides having single exchanges (mismatch primers) to be synthesized and hybridized with the gene in single-stranded form; subsequent DNA polymerization then affords corresponding point mutants. It is possible to use for this purpose the respective species-specific sequences of these genes. Owing to the high homologies, it is possible and particularly advantageous according to the invention to carry out this reaction on the basis of the nucleotide sequences provided in the sequence listing. These sequences can also serve to design appropriate mismatch primers for related species.

In one alternative, all these uses of genes and/or of the described nucleic acids of the invention are ones where in each case a nucleic acid with a deletion mutation or insertion mutation is employed, preferably comprising the border sequences, in each case comprising at least 70 to 150 nucleic acid positions, of the region coding for the protein.

These methods are also familiar per se to the skilled worker. It is thus possible to prevent the formation of one or more of the described gene products by the host cell by cutting out part of the relevant gene on an appropriate transformation vector via restriction endonucleases, and subsequently transforming the vector into the host of interest, where the active gene is replaced by the inactive copy via the homologous recombination which is still possible until then. In the embodiment of insertion mutation it is possible merely to introduce the intact gene interruptingly or, instead of a gene portion, another gene, for example a selection marker. Phenotypical checking of the mutation event is possible thereby in a manner known per se.

In order to enable these recombination events which are necessary in each case between the defective gene introduced into the cell and the intact gene copy which is endogenously present for example on the chromosome, it is necessary according to the current state of knowledge that in each case there is agreement in at least 70 to 150 connected nucleic acid positions, in each case in the two border sequences to the non-agreeing part, with the part lying between being immaterial. Accordingly, preferred embodiments are those including only two flanking regions with at least one of these sizes.

In an alternative embodiment of this use, nucleic acids having a total of two nucleic acid segments which in each case comprise at least 70 to 150 nucleic acid positions, and thus flank at least partly, preferably completely, the region coding for the protein, are employed. The flanking regions can in this connection be ascertained starting from the known sequences by methods known per se, for example with the aid of outwardly directed PCR primers and a preparation of genomic DNA as template (anchored PCR). This is because it is not obligatory for the segments to be protein-encoding in order to make it possible to exchange the two gene copies by homologous recombination. According to the present invention it is possible to design the primers required for this on the basis of the nucleotide sequences indicated in the sequence listing also for other species of Gram-positive bacteria and, among these, in particular for those of the genus Bacillus. As an alternative to this experimental approach it is possible to take such regions which are at least in part non-coding for many of the genes from related species, for example from B. subtilis database entries, for example the SubtiList database of the Institute Pasteur, Paris, France (http://genolist.pasteur.fr/SubtiList/genome.cgi) or the databases specified in Example 2.

The present invention is aimed in particular at providing genetically improved microorganisms for biotechnological production. Thus, every microorganism in which at least one of the genes which corresponds to the nucleic acid which codes for one of the following proteins of B. licheniformis DSM 13 is functionally inactivated represents an embodiment of the present invention:

putative branched-chain amino acid aminotransferase (E.C. 2.6.1.42) defined by SEQ ID NO. 1,
putative branched-chain amino acid aminotransferase (E.C. 2.6.1.42) defined by SEQ ID NO. 3,
lysine and/or arginine decarboxylase (protein SpeA; E.C. 4.1.1.18 or E.C. 4.1.1.19) defined by SEQ ID NO. 5 (speA gene),
NADH-dependent butanol dehydrogenase A (protein YugJ; E.C. 1.1.1.-) defined by SEQ ID NO. 7 (yugJ gene),
butyryl-CoA dehydrogenase (E.C. 1.3.99.25) or acyl-CoA dehydrogenase (E.C. 1.3.99.-) defined by SEQ ID NO. 9,
butyryl-CoA dehydrogenase (E.C. 1.3.99.25) or acyl-CoA dehydrogenase (E.C. 1.3.99.-) defined by SEQ ID NO. 11,
3-hydroxybutyryl-CoA dehydrogenase (E.C. 1.1.1.157) defined by SEQ ID NO. 13,
putative enoyl-CoA hydratase protein (E.C. 4.2.1.17) defined by SEQ ID NO. 15,
probable enoyl-(3-hydroxyisobutyryl)-CoA hydrolase protein defined by SEQ ID NO. 17,
probable enoyl-CoA hydratase (protein EchA8; E.C. 4.2.1.17) defined by SEQ ID NO. 19 (echA8 gene),
acyl-CoA dehydrogenase (E.C. 1.3.99.-) defined by SEQ ID NO. 21,
acetate-CoA ligase or propionate-CoA ligase (or synthetase; protein AcsA; E.C. 6.2.1.1) defined by SEQ ID NO. 23 (acsA gene),
3-hydroxybutyryl-CoA dehydratase (protein YngF; E.C. 4.2.1.55) defined by SEQ ID NO. 25 (yngF gene),
butyryl-CoA dehydrogenase (protein YusJ; E.C. 1.3.99.25) or acyl-CoA dehydrogenase (E.C. 1.3.99.-) defined by SEQ ID NO. 27 (yusJ gene),
3-hydroxyisobutyrate dehydrogenase (protein YkwC; E.C. 1.1.1.31) or oxidoreductase (E.C. 1.1.-.-) defined by SEQ ID NO. 29 (ykwC gene),
probable phosphate butyryltransferase (E.C. 2.3.1.19) defined by SEQ ID NO. 31,
probable butyrate kinase (E.C. 2.7.2.7) defined by SEQ ID NO. 33,
acetate-CoA ligase or synthetase or propionate-CoA ligase or synthetase (protein AcsA; E.C. 6.2.1.1) defined by SEQ ID NO. 35 (acsA gene),
acetate-CoA ligase or propionate-CoA ligase (protein YtcI; E.C. 6.2.1.1) defined by SEQ ID NO. 37 (ytcI gene), lysine and/or arginine decarboxylase (protein speA; E.C. 4.1.1.18 or E.C. 4.1.1.19) defined by SEQ ID NO. 39 (speA gene), probable enoyl-CoA hydratase (E.C. 4.2.1.17) defined by SEQ ID NO. 41 (ysiB gene), similar to 3-hydroxyacyl-CoA dehydrogenase (E.C. 1.1.1.35) defined by SEQ ID NO. 43, 3-methyl-2-oxobutanoate dehydrogenase or 2-oxoglutarate dehydrogenase E1 (E.C. 1.2.4.2) defined by SEQ ID NO. 45, probable acetate-CoA ligase or propionate-CoA ligase (protein YhfL; E.C. 6.2.1.1) or acid-CoA ligase (E.C. 6.2.1.-) defined by SEQ ID NO. 47 (yhfL gene) or agmatinase (E.C. 3.5.1.11) defined by SEQ ID NO. 49 (ywhG gene).

"Corresponds" means in this connection in each case a gene of the organism under consideration which codes for a gene product having the same biochemical activity as defined above in connection with the respective metabolic pathways. This is generally at the same time the gene of all those of this organism which are translated in vivo which shows the greatest homology in each case to the stated gene from *B. licheniformis* (usually more than 40% identity, as can be found by an alignment of the two sequences as carried out in Example 2).

Among these, in accordance with the above statements, there is increasing preference in each case for a microorganism in which 2, 3 or 4 of the genes mentioned for each metabolic pathway ((1.) for synthesizing isovaleric acid, (2.) for synthesizing 2-methylbutyric acid and/or isobutyric acid, (3.) for synthesizing butanol and/or butyric acid, (4.) for synthesizing propionic acid and/or (5.) for synthesizing cadaverine and/or putrescine) are inactivated.

In addition, in accordance with the above statements, there is increasing preference in each case for a microorganism in which 2, 3, 4 or 5 of the metabolic pathways (1.) for synthesizing isovaleric acid, (2.) for synthesizing 2-methylbutyric acid and/or isobutyric acid, (3.) for synthesizing butanol and/or butyric acid, (4.) for synthesizing propionic acid and/or (5.) for synthesizing cadaverine and/or putrescine are blocked at least in part.

In addition, among these in each case a microorganism which is a bacterium is preferred.

This is because they have particular importance for biotechnological production. On the other hand, the relevant pathways have been described for microorganisms of the genus *Bacillus*.

A microorganism which is preferred among these is in each case a Gram-negative bacterium, in particular one of the genera *Escherichia Coli, Klebsiella, Pseudomonas* or *Xanthomonas*, in particular strains of *E. coli* K12, *E. coli* B or *Klebsiella planticola*, and very especially derivatives of the strains *Escherichia coli* BL21 (DE3), *E. coli* RV308, *E. coli* DH5α, *E. coli* JM109, *E. coli* XL-1 or *Klebsiella planticola* (Rf).

This is because these are important strains for molecular biological operations on genes, for instance for cloning (see examples), and additionally important producer strains.

As alternative thereto, in each case a microorganism which is a Gram-positive bacterium is preferred, in particular one of the genera *Bacillus, Staphylococcus* or *Corynebacterium*, very especially of the species *Bacillus lentus, B. licheniformis, B. amyloliquefaciens, B. subtilis, B. globigii* or *B. alcalophilus, Staphylococcus carnosus* or *Corynebacterium glutamicum*, and among these very particularly preferably *B. licheniformis* DSM 13.

This is because these are particularly important for the biotechnological production of valuable products and proteins because they are naturally able to secrete them into the surrounding medium. On the other hand, they are increasingly related to the *B. licheniformis* employed for the present application, so that the working steps described and derived from the sequences disclosed in each case should proceed more successfully as the extent of relationship to *B. licheniformis* DSM 13 increases. It is thus to be assumed for example that a gene indicated in the sequence listing can, after point mutation, be used in a related species directly for a deletion mutation without the need to isolate the homologous gene from the strain itself for this purpose.

The present invention is aimed in particular at improving fermentation processes. Thus, every process for fermenting a microorganism of the invention described above represents an embodiment of the present invention.

These processes and the processes described above in each case in connection with an influence on one of the five metabolic pathways described are in particular processes where a valuable product is produced, in particular a low molecular weight compound or a protein.

This is because these are the essential areas of use of biotechnological production by fermentation of microorganisms.

Among these, preference is given in each case to a process where the low molecular weight compound is a natural product, a dietary supplement or a pharmaceutically relevant compound.

This is because they are important product groups for biotechnological production by fermentation of microorganisms.

Among such biotechnological processes for producing proteins by fermentation of microorganisms, preference is given in each case to a process where the protein is an enzyme, in particular one from the group of α-amylases, proteases, cellulases, lipases, oxidoreductases, peroxidases, laccases, oxidases and hemicellulases.

This is because these are important enzymes produced on the industrial scale, for example for incorporation in detergent or cleaning compositions.

In addition, the gene products provided according to the invention are available for further applications. Thus, the present invention is also implemented by any use of any gene product of the invention in a reaction mixture or process appropriate for its biochemical properties, which is defined as described above with reference to SEQ ID NO. 2, 4, 6, 8, 10, 12, 14, 16, 18, 20, 22, 24, 26, 28, 30, 32, 34, 36, 38, 40, 42, 44, 46, 48 or 50.

Among these are preferably included uses (1.) for synthesizing isovaleric acid, (2.) for synthesizing 2-methylbutyric acid and/or isobutyric acid, (3.) for synthesizing butanol and/or butyric acid, (4.) for synthesizing propionic acid and/or (5.) for synthesizing cadaverine and/or putrescine, where appropriate in suitable combination with further enzymes.

Thus, the products of the metabolic pathways described are simple organic chemical compounds for which there is certainly a need in chemistry, for example to employ them as starting materials for more complex syntheses. Preparation thereof can be considerably simplified, especially when stereochemical reactions are involved, by the use of appropriate enzymes, because they in most cases specifically form one enantiomer. The term used when such synthetic routes are undertaken in at least one reaction step by biological catalysts is biotransformation. All gene products of the invention are suitable in principle therefor.

The following examples illustrate the present invention further.

EXAMPLES

All molecular biological working steps follow standard methods as indicated for example in the handbook by Fritsch, Sambrook and Maniatis "Molecular cloning: a laboratory manual", Cold Spring Harbour Laboratory Press, New York, 1989, or comparable relevant works. Enzymes and construction kits are employed in accordance with the respective manufacturer's instructions.

Example 1

Identification of the Nucleic Acids Shown in SEQ ID NO. 1, 3, 5, 7, 9, 11, 13, 15, 17, 19, 21, 23, 25, 27, 29, 31, 33, 35, 37, 39, 41, 43, 45, 47 and 49 from *B. licheniformis* DSM 13

The genomic DNA was prepared by standard methods from the strain *B. licheniformis* DSM 13, which is available to anyone from the Deutsche Sammiung von Mikroorganismen and Zelikulturen GmbH, Mascheroder Weg 1b, 38124 Brunswick, mechanically fractionated and fractionated by electrophoresis in a 0.8% agarose gel. For a shotgun cloning of the smaller fragments, the fragments 2 to 2.5 kb in size were eluted from the agarose gel, dephosphorylated and ligated as blunt-ended fragments into the SmaI restriction cleavage site of the vector pTZ19R-Cm. This is a derivative which confers chloramphenicol resistance of the plasmid pTZ19R which is obtainable from Fermentas (St. Leon-Rot). A gene library of the smaller fragments was obtained thereby. As second shotgun cloning, the genomic fragments obtained by a partial restriction with the enzyme SauIIIaI were ligated into the SuperCos 1 vector system ("Cosmid Vector Kit") from Stratagene, La Jolla, USA, resulting in a gene library over the predominantly larger fragments.

The relevant recombinant plasmids were isolated and sequenced from the bacteria *E. Coli* DH5α (D. Hannahan (1983): "Studies on transformation on *Escherichia coli*"; *J. Mol. Microbiol.*, volume 166, pages 557-580) obtainable by transformation with the relevant gene libraries. The dye termination method (dye terminator chemistry) was employed in this case, carried out by the automatic sequencers MegaBACE 1000/4000 (Amersham Bioscience, Piscataway, USA) and ABI Prism 377 (Applied Biosystems, Foster City, USA).

In this way, inter alia, the sequences SEQ ID NO. 1, 3, 5, 7, 9, 11, 13, 15, 17, 19, 21, 23, 25, 27, 29, 31, 33, 35, 37, 39, 41, 43, 45, 47 and 49 indicated in the sequence listing of the present application were obtained. The amino acid sequences derived therefrom are indicated—the relevant ones under the higher number in each case—under SEQ ID NO. 2, 4, 6, 8, 10, 12, 14, 16, 18, 20, 22, 24, 26, 28, 30, 32, 34, 36, 38, 40, 42, 44, 46, 48 and 50.

Example 2

Sequence Homologies

After ascertaining the DNA and amino acid sequences as in Example 1, in each case the most similar homologs disclosed to date were ascertained by searching the databases GenBank (National Center for Biotechnology Information NCBI, National Institute of Health, Bethesda, Md., USA), EMBL European Bioinformatics Institute (EBI) in Cambridge, Great Britain (http://www.ebi.ac.uk), Swiss-Prot (Geneva Bioinformatics (GeneBio) S.A., Geneva, Switzerland; http://www.genebio.com/sprot.html) and PIR (Protein Information Resource, National Biomedical Research Foundation, Georgetown University Medical Center, Washington, D.C., USA; http://www.pir.georgetown.edu). The nr (nonredundant) option was chosen in this connection.

The ascertained DNA and amino acid sequences were compared with one another via alignments in order to determine the degree of homology; the computer program used for this was Vector NTI® Suite Version 7, which is obtainable from Informax Inc., Bethesda, USA. In this case, the standard parameters of this program were used, meaning for comparison of the DNA sequences: K-tuple size: 2; Number of best Diagonals: 4; Window size: 4; Gap penalty: 5; Gap opening penalty: 15 and Gap extension penalty: 6.66. The following standard parameters applied to the comparison of the amino acid sequences: K-tuple size: 1; Number of best Diagonals: 5; Window size: 5; Gap penalty: 3; Gap opening penalty: 10 and Gap extension penalty: 0.1. The results of these sequence comparisons are compiled in Table 1 below, together with an indication of the respective enzyme names, meaning functions, E.C. numbers and the relevant metabolic pathways. The numbering of enzymes known in the prior art is the consistent nomenclature of the abovementioned databases.

TABLE 1

Genes and proteins of most similarity to the genes and proteins respectively ascertained in Example 1.
The meanings therein are:
ID the SEQ ID NO. indicated in the sequence listing in the present application;
E.C. No. the number according to the international enzyme classification
(Enzyme Nomenclature of the IUBMB).

| ID | Name of the enzyme (where possible of the gene) and additional information where appropriate | E.C. No. | Metabolic pathway | Identity to the most closely related at the DNA level % | Identity to the most closely related at the protein level % |
|---|---|---|---|---|---|
| 1, 2 | putative branched-chain amino acid aminotransferase | 2.6.1.42 | valine/isoleucine catabolism | 62.40% to gb|AE017003.1|, *B. cereus* ATCC 14579, section 6 of 18 of the complete genome | 69% to aminotransferase IV from *B. anthracis* Ames (NP_655296.1) |
| 3, 4 | putative branched-chain amino acid aminotransferase | 2.6.1.42 | valine/isoleucine catabolism | 73.80% to emb|Z49992.1|BS CELABCD, | 79% to branched-chain amino acid |

TABLE 1-continued

Genes and proteins of most similarity to the genes and proteins respectively ascertained in Example 1.
The meanings therein are:
ID the SEQ ID NO. indicated in the sequence listing in the present application;
E.C. No. the number according to the international enzyme classification
(Enzyme Nomenclature of the IUBMB).

| ID | Name of the enzyme (where possible of the gene) and additional information where appropriate | E.C. No. | Metabolic pathway | Identity to the most closely related at the DNA level % | Identity to the most closely related at the protein level % |
|---|---|---|---|---|---|
| | | | | *B. subtilis* genes celA, celB, celC, celD and ywaA | aminotransferase from *B. subtilis* 168 (NP_391734.1) |
| 5, 6 | lysine and/or arginine decarboxylase (speA) | 4.1.1.18 or 4.1.1.19 | cadaverine and/or putrescine synthesis (lysine and/or arginine catabolism) | 74.00% to emb\|X58433.1\|BS CADDNA *B. subtilis*, cad gene for lysine decarboxylase | 85% to lysine decarboxylase from *B. subtilis* (NP_389346; A54546) |
| 7, 8 | NADH-dependent butanol dehydrogenase A (yugJ) | 1.1.1.- | butyric acid metabolism | 76.30% to emb\|Z93934.1\|BS Z93934, *B. subtilis*, genomic DNA fragment from patB to yugK | 89% to NADH-dependent butanol dehydrogenase from *B. subtilis* 168 (NP_391015.1) |
| 9, 10 | acyl-CoA dehydrogenase (sic, i.e. more generally indicated in the sequence listing)/butyryl-CoA dehydrogenase | 1.3.99.-/ 1.3.99.25 | leucine catabolism valine/ isoleucine catabolism, butyric acid metabolism | 74.70% to emb\|Z49782.1\|BS DNA320D, *B. subtilis*, chromosomal DNA (region 320-321 degrees) | 82% to short-chain specific acyl-CoA dehydrogenase from *B. cereus* ATCC 14579 (NP_835003.1) |
| 11, 12 | acyl-CoA dehydrogenase (sic, i.e. more generally indicated in the sequence listing)/butyryl-CoA dehydrogenase. The first codon ought to be translated in vivo as methionine | 1.3.99.- | leucine catabolism | 59.30% to emb\|Z49782.1\|BS DNA320D, *B. subtilis*, chromosomal DNA (region 320-321 degrees) | 63% to C-terminal domain of acyl-CoA dehydrogenase from *B. anthracis* Ames (NP_653803.1) |
| 13, 14 | 3-hydroxyburyryl-CoA dehydrogenase | 1.1.1.157 | butyric cid metabolism | 62.40% to gb\|AE017015.1\|, *B. cereus* ATCC 14579, section 18 of 18 of the complete genome | 65% to the NAD-binding domain of 3-hydroxyacyl-CoA dehydrogenase, from *B. anthracis* Ames (NP_653804.1) |
| 15, 16 | putative enoyl-CoA hydratase protein | 4.2.1.17 | leucine catabolism, valine/ isoleucine catabolism | 61.00% to emb\|Y14078.1\|BS Y14078, *B. subtilis*, 8.7 Kb chromosomal DNA: downstream of the glyB-prsA region | 58% to YhaR from *B. subtilis* 168 (CAB12828.2) |
| 17, 18 | probable enoyl-(3-hydroxy-isobutyryl)-coenzyme A hydrolase protein | not yet allocated | leucine catabolism, valine/ isoleucine catabolism | 61.90% to gb\|AE017031.1\|, *B. anthracis* Ames, section 8 of 18 of the complete genome | 62% to 3-hydroxy-isobutyryl-coenzyme A hydrolase from *B. cereus* ATCC 14579 (NP_832055.1; AAP09256) |
| 19, 20 | probable enoyl-CoA hydratase (echA8). The first codon ought to be | 4.2.1.17 | leucine catabolism, valine/ isoleucine | 43.50% to gb\|AC084761.2\|, *Gallus gallus*, clone WAG-69H2, | 48% to 3-hydroxy-butyryl-CoA dehydratase from *B subtilis* 168 |

TABLE 1-continued

Genes and proteins of most similarity to the genes and proteins
respectively ascertained in Example 1.
The meanings therein are:
ID the SEQ ID NO. indicated in the sequence listing in the present application;
E.C. No. the number according to the international enzyme classification
(Enzyme Nomenclature of the IUBMB).

| ID | Name of the enzyme (where possible of the gene) and additional information where appropriate | E.C. No. | Metabolic pathway | Identity to the most closely related at the DNA level % | Identity to the most closely related at the protein level % |
|---|---|---|---|---|---|
| | translated in vivo as methionine | | catabolism | complete sequence | (NP_390732.1) |
| 21, 22 | actyl-CoA dehydrogenase | 1.3.99.- | leucine catabolism, valine/ isoleucine catabolism | 49.90% to gb|AE015940.1|, *Clostridium tetani* E88, section 5 of 10 of the complete genome | 61% to acyl-CoA dehydrogenase from *B. cereus* ATCC 14579 (NP_832051.1) |
| 23, 24 | acetyl-coenzyme A synthetase (indicated thus in the sequence listing) or propionate-CoA ligase (acsA) | 6.2.1.1 | propionate metabolism | 63.00% to dbj|AP001511.1|, *B. halodurans*, genomic DNA, section 5/14 | 61% to acetyl-CoA synthetase from *B. halodurans* (NP_242003.1) |
| 25, 26 | 3-hydroxybutyryl-CoA dehydratase (yngF) | 4.2.1.55 | butyric acid metabolism | 63.80% to emb|Y13917.1|BS Y13917, *B. subtilis*, genes ppsE, yngL, yngK, yotB, yngJ, yngI, yngH, yngG and yngF and partial genes ppsD and yngE | 65% to hydroxybutyryl dehydratase from *B. subtilis* (AAF32340.1) |
| 27, 28 | acyl-CoA dehydrogenase (sic, i.e. more generally, indicated in the sequence listing)/ butyryl-CoA dehydrogenase (yusJ) | 1.3.99./ 1.3.99.25 | leucine catabolism, valine/ isoleucine catabolism, butyric acid metabolism | 72.90% to emb|Y13917.1|BS Y13917, *B. subtilis*, genes ppsE, yngL, yngK, yotB, yngJ, yngI, yngH, yngG and yngF and partial genes ppsD and yngE | 82% of butyryl-CoA dehydrogenase from *B. subtilis* 168 (NP_389708.1) |
| 29, 30 | 3-hydroxy-isobutyrate dehydrogenase/ hypothetical oxidoreductase (sic, i.e. more generally, indicated in the sequence listing) (ykwC) | 1.1.1.31 or 1.1.-.- | valine catabolism | 72.80% to emb|AJ222587.1| BS16829KB, *B. subtilis*, 29 kB DNA fragment from the gene ykwC to the gene cse15 | 81% to 3-hydroxy isobutyrate dehydrogenase from *B. subtilis* 168 (NP_389279.1) |
| 31, 32 | probable phosphate butyryl-transferase | 2.3.1.19 | butyric acid metabolism | 46.30% to gb|S81735.1|S81 735, leucine dehydrogenase | 65% to phosphate butyryl-transferase from *B. subtilis* 168 (NP_390289.1) |
| 33, 34 | probable butyrate kinase | 2.7.2.7 | butyric acid metabolism | 72.50% to emb|Z99116.2|BS UB0013, *B. subtilis*, complete genome (section 13 of 21): from 2409151 to 2613687 | 80% to branched-chain fatty acid kinase from *B. subtilis* 168 (NP_390287.1) |
| 35, 36 | acetyl-coenzyme A synthetase (indicated thus in the sequence listing) or | 6.2.1.1 | propionate metabolism | 74.90% to emb|Z99119.2|BS UB0016, *B. subtilis*, complete genome | 81% to acetyl-CoA synthetase from *B. subtilis* 168 (NP_390846.1) |

TABLE 1-continued

Genes and proteins of most similarity to the genes and proteins
respectively ascertained in Example 1.
The meanings therein are:
ID the SEQ ID NO. indicated in the sequence listing in the present application;
E.C. No. the number according to the international enzyme classification
(Enzyme Nomenclature of the IUBMB).

| ID | Name of the enzyme (where possible of the gene) and additional information where appropriate | E.C. No. | Metabolic pathway | Identity to the most closely related at the DNA level % | Identity to the most closely related at the protein level % |
|---|---|---|---|---|---|
| | propionate-CoA ligase (acsA) | | | (section 16 of 21): from 3013458 to 3213379 | and to acetate-CoA ligase from *B. subtilis* (P39062, S39646) |
| 37, 38 | acetate-CoA ligase (indicated thus in the sequence listing) or propionate-CoA ligase (ytcI). The first codon ought to be translated in vivo as methionine | 6.2.1.1 | propionate metabolism | 70% to emb\|Z99119.2\|BS UB0016, *B. subtilis*, complete genome (section 16 of 21): from 3013458 to 3213379 | 73% to acetate-CoA ligase from *B. subtilis* 168 (NP_390834.1, E69989) |
| 39, 40 | lysine and/or arginine decarboxylase (speA) | 4.1.1.18 or 4.1.1.19 | cadaverine and/or putrescine synthesis (lysine and/or arginine catabolism) | 63.40% to emb\|Z99104.2\|BS UB0001, *B. subtilis*, complete genome (section 1 of 21): from 1 to 213080 | 62% to lysine decarboxylase from *B. subtilis* 168 (NP_387908.1) and *B. perfrigens* (NP_976355) |
| 41, 42 | probable enoyl-CoA hydratase (ysiB) | 4.2.1.17 | leucine catabolism, valine/ isoleucine catabolism | 70.30% to emb\|Z75208.1\|BS Z75208, *B. subtilis*, genomic sequence, 89009 bp | 73% to 3-hydroxybutyryl-CoA dehydratase from *B. subtilis* 168 (NP_390732.1) |
| 43, 44 | similar to 3-hydroxyacyl-CoA dehydrogenase | 1.1.1.35 | isoleucine catabolism | 71.60% to emb\|Z99120.2\|BS UB0017, *B. subtilis*, complete genome (section 17 of 21): from 3213330 to 3414388 | 76% to 3-hydroxyacyl-CoA dehydrogenase from *B. subtilis* 168 (NP_391163.1) |
| 45, 46 | 3-methyl-2-oxobutanoate dehydrogenase/ 2-oxoglutarate dehydrogenase E1 component (sic, i.e. indicated more generally in the sequence listing) | 1.2.4.2 | leucine catabolism, valine/ isoleucine catabolism | 75.70% to emb\|X54805.1\|BS ODHA, *B. subtilis*, odhA gene for 2-oxoglutarate dehydrogenase | 78% to E1 subunit of 2-oxoglutarate dehydrogenase from *B. subtilis* (CAB13829.2) |
| 47, 48 | probable acid-CoA ligase (yhfL) | 6.2.1.- | propionate metabolism | 62.20% to gb\|AE017001.1\|, *B. cereus* ATCC 14579, section 4 of 18 of the complete genome | 72% to long-chain fatty acid-CoA ligase from *B. subtilis* 168 (NP_388908.1) |
| 49, 50 | agmatinase (ywhG) | 3.5.1.11 | cadaverine and/or putrescine synthesis (lysine and/or arginine catabolism) | 80.9% to *B. subtilis*, gene BSUB0020 (Genebank, complete genome) | 95% to agmatinase (agmatine ureohydrolase) from *B. subtilis* 168 (P70999) |

It is evident that the genes found and the gene products derived therefrom are respectively novel genes and proteins with a clear distance from the prior art disclosed to date.

Example 3

Functional Inactivation of One or More of the Genes Shown in SEQ ID NO. 1, 3, 5, 7, 9, 11, 13, 15, 17, 19, 21, 23, 25, 27, 29, 31, 33, 35, 37, 39, 41, 43, 45, 47 and 49 in *B. licheniformis* Principle of the Preparation of a Deletion Vector Each of these genes can be functionally inactivated for example by means of a so-called deletion vector. This procedure is described per se for example by J. Vehmaanperä et al. (1991) in the publication "Genetic manipulation of *Bacillus amyloliquefaciens*"; *J. Biotechnol.*, volume 19, pages 221-240.

A suitable vector for this is pE194 which is characterized in the publication "Replication and incompatibility properties of plasmid pE194 in *Bacillus subtilis*" by T. J. Gryczan et al. (1982), *J. Bacteriol.*, volume 152, pages 722-735. The advantage of this deletion vector is that it possesses a temperature-dependent origin of replication. pE194 is able to replicate in the transformed cell at 33° C., so that initial selection for successful transformation takes place at this temperature. Subsequently, the cells comprising the vector are incubated at 42° C. The deletion vector no longer replicates at this temperature, and a selection pressure is exerted on the integration of the plasmid via a previously selected homologous region into the chromosome. A second homologous recombination via a second homologous region then leads to excision of the vector together with the intact gene copy from the chromosome and thus to deletion of the gene which is located in the chromosome in vivo. Another possibility as second recombination would be the reverse reaction to integration, meaning recombination of the vector out of the chromosome, so that the chromosomal gene would remain intact. The gene deletion must therefore be detected by methods known per se, for instance in a southern blot after restriction of the chromosomal DNA with suitable enzymes or with the aid of the PCR technique on the basis of the size of the amplified region.

It is thus necessary to select two homologous regions of the gene to be deleted, each of which should include at least 70 base pairs in each case, for example the 5' region and the 3' region of the selected gene. These are cloned into the vector in such a way that they flank a part coding for an inactive protein, or are in direct succession, omitting the region in between. The deletion vector is obtained thereby.

Deletion of the Genes Considered Here

A deletion vector of the invention is constructed by PCR amplification of the 5' and 3' regions of one of these genes of interest in each case. The sequences SEQ ID NO. 1, 3, 5, 7, 9, 11, 13, 15, 17, 19, 21, 23, 25, 27, 29, 31, 33, 35, 37, 39, 41, 43, 45, 47 and 49 indicated in the sequence listing are available for designing suitable primers and originate from *B. licheniformis*, but ought also to be suitable, because of the homologies to be expected, for other species, especially of the genus *Bacillus*.

The two amplified regions suitably undergo intermediate cloning in direct succession on a vector useful for these operations, for example on the vector pUC18 which is suitable for cloning steps in *E. coli*.

The next step is a subcloning into the vector pE194 selected for deletion, and transformation thereof into *B. subtilis* DB104, for instance by the method of protoplast transformation according to Chang & Cohen (1979; "High Frequency Transformation of *Bacillus subtilis* Protoplasts by Plasmid DNA"; *Molec. Gen. Genet.* (1979), volume 168, pages 111-115). All working steps must be carried out at 33° C. in order to ensure replication of the vector.

In a next step, the vector which has undergone intermediate cloning is likewise transformed by the method of protoplast transformation into the desired host strain, in this case *B. licheniformis*. The transformants obtained in this way and identified as positive by conventional methods (selection via the resistance marker of the plasmid; check by plasmid preparation and PCR for the insert) are subsequently cultured at 42° C. under selection pressure for presence of the plasmid through addition of erythromycin. The deletion vector is unable to replicate at this temperature, and the only cells to survive are those in which the vector is integrated into the chromosome, and this integration most probably takes place in homologous or identical regions. Excision of the deletion vector can then be induced subsequently by culturing at 33° C. without erythromycin selection pressure, the chromosomally encoded gene being completely deleted from the chromosome. The success of the deletion is subsequently checked by southern blotting after restriction of the chromosomal DNA with suitable Such transformants in which the relevant gene is deleted are normally additionally distinguished by a limitation on the formation of the odorous or poisonous substance resulting from the relevant metabolic pathway. In the cases where the cell has no substitute pathway for synthesizing the relevant compound, the relevant metabolic pathway is completely blocked so that this compound is no longer formed at all, and the strain modified in this way no longer has the relevant odorous component.

The invention claimed is:

1. A process for fermenting a substrate using a microorganism, the process comprising:
   (a) providing the microorganism having (1) a butyryl-CoA dehydrogenase gene and (2) a lysine and/or arginine decarboxylase gene involved in metabolic pathways for synthesizing odorous substances;
   (b) functionally inactivating (1) the butyryl-CoA dehydrogenase gene and (2) the lysine and/or arginine decarboxylase gene to form functionally inactivated genes;
   (c) providing a fermentable substrate; and
   (d) permitting the microorganism to ferment the substrate, wherein the microorganism is of a genus *Bacillus*, and
   wherein the metabolic pathways for synthesizing the odorous substances are at least partially blocked, thereby reducing odor produced during fermentation.

2. The process according to claim 1, wherein the microorganism having the functionally inactivated genes forms less than 50% of the amount of the odorous substances formed in the microorganism in which (1) the butyryl-CoA dehydrogenase gene and (2) the lysine and/or arginine decarboxylase gene on the metabolic pathways for synthesizing the odorous substance are not functionally inactivated, wherein the odorous substances are (1) butanol and/or butyric acid and (2) cadaverine and/or putrescine, respectively.

3. The process according to claim 2, wherein the microorganism having the functionally inactivated genes forms less than 10% of the amount of the odorous substances in the microorganism in which the butyryl-CoA dehydrogenase gene and the lysine and/or arginine decarboxylase gene on the metabolic pathways for synthesizing the odorous substances are not functionally inactivated.

4. The process according to claim 3, wherein the microorganism having the functionally inactivated genes forms none of the odorous substances in the microorganism in which the butyryl-CoA dehydrogenase gene and the lysine and/or arginine decarboxylase gene on the metabolic pathways for synthesizing the odorous substances are not functionally inactivated.

5. The process according to claim 1, wherein the butyryl-CoA dehydrogenase gene encodes an amino acid sequence as defined by SEQ ID NO. 10 and wherein the lysine and/or arginine decarboxylase gene encodes an amino acid sequence selected from SEQ ID NOS: 6 or 40.

6. The process according to claim 1 wherein the functionally inactivated genes are functionally inactivated by a point mutation.

7. The process according to claim 1 wherein the functionally inactivated genes are functionally inactivated by a deletion mutation.

8. The process according to claim 1 wherein the functionally inactivated genes are functionally inactivated by an insertion mutation.

9. The process according to claim 1 wherein a low molecular weight compound is produced selected from the group consisting of natural products, dietary supplements and pharmaceutically relevant compounds, and enzymes.

10. The process according to claim 9, wherein the enzymes are selected from the group consisting of a-amylases, proteases, cellulases, lipases, oxidoreductases, peroxidases, laccases, oxidases and hemicellulases.

11. The process according to claim 1,
    wherein (1) the functionally inactivated butyryl-CoA dehydrogenase gene and (2) the lysine and/or arginine decarboxylase gene are on the metabolic pathways for synthesizing (1) butanol and/or butyric acid and (2) cadaverine and/or putrescine, respectively.

12. A process for fermenting a substrate using a microorganism, the process comprising:
    (a) providing the microorganism having (1) a butyryl-CoA dehydrogenase gene and (2) a lysine and/or arginine decarboxylase gene involved in metabolic pathways for synthesizing predetermined products, wherein the butyryl-CoA dehydrogenase gene and the lysine and/or arginine decarboxylase gene are functionally inactivated to at least partially block the metabolic pathways for synthesizing (1) butanol and/or butyric acid and (2) cadaverine and/or putrescine, respectively,
    (b) providing a fermentable substrate; and
    (c) permitting the microorganism to ferment the substrate, wherein the microorganism is a genus *Bacillus*.

13. A process of preparing a microorganism of a genus *Bacillus*, the process comprising:
    (a) providing the microorganism having (1) a butyryl-CoA dehydrogenase gene and (2) a lysine and/or arginine decarboxylase gene involved in metabolic pathways for synthesizing odorous substances; and
    (b) functionally inactivating the butyryl-CoA dehydrogenase gene and the lysine and/or arginine decarboxylase gene effective to at least partially block the metabolic pathways for synthesizing the odorous substances.

* * * * *

SEQUENCE LISTING

```
<160> NUMBER OF SEQ ID NOS: 50

<210> SEQ ID NO 1
<211> LENGTH: 918
<212> TYPE: DNA
<213> ORGANISM: Bacillus licheniformis DSM 13
<220> FEATURE:
<221> NAME/KEY: gene
<222> LOCATION: (1)..(918)
<223> OTHER INFORMATION: Putative branched-chain amino acid
      aminotransferase (E.C. 2.6.1.42)
<220> FEATURE:
<221> NAME/KEY: CDS
<222> LOCATION: (1)..(915)

<400> SEQUENCE: 1
```

| | | | | | | | | | | | | | | | | |
|---|---|---|---|---|---|---|---|---|---|---|---|---|---|---|---|---|
| atg | ggg | gac | cag | aaa | gac | cag | tgg | atc | ttc | cta | aac | gac | aaa | ctc | gtt | 48 |
| Met | Gly | Asp | Gln | Lys | Asp | Gln | Trp | Ile | Phe | Leu | Asn | Asp | Lys | Leu | Val | |
| 1 | | | | 5 | | | | | 10 | | | | | 15 | | |

| aaa | aaa | gaa | gac | gct | aaa | ata | tca | gtc | tat | gat | cac | gga | ttt | tta | tac | 96 |
|---|---|---|---|---|---|---|---|---|---|---|---|---|---|---|---|---|
| Lys | Lys | Glu | Asp | Ala | Lys | Ile | Ser | Val | Tyr | Asp | His | Gly | Phe | Leu | Tyr | |
| | | | 20 | | | | | 25 | | | | | 30 | | | |

| ggg | gac | ggc | gtg | ttt | gaa | ggg | atc | agg | gta | tac | gac | ggc | aac | atc | ttc | 144 |
|---|---|---|---|---|---|---|---|---|---|---|---|---|---|---|---|---|
| Gly | Asp | Gly | Val | Phe | Glu | Gly | Ile | Arg | Val | Tyr | Asp | Gly | Asn | Ile | Phe | |
| | | 35 | | | | | 40 | | | | | 45 | | | | |

| aga | atg | caa | gag | cac | atg | gac | cgc | ctc | tac | gat | tct | gcg | aga | tcg | atc | 192 |
|---|---|---|---|---|---|---|---|---|---|---|---|---|---|---|---|---|
| Arg | Met | Gln | Glu | His | Met | Asp | Arg | Leu | Tyr | Asp | Ser | Ala | Arg | Ser | Ile | |
| | 50 | | | | | 55 | | | | | 60 | | | | | |

| atg | ctg | gag | att | cca | tat | cca | cag | gaa | gaa | ctg | aca | cag | cac | gta | ctc | 240 |
|---|---|---|---|---|---|---|---|---|---|---|---|---|---|---|---|---|
| Met | Leu | Glu | Ile | Pro | Tyr | Pro | Gln | Glu | Glu | Leu | Thr | Gln | His | Val | Leu | |
| 65 | | | | | 70 | | | | | 75 | | | | | 80 | |

| aaa | aca | gtc | gaa | aaa | aac | ggg | ctg | aaa | gac | gct | tac | atc | cgc | ttg | gtc | 288 |
|---|---|---|---|---|---|---|---|---|---|---|---|---|---|---|---|---|
| Lys | Thr | Val | Glu | Lys | Asn | Gly | Leu | Lys | Asp | Ala | Tyr | Ile | Arg | Leu | Val | |
| | | | | 85 | | | | | 90 | | | | | 95 | | |

| gtt | tca | aga | gga | gca | ggt | gac | ctc | gga | ctc | gat | cca | aac | aat | tgt | tca | 336 |
|---|---|---|---|---|---|---|---|---|---|---|---|---|---|---|---|---|
| Val | Ser | Arg | Gly | Ala | Gly | Asp | Leu | Gly | Leu | Asp | Pro | Asn | Asn | Cys | Ser | |
| | | | 100 | | | | | 105 | | | | | 110 | | | |

| aac | ccg | agt | gtc | atc | ata | att | gtc | gaa | cca | ttg | gca | ata | ttc | ccg | aaa | 384 |
|---|---|---|---|---|---|---|---|---|---|---|---|---|---|---|---|---|
| Asn | Pro | Ser | Val | Ile | Ile | Ile | Val | Glu | Pro | Leu | Ala | Ile | Phe | Pro | Lys | |
| | | 115 | | | | | 120 | | | | | 125 | | | | |

| cat | tta | tat | gaa | acg | ggg | att | gac | att | gtt | acg | gtt | ccg | aca | aga | agg | 432 |
|---|---|---|---|---|---|---|---|---|---|---|---|---|---|---|---|---|
| His | Leu | Tyr | Glu | Thr | Gly | Ile | Asp | Ile | Val | Thr | Val | Pro | Thr | Arg | Arg | |
| | 130 | | | | | 135 | | | | | 140 | | | | | |

| aac | aga | ccc | gat | gtg | ctg | agc | cct | aaa | gta | aaa | tcg | ctg | aac | tac | tta | 480 |
|---|---|---|---|---|---|---|---|---|---|---|---|---|---|---|---|---|
| Asn | Arg | Pro | Asp | Val | Leu | Ser | Pro | Lys | Val | Lys | Ser | Leu | Asn | Tyr | Leu | |
| 145 | | | | | 150 | | | | | 155 | | | | | 160 | |

| aac | aat | att | ctt | gtc | cgg | atc | gag | gcg | cat | atg | gcg | ggt | gtg | acg | gaa | 528 |
|---|---|---|---|---|---|---|---|---|---|---|---|---|---|---|---|---|
| Asn | Asn | Ile | Leu | Val | Arg | Ile | Glu | Ala | His | Met | Ala | Gly | Val | Thr | Glu | |
| | | | | 165 | | | | | 170 | | | | | 175 | | |

| gcg | ctc | atg | ctc | aat | gat | caa | ggc | tat | gtc | gcc | gaa | ggg | tct | gcg | gat | 576 |
|---|---|---|---|---|---|---|---|---|---|---|---|---|---|---|---|---|
| Ala | Leu | Met | Leu | Asn | Asp | Gln | Gly | Tyr | Val | Ala | Glu | Gly | Ser | Ala | Asp | |
| | | | 180 | | | | | 185 | | | | | 190 | | | |

| aac | gta | ttt | att | tat | aaa | aac | gga | aag | ctc | ttg | acg | cct | ccg | ggc | tat | 624 |
|---|---|---|---|---|---|---|---|---|---|---|---|---|---|---|---|---|
| Asn | Val | Phe | Ile | Tyr | Lys | Asn | Gly | Lys | Leu | Leu | Thr | Pro | Pro | Gly | Tyr | |
| | | 195 | | | | | 200 | | | | | 205 | | | | |

| atc | gga | gcg | ctt | gaa | gga | atc | acc | cgg | aat | gcc | atc | atc | gaa | ata | gcg | 672 |
|---|---|---|---|---|---|---|---|---|---|---|---|---|---|---|---|---|
| Ile | Gly | Ala | Leu | Glu | Gly | Ile | Thr | Arg | Asn | Ala | Ile | Ile | Glu | Ile | Ala | |
| | 210 | | | | | 215 | | | | | 220 | | | | | |

| cga | gag | ctc | ggc | tat | gaa | gtg | aaa | gaa | gag | ccg | ttt | acc | cgc | cat | gac | 720 |
|---|---|---|---|---|---|---|---|---|---|---|---|---|---|---|---|---|
| Arg | Glu | Leu | Gly | Tyr | Glu | Val | Lys | Glu | Glu | Pro | Phe | Thr | Arg | His | Asp | |
| 225 | | | | | 230 | | | | | 235 | | | | | 240 | |

| gta | tac | aca | gcc | gag | gaa | gtg | ttt | tta | acc | gga | acg | gct | gca | gaa | gtc | 768 |
|---|---|---|---|---|---|---|---|---|---|---|---|---|---|---|---|---|
| Val | Tyr | Thr | Ala | Glu | Glu | Val | Phe | Leu | Thr | Gly | Thr | Ala | Ala | Glu | Val | |
| | | | | 245 | | | | | 250 | | | | | 255 | | |

| atc | gcg | gtc | gta | aaa | gtt | gac | ggc | cgc | aag | atc | ggg | gac | ggc | aaa | ccg | 816 |
|---|---|---|---|---|---|---|---|---|---|---|---|---|---|---|---|---|
| Ile | Ala | Val | Val | Lys | Val | Asp | Gly | Arg | Lys | Ile | Gly | Asp | Gly | Lys | Pro | |
| | | | 260 | | | | | 265 | | | | | 270 | | | |

| gga | gtc | cac | aca | aac | cgg | atg | ctt | gaa | aag | ttc | cgc | gag | cgc | gtc | gtc | 864 |
|---|---|---|---|---|---|---|---|---|---|---|---|---|---|---|---|---|
| Gly | Val | His | Thr | Asn | Arg | Met | Leu | Glu | Lys | Phe | Arg | Glu | Arg | Val | Val | |
| | | 275 | | | | | 280 | | | | | 285 | | | | |

| cgt | gaa | ggg | tta | aaa | gtc | agc | ctc | aaa | gat | caa | agc | tta | agt | gtc | agc | 912 |
|---|---|---|---|---|---|---|---|---|---|---|---|---|---|---|---|---|
| Arg | Glu | Gly | Leu | Lys | Val | Ser | Leu | Lys | Asp | Gln | Ser | Leu | Ser | Val | Ser | |
| | 290 | | | | | 295 | | | | | 300 | | | | | |

| tga | ata | | | | | | | | | | | | | | | 918 |

<210> SEQ ID NO 2
<211> LENGTH: 304
<212> TYPE: PRT
<213> ORGANISM: Bacillus licheniformis DSM 13

<400> SEQUENCE: 2

```
Met Gly Asp Gln Lys Asp Gln Trp Ile Phe Leu Asn Asp Lys Leu Val
1               5                   10                  15

Lys Lys Glu Asp Ala Lys Ile Ser Val Tyr Asp His Gly Phe Leu Tyr
            20                  25                  30

Gly Asp Gly Val Phe Glu Gly Ile Arg Val Tyr Asp Gly Asn Ile Phe
        35                  40                  45

Arg Met Gln Glu His Met Asp Arg Leu Tyr Asp Ser Ala Arg Ser Ile
50                  55                  60

Met Leu Glu Ile Pro Tyr Pro Gln Glu Leu Thr Gln His Val Leu
65                  70                  75                  80

Lys Thr Val Glu Lys Asn Gly Leu Lys Asp Ala Tyr Ile Arg Leu Val
                85                  90                  95

Val Ser Arg Gly Ala Gly Asp Leu Gly Leu Asp Pro Asn Asn Cys Ser
            100                 105                 110

Asn Pro Ser Val Ile Ile Val Glu Pro Leu Ala Ile Phe Pro Lys
        115                 120                 125

His Leu Tyr Glu Thr Gly Ile Asp Ile Val Thr Val Pro Thr Arg Arg
130                 135                 140

Asn Arg Pro Asp Val Leu Ser Pro Lys Val Lys Ser Leu Asn Tyr Leu
145                 150                 155                 160

Asn Asn Ile Leu Val Arg Ile Glu Ala His Met Ala Gly Val Thr Glu
                165                 170                 175

Ala Leu Met Leu Asn Asp Gln Gly Tyr Val Ala Glu Gly Ser Ala Asp
            180                 185                 190

Asn Val Phe Ile Tyr Lys Asn Gly Lys Leu Leu Thr Pro Pro Gly Tyr
        195                 200                 205

Ile Gly Ala Leu Glu Gly Ile Thr Arg Asn Ala Ile Ile Glu Ile Ala
210                 215                 220

Arg Glu Leu Gly Tyr Glu Val Lys Glu Glu Pro Phe Thr Arg His Asp
225                 230                 235                 240

Val Tyr Thr Ala Glu Glu Val Phe Leu Thr Gly Thr Ala Ala Glu Val
                245                 250                 255

Ile Ala Val Val Lys Val Asp Gly Arg Lys Ile Gly Asp Gly Lys Pro
            260                 265                 270

Gly Val His Thr Asn Arg Met Leu Glu Lys Phe Arg Glu Arg Val Val
        275                 280                 285

Arg Glu Gly Leu Lys Val Ser Leu Lys Asp Gln Ser Leu Ser Val Ser
290                 295                 300
```

<210> SEQ ID NO 3
<211> LENGTH: 1095
<212> TYPE: DNA
<213> ORGANISM: Bacillus licheniformis DSM 13
<220> FEATURE:
<221> NAME/KEY: gene
<222> LOCATION: (1)..(1095)
<223> OTHER INFORMATION: Putative branched-chain amino acid
      aminotransferase (E.C. 2.6.1.42)
<220> FEATURE:
<221> NAME/KEY: CDS
<222> LOCATION: (1)..(1092)

<400> SEQUENCE: 3

| | | |
|---|---|---|
| atg aca aaa caa acg atc agc gta cag ctc agt aca gca aaa aag caa<br>Met Thr Lys Gln Thr Ile Ser Val Gln Leu Ser Thr Ala Lys Lys Gln<br>1                        5                     10                   15 | 48 |
| aag cca gag gct gac aag ctc gaa ttc ggc cgg acc ttt acc gac cac<br>Lys Pro Glu Ala Asp Lys Leu Glu Phe Gly Arg Thr Phe Thr Asp His<br>                   20                     25                   30 | 96 |
| atg ttt atc atg gac tat acg gct gaa aac ggc tgg cac gat ccg aga<br>Met Phe Ile Met Asp Tyr Thr Ala Glu Asn Gly Trp His Asp Pro Arg<br>      35                   40                     45 | 144 |
| atc gtt cct tac cag ccg att gaa atg gac ccg gct gca atg gtt tac<br>Ile Val Pro Tyr Gln Pro Ile Glu Met Asp Pro Ala Ala Met Val Tyr<br>    50                     55                     60 | 192 |
| cac tac gga caa tcc gtt ttt gaa gga tta aaa gct tat tta tca agc<br>His Tyr Gly Gln Ser Val Phe Glu Gly Leu Lys Ala Tyr Leu Ser Ser<br>65                       70                     75                   80 | 240 |
| gaa ggc aga gtt ctt ctg ttc aga cct gaa aaa aac ttc gag aga ctc<br>Glu Gly Arg Val Leu Leu Phe Arg Pro Glu Lys Asn Phe Glu Arg Leu<br>                   85                     90                   95 | 288 |
| aat aaa tcc aac gac cgc ctc tgc att ccc cgg gtt gat cct gaa atc<br>Asn Lys Ser Asn Asp Arg Leu Cys Ile Pro Arg Val Asp Pro Glu Ile<br>                100                   105                110 | 336 |
| gtt ctg gaa ggg ctg aag cag ctg gtt cag atc gac aag gaa tgg att<br>Val Leu Glu Gly Leu Lys Gln Leu Val Gln Ile Asp Lys Glu Trp Ile<br>    115                     120                   125 | 384 |
| cct caa gct gag ggg aca tcc ctt tat atc cgt ccg ttc att att tca<br>Pro Gln Ala Glu Gly Thr Ser Leu Tyr Ile Arg Pro Phe Ile Ile Ser<br>130                      135                    140 | 432 |
| aca gaa ccg tac ctt ggc gtc gcc cca tcc aat atg tat aaa atg ctg<br>Thr Glu Pro Tyr Leu Gly Val Ala Pro Ser Asn Met Tyr Lys Met Leu<br>145                      150                    155               160 | 480 |
| atc att tta tcg ccg gtc gga tct tat tac aaa gaa ggc atc cgc cct<br>Ile Ile Leu Ser Pro Val Gly Ser Tyr Tyr Lys Glu Gly Ile Arg Pro<br>                   165                   170                175 | 528 |
| gtg aaa att gct gtt gaa agc gaa ttt gtc cgt gct gtg gca ggc ggt<br>Val Lys Ile Ala Val Glu Ser Glu Phe Val Arg Ala Val Ala Gly Gly<br>    180                     185                    190 | 576 |
| aca ggc aat gca aaa acg gcc gga aac tac gct gcg agc ctg aag gct<br>Thr Gly Asn Ala Lys Thr Ala Gly Asn Tyr Ala Ala Ser Leu Lys Ala<br>195                      200                    205 | 624 |
| cag gaa gtt gcg gaa agc aaa ggc ttc tca caa gtg ctg tgg ctt gac<br>Gln Glu Val Ala Glu Ser Lys Gly Phe Ser Gln Val Leu Trp Leu Asp<br>          210                    215                    220 | 672 |
| gga gtt gaa aag aaa tac att gaa gaa gta ggc agc atg aac atc ttc<br>Gly Val Glu Lys Lys Tyr Ile Glu Glu Val Gly Ser Met Asn Ile Phe<br>225                      230                    235               240 | 720 |
| ttc aaa atc agc ggt gaa att gtc act ccg gct cta aac gga agc att<br>Phe Lys Ile Ser Gly Glu Ile Val Thr Pro Ala Leu Asn Gly Ser Ile<br>                   245                   250                255 | 768 |
| ttg gaa ggc att acg aga aac tcc gtc atc cat ctc tta aaa caa tgg<br>Leu Glu Gly Ile Thr Arg Asn Ser Val Ile His Leu Leu Lys Gln Trp<br>    260                     265                    270 | 816 |
| gga ctc tcc gta acc gaa aga aaa att tca gtt gat gaa ctg gtt cag<br>Gly Leu Ser Val Thr Glu Arg Lys Ile Ser Val Asp Glu Leu Val Gln<br>275                      280                    285 | 864 |
| gct cac aaa gac ggc ctg ctt gag gaa gca ttc ggc acc gga acc gcc<br>Ala His Lys Asp Gly Leu Leu Glu Glu Ala Phe Gly Thr Gly Thr Ala<br>          290                    295                    300 | 912 |
| gct gtc att tcc ccc gtc ggc gag ctg atc tgg aaa gac gaa agc ctt | 960 |

```
Ala Val Ile Ser Pro Val Gly Glu Leu Ile Trp Lys Asp Glu Ser Leu
305                 310                 315                 320 gtg atc aac aac ggt caa act gga gaa atc gcc aaa agg ctc tac caa      1008
Val Ile Asn Asn Gly Gln Thr Gly Glu Ile Ala Lys Arg Leu Tyr Gln
                325                 330                 335 acg atc acc ggt att caa aaa ggc gct ttg cct gac aca ttc ggc tgg      1056
Thr Ile Thr Gly Ile Gln Lys Gly Ala Leu Pro Asp Thr Phe Gly Trp
            340                 345                 350 aca gtt gaa gtt gat aaa gta agc cag tcc tgc taa gcg                  1095
Thr Val Glu Val Asp Lys Val Ser Gln Ser Cys
        355                 360

<210> SEQ ID NO 4
<211> LENGTH: 363
<212> TYPE: PRT
<213> ORGANISM: Bacillus licheniformis DSM 13

<400> SEQUENCE: 4
```

Met Thr Lys Gln Thr Ile Ser Val Gln Leu Ser Thr Ala Lys Lys Gln
1               5                   10                  15

Lys Pro Glu Ala Asp Lys Leu Glu Phe Gly Arg Thr Phe Thr Asp His
            20                  25                  30

Met Phe Ile Met Asp Tyr Thr Ala Glu Asn Gly Trp His Asp Pro Arg
        35                  40                  45

Ile Val Pro Tyr Gln Pro Ile Glu Met Asp Pro Ala Ala Met Val Tyr
    50                  55                  60

His Tyr Gly Gln Ser Val Phe Glu Gly Leu Lys Ala Tyr Leu Ser Ser
65                  70                  75                  80

Glu Gly Arg Val Leu Leu Phe Arg Pro Glu Lys Asn Phe Glu Arg Leu
                85                  90                  95

Asn Lys Ser Asn Asp Arg Leu Cys Ile Pro Arg Val Asp Pro Glu Ile
            100                 105                 110

Val Leu Glu Gly Leu Lys Gln Leu Val Gln Ile Asp Lys Glu Trp Ile
        115                 120                 125

Pro Gln Ala Glu Gly Thr Ser Leu Tyr Ile Arg Pro Phe Ile Ile Ser
    130                 135                 140

Thr Glu Pro Tyr Leu Gly Val Ala Pro Ser Asn Met Tyr Lys Met Leu
145                 150                 155                 160

Ile Ile Leu Ser Pro Val Gly Ser Tyr Tyr Lys Glu Gly Ile Arg Pro
                165                 170                 175

Val Lys Ile Ala Val Glu Ser Glu Phe Val Arg Ala Val Ala Gly Gly
            180                 185                 190

Thr Gly Asn Ala Lys Thr Ala Gly Asn Tyr Ala Ala Ser Leu Lys Ala
        195                 200                 205

Gln Glu Val Ala Glu Ser Lys Gly Phe Ser Gln Val Leu Trp Leu Asp
    210                 215                 220

Gly Val Glu Lys Lys Tyr Ile Glu Glu Val Gly Ser Met Asn Ile Phe
225                 230                 235                 240

Phe Lys Ile Ser Gly Glu Ile Val Thr Pro Ala Leu Asn Gly Ser Ile
                245                 250                 255

Leu Glu Gly Ile Thr Arg Asn Ser Val Ile His Leu Leu Lys Gln Trp
            260                 265                 270

Gly Leu Ser Val Thr Glu Arg Lys Ile Ser Val Asp Glu Leu Val Gln
        275                 280                 285

Ala His Lys Asp Gly Leu Leu Glu Glu Ala Phe Gly Thr Gly Thr Ala
    290                 295                 300

```
Ala Val Ile Ser Pro Val Gly Glu Leu Ile Trp Lys Asp Glu Ser Leu
305                 310                 315                 320

Val Ile Asn Asn Gly Gln Thr Gly Glu Ile Ala Lys Arg Leu Tyr Gln
                325                 330                 335

Thr Ile Thr Gly Ile Gln Lys Gly Ala Leu Pro Asp Thr Phe Gly Trp
            340                 345                 350

Thr Val Glu Val Asp Lys Val Ser Gln Ser Cys
        355                 360

<210> SEQ ID NO 5
<211> LENGTH: 1494
<212> TYPE: DNA
<213> ORGANISM: Bacillus licheniformis DSM 13
<220> FEATURE:
<221> NAME/KEY: gene
<222> LOCATION: (1)..(1494)
<223> OTHER INFORMATION: Lysine and/or Arginine decarboxylase
      (E.C. 4.1.1.18 or E.C. 4.1.1.19, respectively), speA
<220> FEATURE:
<221> NAME/KEY: CDS
<222> LOCATION: (1)..(1491)

<400> SEQUENCE: 5 atg aag gtg gga aaa caa ttg ttg cag cac gaa aca ccc cta tat acc      48
Met Lys Val Gly Lys Gln Leu Leu Gln His Glu Thr Pro Leu Tyr Thr
1               5                   10                  15 gga tta aaa aaa cac gcc ggc aaa aac ccg atc cag ttc cat ata ccg      96
Gly Leu Lys Lys His Ala Gly Lys Asn Pro Ile Gln Phe His Ile Pro
            20                  25                  30 ggg cac aaa aaa ggc tct ggg atg gac cct gaa ttc agg gag ttt atc     144
Gly His Lys Lys Gly Ser Gly Met Asp Pro Glu Phe Arg Glu Phe Ile
        35                  40                  45 gga gaa aat gca tta agc ata gat tta atc aac atc gag cct ctc gac     192
Gly Glu Asn Ala Leu Ser Ile Asp Leu Ile Asn Ile Glu Pro Leu Asp
    50                  55                  60 gat ctg cac gcg ccg aaa gga ata atc aaa cag gcg cag gat ctg gcg     240
Asp Leu His Ala Pro Lys Gly Ile Ile Lys Gln Ala Gln Asp Leu Ala
65                  70                  75                  80 gct gaa gca ttc gga gcc gac tac acg ttc ttt tcc gtc cag gga acg     288
Ala Glu Ala Phe Gly Ala Asp Tyr Thr Phe Phe Ser Val Gln Gly Thr
                85                  90                  95 agc ggc gcc atc atg acg atg gtc atg gcc gta tgc gga ccc gga gac     336
Ser Gly Ala Ile Met Thr Met Val Met Ala Val Cys Gly Pro Gly Asp
            100                 105                 110 aaa atc atc gtc ccg aga aat gtt cat aaa tcg gtg atg tca gcg atc     384
Lys Ile Ile Val Pro Arg Asn Val His Lys Ser Val Met Ser Ala Ile
        115                 120                 125 gtc ttc tca ggc gcc gta ccg atc ttc atc cat ccg gaa atc gac gat     432
Val Phe Ser Gly Ala Val Pro Ile Phe Ile His Pro Glu Ile Asp Asp
    130                 135                 140 gag ctg ggg att tca cac ggg atc acc cct gaa tca gcg aaa aaa gcg     480
Glu Leu Gly Ile Ser His Gly Ile Thr Pro Glu Ser Ala Lys Lys Ala
145                 150                 155                 160 ctg ctt gag cat cct gac gca aaa gga ctg ctc gtc atc aac ccg act     528
Leu Leu Glu His Pro Asp Ala Lys Gly Leu Leu Val Ile Asn Pro Thr
                165                 170                 175 tat ttc ggc ata gct gca gac tta aaa agc atc gtc gag ctg gct cat     576
Tyr Phe Gly Ile Ala Ala Asp Leu Lys Ser Ile Val Glu Leu Ala His
            180                 185                 190 tct ttt cat gtc ccg gtg cta gtt gac gag gcg cac ggc gtt cat atc     624
Ser Phe His Val Pro Val Leu Val Asp Glu Ala His Gly Val His Ile
```

-continued

```
                195                 200                 205
cac ttc cat gaa gat ctg cct ctt tcg gca atg cag gcc gga gcg gat    672
His Phe His Glu Asp Leu Pro Leu Ser Ala Met Gln Ala Gly Ala Asp
    210                 215                 220 atg gcg gcg acg agc gtt cat aag ctc gga gga tcc ctt aca caa agt    720
Met Ala Ala Thr Ser Val His Lys Leu Gly Gly Ser Leu Thr Gln Ser
225                 230                 235                 240 tcg att ctc aat atg aaa gaa ggt ctg gtt tca aag gaa agg gtg caa    768
Ser Ile Leu Asn Met Lys Glu Gly Leu Val Ser Lys Glu Arg Val Gln
                245                 250                 255 tcg att tta agc atg ctg acg acg aca tcg acc tcc tat cta ttg ctc    816
Ser Ile Leu Ser Met Leu Thr Thr Thr Ser Thr Ser Tyr Leu Leu Leu
            260                 265                 270 gct tcg ctt gat gtc gcc aga aaa cgc tta gcc aca gag gga cac gaa    864
Ala Ser Leu Asp Val Ala Arg Lys Arg Leu Ala Thr Glu Gly His Glu
        275                 280                 285 ctg atc gaa caa acg att aag ctc gcc aac gaa aca agg gaa cgc atc    912
Leu Ile Glu Gln Thr Ile Lys Leu Ala Asn Glu Thr Arg Glu Arg Ile
    290                 295                 300 aat aat atc aac ggg att tca tgc gtc ggg agg gaa atc ctc ggc tcc    960
Asn Asn Ile Asn Gly Ile Ser Cys Val Gly Arg Glu Ile Leu Gly Ser
305                 310                 315                 320 aaa gcg gct ttt gac tat gat ccg acc aaa ttg atc ata tct gtg aaa   1008
Lys Ala Ala Phe Asp Tyr Asp Pro Thr Lys Leu Ile Ile Ser Val Lys
                325                 330                 335 gac ctc ggc ctg acc ggt cat gat gtg gaa aaa tgg ctg cgc gag tca   1056
Asp Leu Gly Leu Thr Gly His Asp Val Glu Lys Trp Leu Arg Glu Ser
            340                 345                 350 tgc caa atc gaa gtg gag ctt tct gac tta tac aac atc ctg tgc att   1104
Cys Gln Ile Glu Val Glu Leu Ser Asp Leu Tyr Asn Ile Leu Cys Ile
        355                 360                 365 ttt aca ccg gga gac cgg aaa gag gat gca gat gcg tta att aaa gga   1152
Phe Thr Pro Gly Asp Arg Lys Glu Asp Ala Asp Ala Leu Ile Lys Gly
    370                 375                 380 tta acc gag att gct caa cag gcc gct tca tct gcg gaa aac aga cgc   1200
Leu Thr Glu Ile Ala Gln Gln Ala Ala Ser Ser Ala Glu Asn Arg Arg
385                 390                 395                 400 aag cct gaa gtg ctt ctg cca aac att ccg gcg ctt gcg atg aca ccg   1248
Lys Pro Glu Val Leu Leu Pro Asn Ile Pro Ala Leu Ala Met Thr Pro
                405                 410                 415 cgt gac gct ttt tac gca aac acg gag atc att ccg ttc aaa aaa gca   1296
Arg Asp Ala Phe Tyr Ala Asn Thr Glu Ile Ile Pro Phe Lys Lys Ala
            420                 425                 430 gct ggc aga atg att gcc gag ttt gtt atg gtt tat ccg cca ggg ata   1344
Ala Gly Arg Met Ile Ala Glu Phe Val Met Val Tyr Pro Pro Gly Ile
        435                 440                 445 ccg atc ttc att ccg ggc gag atc att acc gag gat aat atc aac tac   1392
Pro Ile Phe Ile Pro Gly Glu Ile Ile Thr Glu Asp Asn Ile Asn Tyr
    450                 455                 460 atc gaa aag aac ctg gaa gct ggg ctg cct gtt cag gga ccg gaa gat   1440
Ile Glu Lys Asn Leu Glu Ala Gly Leu Pro Val Gln Gly Pro Glu Asp
465                 470                 475                 480 gac acc ctc cat atg atc cgc gtt att aaa gaa cag cag gca atc ctg   1488
Asp Thr Leu His Met Ile Arg Val Ile Lys Glu Gln Gln Ala Ile Leu
                485                 490                 495 taa aaa                                                            1494
```

<210> SEQ ID NO 6
<211> LENGTH: 496

<212> TYPE: PRT
<213> ORGANISM: Bacillus licheniformis DSM 13

<400> SEQUENCE: 6

```
Met Lys Val Gly Lys Gln Leu Leu Gln His Glu Thr Pro Leu Tyr Thr
1               5                   10                  15

Gly Leu Lys Lys His Ala Gly Lys Asn Pro Ile Gln Phe His Ile Pro
            20                  25                  30

Gly His Lys Lys Gly Ser Gly Met Asp Pro Glu Phe Arg Glu Phe Ile
        35                  40                  45

Gly Glu Asn Ala Leu Ser Ile Asp Leu Ile Asn Ile Glu Pro Leu Asp
    50                  55                  60

Asp Leu His Ala Pro Lys Gly Ile Ile Lys Gln Ala Gln Asp Leu Ala
65                  70                  75                  80

Ala Glu Ala Phe Gly Ala Asp Tyr Thr Phe Phe Ser Val Gln Gly Thr
                85                  90                  95

Ser Gly Ala Ile Met Thr Met Val Met Ala Val Cys Gly Pro Gly Asp
            100                 105                 110

Lys Ile Ile Val Pro Arg Asn Val His Lys Ser Val Met Ser Ala Ile
        115                 120                 125

Val Phe Ser Gly Ala Val Pro Ile Phe Ile His Pro Glu Ile Asp Asp
130                 135                 140

Glu Leu Gly Ile Ser His Gly Ile Thr Pro Glu Ser Ala Lys Lys Ala
145                 150                 155                 160

Leu Leu Glu His Pro Asp Ala Lys Gly Leu Leu Val Ile Asn Pro Thr
                165                 170                 175

Tyr Phe Gly Ile Ala Ala Asp Leu Lys Ser Ile Val Glu Leu Ala His
            180                 185                 190

Ser Phe His Val Pro Val Leu Val Asp Glu Ala His Gly Val His Ile
        195                 200                 205

His Phe His Glu Asp Leu Pro Leu Ser Ala Met Gln Ala Gly Ala Asp
    210                 215                 220

Met Ala Ala Thr Ser Val His Lys Leu Gly Gly Ser Leu Thr Gln Ser
225                 230                 235                 240

Ser Ile Leu Asn Met Lys Glu Gly Leu Val Ser Lys Glu Arg Val Gln
                245                 250                 255

Ser Ile Leu Ser Met Leu Thr Thr Ser Thr Ser Tyr Leu Leu Leu
            260                 265                 270

Ala Ser Leu Asp Val Ala Arg Lys Arg Leu Ala Thr Glu Gly His Glu
        275                 280                 285

Leu Ile Glu Gln Thr Ile Lys Leu Ala Asn Glu Thr Arg Glu Arg Ile
    290                 295                 300

Asn Asn Ile Asn Gly Ile Ser Cys Val Gly Arg Glu Ile Leu Gly Ser
305                 310                 315                 320

Lys Ala Ala Phe Asp Tyr Asp Pro Thr Lys Leu Ile Ile Ser Val Lys
                325                 330                 335

Asp Leu Gly Leu Thr Gly His Asp Val Glu Lys Trp Leu Arg Glu Ser
            340                 345                 350

Cys Gln Ile Glu Val Glu Leu Ser Asp Leu Tyr Asn Ile Leu Cys Ile
        355                 360                 365

Phe Thr Pro Gly Asp Arg Lys Glu Asp Ala Asp Ala Leu Ile Lys Gly
    370                 375                 380

Leu Thr Glu Ile Ala Gln Gln Ala Ala Ser Ser Ala Glu Asn Arg Arg
385                 390                 395                 400
```

```
Lys Pro Glu Val Leu Leu Pro Asn Ile Pro Ala Leu Ala Met Thr Pro
            405                 410                 415

Arg Asp Ala Phe Tyr Ala Asn Thr Glu Ile Ile Pro Phe Lys Lys Ala
            420                 425                 430

Ala Gly Arg Met Ile Ala Glu Phe Val Met Val Tyr Pro Pro Gly Ile
            435                 440                 445

Pro Ile Phe Ile Pro Gly Glu Ile Ile Thr Glu Asp Asn Ile Asn Tyr
    450                 455                 460

Ile Glu Lys Asn Leu Glu Ala Gly Leu Pro Val Gln Gly Pro Glu Asp
465                 470                 475                 480

Asp Thr Leu His Met Ile Arg Val Ile Lys Glu Gln Gln Ala Ile Leu
            485                 490                 495

<210> SEQ ID NO 7
<211> LENGTH: 1167
<212> TYPE: DNA
<213> ORGANISM: Bacillus licheniformis DSM 13
<220> FEATURE:
<221> NAME/KEY: gene
<222> LOCATION: (1)..(1167)
<223> OTHER INFORMATION: NADH-dependent butanol dehydrogenase A
      (E.C. 1.1.1.-), yugJ
<220> FEATURE:
<221> NAME/KEY: CDS
<222> LOCATION: (1)..(1164)

<400> SEQUENCE: 7 atg gat aac ttt aca tat tgg aat ccc aca aag ctg ata ttc ggc cgg      48
Met Asp Asn Phe Thr Tyr Trp Asn Pro Thr Lys Leu Ile Phe Gly Arg
1               5                   10                  15 gga gaa gtt gaa aag ctg gca gaa gag gtg aaa caa tac ggc cgc aat      96
Gly Glu Val Glu Lys Leu Ala Glu Glu Val Lys Gln Tyr Gly Arg Asn
            20                  25                  30 gtc ctg ctc gta tac ggc gga ggc agc att aag cga aac ggt tta tac     144
Val Leu Leu Val Tyr Gly Gly Gly Ser Ile Lys Arg Asn Gly Leu Tyr
        35                  40                  45 gat caa gtc att tca atc ctt gaa aag gcg ggc gcg acc gtc cat gaa     192
Asp Gln Val Ile Ser Ile Leu Glu Lys Ala Gly Ala Thr Val His Glu
    50                  55                  60 ctg ccc ggc gtc gaa ccg aat ccg cgt gtt gcc act gtg aat aaa gga     240
Leu Pro Gly Val Glu Pro Asn Pro Arg Val Ala Thr Val Asn Lys Gly
65                  70                  75                  80 gtt gcg atc tgc aaa gag aac gat att gac ttt ctt ttg gca gtc ggc     288
Val Ala Ile Cys Lys Glu Asn Asp Ile Asp Phe Leu Leu Ala Val Gly
            85                  90                  95 ggc gga agc gtc att gat tgt acg aaa gca att gct gcc gga gcg aaa     336
Gly Gly Ser Val Ile Asp Cys Thr Lys Ala Ile Ala Ala Gly Ala Lys
        100                 105                 110 tac gac ggc gat gcg tgg gat att gtg acg aaa aaa cat att ccg gct     384
Tyr Asp Gly Asp Ala Trp Asp Ile Val Thr Lys Lys His Ile Pro Ala
    115                 120                 125 gat gcg ctg ccg ttt gga aca gtt tta acg tta gca gca aca ggc tct     432
Asp Ala Leu Pro Phe Gly Thr Val Leu Thr Leu Ala Ala Thr Gly Ser
130                 135                 140 gaa atg aac tcg gga tct gtg atc aca aat tgg gaa acc aat gaa aaa     480
Glu Met Asn Ser Gly Ser Val Ile Thr Asn Trp Glu Thr Asn Glu Lys
145                 150                 155                 160 tac ggc tgg gga agc ccg ctc gta ttc cct aaa ttt tca att ctt gat     528
Tyr Gly Trp Gly Ser Pro Leu Val Phe Pro Lys Phe Ser Ile Leu Asp
            165                 170                 175
```

```
ccg gtc aac acg ttt acc gtc ccg aaa gac cac acg att tac ggc att    576
Pro Val Asn Thr Phe Thr Val Pro Lys Asp His Thr Ile Tyr Gly Ile
        180                 185                 190 gtc gac atg atg tcc cac gtg ttt gag caa tat ttt cac cat acc gaa    624
Val Asp Met Met Ser His Val Phe Glu Gln Tyr Phe His His Thr Glu
            195                 200                 205 aat acc cct tat cag gac cgg atg tgc gaa tcc ctg ctt aaa acg gta    672
Asn Thr Pro Tyr Gln Asp Arg Met Cys Glu Ser Leu Leu Lys Thr Val
210                 215                 220 att gaa aca gct cct aag ctc att gaa gac cta gaa aac tat gag ctg    720
Ile Glu Thr Ala Pro Lys Leu Ile Glu Asp Leu Glu Asn Tyr Glu Leu
225                 230                 235                 240 cgt gaa acg att ctg tat aca ggc acc att gcg ctg aac ggc atg cta    768
Arg Glu Thr Ile Leu Tyr Thr Gly Thr Ile Ala Leu Asn Gly Met Leu
                245                 250                 255 tca atg ggc gca cgc gga gac tgg gca acg cac aat atc gag cac gct    816
Ser Met Gly Ala Arg Gly Asp Trp Ala Thr His Asn Ile Glu His Ala
            260                 265                 270 gtt tca gcc gta tac gat att ccg cat gcg gga ggg ctt gcg att ctg    864
Val Ser Ala Val Tyr Asp Ile Pro His Ala Gly Gly Leu Ala Ile Leu
        275                 280                 285 ttc ccg aat tgg atg aag cac acg ctt tcc gag aac gtc ggc cgc ttt    912
Phe Pro Asn Trp Met Lys His Thr Leu Ser Glu Asn Val Gly Arg Phe
    290                 295                 300 aaa cag ctt gcc gtc cgt gtt ttt gac gta gat gaa aca gga aaa acc    960
Lys Gln Leu Ala Val Arg Val Phe Asp Val Asp Glu Thr Gly Lys Thr
305                 310                 315                 320 gat cgc gaa gtg gcg ctt gtt gga atc gag aaa ctg tct gaa ttc tgg   1008
Asp Arg Glu Val Ala Leu Val Gly Ile Glu Lys Leu Ser Glu Phe Trp
                325                 330                 335 acc agc ctt ggc gcg cca aat cgt ctt gcc gat tat gac att aca gat   1056
Thr Ser Leu Gly Ala Pro Asn Arg Leu Ala Asp Tyr Asp Ile Thr Asp
            340                 345                 350 gag aag ctt gat ctc att gcc gac aaa gcg atg gca aac ggc gaa ttc   1104
Glu Lys Leu Asp Leu Ile Ala Asp Lys Ala Met Ala Asn Gly Glu Phe
        355                 360                 365 ggc cgc ttt aaa acg ctg aat aaa gac gat gtt ctg tct att ttg aag   1152
Gly Arg Phe Lys Thr Leu Asn Lys Asp Asp Val Leu Ser Ile Leu Lys
    370                 375                 380 gct tct tta taa gat                                               1167
Ala Ser Leu
385

<210> SEQ ID NO 8
<211> LENGTH: 387
<212> TYPE: PRT
<213> ORGANISM: Bacillus licheniformis DSM 13

<400> SEQUENCE: 8

Met Asp Asn Phe Thr Tyr Trp Asn Pro Thr Lys Leu Ile Phe Gly Arg
1               5                   10                  15

Gly Glu Val Glu Lys Leu Ala Glu Val Lys Gln Tyr Gly Arg Asn
                20                  25                  30

Val Leu Leu Val Tyr Gly Gly Gly Ser Ile Lys Arg Asn Gly Leu Tyr
            35                  40                  45

Asp Gln Val Ile Ser Ile Leu Glu Lys Ala Gly Ala Thr Val His Glu
        50                  55                  60

Leu Pro Gly Val Glu Pro Asn Pro Arg Val Ala Thr Val Asn Lys Gly
65                  70                  75                  80
```

```
Val Ala Ile Cys Lys Glu Asn Asp Ile Asp Phe Leu Leu Ala Val Gly
                85                  90                  95

Gly Gly Ser Val Ile Asp Cys Thr Lys Ala Ile Ala Ala Gly Ala Lys
            100                 105                 110

Tyr Asp Gly Asp Ala Trp Asp Ile Val Thr Lys Lys His Ile Pro Ala
        115                 120                 125

Asp Ala Leu Pro Phe Gly Thr Val Leu Thr Leu Ala Ala Thr Gly Ser
    130                 135                 140

Glu Met Asn Ser Gly Ser Val Ile Thr Asn Trp Glu Thr Asn Glu Lys
145                 150                 155                 160

Tyr Gly Trp Gly Ser Pro Leu Val Phe Pro Lys Phe Ser Ile Leu Asp
                165                 170                 175

Pro Val Asn Thr Phe Thr Val Pro Lys Asp His Thr Ile Tyr Gly Ile
            180                 185                 190

Val Asp Met Met Ser His Val Phe Glu Gln Tyr Phe His His Thr Glu
        195                 200                 205

Asn Thr Pro Tyr Gln Asp Arg Met Cys Glu Ser Leu Leu Lys Thr Val
    210                 215                 220

Ile Glu Thr Ala Pro Lys Leu Ile Glu Asp Leu Glu Asn Tyr Glu Leu
225                 230                 235                 240

Arg Glu Thr Ile Leu Tyr Thr Gly Thr Ile Ala Leu Asn Gly Met Leu
                245                 250                 255

Ser Met Gly Ala Arg Gly Asp Trp Ala Thr His Asn Ile Glu His Ala
            260                 265                 270

Val Ser Ala Val Tyr Asp Ile Pro His Ala Gly Gly Leu Ala Ile Leu
        275                 280                 285

Phe Pro Asn Trp Met Lys His Thr Leu Ser Glu Asn Val Gly Arg Phe
    290                 295                 300

Lys Gln Leu Ala Val Arg Val Phe Asp Val Asp Glu Thr Gly Lys Thr
305                 310                 315                 320

Asp Arg Glu Val Ala Leu Val Gly Ile Glu Lys Leu Ser Glu Phe Trp
                325                 330                 335

Thr Ser Leu Gly Ala Pro Asn Arg Leu Ala Asp Tyr Asp Ile Thr Asp
            340                 345                 350

Glu Lys Leu Asp Leu Ile Ala Asp Lys Ala Met Ala Asn Gly Glu Phe
        355                 360                 365

Gly Arg Phe Lys Thr Leu Asn Lys Asp Asp Val Leu Ser Ile Leu Lys
    370                 375                 380

Ala Ser Leu
385

<210> SEQ ID NO 9
<211> LENGTH: 1143
<212> TYPE: DNA
<213> ORGANISM: Bacillus licheniformis DSM 13
<220> FEATURE:
<221> NAME/KEY: gene
<222> LOCATION: (1)..(1143)
<223> OTHER INFORMATION: Acyl-CoA dehydrogenase (E.C. 1.3.99.-)
<220> FEATURE:
<221> NAME/KEY: CDS
<222> LOCATION: (1)..(1140)

<400> SEQUENCE: 9 atg atc ttt aag ctg agc gaa gag cac caa atg ata cag aag atg gtg      48
Met Ile Phe Lys Leu Ser Glu Glu His Gln Met Ile Gln Lys Met Val
1               5                   10                  15
```

| | | |
|---|---|---|
| cgc gac ttt gcc cat cac gag gtg gag ccg act gcg aaa gag cgg gat<br>Arg Asp Phe Ala His His Glu Val Glu Pro Thr Ala Lys Glu Arg Asp<br>20 25 30 | | 96 |
| gag gaa gag cgg ttt gac atg gaa ctg ttt gca aaa atg gcg gaa ttg<br>Glu Glu Glu Arg Phe Asp Met Glu Leu Phe Ala Lys Met Ala Glu Leu<br>35 40 45 | | 144 |
| ggg ctc acg ggt ata ccg tgg cca gag gaa tac ggg gga atc ggc agc<br>Gly Leu Thr Gly Ile Pro Trp Pro Glu Glu Tyr Gly Gly Ile Gly Ser<br>50 55 60 | | 192 |
| gac tat ctc gcc tac gtc atc gcg gtt gaa gag ctt tcg aaa gtc tgc<br>Asp Tyr Leu Ala Tyr Val Ile Ala Val Glu Glu Leu Ser Lys Val Cys<br>65 70 75 80 | | 240 |
| gcc tca acg ggt gtc acc ttg tct gcc cat aca tcg ctt gcg ggc tgg<br>Ala Ser Thr Gly Val Thr Leu Ser Ala His Thr Ser Leu Ala Gly Trp<br>85 90 95 | | 288 |
| ccg att tat gca ttt gga aca gaa gaa cag aaa cag gaa tat tta aag<br>Pro Ile Tyr Ala Phe Gly Thr Glu Glu Gln Lys Gln Glu Tyr Leu Lys<br>100 105 110 | | 336 |
| ccg atg gcc cgc ggc gaa aag ata gga gcc tac gga ttg acg gag ccc<br>Pro Met Ala Arg Gly Glu Lys Ile Gly Ala Tyr Gly Leu Thr Glu Pro<br>115 120 125 | | 384 |
| ggt tca ggc tcc gat gcc ggc ggc atg aaa acg acc gca gaa aaa aaa<br>Gly Ser Gly Ser Asp Ala Gly Gly Met Lys Thr Thr Ala Glu Lys Lys<br>130 135 140 | | 432 |
| ggc gat gaa tat att ttg aac ggg acg aag atc ttt atc aca aac ggc<br>Gly Asp Glu Tyr Ile Leu Asn Gly Thr Lys Ile Phe Ile Thr Asn Gly<br>145 150 155 160 | | 480 |
| gga atc gcg gac ttc tac atc gtg ttt gcc aac ctt gcc ccg gaa cag<br>Gly Ile Ala Asp Phe Tyr Ile Val Phe Ala Asn Leu Ala Pro Glu Gln<br>165 170 175 | | 528 |
| aaa cac aaa ggc aca acc gcc ttt atc gtt gaa aag gac ttc ccc ggc<br>Lys His Lys Gly Thr Thr Ala Phe Ile Val Glu Lys Asp Phe Pro Gly<br>180 185 190 | | 576 |
| ttt tct gtc gga aaa aaa gag agg aaa ctg ggc atc cgt tca tca ccg<br>Phe Ser Val Gly Lys Lys Glu Arg Lys Leu Gly Ile Arg Ser Ser Pro<br>195 200 205 | | 624 |
| aca acc gaa atc atc ttt cag gac tgc cgc gtg cct tta aaa aac cgc<br>Thr Thr Glu Ile Ile Phe Gln Asp Cys Arg Val Pro Leu Lys Asn Arg<br>210 215 220 | | 672 |
| ctt ggc ggg gaa ggt gaa ggc ttt aaa atc gcg atg aag acg ctc gat<br>Leu Gly Gly Glu Gly Glu Gly Phe Lys Ile Ala Met Lys Thr Leu Asp<br>225 230 235 240 | | 720 |
| gga ggc aga aac gga att gcc gct caa gcc gtc ggg att gcc cag ggc<br>Gly Gly Arg Asn Gly Ile Ala Ala Gln Ala Val Gly Ile Ala Gln Gly<br>245 250 255 | | 768 |
| gca ttt gag gcg gcg aag gcg tat gcg aaa gag cgg aag caa ttc ggc<br>Ala Phe Glu Ala Ala Lys Ala Tyr Ala Lys Glu Arg Lys Gln Phe Gly<br>260 265 270 | | 816 |
| agg ccg atc gcc gag cag cag ggc atc gct ttt aaa ctg gct gat atg<br>Arg Pro Ile Ala Glu Gln Gln Gly Ile Ala Phe Lys Leu Ala Asp Met<br>275 280 285 | | 864 |
| gcg acg gag att gaa gct tca agg ctt tta acc tac cag gcg gca tgg<br>Ala Thr Glu Ile Glu Ala Ser Arg Leu Leu Thr Tyr Gln Ala Ala Trp<br>290 295 300 | | 912 |
| ctg gaa tca gaa gga ctg cct tat gga aag gct tct gcc atg tca aag<br>Leu Glu Ser Glu Gly Leu Pro Tyr Gly Lys Ala Ser Ala Met Ser Lys<br>305 310 315 320 | | 960 |
| ctt tac gca ggg gat acg gcc atg aaa gtg acg acg gag gcc gtg caa<br>Leu Tyr Ala Gly Asp Thr Ala Met Lys Val Thr Thr Glu Ala Val Gln<br>325 330 335 | | 1008 |

```
ata ttc ggc ggg tac ggc tac aca aag gat tat ccg gtc gag cgc ttt      1056
Ile Phe Gly Gly Tyr Gly Tyr Thr Lys Asp Tyr Pro Val Glu Arg Phe
        340                 345                 350 atg cgc gat gca aaa atc aca cag atc tat gaa ggt acg cag gaa att      1104
Met Arg Asp Ala Lys Ile Thr Gln Ile Tyr Glu Gly Thr Gln Glu Ile
    355                 360                 365 cag aag ctc gtc att tcg aga atg ctg atg aaa taa ggg                  1143
Gln Lys Leu Val Ile Ser Arg Met Leu Met Lys
    370                 375
```

<210> SEQ ID NO 10
<211> LENGTH: 379
<212> TYPE: PRT
<213> ORGANISM: Bacillus licheniformis DSM 13

<400> SEQUENCE: 10

```
Met Ile Phe Lys Leu Ser Glu Glu His Gln Met Ile Gln Lys Met Val
1               5                   10                  15

Arg Asp Phe Ala His His Glu Val Glu Pro Thr Ala Lys Glu Arg Asp
            20                  25                  30

Glu Glu Glu Arg Phe Asp Met Glu Leu Phe Ala Lys Met Ala Glu Leu
        35                  40                  45

Gly Leu Thr Gly Ile Pro Trp Pro Glu Glu Tyr Gly Gly Ile Gly Ser
    50                  55                  60

Asp Tyr Leu Ala Tyr Val Ile Ala Val Glu Glu Leu Ser Lys Val Cys
65                  70                  75                  80

Ala Ser Thr Gly Val Thr Leu Ser Ala His Thr Ser Leu Ala Gly Trp
                85                  90                  95

Pro Ile Tyr Ala Phe Gly Thr Glu Glu Gln Lys Gln Glu Tyr Leu Lys
            100                 105                 110

Pro Met Ala Arg Gly Glu Lys Ile Gly Ala Tyr Gly Leu Thr Glu Pro
        115                 120                 125

Gly Ser Gly Ser Asp Ala Gly Gly Met Lys Thr Thr Ala Glu Lys Lys
    130                 135                 140

Gly Asp Glu Tyr Ile Leu Asn Gly Thr Lys Ile Phe Ile Thr Asn Gly
145                 150                 155                 160

Gly Ile Ala Asp Phe Tyr Ile Val Phe Ala Asn Leu Ala Pro Glu Gln
                165                 170                 175

Lys His Lys Gly Thr Thr Ala Phe Ile Val Glu Lys Asp Phe Pro Gly
            180                 185                 190

Phe Ser Val Gly Lys Lys Glu Arg Lys Leu Gly Ile Arg Ser Ser Pro
        195                 200                 205

Thr Thr Glu Ile Ile Phe Gln Asp Cys Arg Val Pro Leu Lys Asn Arg
    210                 215                 220

Leu Gly Gly Glu Gly Glu Gly Phe Lys Ile Ala Met Lys Thr Leu Asp
225                 230                 235                 240

Gly Gly Arg Asn Gly Ile Ala Ala Gln Ala Val Gly Ile Ala Gln Gly
                245                 250                 255

Ala Phe Glu Ala Ala Lys Ala Tyr Ala Lys Glu Arg Lys Gln Phe Gly
            260                 265                 270

Arg Pro Ile Ala Glu Gln Gln Gly Ile Ala Phe Lys Leu Ala Asp Met
        275                 280                 285

Ala Thr Glu Ile Glu Ala Ser Arg Leu Leu Thr Tyr Gln Ala Ala Trp
    290                 295                 300

Leu Glu Ser Glu Gly Leu Pro Tyr Gly Lys Ala Ser Ala Met Ser Lys
```

```
                    305                 310                 315                 320
Leu Tyr Ala Gly Asp Thr Ala Met Lys Val Thr Thr Glu Ala Val Gln
                325                 330                 335

Ile Phe Gly Gly Tyr Gly Tyr Thr Lys Asp Tyr Pro Val Glu Arg Phe
                340                 345                 350

Met Arg Asp Ala Lys Ile Thr Gln Ile Tyr Glu Gly Thr Gln Glu Ile
                355                 360                 365

Gln Lys Leu Val Ile Ser Arg Met Leu Met Lys
                370                 375

<210> SEQ ID NO 11
<211> LENGTH: 1134
<212> TYPE: DNA
<213> ORGANISM: Bacillus licheniformis DSM 13
<220> FEATURE:
<221> NAME/KEY: gene
<222> LOCATION: (1)..(1134)
<223> OTHER INFORMATION: Acyl-CoA dehydrogenase (E.C. 1.3.99.-)
<220> FEATURE:
<221> NAME/KEY: misc_feature
<222> LOCATION: (1)..(3)
<223> OTHER INFORMATION: First codon translated as Met.
<220> FEATURE:
<221> NAME/KEY: CDS
<222> LOCATION: (1)..(1131)

<400> SEQUENCE: 11 ttg aat ttt cag ttt aca gaa gag cag acc cgc atg cag aag gtt gta        48
Leu Asn Phe Gln Phe Thr Glu Glu Gln Thr Arg Met Gln Lys Val Val
1               5                   10                  15 agg gat ttt gtc aaa cag gag gtc gct cct ttt gta cct gaa atg gaa        96
Arg Asp Phe Val Lys Gln Glu Val Ala Pro Phe Val Pro Glu Met Glu
                20                  25                  30 aaa ggc cgt ttt cca acc tct ctt ttg aag aaa atg gcg gag cgc ggc       144
Lys Gly Arg Phe Pro Thr Ser Leu Leu Lys Lys Met Ala Glu Arg Gly
            35                  40                  45 tgg atg ggg ctt ccg ata ccg gct aag tac aac ggg gcc ggt cat gac       192
Trp Met Gly Leu Pro Ile Pro Ala Lys Tyr Asn Gly Ala Gly His Asp
        50                  55                  60 ttt atc acc tat atg atg acc ata cat gag ctg tca aag aaa agc gcc       240
Phe Ile Thr Tyr Met Met Thr Ile His Glu Leu Ser Lys Lys Ser Ala
65                  70                  75                  80 gtt ctt ggt gcg gtt cta tct gta cac acg tca att gtc acc att ccc       288
Val Leu Gly Ala Val Leu Ser Val His Thr Ser Ile Val Thr Ile Pro
                85                  90                  95 att ctt tta aac ggt aat gag cgg caa aaa gag cac tac gtt aaa aag       336
Ile Leu Leu Asn Gly Asn Glu Arg Gln Lys Glu His Tyr Val Lys Lys
            100                 105                 110 ctg gca gca ggg cag tac ttg gga gct ttt tgt tta acc gaa ccg agt       384
Leu Ala Ala Gly Gln Tyr Leu Gly Ala Phe Cys Leu Thr Glu Pro Ser
        115                 120                 125 gcc ggt tcc gat gcg ggc agt cta aaa acc agg gcc gaa aag cgc ggc       432
Ala Gly Ser Asp Ala Gly Ser Leu Lys Thr Arg Ala Glu Lys Arg Gly
    130                 135                 140 gat acc tat gtg ctg aac gga acg aaa gtt ttt att aca aac ggc gga       480
Asp Thr Tyr Val Leu Asn Gly Thr Lys Val Phe Ile Thr Asn Gly Gly
145                 150                 155                 160 gcc gcg gac att tat ctt gtt ttc gct tca acc gat ccg gag gcg gga       528
Ala Ala Asp Ile Tyr Leu Val Phe Ala Ser Thr Asp Pro Glu Ala Gly
                165                 170                 175 acg gga ggc att tcc gct ttt atc gtg gag aag ggc acg ccg ggc ttt       576
Thr Gly Gly Ile Ser Ala Phe Ile Val Glu Lys Gly Thr Pro Gly Phe
```

```
                180                 185                 190
ttc atc gga aaa aat gaa gag aaa atg ggc ctc cac ggt tcg cta acg    624
Phe Ile Gly Lys Asn Glu Glu Lys Met Gly Leu His Gly Ser Leu Thr
        195                 200                 205 gtc act tta aat ttt gat aac gct gtc att ccc gcc cgg cag ctg ctg    672
Val Thr Leu Asn Phe Asp Asn Ala Val Ile Pro Ala Arg Gln Leu Leu
210                 215                 220 ggg gag gaa gga atg gga ttc aaa atg gcc ctg tcc aac ctg gat acc    720
Gly Glu Glu Gly Met Gly Phe Lys Met Ala Leu Ser Asn Leu Asp Thr
225                 230                 235                 240 ggc cgg atc gga att gcg gcg cag gct ctg ggt atc gcc gag gga gcg    768
Gly Arg Ile Gly Ile Ala Ala Gln Ala Leu Gly Ile Ala Glu Gly Ala
                245                 250                 255 ctt tct gaa gcc gtt caa ttt cta aaa aaa cgg tat ccg gac gga gag    816
Leu Ser Glu Ala Val Gln Phe Leu Lys Lys Arg Tyr Pro Asp Gly Glu
            260                 265                 270 ctg tat aag aac ggc caa gcg ctt gcc ttt aag ctg gcc gac atg gcg    864
Leu Tyr Lys Asn Gly Gln Ala Leu Ala Phe Lys Leu Ala Asp Met Ala
        275                 280                 285 gcg agg aca gag gcg gcc agg ctt ctc gtc tac cag gcc gcc tcg ttg    912
Ala Arg Thr Glu Ala Ala Arg Leu Leu Val Tyr Gln Ala Ala Ser Leu
290                 295                 300 aaa cag caa ggc atg cag acg ggg aaa gct gct tca atg gcc aaa ttg    960
Lys Gln Gln Gly Met Gln Thr Gly Lys Ala Ala Ser Met Ala Lys Leu
305                 310                 315                 320 ttc gct tcg gaa acg gcg atg tat gtc gcc gga gag gcc gtg cag ctg   1008
Phe Ala Ser Glu Thr Ala Met Tyr Val Ala Gly Glu Ala Val Gln Leu
                325                 330                 335 ctc gga gat ttc gga tac aca aag gat ttc agc gct gaa cga tat ttc   1056
Leu Gly Asp Phe Gly Tyr Thr Lys Asp Phe Ser Ala Glu Arg Tyr Phe
            340                 345                 350 agg gat gcg aaa gtg tgt gaa att tat gag ggc acg agc gag atc cag   1104
Arg Asp Ala Lys Val Cys Glu Ile Tyr Glu Gly Thr Ser Glu Ile Gln
        355                 360                 365 cgg atc gtc atc ggt aaa cat tta taa ggt                           1134
Arg Ile Val Ile Gly Lys His Leu
370                 375

<210> SEQ ID NO 12
<211> LENGTH: 376
<212> TYPE: PRT
<213> ORGANISM: Bacillus licheniformis DSM 13
<220> FEATURE:
<221> NAME/KEY: misc_feature
<222> LOCATION: (1)..(3)
<223> OTHER INFORMATION: First codon translated as Met.

<400> SEQUENCE: 12

Leu Asn Phe Gln Phe Thr Glu Glu Gln Thr Arg Met Gln Lys Val Val
1               5                   10                  15

Arg Asp Phe Val Lys Gln Glu Val Ala Pro Phe Val Pro Glu Met Glu
            20                  25                  30

Lys Gly Arg Phe Pro Thr Ser Leu Leu Lys Met Ala Glu Arg Gly
        35                  40                  45

Trp Met Gly Leu Pro Ile Pro Ala Lys Tyr Asn Gly Ala Gly His Asp
50                  55                  60

Phe Ile Thr Tyr Met Met Thr Ile His Glu Leu Ser Lys Lys Ser Ala
65                  70                  75                  80

Val Leu Gly Ala Val Leu Ser Val His Thr Ser Ile Val Thr Ile Pro
                85                  90                  95
```

```
Ile Leu Leu Asn Gly Asn Glu Arg Gln Lys Glu His Tyr Val Lys Lys
                100                 105                 110

Leu Ala Ala Gly Gln Tyr Leu Gly Ala Phe Cys Leu Thr Glu Pro Ser
            115                 120                 125

Ala Gly Ser Asp Ala Gly Ser Leu Lys Thr Arg Ala Glu Lys Arg Gly
130                 135                 140

Asp Thr Tyr Val Leu Asn Gly Thr Lys Val Phe Ile Thr Asn Gly Gly
145                 150                 155                 160

Ala Ala Asp Ile Tyr Leu Val Phe Ala Ser Thr Asp Pro Glu Ala Gly
                165                 170                 175

Thr Gly Gly Ile Ser Ala Phe Ile Val Glu Lys Gly Thr Pro Gly Phe
            180                 185                 190

Phe Ile Gly Lys Asn Glu Glu Lys Met Gly Leu His Gly Ser Leu Thr
        195                 200                 205

Val Thr Leu Asn Phe Asp Asn Ala Val Ile Pro Ala Arg Gln Leu Leu
210                 215                 220

Gly Glu Glu Gly Met Gly Phe Lys Met Ala Leu Ser Asn Leu Asp Thr
225                 230                 235                 240

Gly Arg Ile Gly Ile Ala Ala Gln Ala Leu Gly Ile Ala Glu Gly Ala
                245                 250                 255

Leu Ser Glu Ala Val Gln Phe Leu Lys Lys Arg Tyr Pro Asp Gly Glu
            260                 265                 270

Leu Tyr Lys Asn Gly Gln Ala Leu Ala Phe Lys Leu Ala Asp Met Ala
        275                 280                 285

Ala Arg Thr Glu Ala Ala Arg Leu Leu Val Tyr Gln Ala Ala Ser Leu
290                 295                 300

Lys Gln Gln Gly Met Gln Thr Gly Lys Ala Ala Ser Met Ala Lys Leu
305                 310                 315                 320

Phe Ala Ser Glu Thr Ala Met Tyr Val Ala Gly Glu Ala Val Gln Leu
                325                 330                 335

Leu Gly Asp Phe Gly Tyr Thr Lys Asp Phe Ser Ala Glu Arg Tyr Phe
            340                 345                 350

Arg Asp Ala Lys Val Cys Glu Ile Tyr Glu Gly Thr Ser Glu Ile Gln
        355                 360                 365

Arg Ile Val Ile Gly Lys His Leu
    370                 375

<210> SEQ ID NO 13
<211> LENGTH: 867
<212> TYPE: DNA
<213> ORGANISM: Bacillus licheniformis DSM 13
<220> FEATURE:
<221> NAME/KEY: gene
<222> LOCATION: (1)..(867)
<223> OTHER INFORMATION: 3-hydroxybutyryl-CoA dehydrogenase
      (E.C. 1.1.1.157)
<220> FEATURE:
<221> NAME/KEY: CDS
<222> LOCATION: (1)..(864)

<400> SEQUENCE: 13 atg aaa aaa gac acg atc atg gtc atc gga gcc ggc cag atg ggg tcc      48
Met Lys Lys Asp Thr Ile Met Val Ile Gly Ala Gly Gln Met Gly Ser
1               5                   10                  15 ggg atc gct cag gtc tct gcc cag gcc gga tac aat gtt tac atg tat      96
Gly Ile Ala Gln Val Ser Ala Gln Ala Gly Tyr Asn Val Tyr Met Tyr
            20                  25                  30
```

-continued

```
gac gta tca cct gaa caa att gaa aaa gga atg aag cgc att tcc ggc       144
Asp Val Ser Pro Glu Gln Ile Glu Lys Gly Met Lys Arg Ile Ser Gly
    35                  40                  45 cag ctt ttc aga cag gcg gaa aaa ggc aag ctg ccg cat gaa gat gtg       192
Gln Leu Phe Arg Gln Ala Glu Lys Gly Lys Leu Pro His Glu Asp Val
 50                  55                  60 aag caa atc tac cag cgc ctt tct ccg tcg gct gcg ctc gac gaa gcg       240
Lys Gln Ile Tyr Gln Arg Leu Ser Pro Ser Ala Ala Leu Asp Glu Ala
 65                  70                  75                  80 cgg gaa gct ttt ctc atc att gaa gcg gct gtt gaa caa atg gac gta       288
Arg Glu Ala Phe Leu Ile Ile Glu Ala Ala Val Glu Gln Met Asp Val
                 85                  90                  95 aaa aaa gac att ttc acg cgg ctt gat gaa gtg acc gaa gac tca gcg       336
Lys Lys Asp Ile Phe Thr Arg Leu Asp Glu Val Thr Glu Asp Ser Ala
                100                 105                 110 ata ttg gca tca aat aca tcg tcc ctg tcg att acg gaa ctt gct gcc       384
Ile Leu Ala Ser Asn Thr Ser Ser Leu Ser Ile Thr Glu Leu Ala Ala
            115                 120                 125 gtc aca aaa aaa cct caa aac gtc atc ggc atg cat ttt atg aac ccg       432
Val Thr Lys Lys Pro Gln Asn Val Ile Gly Met His Phe Met Asn Pro
130                 135                 140 gtt ccc gtc atg cag ctt gtc gaa gtc atc agg ggg ctt gag acg agc       480
Val Pro Val Met Gln Leu Val Glu Val Ile Arg Gly Leu Glu Thr Ser
145                 150                 155                 160 ggc gaa aca tat gaa acc gtc gtg gct gcg gcg gag cgg atg aac aag       528
Gly Glu Thr Tyr Glu Thr Val Val Ala Ala Glu Arg Met Asn Lys
                165                 170                 175 gtt ccg ata gag gtg cgg gat ttc ccg gga ttt atc tcc aac cgc atc       576
Val Pro Ile Glu Val Arg Asp Phe Pro Gly Phe Ile Ser Asn Arg Ile
            180                 185                 190 tta atg ccg atg att aat gag gcg gtt ttt gca ctt tat gaa ggc atc       624
Leu Met Pro Met Ile Asn Glu Ala Val Phe Ala Leu Tyr Glu Gly Ile
        195                 200                 205 gcc gag aaa gaa agc ata gac gga atc atg aag ctt ggc atg aac cat       672
Ala Glu Lys Glu Ser Ile Asp Gly Ile Met Lys Leu Gly Met Asn His
    210                 215                 220 ccg atg ggc ccg ttg gct ctc gcc gat ctg atc ggt ctg gat acg tgt       720
Pro Met Gly Pro Leu Ala Leu Ala Asp Leu Ile Gly Leu Asp Thr Cys
225                 230                 235                 240 ctg tat att atg gag acg ctg cat gaa ggc ttt ggc gac gat aag tac       768
Leu Tyr Ile Met Glu Thr Leu His Glu Gly Phe Gly Asp Asp Lys Tyr
                245                 250                 255 agg cct tgt ccg ctc ctt aaa caa tat gtc agc gca gga cga ctc gga       816
Arg Pro Cys Pro Leu Leu Lys Gln Tyr Val Ser Ala Gly Arg Leu Gly
            260                 265                 270 aag aaa acg ggc aga ggg ttt tat acg tat gaa aag cag ccg aca taa       864
Lys Lys Thr Gly Arg Gly Phe Tyr Thr Tyr Glu Lys Gln Pro Thr
        275                 280                 285 gga                                                                   867
```

<210> SEQ ID NO 14
<211> LENGTH: 287
<212> TYPE: PRT
<213> ORGANISM: Bacillus licheniformis DSM 13

<400> SEQUENCE: 14

```
Met Lys Lys Asp Thr Ile Met Val Ile Gly Ala Gly Gln Met Gly Ser
 1               5                  10                  15

Gly Ile Ala Gln Val Ser Ala Gln Ala Gly Tyr Asn Val Tyr Met Tyr
            20                  25                  30
```

```
Asp Val Ser Pro Glu Gln Ile Glu Lys Gly Met Lys Arg Ile Ser Gly
            35                  40                  45

Gln Leu Phe Arg Gln Ala Glu Lys Gly Lys Leu Pro His Glu Asp Val
        50                  55                  60

Lys Gln Ile Tyr Gln Arg Leu Ser Pro Ser Ala Ala Leu Asp Glu Ala
 65                  70                  75                  80

Arg Glu Ala Phe Leu Ile Ile Glu Ala Ala Val Glu Gln Met Asp Val
                85                  90                  95

Lys Lys Asp Ile Phe Thr Arg Leu Asp Glu Val Thr Glu Asp Ser Ala
            100                 105                 110

Ile Leu Ala Ser Asn Thr Ser Ser Leu Ser Ile Thr Glu Leu Ala Ala
        115                 120                 125

Val Thr Lys Lys Pro Gln Asn Val Ile Gly Met His Phe Met Asn Pro
    130                 135                 140

Val Pro Val Met Gln Leu Val Glu Val Ile Arg Gly Leu Glu Thr Ser
145                 150                 155                 160

Gly Glu Thr Tyr Glu Thr Val Ala Ala Ala Glu Arg Met Asn Lys
                165                 170                 175

Val Pro Ile Glu Val Arg Asp Phe Pro Gly Phe Ile Ser Asn Arg Ile
            180                 185                 190

Leu Met Pro Met Ile Asn Glu Ala Val Phe Ala Leu Tyr Glu Gly Ile
        195                 200                 205

Ala Glu Lys Glu Ser Ile Asp Gly Ile Met Lys Leu Gly Met Asn His
    210                 215                 220

Pro Met Gly Pro Leu Ala Leu Ala Asp Leu Ile Gly Leu Asp Thr Cys
225                 230                 235                 240

Leu Tyr Ile Met Glu Thr Leu His Glu Gly Phe Gly Asp Asp Lys Tyr
                245                 250                 255

Arg Pro Cys Pro Leu Leu Lys Gln Tyr Val Ser Ala Gly Arg Leu Gly
            260                 265                 270

Lys Lys Thr Gly Arg Gly Phe Tyr Thr Tyr Glu Lys Gln Pro Thr
        275                 280                 285

<210> SEQ ID NO 15
<211> LENGTH: 780
<212> TYPE: DNA
<213> ORGANISM: Bacillus licheniformis DSM 13
<220> FEATURE:
<221> NAME/KEY: gene
<222> LOCATION: (1)..(780)
<223> OTHER INFORMATION: Putative enoyl-CoA hydratase protein
      (E.C. 4.2.1.17)
<220> FEATURE:
<221> NAME/KEY: CDS
<222> LOCATION: (1)..(777)

<400> SEQUENCE: 15 atg gaa tat atc aaa tgg aaa gac gaa gac ggg att ttt gaa att gta    48
Met Glu Tyr Ile Lys Trp Lys Asp Glu Asp Gly Ile Phe Glu Ile Val
 1               5                  10                  15 ctg aat cgc tct gag gcg tac aat gcc ttg aat gaa aaa atg ctt gaa    96
Leu Asn Arg Ser Glu Ala Tyr Asn Ala Leu Asn Glu Lys Met Leu Glu
            20                  25                  30 gaa ctg aat gaa gct ttg cgt gtt gca gag gaa agc gaa tcg ctg ctt   144
Glu Leu Asn Glu Ala Leu Arg Val Ala Glu Glu Ser Glu Ser Leu Leu
        35                  40                  45 ctc ctt gtg aga ggc agc ggc aaa gga ttt tcg gca ggc gga gac att   192
Leu Leu Val Arg Gly Ser Gly Lys Gly Phe Ser Ala Gly Gly Asp Ile
```

```
      50                  55                  60
aag atg atg ctg tct tcc gga gat caa gac agc tcc gcc cgc gtc att    240
Lys Met Met Leu Ser Ser Gly Asp Gln Asp Ser Ser Ala Arg Val Ile
 65                  70                  75                  80 gac aca att tct gaa att gcg gtg aag ctt tac agc atg ccg aag atg    288
Asp Thr Ile Ser Glu Ile Ala Val Lys Leu Tyr Ser Met Pro Lys Met
                 85                  90                  95 acg aca gcg gct gtc cac ggt gcg gct gcg ggt ctg gga ttg agc ctc    336
Thr Thr Ala Ala Val His Gly Ala Ala Ala Gly Leu Gly Leu Ser Leu
            100                 105                 110 gcg ctc agc tgc gac cat gta ctg gtc gaa aaa gag gcg aag ctg gcg    384
Ala Leu Ser Cys Asp His Val Leu Val Glu Lys Glu Ala Lys Leu Ala
        115                 120                 125 atg aat ttt atc ggc atc ggg ctt gtt ccc gac gga ggc gga cac ttc    432
Met Asn Phe Ile Gly Ile Gly Leu Val Pro Asp Gly Gly Gly His Phe
    130                 135                 140 ttt tta gag cgg aga atc ggt gaa act gcg gcc aaa gaa ttg att tgg    480
Phe Leu Glu Arg Arg Ile Gly Glu Thr Ala Ala Lys Glu Leu Ile Trp
145                 150                 155                 160 agc ggg aaa aaa ttg acg ggg gcc gaa gcg cac gag ctt cgg atc gca    528
Ser Gly Lys Lys Leu Thr Gly Ala Glu Ala His Glu Leu Arg Ile Ala
                165                 170                 175 gac gcc gta ttc agc ggg gac tcc ggc cgt ttt gcg cgc atc tat ctt    576
Asp Ala Val Phe Ser Gly Asp Ser Gly Arg Phe Ala Arg Ile Tyr Leu
            180                 185                 190 gaa aag ctt ctg cac gct ccg ctg gca gcg atg att gag aca aaa aag    624
Glu Lys Leu Leu His Ala Pro Leu Ala Ala Met Ile Glu Thr Lys Lys
        195                 200                 205 atc tat cag gcg ttg aat gga ggc agg ctg cag aaa acg ctt gaa ctc    672
Ile Tyr Gln Ala Leu Asn Gly Gly Arg Leu Gln Lys Thr Leu Glu Leu
    210                 215                 220 gag aaa acg gcc cag atg aaa atg agg ctg aca agc gac cat cag gaa    720
Glu Lys Thr Ala Gln Met Lys Met Arg Leu Thr Ser Asp His Gln Glu
225                 230                 235                 240 ggg atc cgc gca ttt tta gaa aag cgc cag ccg caa ttt aac cgt cag    768
Gly Ile Arg Ala Phe Leu Glu Lys Arg Gln Pro Gln Phe Asn Arg Gln
                245                 250                 255 caa gta taa caa                                                    780
Gln Val

<210> SEQ ID NO 16
<211> LENGTH: 258
<212> TYPE: PRT
<213> ORGANISM: Bacillus licheniformis DSM 13

<400> SEQUENCE: 16

Met Glu Tyr Ile Lys Trp Lys Asp Glu Asp Gly Ile Phe Glu Ile Val
1               5                   10                  15

Leu Asn Arg Ser Glu Ala Tyr Asn Ala Leu Asn Glu Lys Met Leu Glu
            20                  25                  30

Glu Leu Asn Glu Ala Leu Arg Val Ala Glu Glu Ser Glu Ser Leu Leu
        35                  40                  45

Leu Leu Val Arg Gly Ser Gly Lys Gly Phe Ser Ala Gly Gly Asp Ile
    50                  55                  60

Lys Met Met Leu Ser Ser Gly Asp Gln Asp Ser Ser Ala Arg Val Ile
65                  70                  75                  80

Asp Thr Ile Ser Glu Ile Ala Val Lys Leu Tyr Ser Met Pro Lys Met
                85                  90                  95
```

```
Thr Thr Ala Ala Val His Gly Ala Ala Ala Gly Leu Gly Leu Ser Leu
            100                 105                 110

Ala Leu Ser Cys Asp His Val Leu Val Glu Lys Glu Ala Lys Leu Ala
        115                 120                 125

Met Asn Phe Ile Gly Ile Gly Leu Val Pro Asp Gly Gly His Phe
130                 135                 140

Phe Leu Glu Arg Arg Ile Gly Glu Thr Ala Ala Lys Glu Leu Ile Trp
145                 150                 155                 160

Ser Gly Lys Lys Leu Thr Gly Ala Glu Ala His Glu Leu Arg Ile Ala
                165                 170                 175

Asp Ala Val Phe Ser Gly Asp Ser Gly Arg Phe Ala Arg Ile Tyr Leu
            180                 185                 190

Glu Lys Leu Leu His Ala Pro Leu Ala Ala Met Ile Glu Thr Lys Lys
        195                 200                 205

Ile Tyr Gln Ala Leu Asn Gly Gly Arg Leu Gln Lys Thr Leu Glu Leu
    210                 215                 220

Glu Lys Thr Ala Gln Met Lys Met Arg Leu Thr Ser Asp His Gln Glu
225                 230                 235                 240

Gly Ile Arg Ala Phe Leu Glu Lys Arg Gln Pro Gln Phe Asn Arg Gln
                245                 250                 255

Gln Val

<210> SEQ ID NO 17
<211> LENGTH: 1065
<212> TYPE: DNA
<213> ORGANISM: Bacillus licheniformis DSM 13
<220> FEATURE:
<221> NAME/KEY: gene
<222> LOCATION: (1)..(1065)
<223> OTHER INFORMATION: Probable Enoyl(3-hydroxyisobutyryl)-coenzyme A
      hydrolase protein
<220> FEATURE:
<221> NAME/KEY: CDS
<222> LOCATION: (1)..(1062)

<400> SEQUENCE: 17 atg tcc gat gac gtg ctg ttt tcc gtc aat caa aac ggc gcc gca gcg       48
Met Ser Asp Asp Val Leu Phe Ser Val Asn Gln Asn Gly Ala Ala Ala
1               5                   10                  15 att gtt ctg aat cgc ccg aaa gcg ctc aac tca ctc aca tac gac atg       96
Ile Val Leu Asn Arg Pro Lys Ala Leu Asn Ser Leu Thr Tyr Asp Met
                20                  25                  30 gtc cgt ctg att ggt gaa aag tta aac gag tgg gag aca gat caa aac      144
Val Arg Leu Ile Gly Glu Lys Leu Asn Glu Trp Glu Thr Asp Gln Asn
            35                  40                  45 gtt tct atc gtg gtc atc aaa ggt gca gga cca aaa gga cta tgt gcc      192
Val Ser Ile Val Val Ile Lys Gly Ala Gly Pro Lys Gly Leu Cys Ala
        50                  55                  60 gga ggg gat att aag gca ctc tat gaa gct cgt tcg tca aaa cag gcc      240
Gly Gly Asp Ile Lys Ala Leu Tyr Glu Ala Arg Ser Ser Lys Gln Ala
65                  70                  75                  80 ctg caa gat gcc gag cgc ttt ttt gaa aca gag tac gaa gtc gat atg      288
Leu Gln Asp Ala Glu Arg Phe Phe Glu Thr Glu Tyr Glu Val Asp Met
                85                  90                  95 gca gtc cat cga ttt tcg aaa ccg atc atc gcc tgc ttg gac ggg atc      336
Ala Val His Arg Phe Ser Lys Pro Ile Ile Ala Cys Leu Asp Gly Ile
            100                 105                 110 gtc atg ggg gga ggc gtc ggc ctg acg tac ggg gcc agc cac cgg atc      384
Val Met Gly Gly Gly Val Gly Leu Thr Tyr Gly Ala Ser His Arg Ile
        115                 120                 125
```

```
gtc acg gag agg aca aaa tgg gcg atg ccc gaa atg aat atc ggc ttc      432
Val Thr Glu Arg Thr Lys Trp Ala Met Pro Glu Met Asn Ile Gly Phe
    130                 135                 140 ttt ccg gat gtc ggg gca gcc tat ttt tta aac aaa gcc ccg ggc cgc      480
Phe Pro Asp Val Gly Ala Ala Tyr Phe Leu Asn Lys Ala Pro Gly Arg
145                 150                 155                 160 tta ggg cgg tat ctt gga tta acg gcg tct gtc atc cat gca gcc gac      528
Leu Gly Arg Tyr Leu Gly Leu Thr Ala Ser Val Ile His Ala Ala Asp
                165                 170                 175 gtg ctg tat atc aat ggg gca gac gcc tac atg gag agc ggc gct tta      576
Val Leu Tyr Ile Asn Gly Ala Asp Ala Tyr Met Glu Ser Gly Ala Leu
            180                 185                 190 gaa cga ttg ctt caa gca gtg gaa caa acc gat tgg cgc ctt gca agc      624
Glu Arg Leu Leu Gln Ala Val Glu Gln Thr Asp Trp Arg Leu Ala Ser
        195                 200                 205 gtt gaa gaa aag ctc gat cag ctg atc cgc gaa tcg aaa acg gag ccc      672
Val Glu Glu Lys Leu Asp Gln Leu Ile Arg Glu Ser Lys Thr Glu Pro
    210                 215                 220 tcc cag gag agc acg ctc gcc cgt gat cag caa gcg att gac cgt cat      720
Ser Gln Glu Ser Thr Leu Ala Arg Asp Gln Gln Ala Ile Asp Arg His
225                 230                 235                 240 ttt aag tat gat aag ctg gaa gag atc ctt caa tcg ctc gaa agc gag      768
Phe Lys Tyr Asp Lys Leu Glu Glu Ile Leu Gln Ser Leu Glu Ser Glu
                245                 250                 255 gga agc acc ttt agc tcg aat gtg aaa aaa aca atg ctt tcc aaa tcg      816
Gly Ser Thr Phe Ser Ser Asn Val Lys Lys Thr Met Leu Ser Lys Ser
            260                 265                 270 cca ttt tca tta aaa atc aca ttg aaa cag ctg gcg gac gga cgt caa      864
Pro Phe Ser Leu Lys Ile Thr Leu Lys Gln Leu Ala Asp Gly Arg Gln
        275                 280                 285 aaa aca ctg gaa gaa tgc ttt gcc acg gat ctg gtg ctg gca aag aac      912
Lys Thr Leu Glu Glu Cys Phe Ala Thr Asp Leu Val Leu Ala Lys Asn
    290                 295                 300 ttt ttg aag cac aat gat ttc ttc gaa ggc gtc agg tcc gtc ctg atc      960
Phe Leu Lys His Asn Asp Phe Phe Glu Gly Val Arg Ser Val Leu Ile
305                 310                 315                 320 gac cgt gat caa tca ccg aac tac aag tac cgg aac gtt tca gat gta     1008
Asp Arg Asp Gln Ser Pro Asn Tyr Lys Tyr Arg Asn Val Ser Asp Val
                325                 330                 335 acc gat gaa gcg gtg gac cgg ttt ttc caa ccc tct gaa tct gtc cgg     1056
Thr Asp Glu Ala Val Asp Arg Phe Phe Gln Pro Ser Glu Ser Val Arg
            340                 345                 350 ttt taa aag                                                          1065
Phe

<210> SEQ ID NO 18
<211> LENGTH: 353
<212> TYPE: PRT
<213> ORGANISM: Bacillus licheniformis DSM 13

<400> SEQUENCE: 18

Met Ser Asp Asp Val Leu Phe Ser Val Asn Gln Asn Gly Ala Ala Ala
1               5                   10                  15

Ile Val Leu Asn Arg Pro Lys Ala Leu Asn Ser Leu Thr Tyr Asp Met
            20                  25                  30

Val Arg Leu Ile Gly Glu Lys Leu Asn Glu Trp Glu Thr Asp Gln Asn
        35                  40                  45

Val Ser Ile Val Val Ile Lys Gly Ala Gly Pro Lys Gly Leu Cys Ala
    50                  55                  60
```

Gly Gly Asp Ile Lys Ala Leu Tyr Glu Ala Arg Ser Ser Lys Gln Ala
 65                  70                  75                  80

Leu Gln Asp Ala Glu Arg Phe Phe Glu Thr Glu Tyr Glu Val Asp Met
                 85                  90                  95

Ala Val His Arg Phe Ser Lys Pro Ile Ile Ala Cys Leu Asp Gly Ile
            100                 105                 110

Val Met Gly Gly Gly Val Gly Leu Thr Tyr Gly Ala Ser His Arg Ile
        115                 120                 125

Val Thr Glu Arg Thr Lys Trp Ala Met Pro Glu Met Asn Ile Gly Phe
130                 135                 140

Phe Pro Asp Val Gly Ala Ala Tyr Phe Leu Asn Lys Ala Pro Gly Arg
145                 150                 155                 160

Leu Gly Arg Tyr Leu Gly Leu Thr Ala Ser Val Ile His Ala Ala Asp
                165                 170                 175

Val Leu Tyr Ile Asn Gly Ala Asp Ala Tyr Met Glu Ser Gly Ala Leu
            180                 185                 190

Glu Arg Leu Leu Gln Ala Val Glu Gln Thr Asp Trp Arg Leu Ala Ser
        195                 200                 205

Val Glu Glu Lys Leu Asp Gln Leu Ile Arg Glu Ser Lys Thr Glu Pro
210                 215                 220

Ser Gln Glu Ser Thr Leu Ala Arg Asp Gln Gln Ala Ile Asp Arg His
225                 230                 235                 240

Phe Lys Tyr Asp Lys Leu Glu Glu Ile Leu Gln Ser Leu Glu Ser Glu
                245                 250                 255

Gly Ser Thr Phe Ser Ser Asn Val Lys Lys Thr Met Leu Ser Lys Ser
            260                 265                 270

Pro Phe Ser Leu Lys Ile Thr Leu Lys Gln Leu Ala Asp Gly Arg Gln
        275                 280                 285

Lys Thr Leu Glu Glu Cys Phe Ala Thr Asp Leu Val Leu Ala Lys Asn
290                 295                 300

Phe Leu Lys His Asn Asp Phe Phe Glu Gly Val Arg Ser Val Leu Ile
305                 310                 315                 320

Asp Arg Asp Gln Ser Pro Asn Tyr Lys Tyr Arg Asn Val Ser Asp Val
                325                 330                 335

Thr Asp Glu Ala Val Asp Arg Phe Phe Gln Pro Ser Glu Ser Val Arg
            340                 345                 350

Phe

<210> SEQ ID NO 19
<211> LENGTH: 789
<212> TYPE: DNA
<213> ORGANISM: Bacillus licheniformis DSM 13
<220> FEATURE:
<221> NAME/KEY: gene
<222> LOCATION: (1)..(789)
<223> OTHER INFORMATION: Probable enoyl-CoA hydratase (E.C. 4.2.1.17),
      echA8
<220> FEATURE:
<221> NAME/KEY: misc_feature
<222> LOCATION: (1)..(3)
<223> OTHER INFORMATION: First codon translated as Met.
<220> FEATURE:
<221> NAME/KEY: CDS
<222> LOCATION: (1)..(786)

<400> SEQUENCE: 19 ttg aac ttg aaa tat gcc aca ctt aaa aca gaa cat ggc atc aca acc     48
Leu Asn Leu Lys Tyr Ala Thr Leu Lys Thr Glu His Gly Ile Thr Thr

```
1               5                  10                 15
gtg acg ttg aac aat ccg ccg gca aat aca ctt tct tct tcc tgt atc        96
Val Thr Leu Asn Asn Pro Pro Ala Asn Thr Leu Ser Ser Ser Cys Ile
            20                  25                  30 gcc gaa ttg cgc tct ctt ttt cgg gaa ttg gcc cgc gac gag gag aca       144
Ala Glu Leu Arg Ser Leu Phe Arg Glu Leu Ala Arg Asp Glu Glu Thr
            35                  40                  45 aaa gca atc atc att act gga gaa ggc cgc ttt ttt gtg gcg gga gcg       192
Lys Ala Ile Ile Ile Thr Gly Glu Gly Arg Phe Phe Val Ala Gly Ala
50                  55                  60 gat ata aaa gaa ttc gtt tca aaa ctt ggg gac caa aaa caa gga ttg       240
Asp Ile Lys Glu Phe Val Ser Lys Leu Gly Asp Gln Lys Gln Gly Leu
65                  70                  75                  80 gcg ctc gca caa ggg ggc cag gcg ctc tgc gat gaa atc gaa gct tcc       288
Ala Leu Ala Gln Gly Gly Gln Ala Leu Cys Asp Glu Ile Glu Ala Ser
                85                  90                  95 aaa aaa ccc gtc att gcg gcg ata aac gga ccg gct ctt ggc gga ggc       336
Lys Lys Pro Val Ile Ala Ala Ile Asn Gly Pro Ala Leu Gly Gly Gly
            100                 105                 110 ctg gaa ctc gcg atg agc tgc cac ttc aga atc gta tca gac gat gca       384
Leu Glu Leu Ala Met Ser Cys His Phe Arg Ile Val Ser Asp Asp Ala
            115                 120                 125 aca gtc ggt ctt ccc gaa tta aag ctc ggc ttg att cct gca ttt ggt       432
Thr Val Gly Leu Pro Glu Leu Lys Leu Gly Leu Ile Pro Ala Phe Gly
130                 135                 140 ggt aca cag cgg ctt cgc aac ata acg gac aca gcg aca gca ctc gac       480
Gly Thr Gln Arg Leu Arg Asn Ile Thr Asp Thr Ala Thr Ala Leu Asp
145                 150                 155                 160 ctt atc ctg acg ggc cga tcg ctt tca gct caa gag gcg gta gag ctg       528
Leu Ile Leu Thr Gly Arg Ser Leu Ser Ala Gln Glu Ala Val Glu Leu
                165                 170                 175 aaa att gca cag atg gct gta aag gga gag gaa ctg atg aag acg gca       576
Lys Ile Ala Gln Met Ala Val Lys Gly Glu Glu Leu Met Lys Thr Ala
            180                 185                 190 gct gct gtc gcg tcg tct ttt atc gaa gga aaa agc atg acc agc gtg       624
Ala Ala Val Ala Ser Ser Phe Ile Glu Gly Lys Ser Met Thr Ser Val
            195                 200                 205 agg cgc gcc gtc gaa tgt gtc gta cag ggc gcc agc gaa agc atg gaa       672
Arg Arg Ala Val Glu Cys Val Val Gln Gly Ala Ser Glu Ser Met Glu
            210                 215                 220 caa gca ctg gag agg gag cga aac aga ttc gcc gag ctg ttt gtc act       720
Gln Ala Leu Glu Arg Glu Arg Asn Arg Phe Ala Glu Leu Phe Val Thr
225                 230                 235                 240 tca gat gcc aaa gaa gga att cac gca ttt gtc gaa aag cgc aaa cca       768
Ser Asp Ala Lys Glu Gly Ile His Ala Phe Val Glu Lys Arg Lys Pro
                245                 250                 255 aac ttt cat cat tca taa aag                                            789
Asn Phe His His Ser
            260
```

<210> SEQ ID NO 20
<211> LENGTH: 261
<212> TYPE: PRT
<213> ORGANISM: Bacillus licheniformis DSM 13
<220> FEATURE:
<221> NAME/KEY: misc_feature
<222> LOCATION: (1)..(3)
<223> OTHER INFORMATION: First codon translated as Met.

<400> SEQUENCE: 20

Leu Asn Leu Lys Tyr Ala Thr Leu Lys Thr Glu His Gly Ile Thr Thr

```
                1               5              10              15
            Val Thr Leu Asn Asn Pro Pro Ala Asn Thr Leu Ser Ser Cys Ile
                             20                  25                  30

Ala Glu Leu Arg Ser Leu Phe Arg Glu Leu Ala Arg Asp Glu Glu Thr
                         35                  40                  45

Lys Ala Ile Ile Ile Thr Gly Glu Gly Arg Phe Phe Val Ala Gly Ala
                 50                  55                  60

Asp Ile Lys Glu Phe Val Ser Lys Leu Gly Asp Gln Lys Gln Gly Leu
             65                  70                  75                  80

Ala Leu Ala Gln Gly Gly Gln Ala Leu Cys Asp Glu Ile Glu Ala Ser
                             85                  90                  95

Lys Lys Pro Val Ile Ala Ala Ile Asn Gly Pro Ala Leu Gly Gly Gly
                        100                 105                 110

Leu Glu Leu Ala Met Ser Cys His Phe Arg Ile Val Ser Asp Asp Ala
                    115                 120                 125

Thr Val Gly Leu Pro Glu Leu Lys Leu Gly Leu Ile Pro Ala Phe Gly
                130                 135                 140

Gly Thr Gln Arg Leu Arg Asn Ile Thr Asp Thr Ala Thr Ala Leu Asp
            145                 150                 155                 160

Leu Ile Leu Thr Gly Arg Ser Leu Ser Ala Gln Glu Ala Val Glu Leu
                            165                 170                 175

Lys Ile Ala Gln Met Ala Val Lys Gly Glu Glu Leu Met Lys Thr Ala
                        180                 185                 190

Ala Ala Val Ala Ser Ser Phe Ile Glu Gly Lys Ser Met Thr Ser Val
                    195                 200                 205

Arg Arg Ala Val Glu Cys Val Val Gln Gly Ala Ser Glu Ser Met Glu
                210                 215                 220

Gln Ala Leu Glu Arg Glu Arg Asn Arg Phe Ala Glu Leu Phe Val Thr
            225                 230                 235                 240

Ser Asp Ala Lys Glu Gly Ile His Ala Phe Val Glu Lys Arg Lys Pro
                            245                 250                 255

Asn Phe His His Ser
                        260

<210> SEQ ID NO 21
<211> LENGTH: 1719
<212> TYPE: DNA
<213> ORGANISM: Bacillus licheniformis DSM 13
<220> FEATURE:
<221> NAME/KEY: gene
<222> LOCATION: (1)..(1719)
<223> OTHER INFORMATION: Acyl-CoA dehydrogenase (E.C. 1.3.99.-)
<220> FEATURE:
<221> NAME/KEY: CDS
<222> LOCATION: (1)..(1716)

<400> SEQUENCE: 21 atg ggg aaa gca aaa ctt cga tgg aat gaa ccc ttg att tct caa cac      48
Met Gly Lys Ala Lys Leu Arg Trp Asn Glu Pro Leu Ile Ser Gln His
  1               5                  10                  15 gaa tcg gct gct gaa gga ttt aca ccg gaa gat ttc aca gag gaa gat      96
Glu Ser Ala Ala Glu Gly Phe Thr Pro Glu Asp Phe Thr Glu Glu Asp
                 20                  25                  30 cga ctg att tca aaa acg aca gaa tca ttt gtc aaa aac gaa gtc atg     144
Arg Leu Ile Ser Lys Thr Thr Glu Ser Phe Val Lys Asn Glu Val Met
             35                  40                  45 ccc ctt ctt gaa tcg att gat cag cag gat cac gaa agc gtg aaa aaa     192
Pro Leu Leu Glu Ser Ile Asp Gln Gln Asp His Glu Ser Val Lys Lys
```

```
                50                  55                  60
ttg ttt caa aaa gca gga gag ctc ggt ttg ctc agt atc gaa gtt ccg       240
Leu Phe Gln Lys Ala Gly Glu Leu Gly Leu Leu Ser Ile Glu Val Pro
 65                  70                  75                  80 gag gat tgc ggc ggc ctt tca ctc agc aag aag ctt tcc ggg ttg gtg       288
Glu Asp Cys Gly Gly Leu Ser Leu Ser Lys Lys Leu Ser Gly Leu Val
                 85                  90                  95 gca gag aaa atg gga gcc ggc gga tcg ttc agc gtc tcc ttt aat att       336
Ala Glu Lys Met Gly Ala Gly Gly Ser Phe Ser Val Ser Phe Asn Ile
            100                 105                 110 cat gcg gga gtc ggg aca ctg ccg tat att tat tat gga aca gag gaa       384
His Ala Gly Val Gly Thr Leu Pro Tyr Ile Tyr Tyr Gly Thr Glu Glu
        115                 120                 125 caa aaa caa aaa tac ctt cca aaa ctg gca tcg ggc gaa tgg atc gga       432
Gln Lys Gln Lys Tyr Leu Pro Lys Leu Ala Ser Gly Glu Trp Ile Gly
    130                 135                 140 gca tat gct ctg aca gag ccg ggc gca gga tcg gat gct tta aac gca       480
Ala Tyr Ala Leu Thr Glu Pro Gly Ala Gly Ser Asp Ala Leu Asn Ala
145                 150                 155                 160 aaa acg aca gcc gtc ttg aat agg gaa ggg aca gcc tgg att tta aat       528
Lys Thr Thr Ala Val Leu Asn Arg Glu Gly Thr Ala Trp Ile Leu Asn
                165                 170                 175 ggg gaa aag cag tgg att acg aac gcg caa gta gct gat gta tat gtt       576
Gly Glu Lys Gln Trp Ile Thr Asn Ala Gln Val Ala Asp Val Tyr Val
            180                 185                 190 gtc ttt gca aaa acg gcg gaa ggc atg aca gca ttt atc gtc gaa cgc       624
Val Phe Ala Lys Thr Ala Glu Gly Met Thr Ala Phe Ile Val Glu Arg
        195                 200                 205 tcg ttt aaa ggt gtt tcc atc gga cct gaa gag aag aag atg gga atc       672
Ser Phe Lys Gly Val Ser Ile Gly Pro Glu Glu Lys Lys Met Gly Ile
    210                 215                 220 aaa ggg tct tcg aca gca acc tta atc ttg gag gaa gtc gag gtg cca       720
Lys Gly Ser Ser Thr Ala Thr Leu Ile Leu Glu Glu Val Glu Val Pro
225                 230                 235                 240 agc gac aat gtt cta ggt cat atc ggg aaa ggt cat cac gtc gct ttg       768
Ser Asp Asn Val Leu Gly His Ile Gly Lys Gly His His Val Ala Leu
                245                 250                 255 aac att tta aac atg gcc cgc tta aag ctc gcg ttt tcg aac att gga       816
Asn Ile Leu Asn Met Ala Arg Leu Lys Leu Ala Phe Ser Asn Ile Gly
            260                 265                 270 acg gca aaa caa gca ttg aac ctt gct gtt agc tac gcc aaa cag cga       864
Thr Ala Lys Gln Ala Leu Asn Leu Ala Val Ser Tyr Ala Lys Gln Arg
        275                 280                 285 aag caa ttt aac aag ccg atc atc ggt ttt tca atg att caa gaa aag       912
Lys Gln Phe Asn Lys Pro Ile Ile Gly Phe Ser Met Ile Gln Glu Lys
    290                 295                 300 att gcc gac atg gcg gtc tcg att ttc ggc gcg gaa agc gct gct tac       960
Ile Ala Asp Met Ala Val Ser Ile Phe Gly Ala Glu Ser Ala Ala Tyr
305                 310                 315                 320 aga acg gca gat tgc ttg gac aat gtt tta gat tcg gct ctc cca tta      1008
Arg Thr Ala Asp Cys Leu Asp Asn Val Leu Asp Ser Ala Leu Pro Leu
                325                 330                 335 gac gat aga ctg aga aaa ctc aca aac tat gca tcc gaa tgt gcg atc      1056
Asp Asp Arg Leu Arg Lys Leu Thr Asn Tyr Ala Ser Glu Cys Ala Ile
            340                 345                 350 aat aaa gtt tac tgc tcc gaa atc ctc ggc cgg atc gca gac gaa gcg      1104
Asn Lys Val Tyr Cys Ser Glu Ile Leu Gly Arg Ile Ala Asp Glu Ala
        355                 360                 365 gtg cag att cat ggc ggc tac gga tac atg cag gag tac gaa gtc gaa      1152
```

```
Val Gln Ile His Gly Gly Tyr Gly Tyr Met Gln Glu Tyr Glu Val Glu
    370                 375                 380 cga ttg tac cgg gac gcg agg atc agc cgg att ttc gag ggg aca aat      1200
Arg Leu Tyr Arg Asp Ala Arg Ile Ser Arg Ile Phe Glu Gly Thr Asn
385                 390                 395                 400 gaa ata aac cgc tta acg atc gcc aaa ctg ctc atg aaa gaa gtg cag      1248
Glu Ile Asn Arg Leu Thr Ile Ala Lys Leu Leu Met Lys Glu Val Gln
                405                 410                 415 caa aac ggc atc tca gag ccg gaa gct caa cta ggc agc gag gga aat      1296
Gln Asn Gly Ile Ser Glu Pro Glu Ala Gln Leu Gly Ser Glu Gly Asn
            420                 425                 430 cga aac cgg cga ttt att cag ctg tcc aac agg ctt ttc ggc aag aca      1344
Arg Asn Arg Arg Phe Ile Gln Leu Ser Asn Arg Leu Phe Gly Lys Thr
        435                 440                 445 ctg aaa gcg ctt atc cgc tct cgc gtg aac act caa gaa gat cag gaa      1392
Leu Lys Ala Leu Ile Arg Ser Arg Val Asn Thr Gln Glu Asp Gln Glu
    450                 455                 460 tac gca cgg ctt ctc gcc gac atg aaa aaa gaa atc tat gtg atg gaa      1440
Tyr Ala Arg Leu Leu Ala Asp Met Lys Lys Glu Ile Tyr Val Met Glu
465                 470                 475                 480 tcc gcc gcc cgc cga acc gaa aaa gct agg caa ata tac ggt ggt gaa      1488
Ser Ala Ala Arg Arg Thr Glu Lys Ala Arg Gln Ile Tyr Gly Gly Glu
                485                 490                 495 aaa gca cgg ttg aaa gaa atg atg acg aat gtc att tgt gaa gaa ggc      1536
Lys Ala Arg Leu Lys Glu Met Met Thr Asn Val Ile Cys Glu Glu Gly
            500                 505                 510 tac cgc aga atc gaa gag atg gcg gtg acc gcc tta tca agc ata gca      1584
Tyr Arg Arg Ile Glu Glu Met Ala Val Thr Ala Leu Ser Ser Ile Ala
        515                 520                 525 tct gat gaa gcc gaa aga aaa ctc gca ttt gaa gag gct cgc agc gtt      1632
Ser Asp Glu Ala Glu Arg Lys Leu Ala Phe Glu Glu Ala Arg Ser Val
    530                 535                 540 tct ttg cct ctt ttc agc aat ctg ttt act caa aaa cgc gaa atc gca      1680
Ser Leu Pro Leu Phe Ser Asn Leu Phe Thr Gln Lys Arg Glu Ile Ala
545                 550                 555                 560 gaa aaa ata gcc gct cat gaa aaa tat acg gtg tga tcg                  1719
Glu Lys Ile Ala Ala His Glu Lys Tyr Thr Val
                565                 570

<210> SEQ ID NO 22
<211> LENGTH: 571
<212> TYPE: PRT
<213> ORGANISM: Bacillus licheniformis DSM 13

<400> SEQUENCE: 22

Met Gly Lys Ala Lys Leu Arg Trp Asn Glu Pro Leu Ile Ser Gln His
1               5                   10                  15

Glu Ser Ala Ala Glu Gly Phe Thr Pro Glu Asp Phe Thr Glu Glu Asp
                20                  25                  30

Arg Leu Ile Ser Lys Thr Thr Glu Ser Phe Val Lys Asn Glu Val Met
            35                  40                  45

Pro Leu Leu Glu Ser Ile Asp Gln Gln Asp His Glu Ser Val Lys Lys
        50                  55                  60

Leu Phe Gln Lys Ala Gly Glu Leu Gly Leu Leu Ser Ile Glu Val Pro
65                  70                  75                  80

Glu Asp Cys Gly Gly Leu Ser Leu Ser Lys Lys Leu Ser Gly Leu Val
                85                  90                  95

Ala Glu Lys Met Gly Ala Gly Gly Ser Phe Ser Val Ser Phe Asn Ile
                100                 105                 110
```

-continued

His Ala Gly Val Gly Thr Leu Pro Tyr Ile Tyr Tyr Gly Thr Glu Glu
            115                 120                 125

Gln Lys Gln Lys Tyr Leu Pro Lys Leu Ala Ser Gly Glu Trp Ile Gly
        130                 135                 140

Ala Tyr Ala Leu Thr Glu Pro Gly Ala Gly Ser Asp Ala Leu Asn Ala
145                 150                 155                 160

Lys Thr Thr Ala Val Leu Asn Arg Glu Gly Thr Ala Trp Ile Leu Asn
                165                 170                 175

Gly Glu Lys Gln Trp Ile Thr Asn Ala Gln Val Ala Asp Val Tyr Val
            180                 185                 190

Val Phe Ala Lys Thr Ala Glu Gly Met Thr Ala Phe Ile Val Glu Arg
        195                 200                 205

Ser Phe Lys Gly Val Ser Ile Gly Pro Glu Glu Lys Lys Met Gly Ile
210                 215                 220

Lys Gly Ser Ser Thr Ala Thr Leu Ile Leu Glu Glu Val Glu Val Pro
225                 230                 235                 240

Ser Asp Asn Val Leu Gly His Ile Gly Lys Gly His His Val Ala Leu
                245                 250                 255

Asn Ile Leu Asn Met Ala Arg Leu Lys Leu Ala Phe Ser Asn Ile Gly
            260                 265                 270

Thr Ala Lys Gln Ala Leu Asn Leu Ala Val Ser Tyr Ala Lys Gln Arg
        275                 280                 285

Lys Gln Phe Asn Lys Pro Ile Ile Gly Phe Ser Met Ile Gln Glu Lys
        290                 295                 300

Ile Ala Asp Met Ala Val Ser Ile Phe Gly Ala Glu Ser Ala Ala Tyr
305                 310                 315                 320

Arg Thr Ala Asp Cys Leu Asp Asn Val Leu Asp Ser Ala Leu Pro Leu
                325                 330                 335

Asp Asp Arg Leu Arg Lys Leu Thr Asn Tyr Ala Ser Glu Cys Ala Ile
            340                 345                 350

Asn Lys Val Tyr Cys Ser Glu Ile Leu Gly Arg Ile Ala Asp Glu Ala
        355                 360                 365

Val Gln Ile His Gly Gly Tyr Gly Tyr Met Gln Glu Tyr Glu Val Glu
        370                 375                 380

Arg Leu Tyr Arg Asp Ala Arg Ile Ser Arg Ile Phe Glu Gly Thr Asn
385                 390                 395                 400

Glu Ile Asn Arg Leu Thr Ile Ala Lys Leu Leu Met Lys Glu Val Gln
                405                 410                 415

Gln Asn Gly Ile Ser Glu Pro Glu Ala Gln Leu Gly Ser Glu Gly Asn
            420                 425                 430

Arg Asn Arg Arg Phe Ile Gln Leu Ser Asn Arg Leu Phe Gly Lys Thr
        435                 440                 445

Leu Lys Ala Leu Ile Arg Ser Arg Val Asn Thr Gln Glu Asp Gln Glu
450                 455                 460

Tyr Ala Arg Leu Leu Ala Asp Met Lys Lys Glu Ile Tyr Val Met Glu
465                 470                 475                 480

Ser Ala Ala Arg Arg Thr Glu Lys Ala Arg Gln Ile Tyr Gly Gly Glu
                485                 490                 495

Lys Ala Arg Leu Lys Glu Met Met Thr Asn Val Ile Cys Glu Glu Gly
            500                 505                 510

Tyr Arg Arg Ile Glu Glu Met Ala Val Thr Ala Leu Ser Ser Ile Ala
        515                 520                 525

```
Ser Asp Glu Ala Glu Arg Lys Leu Ala Phe Glu Glu Ala Arg Ser Val
    530             535                 540

Ser Leu Pro Leu Phe Ser Asn Leu Phe Thr Gln Lys Arg Glu Ile Ala
545             550                 555                 560

Glu Lys Ile Ala Ala His Glu Lys Tyr Thr Val
                565                 570

<210> SEQ ID NO 23
<211> LENGTH: 1956
<212> TYPE: DNA
<213> ORGANISM: Bacillus licheniformis DSM 13
<220> FEATURE:
<221> NAME/KEY: gene
<222> LOCATION: (1)..(1956)
<223> OTHER INFORMATION: Acetyl-coenzyme A synthetase (E.C. 6.2.1.1),
      acsA
<220> FEATURE:
<221> NAME/KEY: CDS
<222> LOCATION: (1)..(1953)

<400> SEQUENCE: 23 atg ggc gaa aaa gcg gtt tgg cag cct gat ccg gaa ttt gta aaa aca      48
Met Gly Glu Lys Ala Val Trp Gln Pro Asp Pro Glu Phe Val Lys Thr
1               5                   10                  15 acc cgg ctg ttt caa tgg atg aca gcc ctc ggt ttt tcc gac tat gat      96
Thr Arg Leu Phe Gln Trp Met Thr Ala Leu Gly Phe Ser Asp Tyr Asp
                20                  25                  30 gat ttt ttg aaa gca agt aca aac gat atc gcc tgg ttc tgg gaa gag    144
Asp Phe Leu Lys Ala Ser Thr Asn Asp Ile Ala Trp Phe Trp Glu Glu
            35                  40                  45 gcc gaa aaa gcg ctc ggg atc agc tgg tac aag cgg tac agc caa aca    192
Ala Glu Lys Ala Leu Gly Ile Ser Trp Tyr Lys Arg Tyr Ser Gln Thr
        50                  55                  60 ttg aat ctc gac aaa ggc ata aaa tgg ccg caa tgg ttt acc ggc ggc    240
Leu Asn Leu Asp Lys Gly Ile Lys Trp Pro Gln Trp Phe Thr Gly Gly
65                  70                  75                  80 cgc tta aat gcc gtt tac aac gcc gtg gaa aaa tgg gcc cgc cgg cct    288
Arg Leu Asn Ala Val Tyr Asn Ala Val Glu Lys Trp Ala Arg Arg Pro
                85                  90                  95 gat acg gcc ggc agg acg gca ctc atc tgg gaa agt gaa gac gga aaa    336
Asp Thr Ala Gly Arg Thr Ala Leu Ile Trp Glu Ser Glu Asp Gly Lys
                100                 105                 110 aca gaa cag atc acc tat tct tct tta cac caa caa gtc gcc cgt gcg    384
Thr Glu Gln Ile Thr Tyr Ser Ser Leu His Gln Gln Val Ala Arg Ala
            115                 120                 125 gcg gca ggc ttt aaa aag caa ggc atc tca aaa ggg gat gtc att gcg    432
Ala Ala Gly Phe Lys Lys Gln Gly Ile Ser Lys Gly Asp Val Ile Ala
        130                 135                 140 att tac atg ccg atg atc ccc gaa acg gtc atc gcc atg ctg gcc gcc    480
Ile Tyr Met Pro Met Ile Pro Glu Thr Val Ile Ala Met Leu Ala Ala
145                 150                 155                 160 gct aaa atc gga gcg gta ttc tca ccg gtt ttt tca ggc tac ggc gcc    528
Ala Lys Ile Gly Ala Val Phe Ser Pro Val Phe Ser Gly Tyr Gly Ala
                165                 170                 175 cat gca gca gcg gcg aga ctt acc gct gcc gga gcg aaa atc ctt gtc    576
His Ala Ala Ala Ala Arg Leu Thr Ala Ala Gly Ala Lys Ile Leu Val
            180                 185                 190 aca gca gat gcc ttt ttg cga agg gga aag aag gtc tgc atg aag aaa    624
Thr Ala Asp Ala Phe Leu Arg Arg Gly Lys Lys Val Cys Met Lys Lys
        195                 200                 205 gaa gct gac aaa gcc gcg gac cgt tcc ccc act gtt caa aaa gtc gtc    672
Glu Ala Asp Lys Ala Ala Asp Arg Ser Pro Thr Val Gln Lys Val Val
```

```
                210                215                220
gtc tgc aag ctt cac ggc ggc gat caa gat tgg aat tat aag aga gat    720
Val Cys Lys Leu His Gly Gly Asp Gln Asp Trp Asn Tyr Lys Arg Asp
225             230                235                240 atc gac tgg aat gaa ttg atg aaa aac gag ccc atg caa aac acc gaa    768
Ile Asp Trp Asn Glu Leu Met Lys Asn Glu Pro Met Gln Asn Thr Glu
                245                250                255 gaa atg gac agt tca gat ccg ctc atg ctg cta tac aca tca ggg acg    816
Glu Met Asp Ser Ser Asp Pro Leu Met Leu Leu Tyr Thr Ser Gly Thr
            260                265                270 aca gga cag tcg aag gga gcg gtt cat acc cat gcc ggt ttt ccg ctg    864
Thr Gly Gln Ser Lys Gly Ala Val His Thr His Ala Gly Phe Pro Leu
        275                280                285 aaa gct gca ttt gat gcg gga ttc ggg atg gat gtc aaa caa ggg gac    912
Lys Ala Ala Phe Asp Ala Gly Phe Gly Met Asp Val Lys Gln Gly Asp
    290                295                300 aca ttt ttc tgg ttt aca gac atg ggc tgg atg atg ggg ccg ttt tta    960
Thr Phe Phe Trp Phe Thr Asp Met Gly Trp Met Met Gly Pro Phe Leu
305             310                315                320 ata ttc ggg ggc ctc ata aac gga gcg gct gtt ttg ctg ttt gac gga    1008
Ile Phe Gly Gly Leu Ile Asn Gly Ala Ala Val Leu Leu Phe Asp Gly
                325                330                335 gca ccg gac tac ccg gcc ccg gat cgg ctg tgg gag ctt gtc agc aga    1056
Ala Pro Asp Tyr Pro Ala Pro Asp Arg Leu Trp Glu Leu Val Ser Arg
            340                345                350 cac cgg gtg acg cat ctc ggc gtc tct ccg acg ctc att cgc tcg ctg    1104
His Arg Val Thr His Leu Gly Val Ser Pro Thr Leu Ile Arg Ser Leu
        355                360                365 atg cag cac ggc gaa gat ttt ctc tat caa tac aat ctg aac agt ctg    1152
Met Gln His Gly Glu Asp Phe Leu Tyr Gln Tyr Asn Leu Asn Ser Leu
    370                375                380 aag gca atc ggc tca acg ggc gaa cca tgg aat tat gag ccg tgg atg    1200
Lys Ala Ile Gly Ser Thr Gly Glu Pro Trp Asn Tyr Glu Pro Trp Met
385             390                395                400 tgg ctg ttc cgc cat gtt gga aaa gaa cgg att cct ata ttt aat tat    1248
Trp Leu Phe Arg His Val Gly Lys Glu Arg Ile Pro Ile Phe Asn Tyr
                405                410                415 tca gga gga aca gag atc tca ggc gga att tta ggc aat gtg ctc ctg    1296
Ser Gly Gly Thr Glu Ile Ser Gly Gly Ile Leu Gly Asn Val Leu Leu
            420                425                430 cgg ccg atc acg ccg atg acg ttt aat tcg cct ctt ccc ggc atg gcg    1344
Arg Pro Ile Thr Pro Met Thr Phe Asn Ser Pro Leu Pro Gly Met Ala
        435                440                445 gcc aat gtc ttc aat gaa aaa gga gag gaa gtc gtc aat gaa gtc gga    1392
Ala Asn Val Phe Asn Glu Lys Gly Glu Glu Val Val Asn Glu Val Gly
    450                455                460 gag ctt gtc ctg aca aag ccc tgg gtc ggc atg acg aac ggt ttt tgg    1440
Glu Leu Val Leu Thr Lys Pro Trp Val Gly Met Thr Asn Gly Phe Trp
465             470                475                480 aag gag ccg tca aga tac gaa gaa gca tat tgg agc cgc tgg acc gac    1488
Lys Glu Pro Ser Arg Tyr Glu Glu Ala Tyr Trp Ser Arg Trp Thr Asp
                485                490                495 gtc tgg gtg cac ggc gat tgg gca aaa cgg gat gaa aac ggc tac tgg    1536
Val Trp Val His Gly Asp Trp Ala Lys Arg Asp Glu Asn Gly Tyr Trp
            500                505                510 acg atc agc gga cgc tct gat gat gtg atc aat gct gcc ggg aaa agg    1584
Thr Ile Ser Gly Arg Ser Asp Asp Val Ile Asn Ala Ala Gly Lys Arg
        515                520                525 atc ggc ccc gcc gaa ata gag tcc gtt ctg gtc ggc cat cca gcg gtg    1632
```

```
                Ile Gly Pro Ala Glu Ile Glu Ser Val Leu Val Gly His Pro Ala Val
                530                 535                 540 gcg gaa gca ggc gtc atc ggc gtt ccg gat aag ctc aaa ggc cag gct          1680
Ala Glu Ala Gly Val Ile Gly Val Pro Asp Lys Leu Lys Gly Gln Ala
545                 550                 555                 560 gcc gtc tgc ttc gtc gtc ctc aga cag tcg gaa aag ccg tcg gaa gaa          1728
Ala Val Cys Phe Val Val Leu Arg Gln Ser Glu Lys Pro Ser Glu Glu
                565                 570                 575 tta aaa gat gat ttg ctg aac ctt gca tct gat gcg atc ggt aaa gcg          1776
Leu Lys Asp Asp Leu Leu Asn Leu Ala Ser Asp Ala Ile Gly Lys Ala
            580                 585                 590 gtc aag ccc aaa gcg gtt tat ttt gtc agc ggt ttg ccg aag acg aga          1824
Val Lys Pro Lys Ala Val Tyr Phe Val Ser Gly Leu Pro Lys Thr Arg
        595                 600                 605 aat gca aaa gtg atg aga cgg ctg atc aga gct gcc tat atg aac gag          1872
Asn Ala Lys Val Met Arg Arg Leu Ile Arg Ala Ala Tyr Met Asn Glu
    610                 615                 620 ccc gca ggc gat ttg tca act ttg gaa aac cgc gaa aca tat gat gaa          1920
Pro Ala Gly Asp Leu Ser Thr Leu Glu Asn Arg Glu Thr Tyr Asp Glu
625                 630                 635                 640 att gcc ggt ctt tca gtg cga aaa aat ctg tag tat                          1956
Ile Ala Gly Leu Ser Val Arg Lys Asn Leu
                645                 650

<210> SEQ ID NO 24
<211> LENGTH: 650
<212> TYPE: PRT
<213> ORGANISM: Bacillus licheniformis DSM 13

<400> SEQUENCE: 24

Met Gly Glu Lys Ala Val Trp Gln Pro Asp Pro Glu Phe Val Lys Thr
1               5                   10                  15

Thr Arg Leu Phe Gln Trp Met Thr Ala Leu Gly Phe Ser Asp Tyr Asp
            20                  25                  30

Asp Phe Leu Lys Ala Ser Thr Asn Asp Ile Ala Trp Phe Trp Glu Glu
        35                  40                  45

Ala Glu Lys Ala Leu Gly Ile Ser Trp Tyr Lys Arg Tyr Ser Gln Thr
    50                  55                  60

Leu Asn Leu Asp Lys Gly Ile Lys Trp Pro Gln Trp Phe Thr Gly Gly
65                  70                  75                  80

Arg Leu Asn Ala Val Tyr Asn Ala Val Glu Lys Trp Ala Arg Arg Pro
                85                  90                  95

Asp Thr Ala Gly Arg Thr Ala Leu Ile Trp Glu Ser Glu Asp Gly Lys
            100                 105                 110

Thr Glu Gln Ile Thr Tyr Ser Ser Leu His Gln Gln Val Ala Arg Ala
        115                 120                 125

Ala Ala Gly Phe Lys Lys Gln Gly Ile Ser Lys Gly Asp Val Ile Ala
    130                 135                 140

Ile Tyr Met Pro Met Ile Pro Glu Thr Val Ile Ala Met Leu Ala Ala
145                 150                 155                 160

Ala Lys Ile Gly Ala Val Phe Ser Pro Val Phe Ser Gly Tyr Gly Ala
                165                 170                 175

His Ala Ala Ala Ala Arg Leu Thr Ala Gly Ala Lys Ile Leu Val
            180                 185                 190

Thr Ala Asp Ala Phe Leu Arg Arg Gly Lys Lys Val Cys Met Lys Lys
        195                 200                 205

Glu Ala Asp Lys Ala Ala Asp Arg Ser Pro Thr Val Gln Lys Val Val
```

```
            210                 215                 220
Val Cys Lys Leu His Gly Gly Asp Gln Asp Trp Asn Tyr Lys Arg Asp
225                 230                 235                 240

Ile Asp Trp Asn Glu Leu Met Lys Asn Glu Pro Met Gln Asn Thr Glu
                245                 250                 255

Glu Met Asp Ser Ser Asp Pro Leu Met Leu Leu Tyr Thr Ser Gly Thr
                260                 265                 270

Thr Gly Gln Ser Lys Gly Ala Val His Thr His Ala Gly Phe Pro Leu
                275                 280                 285

Lys Ala Ala Phe Asp Ala Gly Phe Gly Met Asp Val Lys Gln Gly Asp
                290                 295                 300

Thr Phe Phe Trp Phe Thr Asp Met Gly Trp Met Met Gly Pro Phe Leu
305                 310                 315                 320

Ile Phe Gly Gly Leu Ile Asn Gly Ala Ala Val Leu Leu Phe Asp Gly
                325                 330                 335

Ala Pro Asp Tyr Pro Ala Pro Asp Arg Leu Trp Glu Leu Val Ser Arg
                340                 345                 350

His Arg Val Thr His Leu Gly Val Ser Pro Thr Leu Ile Arg Ser Leu
                355                 360                 365

Met Gln His Gly Glu Asp Phe Leu Tyr Gln Tyr Asn Leu Asn Ser Leu
                370                 375                 380

Lys Ala Ile Gly Ser Thr Gly Glu Pro Trp Asn Tyr Glu Pro Trp Met
385                 390                 395                 400

Trp Leu Phe Arg His Val Gly Lys Glu Arg Ile Pro Ile Phe Asn Tyr
                405                 410                 415

Ser Gly Gly Thr Glu Ile Ser Gly Gly Ile Leu Gly Asn Val Leu Leu
                420                 425                 430

Arg Pro Ile Thr Pro Met Thr Phe Asn Ser Pro Leu Pro Gly Met Ala
                435                 440                 445

Ala Asn Val Phe Asn Glu Lys Gly Glu Val Val Asn Glu Val Gly
                450                 455                 460

Glu Leu Val Leu Thr Lys Pro Trp Val Gly Met Thr Asn Gly Phe Trp
465                 470                 475                 480

Lys Glu Pro Ser Arg Tyr Glu Glu Ala Tyr Trp Ser Arg Trp Thr Asp
                485                 490                 495

Val Trp Val His Gly Asp Trp Ala Lys Arg Asp Glu Asn Gly Tyr Trp
                500                 505                 510

Thr Ile Ser Gly Arg Ser Asp Asp Val Ile Asn Ala Ala Gly Lys Arg
                515                 520                 525

Ile Gly Pro Ala Glu Ile Glu Ser Val Leu Val Gly His Pro Ala Val
                530                 535                 540

Ala Glu Ala Gly Val Ile Gly Val Pro Asp Lys Leu Lys Gly Gln Ala
545                 550                 555                 560

Ala Val Cys Phe Val Val Leu Arg Gln Ser Glu Lys Pro Ser Glu Glu
                565                 570                 575

Leu Lys Asp Asp Leu Leu Asn Leu Ala Ser Asp Ala Ile Gly Lys Ala
                580                 585                 590

Val Lys Pro Lys Ala Val Tyr Phe Val Ser Gly Leu Pro Lys Thr Arg
                595                 600                 605

Asn Ala Lys Val Met Arg Arg Leu Ile Arg Ala Ala Tyr Met Asn Glu
                610                 615                 620

Pro Ala Gly Asp Leu Ser Thr Leu Glu Asn Arg Glu Thr Tyr Asp Glu
625                 630                 635                 640
```

<210> SEQ ID NO 25
<211> LENGTH: 786
<212> TYPE: DNA
<213> ORGANISM: Bacillus licheniformis DSM 13
<220> FEATURE:
<221> NAME/KEY: gene
<222> LOCATION: (1)..(786)
<223> OTHER INFORMATION: 3-hydroxybutyryl-CoA dehydratase
(E.C. 4.2.1.55), yngF
<220> FEATURE:
<221> NAME/KEY: CDS
<222> LOCATION: (1)..(783)

<400> SEQUENCE: 25

```
atg gag ccc aat gtt ctt tat tcc ata aac gag cag tcg gtc gcc gtg      48
Met Glu Pro Asn Val Leu Tyr Ser Ile Asn Glu Gln Ser Val Ala Val
1               5                   10                  15 ttg acg ctg aac agg ccg cag gct gca aat gcc ctc tcg ctt ggg ctt      96
Leu Thr Leu Asn Arg Pro Gln Ala Ala Asn Ala Leu Ser Leu Gly Leu
            20                  25                  30 ctc gac gac ttt cag cgc atc ctt cga gat att cgt tca aac ccg gcc     144
Leu Asp Asp Phe Gln Arg Ile Leu Arg Asp Ile Arg Ser Asn Pro Ala
        35                  40                  45 gtc cgc tgt gtc atc ata acg gga aaa ggg gac agg acg ttt tgt gca     192
Val Arg Cys Val Ile Ile Thr Gly Lys Gly Asp Arg Thr Phe Cys Ala
    50                  55                  60 ggc gcc gat tta aag gaa aga gcc cgc atg agc caa aca gaa gcg aag     240
Gly Ala Asp Leu Lys Glu Arg Ala Arg Met Ser Gln Thr Glu Ala Lys
65                  70                  75                  80 cag gct gtt tcc ctg att caa cgc gtg gtc agc gaa acg gaa aaa ctg     288
Gln Ala Val Ser Leu Ile Gln Arg Val Val Ser Glu Thr Glu Lys Leu
                85                  90                  95 ccg cag ccc gtc atc gct tca tta aac gga agc gct tta gga ggg ggg     336
Pro Gln Pro Val Ile Ala Ser Leu Asn Gly Ser Ala Leu Gly Gly Gly
            100                 105                 110 ctg gag ctt gca ttg gcg tgc gac atc agg atc gca gcc gaa cat att     384
Leu Glu Leu Ala Leu Ala Cys Asp Ile Arg Ile Ala Ala Glu His Ile
        115                 120                 125 gaa ctc ggc ctc ccc gaa aca acg ctc gca atc att cca ggg gca gga     432
Glu Leu Gly Leu Pro Glu Thr Thr Leu Ala Ile Ile Pro Gly Ala Gly
    130                 135                 140 ggg aca cag cgg ctg ccc cgc ttg atc ggc agg gga aag gca aaa gaa     480
Gly Thr Gln Arg Leu Pro Arg Leu Ile Gly Arg Gly Lys Ala Lys Glu
145                 150                 155                 160 atg atc ttt acc ggc tgc cgc atc agc gcc gaa gaa gcg caa aag atc     528
Met Ile Phe Thr Gly Cys Arg Ile Ser Ala Glu Glu Ala Gln Lys Ile
                165                 170                 175 agc ctg gtt gaa cat gtc gtt ccg ctt tcg aag tta aag gaa gcg agt     576
Ser Leu Val Glu His Val Val Pro Leu Ser Lys Leu Lys Glu Ala Ser
            180                 185                 190 gaa agc atc gcg gcg aac atc gcg gcg aac gga ccg gta gcc gtc aga     624
Glu Ser Ile Ala Ala Asn Ile Ala Ala Asn Gly Pro Val Ala Val Arg
        195                 200                 205 caa gcg aag ttt gcc atc aat caa ggc ctt gag aca gct atc gaa aca     672
Gln Ala Lys Phe Ala Ile Asn Gln Gly Leu Glu Thr Ala Ile Glu Thr
    210                 215                 220 ggg ctt gcc att gaa caa aaa gcc tat gaa ctg acg att ccg acg aaa     720
Gly Leu Ala Ile Glu Gln Lys Ala Tyr Glu Leu Thr Ile Pro Thr Lys
225                 230                 235                 240
```

```
gac agg aca gaa ggg ctg aaa gct ttt gca gaa aag cgg aag ccg gat    768
Asp Arg Thr Glu Gly Leu Lys Ala Phe Ala Glu Lys Arg Lys Pro Asp
            245                 250                 255 tat acg gga gaa taa aac                                            786
Tyr Thr Gly Glu
            260

<210> SEQ ID NO 26
<211> LENGTH: 260
<212> TYPE: PRT
<213> ORGANISM: Bacillus licheniformis DSM 13

<400> SEQUENCE: 26

Met Glu Pro Asn Val Leu Tyr Ser Ile Asn Glu Gln Ser Val Ala Val
1               5                   10                  15

Leu Thr Leu Asn Arg Pro Gln Ala Ala Asn Ala Leu Ser Leu Gly Leu
            20                  25                  30

Leu Asp Asp Phe Gln Arg Ile Leu Arg Asp Ile Arg Ser Asn Pro Ala
        35                  40                  45

Val Arg Cys Val Ile Ile Thr Gly Lys Gly Asp Arg Thr Phe Cys Ala
50                  55                  60

Gly Ala Asp Leu Lys Glu Arg Ala Arg Met Ser Gln Thr Glu Ala Lys
65                  70                  75                  80

Gln Ala Val Ser Leu Ile Gln Arg Val Val Ser Glu Thr Glu Lys Leu
                85                  90                  95

Pro Gln Pro Val Ile Ala Ser Leu Asn Gly Ser Ala Leu Gly Gly Gly
            100                 105                 110

Leu Glu Leu Ala Leu Ala Cys Asp Ile Arg Ile Ala Ala Glu His Ile
        115                 120                 125

Glu Leu Gly Leu Pro Glu Thr Thr Leu Ala Ile Ile Pro Gly Ala Gly
    130                 135                 140

Gly Thr Gln Arg Leu Pro Arg Leu Ile Gly Arg Gly Lys Ala Lys Glu
145                 150                 155                 160

Met Ile Phe Thr Gly Cys Arg Ile Ser Ala Glu Glu Ala Gln Lys Ile
                165                 170                 175

Ser Leu Val Glu His Val Val Pro Leu Ser Lys Leu Lys Glu Ala Ser
            180                 185                 190

Glu Ser Ile Ala Ala Asn Ile Ala Ala Asn Gly Pro Val Ala Val Arg
        195                 200                 205

Gln Ala Lys Phe Ala Ile Asn Gln Gly Leu Glu Thr Ala Ile Glu Thr
    210                 215                 220

Gly Leu Ala Ile Glu Gln Lys Ala Tyr Glu Leu Thr Ile Pro Thr Lys
225                 230                 235                 240

Asp Arg Thr Glu Gly Leu Lys Ala Phe Ala Glu Lys Arg Lys Pro Asp
                245                 250                 255

Tyr Thr Gly Glu
            260

<210> SEQ ID NO 27
<211> LENGTH: 1164
<212> TYPE: DNA
<213> ORGANISM: Bacillus licheniformis DSM 13
<220> FEATURE:
<221> NAME/KEY: gene
<222> LOCATION: (1)..(1164)
<223> OTHER INFORMATION: Acyl-CoA dehydrogenase (E.C. 1.3.99.-), yusJ
<220> FEATURE:
<221> NAME/KEY: CDS
```

```
<222> LOCATION: (1)..(1161)

<400> SEQUENCE: 27 atg aat ttt gaa cta acc aga gaa cag caa atg att cgt gaa ctc gca      48
Met Asn Phe Glu Leu Thr Arg Glu Gln Gln Met Ile Arg Glu Leu Ala
1               5                   10                  15 aga gat ttt gcg aaa cag gaa att gca ccg cac gcc gaa cat gtt gac      96
Arg Asp Phe Ala Lys Gln Glu Ile Ala Pro His Ala Glu His Val Asp
            20                  25                  30 agg acg gga gaa ttt ccg att gag aca ttt aaa aaa atg ggg gag ctc     144
Arg Thr Gly Glu Phe Pro Ile Glu Thr Phe Lys Lys Met Gly Glu Leu
        35                  40                  45 ggc ctc ttg ggg att ccg ttt cct gaa agc tac ggc ggt tca ggc gga     192
Gly Leu Leu Gly Ile Pro Phe Pro Glu Ser Tyr Gly Gly Ser Gly Gly
    50                  55                  60 gat acg att tcc tat gca ctt agc gtc gaa gaa atc ggc aaa gcg tgc     240
Asp Thr Ile Ser Tyr Ala Leu Ser Val Glu Glu Ile Gly Lys Ala Cys
65                  70                  75                  80 gga agc acc ggt ctt agc tat gct gcg gct gta tcg ctc ggg gct gcg     288
Gly Ser Thr Gly Leu Ser Tyr Ala Ala Ala Val Ser Leu Gly Ala Ala
                85                  90                  95 ccg att tat tat ttc ggc act gaa gaa caa aaa caa gaa tat ctc gtc     336
Pro Ile Tyr Tyr Phe Gly Thr Glu Glu Gln Lys Gln Glu Tyr Leu Val
            100                 105                 110 ccg ctt gcg acg ggc cgg gcg ctc gga gca ttt ggg ctg acc gaa ccg     384
Pro Leu Ala Thr Gly Arg Ala Leu Gly Ala Phe Gly Leu Thr Glu Pro
        115                 120                 125 aat gca ggt tcc gat gcg ggc ggc acc cgg aca aaa gcc cgc tcg gaa     432
Asn Ala Gly Ser Asp Ala Gly Gly Thr Arg Thr Lys Ala Arg Ser Glu
    130                 135                 140 ggg gac agc tat gtg atc agc ggt gag aaa tgc tgg atc aca aat gca     480
Gly Asp Ser Tyr Val Ile Ser Gly Glu Lys Cys Trp Ile Thr Asn Ala
145                 150                 155                 160 gga ttt gcc agg acc gtc atc gtc acc gcc gtc acc gga ata gat gac     528
Gly Phe Ala Arg Thr Val Ile Val Thr Ala Val Thr Gly Ile Asp Asp
                165                 170                 175 aac gga aaa aac atc att tcc gcc atc atc gtt ccg aca gat tcg gag     576
Asn Gly Lys Asn Ile Ile Ser Ala Ile Ile Val Pro Thr Asp Ser Glu
            180                 185                 190 ggc ttc acc att aaa agc gaa tat gac aaa atg ggt gtc cgc ggc tcc     624
Gly Phe Thr Ile Lys Ser Glu Tyr Asp Lys Met Gly Val Arg Gly Ser
        195                 200                 205 aat aca tca cag ctc ata ttg gac aat gtc cgc gta cca aaa caa aat     672
Asn Thr Ser Gln Leu Ile Leu Asp Asn Val Arg Val Pro Lys Gln Asn
    210                 215                 220 cta ttg gga agc ccg gaa aaa ggg ttt aaa caa ttt ctc aat aca ctt     720
Leu Leu Gly Ser Pro Glu Lys Gly Phe Lys Gln Phe Leu Asn Thr Leu
225                 230                 235                 240 gac ggc ggc aga att tcg atc gca gcg ctg gct gtc ggt att gcc caa     768
Asp Gly Gly Arg Ile Ser Ile Ala Ala Leu Ala Val Gly Ile Ala Gln
                245                 250                 255 ggc gca ttt gag gcg gcg ctc aca tac gcg cgc gaa cga aaa caa ttc     816
Gly Ala Phe Glu Ala Ala Leu Thr Tyr Ala Arg Glu Arg Lys Gln Phe
            260                 265                 270 ggc cga ccg atc tct tat ttc cag gcg att cag ttc aag ctt gcc gac     864
Gly Arg Pro Ile Ser Tyr Phe Gln Ala Ile Gln Phe Lys Leu Ala Asp
        275                 280                 285 atg gcc atg gaa att gag ctc gcc cgc aat atg gtg ctg aag gcc gcc     912
Met Ala Met Glu Ile Glu Leu Ala Arg Asn Met Val Leu Lys Ala Ala
    290                 295                 300
```

```
tgg ctg aaa gat caa gga cgt ccg ttt aca aaa gaa gcg gct ttt gcc      960
Trp Leu Lys Asp Gln Gly Arg Pro Phe Thr Lys Glu Ala Ala Phe Ala
305                 310                 315                 320 aag ctt tat gcc tca gaa atg gcg ttc agg aca tgc aat cag tcc att     1008
Lys Leu Tyr Ala Ser Glu Met Ala Phe Arg Thr Cys Asn Gln Ser Ile
                325                 330                 335 caa ata cac gga gga tac ggg tat atg aaa gag tat gga gtg gag cgc     1056
Gln Ile His Gly Gly Tyr Gly Tyr Met Lys Glu Tyr Gly Val Glu Arg
            340                 345                 350 atg ctg cgg gac gca aaa tta atg gaa atc ggt gaa ggc act tca gaa     1104
Met Leu Arg Asp Ala Lys Leu Met Glu Ile Gly Glu Gly Thr Ser Glu
        355                 360                 365 att caa cgg ctc gtc atc gca agg cag ctc ggc atc ggc aaa caa gcg     1152
Ile Gln Arg Leu Val Ile Ala Arg Gln Leu Gly Ile Gly Lys Gln Ala
    370                 375                 380 ctg aaa tga aaa                                                     1164
Leu Lys
385
```

<210> SEQ ID NO 28
<211> LENGTH: 386
<212> TYPE: PRT
<213> ORGANISM: Bacillus licheniformis DSM 13

<400> SEQUENCE: 28

```
Met Asn Phe Glu Leu Thr Arg Glu Gln Gln Met Ile Arg Glu Leu Ala
1               5                   10                  15

Arg Asp Phe Ala Lys Gln Glu Ile Ala Pro His Ala Glu His Val Asp
            20                  25                  30

Arg Thr Gly Glu Phe Pro Ile Glu Thr Phe Lys Lys Met Gly Glu Leu
        35                  40                  45

Gly Leu Leu Gly Ile Pro Phe Pro Glu Ser Tyr Gly Gly Ser Gly Gly
    50                  55                  60

Asp Thr Ile Ser Tyr Ala Leu Ser Val Glu Ile Gly Lys Ala Cys
65                  70                  75                  80

Gly Ser Thr Gly Leu Ser Tyr Ala Ala Ala Val Ser Leu Gly Ala Ala
            85                  90                  95

Pro Ile Tyr Tyr Phe Gly Thr Glu Glu Gln Lys Gln Glu Tyr Leu Val
        100                 105                 110

Pro Leu Ala Thr Gly Arg Ala Leu Gly Ala Phe Gly Leu Thr Glu Pro
    115                 120                 125

Asn Ala Gly Ser Asp Ala Gly Gly Thr Arg Thr Lys Ala Arg Ser Glu
130                 135                 140

Gly Asp Ser Tyr Val Ile Ser Gly Glu Lys Cys Trp Ile Thr Asn Ala
145                 150                 155                 160

Gly Phe Ala Arg Thr Val Ile Val Thr Ala Val Thr Gly Ile Asp Asp
            165                 170                 175

Asn Gly Lys Asn Ile Ile Ser Ala Ile Ile Val Pro Thr Asp Ser Glu
        180                 185                 190

Gly Phe Thr Ile Lys Ser Glu Tyr Asp Lys Met Gly Val Arg Gly Ser
    195                 200                 205

Asn Thr Ser Gln Leu Ile Leu Asp Asn Val Arg Val Pro Lys Gln Asn
    210                 215                 220

Leu Leu Gly Ser Pro Glu Lys Gly Phe Lys Gln Phe Leu Asn Thr Leu
225                 230                 235                 240

Asp Gly Gly Arg Ile Ser Ile Ala Ala Leu Ala Val Gly Ile Ala Gln
```

```
                       245                 250                 255
Gly Ala Phe Glu Ala Ala Leu Thr Tyr Ala Arg Glu Arg Lys Gln Phe
            260                 265                 270

Gly Arg Pro Ile Ser Tyr Phe Gln Ala Ile Gln Phe Lys Leu Ala Asp
        275                 280                 285

Met Ala Met Glu Ile Glu Leu Ala Arg Asn Met Val Leu Lys Ala Ala
    290                 295                 300

Trp Leu Lys Asp Gln Gly Arg Pro Phe Thr Lys Glu Ala Ala Phe Ala
305                 310                 315                 320

Lys Leu Tyr Ala Ser Glu Met Ala Phe Arg Thr Cys Asn Gln Ser Ile
                325                 330                 335

Gln Ile His Gly Gly Tyr Gly Tyr Met Lys Glu Tyr Gly Val Glu Arg
            340                 345                 350

Met Leu Arg Asp Ala Lys Leu Met Glu Ile Gly Glu Gly Thr Ser Glu
        355                 360                 365

Ile Gln Arg Leu Val Ile Ala Arg Gln Leu Gly Ile Gly Lys Gln Ala
370                 375                 380

Leu Lys
385

<210> SEQ ID NO 29
<211> LENGTH: 876
<212> TYPE: DNA
<213> ORGANISM: Bacillus licheniformis DSM 13
<220> FEATURE:
<221> NAME/KEY: gene
<222> LOCATION: (1)..(876)
<223> OTHER INFORMATION: Hypothetical oxidoreductase (E.C. 1.1.-.-),
      ykwC
<220> FEATURE:
<221> NAME/KEY: CDS
<222> LOCATION: (1)..(873)

<400> SEQUENCE: 29 atg aaa aaa acg gtc gga ttt atc gga ctc ggt gta atg gga aac agc      48
Met Lys Lys Thr Val Gly Phe Ile Gly Leu Gly Val Met Gly Asn Ser
1               5                   10                  15 atg gcc tcg cac att tta gcc gcg ggc tat ccc gtc agc gcc tat acg      96
Met Ala Ser His Ile Leu Ala Ala Gly Tyr Pro Val Ser Ala Tyr Thr
            20                  25                  30 aga acg aaa cac aaa gcg gac agc ctc gtg gaa aaa ggg gcg gaa tgg     144
Arg Thr Lys His Lys Ala Asp Ser Leu Val Glu Lys Gly Ala Glu Trp
        35                  40                  45 aaa tca tcc gtc aaa gca ctg gcg cag tcg tct gat gtg atc atc aca     192
Lys Ser Ser Val Lys Ala Leu Ala Gln Ser Ser Asp Val Ile Ile Thr
    50                  55                  60 atg gtc ggc tac cca aaa gac gtt gaa gag gtt tac ttt gga agc gaa     240
Met Val Gly Tyr Pro Lys Asp Val Glu Glu Val Tyr Phe Gly Ser Glu
65                  70                  75                  80 ggc att att gaa aat gcc aaa aaa ggt tcc tac ctt atc gat atg acg     288
Gly Ile Ile Glu Asn Ala Lys Lys Gly Ser Tyr Leu Ile Asp Met Thr
                85                  90                  95 act tcc aaa cct tcg ctt gcc aaa caa atc gag act gcc gca aaa gag     336
Thr Ser Lys Pro Ser Leu Ala Lys Gln Ile Glu Thr Ala Ala Lys Glu
            100                 105                 110 aaa gga ctt tac gct ttg gat gct ccg gtt tca ggc ggg gac gtc ggc     384
Lys Gly Leu Tyr Ala Leu Asp Ala Pro Val Ser Gly Gly Asp Val Gly
        115                 120                 125 gcg agg aac ggc acg ctc gct atc atg gtc gga gga gaa cgg aaa gct     432
Ala Arg Asn Gly Thr Leu Ala Ile Met Val Gly Gly Glu Arg Lys Ala
```

```
tat gat gaa tgc tac ccg ctc ttt tcg atc atg ggt gaa aac atc cag    480
Tyr Asp Glu Cys Tyr Pro Leu Phe Ser Ile Met Gly Glu Asn Ile Gln
145                 150                 155                 160 tat cag ggg ccg gcc gga agc ggc cag cat acg aaa atg tgc aac cag    528
Tyr Gln Gly Pro Ala Gly Ser Gly Gln His Thr Lys Met Cys Asn Gln
            165                 170                 175 att gcg att gcc gca ggg atg atc ggc gtc gca gaa gcg atg gcc tac    576
Ile Ala Ile Ala Ala Gly Met Ile Gly Val Ala Glu Ala Met Ala Tyr
        180                 185                 190 gcc gaa aaa tcc gga ctc gat ccc gac aac gtg ctg aaa agc att acg    624
Ala Glu Lys Ser Gly Leu Asp Pro Asp Asn Val Leu Lys Ser Ile Thr
    195                 200                 205 acc ggc gct gcg gga agc tgg tcg ctc tca aat cta gcg cct aga atg    672
Thr Gly Ala Ala Gly Ser Trp Ser Leu Ser Asn Leu Ala Pro Arg Met
210                 215                 220 ctg aaa ggc gac ttt gaa ccg ggt ttt tac gtc aaa cac ttt gtt aaa    720
Leu Lys Gly Asp Phe Glu Pro Gly Phe Tyr Val Lys His Phe Val Lys
225                 230                 235                 240 gac atg ggc atc gcg ctt gaa gag gcg gag ctg atg ggc gag aaa atg    768
Asp Met Gly Ile Ala Leu Glu Glu Ala Glu Leu Met Gly Glu Lys Met
            245                 250                 255 ccg ggg ctc gag ctt gcg aaa agc ctt tac gac acc ctt gtt gaa aaa    816
Pro Gly Leu Glu Leu Ala Lys Ser Leu Tyr Asp Thr Leu Val Glu Lys
        260                 265                 270 ggc gaa gaa aac agc ggc acc caa agt ctg tac aag ctt tgg aca gaa    864
Gly Glu Glu Asn Ser Gly Thr Gln Ser Leu Tyr Lys Leu Trp Thr Glu
    275                 280                 285 tac aaa taa cga                                                    876
Tyr Lys
    290

<210> SEQ ID NO 30
<211> LENGTH: 290
<212> TYPE: PRT
<213> ORGANISM: Bacillus licheniformis DSM 13

<400> SEQUENCE: 30

Met Lys Lys Thr Val Gly Phe Ile Gly Leu Gly Val Met Gly Asn Ser
1               5                   10                  15

Met Ala Ser His Ile Leu Ala Ala Gly Tyr Pro Val Ser Ala Tyr Thr
            20                  25                  30

Arg Thr Lys His Lys Ala Asp Ser Leu Val Glu Lys Gly Ala Glu Trp
        35                  40                  45

Lys Ser Ser Val Lys Ala Leu Ala Gln Ser Ser Asp Val Ile Ile Thr
    50                  55                  60

Met Val Gly Tyr Pro Lys Asp Val Glu Glu Val Tyr Phe Gly Ser Glu
65                  70                  75                  80

Gly Ile Ile Glu Asn Ala Lys Lys Gly Ser Tyr Leu Ile Asp Met Thr
                85                  90                  95

Thr Ser Lys Pro Ser Leu Ala Lys Gln Ile Glu Thr Ala Ala Lys Glu
            100                 105                 110

Lys Gly Leu Tyr Ala Leu Asp Ala Pro Val Ser Gly Gly Asp Val Gly
        115                 120                 125

Ala Arg Asn Gly Thr Leu Ala Ile Met Val Gly Gly Glu Arg Lys Ala
    130                 135                 140

Tyr Asp Glu Cys Tyr Pro Leu Phe Ser Ile Met Gly Glu Asn Ile Gln
145                 150                 155                 160
```

```
Tyr Gln Gly Pro Ala Gly Ser Gly Gln His Thr Lys Met Cys Asn Gln
            165                 170                 175
Ile Ala Ile Ala Ala Gly Met Ile Gly Val Ala Glu Ala Met Ala Tyr
            180                 185                 190
Ala Glu Lys Ser Gly Leu Asp Pro Asp Asn Val Leu Lys Ser Ile Thr
            195                 200                 205
Thr Gly Ala Ala Gly Ser Trp Ser Leu Ser Asn Leu Ala Pro Arg Met
            210                 215                 220
Leu Lys Gly Asp Phe Glu Pro Gly Phe Tyr Val Lys His Phe Val Lys
225                 230                 235                 240
Asp Met Gly Ile Ala Leu Glu Glu Ala Glu Leu Met Gly Glu Lys Met
            245                 250                 255
Pro Gly Leu Glu Leu Ala Lys Ser Leu Tyr Asp Thr Leu Val Glu Lys
            260                 265                 270
Gly Glu Glu Asn Ser Gly Thr Gln Ser Leu Tyr Lys Leu Trp Thr Glu
            275                 280                 285
Tyr Lys
    290
```

```
<210> SEQ ID NO 31
<211> LENGTH: 915
<212> TYPE: DNA
<213> ORGANISM: Bacillus licheniformis DSM 13
<220> FEATURE:
<221> NAME/KEY: gene
<222> LOCATION: (1)..(915)
<223> OTHER INFORMATION: Probable phosphate butyryltransferase
      (E.C. 2.3.1.19)
<220> FEATURE:
<221> NAME/KEY: CDS
<222> LOCATION: (1)..(912)

<400> SEQUENCE: 31
```

```
atg aag ctg aaa caa cta ttg caa aaa gcg gcg gag ctt gac aat aaa       48
Met Lys Leu Lys Gln Leu Leu Gln Lys Ala Ala Glu Leu Asp Asn Lys
1               5                   10                  15 acg gtc gcc gtc gca cat gcg gaa gat gac gaa gtg ctg caa gcg gtc       96
Thr Val Ala Val Ala His Ala Glu Asp Asp Glu Val Leu Gln Ala Val
                20                  25                  30 aaa ctt gcg gtc gac aaa caa ttt gcc cgg ttc ttg ctg atc ggg cac      144
Lys Leu Ala Val Asp Lys Gln Phe Ala Arg Phe Leu Leu Ile Gly His
            35                  40                  45 aga gaa aaa ctt aga cat atg atg aca gag cag aat att tca aaa cgg      192
Arg Glu Lys Leu Arg His Met Met Thr Glu Gln Asn Ile Ser Lys Arg
        50                  55                  60 cac gtg gat atc att cat tcg gaa tcg ccg gcg gat tct gcg aga att      240
His Val Asp Ile Ile His Ser Glu Ser Pro Ala Asp Ser Ala Arg Ile
65                  70                  75                  80 gcc gtt caa gct gtc aaa agc ggc aat gcg gat gtt ctt atg aag ggg      288
Ala Val Gln Ala Val Lys Ser Gly Asn Ala Asp Val Leu Met Lys Gly
                85                  90                  95 aat gtc ccg aca gct gtg cta tta aaa gcc gtt ttg aat aaa gag tac      336
Asn Val Pro Thr Ala Val Leu Leu Lys Ala Val Leu Asn Lys Glu Tyr
                100                 105                 110 ggg ctt cgt tcc tcg cac gtg ctg tca cat gta gca gca ttt gaa gtc      384
Gly Leu Arg Ser Ser His Val Leu Ser His Val Ala Ala Phe Glu Val
            115                 120                 125 agc ggg ttt gag agg ctg att tat gta aca gat gcg gcg atg aat atc      432
Ser Gly Phe Glu Arg Leu Ile Tyr Val Thr Asp Ala Ala Met Asn Ile
        130                 135                 140
```

```
agc ccc aag ctt gat gag ctg aag cag att tta gaa aac gca gtc ggc    480
Ser Pro Lys Leu Asp Glu Leu Lys Gln Ile Leu Glu Asn Ala Val Gly
145                 150                 155                 160 gtg gcg agg tcg gtc ggc gtg caa atg ccg aaa gtc gct tgt ctt gcc    528
Val Ala Arg Ser Val Gly Val Gln Met Pro Lys Val Ala Cys Leu Ala
                165                 170                 175 gca gtg gaa aca gtg aat ccc gcg atg gaa gcg aca ttg aat gca gct    576
Ala Val Glu Thr Val Asn Pro Ala Met Glu Ala Thr Leu Asn Ala Ala
            180                 185                 190 gcc ttg acg cag atg aat cat cgg ggc caa atc aaa aac tgc gtt gtt    624
Ala Leu Thr Gln Met Asn His Arg Gly Gln Ile Lys Asn Cys Val Val
        195                 200                 205 gac ggg cct ctt gca ttg gat aac gcg ata tcg ccg ctt gcc gcc cgg    672
Asp Gly Pro Leu Ala Leu Asp Asn Ala Ile Ser Pro Leu Ala Ala Arg
    210                 215                 220 cat aaa aac att tcc ggg atc gta gca ggc gag gcc gat atc ctg ctt    720
His Lys Asn Ile Ser Gly Ile Val Ala Gly Glu Ala Asp Ile Leu Leu
225                 230                 235                 240 gtt cct tca att gaa aca ggc aat gtc ctt tat aaa tca ttg att cat    768
Val Pro Ser Ile Glu Thr Gly Asn Val Leu Tyr Lys Ser Leu Ile His
                245                 250                 255 ttt gcg ggt gca aaa gtg gga gcc att tta gca ggg gca aaa gca ccc    816
Phe Ala Gly Ala Lys Val Gly Ala Ile Leu Ala Gly Ala Lys Ala Pro
            260                 265                 270 atc gcc ttg aca agc agg gcc gat tcc gca gaa aac aag ttg tat tcg    864
Ile Ala Leu Thr Ser Arg Ala Asp Ser Ala Glu Asn Lys Leu Tyr Ser
        275                 280                 285 att gct ttg gcg ctg tgt acg tct gaa gca cga cat gag gag gaa taa   912
Ile Ala Leu Ala Leu Cys Thr Ser Glu Ala Arg His Glu Glu Glu
    290                 295                 300 aaa                                                               915
```

<210> SEQ ID NO 32
<211> LENGTH: 303
<212> TYPE: PRT
<213> ORGANISM: Bacillus licheniformis DSM 13

<400> SEQUENCE: 32

```
Met Lys Leu Lys Gln Leu Leu Gln Lys Ala Glu Leu Asp Asn Lys
1               5                   10                  15

Thr Val Ala Val Ala His Ala Glu Asp Glu Val Leu Gln Ala Val
                20                  25                  30

Lys Leu Ala Val Asp Lys Gln Phe Ala Arg Phe Leu Ile Gly His
            35                  40                  45

Arg Glu Lys Leu Arg His Met Met Thr Glu Gln Asn Ile Ser Lys Arg
50                  55                  60

His Val Asp Ile Ile His Ser Glu Ser Pro Ala Asp Ser Ala Arg Ile
65                  70                  75                  80

Ala Val Gln Ala Val Lys Ser Gly Asn Ala Asp Val Leu Met Lys Gly
                85                  90                  95

Asn Val Pro Thr Ala Val Leu Leu Lys Ala Val Leu Asn Lys Glu Tyr
                100                 105                 110

Gly Leu Arg Ser Ser His Val Leu Ser His Val Ala Ala Phe Glu Val
            115                 120                 125

Ser Gly Phe Glu Arg Leu Ile Tyr Val Thr Asp Ala Ala Met Asn Ile
        130                 135                 140

Ser Pro Lys Leu Asp Glu Leu Lys Gln Ile Leu Glu Asn Ala Val Gly
```

```
                145                 150                 155                 160
        Val Ala Arg Ser Val Gly Val Gln Met Pro Lys Val Ala Cys Leu Ala
                        165                 170                 175

Ala Val Glu Thr Val Asn Pro Ala Met Glu Ala Thr Leu Asn Ala Ala
                        180                 185                 190

Ala Leu Thr Gln Met Asn His Arg Gly Gln Ile Lys Asn Cys Val Val
                        195                 200                 205

Asp Gly Pro Leu Ala Leu Asp Asn Ala Ile Ser Pro Leu Ala Ala Arg
                    210                 215                 220

His Lys Asn Ile Ser Gly Ile Val Ala Gly Glu Ala Asp Ile Leu Leu
        225                 230                 235                 240

Val Pro Ser Ile Glu Thr Gly Asn Val Leu Tyr Lys Ser Leu Ile His
                        245                 250                 255

Phe Ala Gly Ala Lys Val Gly Ala Ile Leu Ala Gly Ala Lys Ala Pro
                        260                 265                 270

Ile Ala Leu Thr Ser Arg Ala Asp Ser Ala Glu Asn Lys Leu Tyr Ser
                        275                 280                 285

Ile Ala Leu Ala Leu Cys Thr Ser Glu Ala Arg His Glu Glu Glu
                        290                 295                 300

<210> SEQ ID NO 33
<211> LENGTH: 1110
<212> TYPE: DNA
<213> ORGANISM: Bacillus licheniformis DSM 13
<220> FEATURE:
<221> NAME/KEY: gene
<222> LOCATION: (1)..(1110)
<223> OTHER INFORMATION: Probable butyrate kinase (E.C. 2.7.2.7)
<220> FEATURE:
<221> NAME/KEY: CDS
<222> LOCATION: (1)..(1107)

<400> SEQUENCE: 33 atg cag gta cag gaa aaa cgt att ctc gtc atc aat ccg gga tct aca      48
Met Gln Val Gln Glu Lys Arg Ile Leu Val Ile Asn Pro Gly Ser Thr
1               5                   10                  15 tct aca aag atc ggc gtt ttt cat gat gac cgt tcg att ttc gaa aaa      96
Ser Thr Lys Ile Gly Val Phe His Asp Asp Arg Ser Ile Phe Glu Lys
                20                  25                  30 tca atc cgt cat gac gag gct gag cta cag caa tat cag acc att att     144
Ser Ile Arg His Asp Glu Ala Glu Leu Gln Gln Tyr Gln Thr Ile Ile
            35                  40                  45 gat caa tat tcg ttc aga aaa cag gcg ata ctc gaa acc ctg cat gaa     192
Asp Gln Tyr Ser Phe Arg Lys Gln Ala Ile Leu Glu Thr Leu His Glu
        50                  55                  60 cag gga atc aat att tct aaa ttg gat gcc gtt tgc gcc agg gga ggg     240
Gln Gly Ile Asn Ile Ser Lys Leu Asp Ala Val Cys Ala Arg Gly Gly
65                  70                  75                  80 ctg ctt cgg ccg att gaa ggc ggc act tac gaa gtc aat gat gcg atg     288
Leu Leu Arg Pro Ile Glu Gly Gly Thr Tyr Glu Val Asn Asp Ala Met
                85                  90                  95 att gtc gat ttg aaa aac ggc tat gcg ggg cag cat gca tca aat ctc     336
Ile Val Asp Leu Lys Asn Gly Tyr Ala Gly Gln His Ala Ser Asn Leu
                100                 105                 110 ggg ggc atc atc gcc agg gag att gcc gac ggg tta aat att ccc gct     384
Gly Gly Ile Ile Ala Arg Glu Ile Ala Asp Gly Leu Asn Ile Pro Ala
            115                 120                 125 ttt atc gtc gac ccc gtt gtt gtg gat gaa atg gct cct atc gca aaa     432
Phe Ile Val Asp Pro Val Val Val Asp Glu Met Ala Pro Ile Ala Lys
        130                 135                 140
```

```
att tcc ggc acc ccg gct att gaa agg cgc agc att ttt cac gcg ctc      480
Ile Ser Gly Thr Pro Ala Ile Glu Arg Arg Ser Ile Phe His Ala Leu
145                 150                 155                 160 aac caa aaa gca gtt gca agg aaa gcg gct tgg cag ttt ggg aag cgt      528
Asn Gln Lys Ala Val Ala Arg Lys Ala Ala Trp Gln Phe Gly Lys Arg
                165                 170                 175 tat gaa gat atg aaa atg atc atc acc cac atg gga ggc ggc att acg      576
Tyr Glu Asp Met Lys Met Ile Ile Thr His Met Gly Gly Gly Ile Thr
            180                 185                 190 atc ggc gtc cat tgc cgc ggc cgg gtg atc gac gtc aac aac ggc ctc      624
Ile Gly Val His Cys Arg Gly Arg Val Ile Asp Val Asn Asn Gly Leu
        195                 200                 205 cac ggg gaa ggt ccg ctc agt cca gag cgg gcc gga acc att cct gcg      672
His Gly Glu Gly Pro Leu Ser Pro Glu Arg Ala Gly Thr Ile Pro Ala
    210                 215                 220 ggt gat ctg atc gat atg tgc ttt tcc ggc gaa tat acg aaa gac gag      720
Gly Asp Leu Ile Asp Met Cys Phe Ser Gly Glu Tyr Thr Lys Asp Glu
225                 230                 235                 240 ctg atg aaa atg ctt gtc ggc ggc gga ggg ctt gcc ggc tat ctc ggc      768
Leu Met Lys Met Leu Val Gly Gly Gly Gly Leu Ala Gly Tyr Leu Gly
                245                 250                 255 acg acg gat gcg gta aaa gtt gag aaa atg atc aag gaa ggc gat caa      816
Thr Thr Asp Ala Val Lys Val Glu Lys Met Ile Lys Glu Gly Asp Gln
            260                 265                 270 aaa gct gcg ctc atc tat gaa gcg atg gct tat caa atc gcc aaa gaa      864
Lys Ala Ala Leu Ile Tyr Glu Ala Met Ala Tyr Gln Ile Ala Lys Glu
        275                 280                 285 atc ggg gcg gcc agc gcc gtc tta aaa ggc gaa gtc gat gtc att att      912
Ile Gly Ala Ala Ser Ala Val Leu Lys Gly Glu Val Asp Val Ile Ile
    290                 295                 300 ttg aca gga gga ctg gca tat gga aaa tcg ttt att tcc tcg atc aga      960
Leu Thr Gly Gly Leu Ala Tyr Gly Lys Ser Phe Ile Ser Ser Ile Arg
305                 310                 315                 320 caa tac ata gac tgg att tcg gat gtc gtc gtc ttt cca gga gaa aat     1008
Gln Tyr Ile Asp Trp Ile Ser Asp Val Val Val Phe Pro Gly Glu Asn
                325                 330                 335 gaa ctt caa gca ttg gct gaa ggt gca ttt cgc gta ttg aac ggc gaa     1056
Glu Leu Gln Ala Leu Ala Glu Gly Ala Phe Arg Val Leu Asn Gly Glu
            340                 345                 350 gaa gag gca aaa cag tat ccg aac cag agg agg gaa agt cat ggc aac     1104
Glu Glu Ala Lys Gln Tyr Pro Asn Gln Arg Arg Glu Ser His Gly Asn
        355                 360                 365 tga ata                                                             1110

<210> SEQ ID NO 34
<211> LENGTH: 368
<212> TYPE: PRT
<213> ORGANISM: Bacillus licheniformis DSM 13

<400> SEQUENCE: 34

Met Gln Val Gln Glu Lys Arg Ile Leu Val Ile Asn Pro Gly Ser Thr
1               5                   10                  15

Ser Thr Lys Ile Gly Val Phe His Asp Asp Arg Ser Ile Phe Glu Lys
            20                  25                  30

Ser Ile Arg His Asp Glu Ala Glu Leu Gln Gln Tyr Gln Thr Ile Ile
        35                  40                  45

Asp Gln Tyr Ser Phe Arg Lys Gln Ala Ile Leu Glu Thr Leu His Glu
    50                  55                  60
```

| | | | | | | | | | | | | | | | |
|---|---|---|---|---|---|---|---|---|---|---|---|---|---|---|---|
|Gln|Gly|Ile|Asn|Ile|Ser|Lys|Leu|Asp|Ala|Val|Cys|Ala|Arg|Gly|Gly|
|65| | | |70| | | |75| | | |80| | | |

Leu Leu Arg Pro Ile Glu Gly Gly Thr Tyr Glu Val Asn Asp Ala Met
               85              90              95

Ile Val Asp Leu Lys Asn Gly Tyr Ala Gly Gln His Ala Ser Asn Leu
       100              105              110

Gly Gly Ile Ile Ala Arg Glu Ile Ala Asp Gly Leu Asn Ile Pro Ala
     115              120              125

Phe Ile Val Asp Pro Val Val Asp Glu Met Ala Pro Ile Ala Lys
   130              135              140

Ile Ser Gly Thr Pro Ala Ile Glu Arg Arg Ser Ile Phe His Ala Leu
145           150             155              160

Asn Gln Lys Ala Val Ala Arg Lys Ala Ala Trp Gln Phe Gly Lys Arg
       165              170              175

Tyr Glu Asp Met Lys Met Ile Ile Thr His Met Gly Gly Ile Thr
        180             185              190

Ile Gly Val His Cys Arg Gly Arg Val Ile Asp Val Asn Asn Gly Leu
     195              200              205

His Gly Glu Gly Pro Leu Ser Pro Glu Arg Ala Gly Thr Ile Pro Ala
   210              215              220

Gly Asp Leu Ile Asp Met Cys Phe Ser Gly Glu Tyr Thr Lys Asp Glu
225           230             235              240

Leu Met Lys Met Leu Val Gly Gly Gly Leu Ala Gly Tyr Leu Gly
       245              250              255

Thr Thr Asp Ala Val Lys Val Glu Lys Met Ile Lys Glu Gly Asp Gln
       260              265              270

Lys Ala Ala Leu Ile Tyr Glu Ala Met Ala Tyr Gln Ile Ala Lys Glu
     275              280              285

Ile Gly Ala Ala Ser Ala Val Leu Lys Gly Glu Val Asp Val Ile Ile
   290              295              300

Leu Thr Gly Gly Leu Ala Tyr Gly Lys Ser Phe Ile Ser Ser Ile Arg
305           310             315              320

Gln Tyr Ile Asp Trp Ile Ser Asp Val Val Phe Pro Gly Glu Asn
       325              330              335

Glu Leu Gln Ala Leu Ala Glu Gly Ala Phe Arg Val Leu Asn Gly Glu
       340              345              350

Glu Glu Ala Lys Gln Tyr Pro Asn Gln Arg Arg Glu Ser His Gly Asn
     355              360              365

<210> SEQ ID NO 35
<211> LENGTH: 1722
<212> TYPE: DNA
<213> ORGANISM: Bacillus licheniformis DSM 13
<220> FEATURE:
<221> NAME/KEY: gene
<222> LOCATION: (1)..(1722)
<223> OTHER INFORMATION: Acetyl-coenzyme A synthetase (E.C. 6.2.1.1),
    acsA
<220> FEATURE:
<221> NAME/KEY: CDS
<222> LOCATION: (1)..(1719)

<400> SEQUENCE: 35 atg aaa ttg aaa gcg ctg cca gca gaa aag gga aat tac aac ttg aaa    48
Met Lys Leu Lys Ala Leu Pro Ala Glu Lys Gly Asn Tyr Asn Leu Lys
1              5                 10               15 gac tat gat gaa aca tac cgg aca ttt gac tgg aag gat gcc gaa aag    96
Asp Tyr Asp Glu Thr Tyr Arg Thr Phe Asp Trp Lys Asp Ala Glu Lys

```
                    20                  25                  30
cat ttt tca tgg cac aaa acg gga aaa atc aat gca gct tat gaa gct    144
His Phe Ser Trp His Lys Thr Gly Lys Ile Asn Ala Ala Tyr Glu Ala
         35                  40                  45 atc gac cgc cac gct gag tca aat ttg aaa aac aaa gtg gca ttt tac    192
Ile Asp Arg His Ala Glu Ser Asn Leu Lys Asn Lys Val Ala Phe Tyr
 50                  55                  60 tac aaa gat ccg gtc cgc gaa gaa aag tac act ttc aga gag atg aaa    240
Tyr Lys Asp Pro Val Arg Glu Glu Lys Tyr Thr Phe Arg Glu Met Lys
 65                  70                  75                  80 aat gaa acc aac aaa gcc ggg aat gtc tta aag cag cat gcc gat gtg    288
Asn Glu Thr Asn Lys Ala Gly Asn Val Leu Lys Gln His Ala Asp Val
                 85                  90                  95 gga aag gga gac cgt gtg ttt gtt ttt atg ccg aga tcg ccc gag ctt    336
Gly Lys Gly Asp Arg Val Phe Val Phe Met Pro Arg Ser Pro Glu Leu
            100                 105                 110 tat ttt att ctt ctc ggc gcc atc aaa ttg gga gcg atc gtc ggg ccg    384
Tyr Phe Ile Leu Leu Gly Ala Ile Lys Leu Gly Ala Ile Val Gly Pro
        115                 120                 125 tta ttt gaa gcg ttt atg gaa ggt gcc gtc aaa gac agg ctt gca aac    432
Leu Phe Glu Ala Phe Met Glu Gly Ala Val Lys Asp Arg Leu Ala Asn
130                 135                 140 agc gga gcg aag gtc atc gtg acg acg ccg gaa ttg ctt gaa cgg gtg    480
Ser Gly Ala Lys Val Ile Val Thr Thr Pro Glu Leu Leu Glu Arg Val
145                 150                 155                 160 ccg gcc gat gaa ctt ccg gat ctt gaa tca atc att gtc gtt gga gaa    528
Pro Ala Asp Glu Leu Pro Asp Leu Glu Ser Ile Ile Val Val Gly Glu
                165                 170                 175 ggc gta aag gaa gaa gga cct gtc att gat tat tac gcg aaa gcg gcg    576
Gly Val Lys Glu Glu Gly Pro Val Ile Asp Tyr Tyr Ala Lys Ala Ala
            180                 185                 190 gaa gca ggc act gat ctt gag att gaa tgg gtg gat cag gaa gac ggg    624
Glu Ala Gly Thr Asp Leu Glu Ile Glu Trp Val Asp Gln Glu Asp Gly
        195                 200                 205 atg ctg ctt cac tat acg tcg ggt tcg acc ggc gcg cca aaa ggg gtt    672
Met Leu Leu His Tyr Thr Ser Gly Ser Thr Gly Ala Pro Lys Gly Val
    210                 215                 220 ctc cac gtc cat aaa gca atg atc cag cat tat caa aca gcc aaa tgg    720
Leu His Val His Lys Ala Met Ile Gln His Tyr Gln Thr Ala Lys Trp
225                 230                 235                 240 gtt ctt gat ctg cat gac gat gac atc tat tgg tgc acc gct gat ccc    768
Val Leu Asp Leu His Asp Asp Asp Ile Tyr Trp Cys Thr Ala Asp Pro
                245                 250                 255 ggc tgg gtc acc gga acg gtt tac ggg att ttc ggt ccg tgg ctg aat    816
Gly Trp Val Thr Gly Thr Val Tyr Gly Ile Phe Gly Pro Trp Leu Asn
            260                 265                 270 gga gct acg aat gtt gtc gta ggc ggc aga ttc agt cct gag gca tgg    864
Gly Ala Thr Asn Val Val Val Gly Gly Arg Phe Ser Pro Glu Ala Trp
        275                 280                 285 tac gaa acg att gaa aaa atg gaa gtg acg gta tgg tac agc gcg cca    912
Tyr Glu Thr Ile Glu Lys Met Glu Val Thr Val Trp Tyr Ser Ala Pro
    290                 295                 300 acg gct ttc cgg atg ctg atg ggt gca ggc gac gat ctt gtg aat aaa    960
Thr Ala Phe Arg Met Leu Met Gly Ala Gly Asp Asp Leu Val Asn Lys
305                 310                 315                 320 tat aat cta agc tcc ttg cgg cat att tta agc gta ggg gag ccg tta   1008
Tyr Asn Leu Ser Ser Leu Arg His Ile Leu Ser Val Gly Glu Pro Leu
                325                 330                 335 aat ccc gaa gtc atc agg tgg ggg cat aaa gtc ttc ggc aac cgg att   1056
```

```
                Asn Pro Glu Val Ile Arg Trp Gly His Lys Val Phe Gly Asn Arg Ile
                                340                 345                 350 cat gat act tgg tgg atg act gaa aca gga tcg cag ctc atc tgc aat             1104
His Asp Thr Trp Trp Met Thr Glu Thr Gly Ser Gln Leu Ile Cys Asn
            355                 360                 365 tac ccg tgc atg gaa att aaa ccg gga tca atg ggc aag ccg att ccc             1152
Tyr Pro Cys Met Glu Ile Lys Pro Gly Ser Met Gly Lys Pro Ile Pro
        370                 375                 380 ggt gta gag gct gca atc gtc gac aac cag gga aat gaa ctg cct cct             1200
Gly Val Glu Ala Ala Ile Val Asp Asn Gln Gly Asn Glu Leu Pro Pro
385                 390                 395                 400 tac aga atg gga aat ctc gcc att aaa aaa ggc tgg ccg tcg atg atg             1248
Tyr Arg Met Gly Asn Leu Ala Ile Lys Lys Gly Trp Pro Ser Met Met
                405                 410                 415 cat tcg atc tgg aac aat cct gaa aaa tat agc tcc tat ttt atg ccg             1296
His Ser Ile Trp Asn Asn Pro Glu Lys Tyr Ser Ser Tyr Phe Met Pro
            420                 425                 430 ggc gat tgg tat gtg tca gga gat tcc gcc tac atg gat gaa gac ggg             1344
Gly Asp Trp Tyr Val Ser Gly Asp Ser Ala Tyr Met Asp Glu Asp Gly
        435                 440                 445 tac ttc tgg ttc cag gga cgg atc gac gat gtc atc atg aca tcg ggc             1392
Tyr Phe Trp Phe Gln Gly Arg Ile Asp Asp Val Ile Met Thr Ser Gly
    450                 455                 460 gaa cgc gtc ggc ccg ttt gaa gtc gag agc aag ctt gtt gag cat cag             1440
Glu Arg Val Gly Pro Phe Glu Val Glu Ser Lys Leu Val Glu His Gln
465                 470                 475                 480 gcc gtc gct gaa gca ggc gtc atc ggc aaa ccg gat ccc gtc cgg ggt             1488
Ala Val Ala Glu Ala Gly Val Ile Gly Lys Pro Asp Pro Val Arg Gly
                485                 490                 495 gaa att att aaa gcg ttc atc gcc ttg agg gac ggt tat gaa ccg tca             1536
Glu Ile Ile Lys Ala Phe Ile Ala Leu Arg Asp Gly Tyr Glu Pro Ser
            500                 505                 510 gat gcg tta aaa gaa gaa atc agg cag ttc gtg aaa caa ggc ttg gcc             1584
Asp Ala Leu Lys Glu Glu Ile Arg Gln Phe Val Lys Gln Gly Leu Ala
        515                 520                 525 gca cat gcc gcg cca agg gaa atc gaa ttt aaa gat aaa ctg ccg aag             1632
Ala His Ala Ala Pro Arg Glu Ile Glu Phe Lys Asp Lys Leu Pro Lys
    530                 535                 540 aca aga agc gga aag atc atg aga cgc gtc ctg aaa gca tgg gag ctg             1680
Thr Arg Ser Gly Lys Ile Met Arg Arg Val Leu Lys Ala Trp Glu Leu
545                 550                 555                 560 aac ctt ccg gca ggc gat ctc tca tcg atg gaa gac tga tgt                     1722
Asn Leu Pro Ala Gly Asp Leu Ser Ser Met Glu Asp
                565                 570

<210> SEQ ID NO 36
<211> LENGTH: 572
<212> TYPE: PRT
<213> ORGANISM: Bacillus licheniformis DSM 13

<400> SEQUENCE: 36

Met Lys Leu Lys Ala Leu Pro Ala Glu Lys Gly Asn Tyr Asn Leu Lys
1               5                   10                  15

Asp Tyr Asp Glu Thr Tyr Arg Thr Phe Asp Trp Lys Asp Ala Glu Lys
            20                  25                  30

His Phe Ser Trp His Lys Thr Gly Lys Ile Asn Ala Ala Tyr Glu Ala
        35                  40                  45

Ile Asp Arg His Ala Glu Ser Asn Leu Lys Asn Lys Val Ala Phe Tyr
    50                  55                  60
```

```
Tyr Lys Asp Pro Val Arg Glu Glu Lys Tyr Thr Phe Arg Glu Met Lys
 65                  70                  75                  80

Asn Glu Thr Asn Lys Ala Gly Asn Val Leu Lys Gln His Ala Asp Val
                 85                  90                  95

Gly Lys Gly Asp Arg Val Phe Val Phe Met Pro Arg Ser Pro Glu Leu
                100                 105                 110

Tyr Phe Ile Leu Leu Gly Ala Ile Lys Leu Gly Ala Ile Val Gly Pro
            115                 120                 125

Leu Phe Glu Ala Phe Met Glu Gly Ala Val Lys Asp Arg Leu Ala Asn
    130                 135                 140

Ser Gly Ala Lys Val Ile Val Thr Thr Pro Glu Leu Leu Glu Arg Val
145                 150                 155                 160

Pro Ala Asp Glu Leu Pro Asp Leu Glu Ser Ile Ile Val Val Gly Glu
                165                 170                 175

Gly Val Lys Glu Glu Gly Pro Val Ile Asp Tyr Tyr Ala Lys Ala Ala
                180                 185                 190

Glu Ala Gly Thr Asp Leu Glu Ile Glu Trp Val Asp Gln Glu Asp Gly
            195                 200                 205

Met Leu Leu His Tyr Thr Ser Gly Ser Thr Gly Ala Pro Lys Gly Val
    210                 215                 220

Leu His Val His Lys Ala Met Ile Gln His Tyr Gln Thr Ala Lys Trp
225                 230                 235                 240

Val Leu Asp Leu His Asp Asp Ile Tyr Trp Cys Thr Ala Asp Pro
                245                 250                 255

Gly Trp Val Thr Gly Thr Val Tyr Gly Ile Phe Gly Pro Trp Leu Asn
                260                 265                 270

Gly Ala Thr Asn Val Val Gly Gly Arg Phe Ser Pro Glu Ala Trp
            275                 280                 285

Tyr Glu Thr Ile Glu Lys Met Glu Val Thr Val Trp Tyr Ser Ala Pro
            290                 295                 300

Thr Ala Phe Arg Met Leu Met Gly Ala Gly Asp Asp Leu Val Asn Lys
305                 310                 315                 320

Tyr Asn Leu Ser Ser Leu Arg His Ile Leu Ser Val Gly Glu Pro Leu
                325                 330                 335

Asn Pro Glu Val Ile Arg Trp Gly His Lys Val Phe Gly Asn Arg Ile
            340                 345                 350

His Asp Thr Trp Trp Met Thr Glu Thr Gly Ser Gln Leu Ile Cys Asn
            355                 360                 365

Tyr Pro Cys Met Glu Ile Lys Pro Gly Ser Met Gly Lys Pro Ile Pro
    370                 375                 380

Gly Val Glu Ala Ala Ile Val Asp Asn Gln Gly Asn Glu Leu Pro Pro
385                 390                 395                 400

Tyr Arg Met Gly Asn Leu Ala Ile Lys Lys Gly Trp Pro Ser Met Met
                405                 410                 415

His Ser Ile Trp Asn Asn Pro Glu Lys Tyr Ser Ser Tyr Phe Met Pro
            420                 425                 430

Gly Asp Trp Tyr Val Ser Gly Asp Ser Ala Tyr Met Asp Glu Asp Gly
            435                 440                 445

Tyr Phe Trp Phe Gln Gly Arg Ile Asp Asp Val Ile Met Thr Ser Gly
    450                 455                 460

Glu Arg Val Gly Pro Phe Glu Val Glu Ser Lys Leu Val Glu His Gln
465                 470                 475                 480

Ala Val Ala Glu Ala Gly Val Ile Gly Lys Pro Asp Pro Val Arg Gly
```

```
                                485                 490                 495
Glu Ile Ile Lys Ala Phe Ile Ala Leu Arg Asp Gly Tyr Glu Pro Ser
                500                 505                 510

Asp Ala Leu Lys Glu Glu Ile Arg Gln Phe Val Lys Gln Gly Leu Ala
                515                 520                 525

Ala His Ala Ala Pro Arg Glu Ile Glu Phe Lys Asp Lys Leu Pro Lys
        530                 535                 540

Thr Arg Ser Gly Lys Ile Met Arg Arg Val Leu Lys Ala Trp Glu Leu
545                 550                 555                 560

Asn Leu Pro Ala Gly Asp Leu Ser Ser Met Glu Asp
                565                 570

<210> SEQ ID NO 37
<211> LENGTH: 1593
<212> TYPE: DNA
<213> ORGANISM: Bacillus licheniformis DSM 13
<220> FEATURE:
<221> NAME/KEY: gene
<222> LOCATION: (1)..(1593)
<223> OTHER INFORMATION: acetate-CoA ligase (E.C. 6.2.1.1), ytcI
<220> FEATURE:
<221> NAME/KEY: misc_feature
<222> LOCATION: (1)..(3)
<223> OTHER INFORMATION: First codon translated as Met.
<220> FEATURE:
<221> NAME/KEY: CDS
<222> LOCATION: (1)..(1590)

<400> SEQUENCE: 37 ttg aga aga gaa gat ttg att gcg ccg gag aag tat aat gcg gtt gat       48
Leu Arg Arg Glu Asp Leu Ile Ala Pro Glu Lys Tyr Asn Ala Val Asp
1               5                  10                  15 gaa att gaa aaa ttt aaa tct tcc cgc gat aag acc gca ttg atc tgg       96
Glu Ile Glu Lys Phe Lys Ser Ser Arg Asp Lys Thr Ala Leu Ile Trp
            20                  25                  30 gaa gat gaa tca ggg cgt caa gtg tca tgg tcc tat gaa aaa ttg att      144
Glu Asp Glu Ser Gly Arg Gln Val Ser Trp Ser Tyr Glu Lys Leu Ile
        35                  40                  45 gaa aag gct tac aaa atc ggc agc ata ttg acc cgt tct gga ctg aaa      192
Glu Lys Ala Tyr Lys Ile Gly Ser Ile Leu Thr Arg Ser Gly Leu Lys
    50                  55                  60 aaa ggt gac aag ctt atc gtg atg atg ccg cgg ata ccg gaa acg tat      240
Lys Gly Asp Lys Leu Ile Val Met Met Pro Arg Ile Pro Glu Thr Tyr
65                  70                  75                  80 gcc gtg tac atg gcc att tta aaa gct gga atg gtg gtc atc cca tgt      288
Ala Val Tyr Met Ala Ile Leu Lys Ala Gly Met Val Val Ile Pro Cys
                85                  90                  95 tcc gaa atg ctt cgg gcg aaa gac ttg gat tac agg atc aag cat gca      336
Ser Glu Met Leu Arg Ala Lys Asp Leu Asp Tyr Arg Ile Lys His Ala
            100                 105                 110 ggc gtc aaa gga gcc gtc gta tat tca gca ttt ctt gat gct ttt cta      384
Gly Val Lys Gly Ala Val Val Tyr Ser Ala Phe Leu Asp Ala Phe Leu
        115                 120                 125 gat gtt cgt tca aaa gag gca ctg tcg tta ttt gcc gtc gga gaa agc      432
Asp Val Arg Ser Lys Glu Ala Leu Ser Leu Phe Ala Val Gly Glu Ser
    130                 135                 140 agc gaa ggg tgg atc aat ctg ctc gaa aaa atg aat cag gcc att gca      480
Ser Glu Gly Trp Ile Asn Leu Leu Glu Lys Met Asn Gln Ala Ile Ala
145                 150                 155                 160 gcg gat ttt caa gcg gcg gat acc tct cgc gat gac atc gca ttt tta      528
Ala Asp Phe Gln Ala Ala Asp Thr Ser Arg Asp Asp Ile Ala Phe Leu
                165                 170                 175
```

-continued

| | | |
|---|---|---|
| tct tac aca tcc ggc acg acc ggt cag cca aaa ggg gtt gta cat aca<br>Ser Tyr Thr Ser Gly Thr Thr Gly Gln Pro Lys Gly Val Val His Thr<br>                    180                    185                    190 | 576 |
| cac ggc tgg gct tat gct cac tta aga acg aca gct tcc gca tgg ctt<br>His Gly Trp Ala Tyr Ala His Leu Arg Thr Thr Ala Ser Ala Trp Leu<br>        195                    200                    205 | 624 |
| gac att tcg gaa ggg gat ctc gtc tgg gcg aca gca ggg ccg ggc tgg<br>Asp Ile Ser Glu Gly Asp Leu Val Trp Ala Thr Ala Gly Pro Gly Trp<br>210                    215                    220 | 672 |
| caa aaa tgg gta tgg agc ccg ttt tta gca gtg ctc ggt agc ggt gca<br>Gln Lys Trp Val Trp Ser Pro Phe Leu Ala Val Leu Gly Ser Gly Ala<br>225                    230                    235                    240 | 720 |
| acc ggc ttt atc tat cat gga aaa ttc acg ccg gaa acg tat ttg cgg<br>Thr Gly Phe Ile Tyr His Gly Lys Phe Thr Pro Glu Thr Tyr Leu Arg<br>                    245                    250                    255 | 768 |
| ctg att gag cgc cat caa gtc aat gtg ctg tgc tgt acg ccg aca gag<br>Leu Ile Glu Arg His Gln Val Asn Val Leu Cys Cys Thr Pro Thr Glu<br>        260                    265                    270 | 816 |
| tac cgg ttc atg gcg aaa gtc aat gat ttg tcc cga ttt gac ctg tct<br>Tyr Arg Phe Met Ala Lys Val Asn Asp Leu Ser Arg Phe Asp Leu Ser<br>275                    280                    285 | 864 |
| tct ctg cac agc gct gtt tcg gcc gga gag ccg ttg aac agg gaa gtc<br>Ser Leu His Ser Ala Val Ser Ala Gly Glu Pro Leu Asn Arg Glu Val<br>            290                    295                    300 | 912 |
| atc gat aca ttt aaa aag cat ttt cat att gct gtg cgg gac gga tac<br>Ile Asp Thr Phe Lys Lys His Phe His Ile Ala Val Arg Asp Gly Tyr<br>305                    310                    315                    320 | 960 |
| gga caa acg gag agc acg ctg ttg gtg ggg att tta aaa ggt atg aaa<br>Gly Gln Thr Glu Ser Thr Leu Leu Val Gly Ile Leu Lys Gly Met Lys<br>                      325                    330                    335 | 1008 |
| atc aag cct gga agc atg gga aaa ccg acg cct gga aac ttg gtt gat<br>Ile Lys Pro Gly Ser Met Gly Lys Pro Thr Pro Gly Asn Leu Val Asp<br>                340                    345                    350 | 1056 |
| att att gac ggg aat gga aag agc tgt ccc ccg ggc gaa aca ggc gat<br>Ile Ile Asp Gly Asn Gly Lys Ser Cys Pro Pro Gly Glu Thr Gly Asp<br>        355                    360                    365 | 1104 |
| att gcc gtt cac tta agc acg ccg gct ctt ttt aaa gaa tat tac aaa<br>Ile Ala Val His Leu Ser Thr Pro Ala Leu Phe Lys Glu Tyr Tyr Lys<br>370                    375                    380 | 1152 |
| gat caa gaa cga acg ctc cga caa aga aga ggg gat tac ttt ata aca<br>Asp Gln Glu Arg Thr Leu Arg Gln Arg Arg Gly Asp Tyr Phe Ile Thr<br>385                    390                    395                    400 | 1200 |
| ggg gat aag gcg cga aag gat gaa gac ggc tat ttt tgg ttt gaa agc<br>Gly Asp Lys Ala Arg Lys Asp Glu Asp Gly Tyr Phe Trp Phe Glu Ser<br>                      405                    410                    415 | 1248 |
| cgc aat gac gat gtg atc atc agc tca gga tat aca atc ggc ccg ttt<br>Arg Asn Asp Asp Val Ile Ile Ser Ser Gly Tyr Thr Ile Gly Pro Phe<br>            420                    425                    430 | 1296 |
| gaa gtt gaa gat gcg ctg atc aag cat cct gag gtc aaa gaa tgt gct<br>Glu Val Glu Asp Ala Leu Ile Lys His Pro Glu Val Lys Glu Cys Ala<br>                435                    440                    445 | 1344 |
| gtt gtg gca agc cct gat gaa atc agg gga tcg atc gtg aaa gca tac<br>Val Val Ala Ser Pro Asp Glu Ile Arg Gly Ser Ile Val Lys Ala Tyr<br>450                    455                    460 | 1392 |
| gtt gtc tta aag gac cca tcc cgc gga aat gaa cac ctg aca aag gaa<br>Val Val Leu Lys Asp Pro Ser Arg Gly Asn Glu His Leu Thr Lys Glu<br>465                    470                    475                    480 | 1440 |
| tta caa gac cat gta aaa gcc atg acg gcc cct tat aaa tac ccc cgg<br>Leu Gln Asp His Val Lys Ala Met Thr Ala Pro Tyr Lys Tyr Pro Arg | 1488 |

-continued

```
                          485                 490                 495
gag ata gaa ttc atc gaa gaa ctg ccg aaa acg cct tcg gcg aaa atc     1536
Glu Ile Glu Phe Ile Glu Glu Leu Pro Lys Thr Pro Ser Ala Lys Ile
        500                 505                 510 aag cgc ttt gaa cta aga caa cgg gaa atc gca ctt aaa acg aaa gct     1584
Lys Arg Phe Glu Leu Arg Gln Arg Glu Ile Ala Leu Lys Thr Lys Ala
        515                 520                 525 gaa taa cca                                                         1593
Glu
```

<210> SEQ ID NO 38
<211> LENGTH: 529
<212> TYPE: PRT
<213> ORGANISM: Bacillus licheniformis DSM 13
<220> FEATURE:
<221> NAME/KEY: misc_feature
<222> LOCATION: (1)..(3)
<223> OTHER INFORMATION: First codon translated as Met.

<400> SEQUENCE: 38

```
Leu Arg Arg Glu Asp Leu Ile Ala Pro Glu Lys Tyr Asn Ala Val Asp
1               5                   10                  15

Glu Ile Glu Lys Phe Lys Ser Ser Arg Asp Lys Thr Ala Leu Ile Trp
            20                  25                  30

Glu Asp Glu Ser Gly Arg Gln Val Ser Trp Ser Tyr Glu Lys Leu Ile
        35                  40                  45

Glu Lys Ala Tyr Lys Ile Gly Ser Ile Leu Thr Arg Ser Gly Leu Lys
    50                  55                  60

Lys Gly Asp Lys Leu Ile Val Met Met Pro Arg Ile Pro Glu Thr Tyr
65                  70                  75                  80

Ala Val Tyr Met Ala Ile Leu Lys Ala Gly Met Val Val Ile Pro Cys
                85                  90                  95

Ser Glu Met Leu Arg Ala Lys Asp Leu Asp Tyr Arg Ile Lys His Ala
            100                 105                 110

Gly Val Lys Gly Ala Val Val Tyr Ser Ala Phe Leu Asp Ala Phe Leu
        115                 120                 125

Asp Val Arg Ser Lys Glu Ala Leu Ser Leu Phe Ala Val Gly Glu Ser
    130                 135                 140

Ser Glu Gly Trp Ile Asn Leu Leu Glu Lys Met Asn Gln Ala Ile Ala
145                 150                 155                 160

Ala Asp Phe Gln Ala Ala Asp Thr Ser Arg Asp Asp Ile Ala Phe Leu
                165                 170                 175

Ser Tyr Thr Ser Gly Thr Thr Gly Gln Pro Lys Gly Val Val His Thr
            180                 185                 190

His Gly Trp Ala Tyr Ala His Leu Arg Thr Thr Ala Ser Ala Trp Leu
        195                 200                 205

Asp Ile Ser Glu Gly Asp Leu Val Trp Ala Thr Ala Gly Pro Gly Trp
    210                 215                 220

Gln Lys Trp Val Trp Ser Pro Phe Leu Ala Val Leu Gly Ser Gly Ala
225                 230                 235                 240

Thr Gly Phe Ile Tyr His Gly Lys Phe Thr Pro Glu Thr Tyr Leu Arg
                245                 250                 255

Leu Ile Glu Arg His Gln Val Asn Val Leu Cys Cys Thr Pro Thr Glu
            260                 265                 270

Tyr Arg Phe Met Ala Lys Val Asn Asp Leu Ser Arg Phe Asp Leu Ser
        275                 280                 285
```

```
Ser Leu His Ser Ala Val Ser Ala Gly Glu Pro Leu Asn Arg Glu Val
    290                 295                 300

Ile Asp Thr Phe Lys Lys His Phe His Ile Ala Val Arg Asp Gly Tyr
305                 310                 315                 320

Gly Gln Thr Glu Ser Thr Leu Leu Val Gly Ile Leu Lys Gly Met Lys
                325                 330                 335

Ile Lys Pro Gly Ser Met Gly Lys Pro Thr Pro Gly Asn Leu Val Asp
            340                 345                 350

Ile Ile Asp Gly Asn Gly Lys Ser Cys Pro Pro Gly Glu Thr Gly Asp
        355                 360                 365

Ile Ala Val His Leu Ser Thr Pro Ala Leu Phe Lys Glu Tyr Tyr Lys
    370                 375                 380

Asp Gln Glu Arg Thr Leu Arg Gln Arg Arg Gly Asp Tyr Phe Ile Thr
385                 390                 395                 400

Gly Asp Lys Ala Arg Lys Asp Glu Asp Gly Tyr Phe Trp Phe Glu Ser
                405                 410                 415

Arg Asn Asp Asp Val Ile Ile Ser Ser Gly Tyr Thr Ile Gly Pro Phe
            420                 425                 430

Glu Val Glu Asp Ala Leu Ile Lys His Pro Glu Val Lys Glu Cys Ala
        435                 440                 445

Val Val Ala Ser Pro Asp Glu Ile Arg Gly Ser Ile Val Lys Ala Tyr
    450                 455                 460

Val Val Leu Lys Asp Pro Ser Arg Gly Asn Glu His Leu Thr Lys Glu
465                 470                 475                 480

Leu Gln Asp His Val Lys Ala Met Thr Ala Pro Tyr Lys Tyr Pro Arg
                485                 490                 495

Glu Ile Glu Phe Ile Glu Glu Leu Pro Lys Thr Pro Ser Ala Lys Ile
            500                 505                 510

Lys Arg Phe Glu Leu Arg Gln Arg Glu Ile Ala Leu Lys Thr Lys Ala
        515                 520                 525

Glu

<210> SEQ ID NO 39
<211> LENGTH: 1524
<212> TYPE: DNA
<213> ORGANISM: Bacillus licheniformis DSM 13
<220> FEATURE:
<221> NAME/KEY: gene
<222> LOCATION: (1)..(1524)
<223> OTHER INFORMATION: Lysine and/or arginine decarboxylase
      (E.C. 4.1.1.18 or E.C. 4.1.1.19, respectively), speA
<220> FEATURE:
<221> NAME/KEY: CDS
<222> LOCATION: (1)..(1521)

<400> SEQUENCE: 39 atg cag aat gtc ata tcg gca tcc ggc agc gcc tgg atg ccg aag aaa        48
Met Gln Asn Val Ile Ser Ala Ser Gly Ser Ala Trp Met Pro Lys Lys
1               5                   10                  15 ata gag aag atg act aaa gga tcg gtt tat atg aag aca cct tta tat       96
Ile Glu Lys Met Thr Lys Gly Ser Val Tyr Met Lys Thr Pro Leu Tyr
            20                  25                  30 aca gca ttg gtg aac cat gct gaa gga cat cat tat tct ttt cac gtt      144
Thr Ala Leu Val Asn His Ala Glu Gly His His Tyr Ser Phe His Val
        35                  40                  45 ccg gga cat cac aat gga gat gtc ttt ttt gat gaa gca aaa act ttt      192
Pro Gly His His Asn Gly Asp Val Phe Phe Asp Glu Ala Lys Thr Phe
    50                  55                  60
```

| | | |
|---|---|---|
| ttt gaa acg att ctc aaa gtg gat cta act gaa ctg aca gga ctg gat<br>Phe Glu Thr Ile Leu Lys Val Asp Leu Thr Glu Leu Thr Gly Leu Asp<br>65                   70                    75                 80 | 240 |
| gat tta cat gag cca tct ggc gtc atc aag gaa gca cag gat tta gtt<br>Asp Leu His Glu Pro Ser Gly Val Ile Lys Glu Ala Gln Asp Leu Val<br>              85                    90                    95 | 288 |
| tcg cgg ctt tac gga gcg gaa gaa agc ttt ttt ctc gtc aat ggt tcg<br>Ser Arg Leu Tyr Gly Ala Glu Glu Ser Phe Phe Leu Val Asn Gly Ser<br>           100                  105                110 | 336 |
| acc gtt ggg aat ctg gct atg atc ctg gct gtt tgt cag ccg ggt gat<br>Thr Val Gly Asn Leu Ala Met Ile Leu Ala Val Cys Gln Pro Gly Asp<br>        115                  120                125 | 384 |
| acg ata ctc gtt cag cgt aac tgc cat aag tct gta ttt cat gcg att<br>Thr Ile Leu Val Gln Arg Asn Cys His Lys Ser Val Phe His Ala Ile<br>130                  135                140 | 432 |
| gaa ctt tca ggc gcc cat ccg gtt ttt ttg aca ccg gaa att gat gag<br>Glu Leu Ser Gly Ala His Pro Val Phe Leu Thr Pro Glu Ile Asp Glu<br>145                  150                155                160 | 480 |
| gcg atg gct gtt ccc aca cat ata ctg tac gaa aca gtt gaa gat gca<br>Ala Met Ala Val Pro Thr His Ile Leu Tyr Glu Thr Val Glu Asp Ala<br>                  165                170                175 | 528 |
| att tca caa tat ccg cac gca aaa ggg atc gtg ttg aca tat cca aat<br>Ile Ser Gln Tyr Pro His Ala Lys Gly Ile Val Leu Thr Tyr Pro Asn<br>        180                  185                190 | 576 |
| tac tac ggc cat gca gtt gat ctg aag ccg atc ata gaa aag gcc cac<br>Tyr Tyr Gly His Ala Val Asp Leu Lys Pro Ile Ile Glu Lys Ala His<br>195                  200                205 | 624 |
| caa cac gat att tcc gtt tta gtc gac gag gct cac ggc gcc cat ttt<br>Gln His Asp Ile Ser Val Leu Val Asp Glu Ala His Gly Ala His Phe<br>        210                  215                220 | 672 |
| gtg ctg ggc cat cca ttt ccc cag tcg tcg ttg aaa gcg ggc gct gat<br>Val Leu Gly His Pro Phe Pro Gln Ser Ser Leu Lys Ala Gly Ala Asp<br>225                  230                235                240 | 720 |
| gcc gtc gtc cag tcc gcg cat aaa acg ctc ccg gcg atg acg atg ggg<br>Ala Val Val Gln Ser Ala His Lys Thr Leu Pro Ala Met Thr Met Gly<br>                  245                250                255 | 768 |
| tcc tat ctg cat ctt aac agc ggc agg atc aac agg gac aga ctg gca<br>Ser Tyr Leu His Leu Asn Ser Gly Arg Ile Asn Arg Asp Arg Leu Ala<br>        260                  265                270 | 816 |
| tac tat ctg tcc gtg ctt caa agc agc agt cct tcc tac cca att atg<br>Tyr Tyr Leu Ser Val Leu Gln Ser Ser Ser Pro Ser Tyr Pro Ile Met<br>275                  280                285 | 864 |
| gca tct ttg gat ata gct agg gca tac gcc gaa gat atc ttg aaa aca<br>Ala Ser Leu Asp Ile Ala Arg Ala Tyr Ala Glu Asp Ile Leu Lys Thr<br>        290                  295                300 | 912 |
| aat cga aca gcc gat att gag aaa gag ctc atc aat atg aga gaa gtc<br>Asn Arg Thr Ala Asp Ile Glu Lys Glu Leu Ile Asn Met Arg Glu Val<br>305                  310                315                320 | 960 |
| ttt tct caa ata aac gga gct gat att gtc gag ccg gct gat gcc cgt<br>Phe Ser Gln Ile Asn Gly Ala Asp Ile Val Glu Pro Ala Asp Ala Arg<br>                  325                330                335 | 1008 |
| atc cgg caa gat ccg ctt aag ctg tgt atc aga tca gcg tac ggc cac<br>Ile Arg Gln Asp Pro Leu Lys Leu Cys Ile Arg Ser Ala Tyr Gly His<br>        340                  345                350 | 1056 |
| tcc ggt ttt gaa ctg aaa tcc ata ttt gaa gca aac ggc atc cat cct<br>Ser Gly Phe Glu Leu Lys Ser Ile Phe Glu Ala Asn Gly Ile His Pro<br>355                  360                365 | 1104 |
| gaa ttg gca gat gaa agg caa gtc ctg ttg atc ctg ccg ctt gaa gga<br>Glu Leu Ala Asp Glu Arg Gln Val Leu Leu Ile Leu Pro Leu Glu Gly<br>370                  375                380 | 1152 |

```
aaa aat atg ccc gcg ccg gaa ctg atc agc aca atc agt aaa gac atg       1200
Lys Asn Met Pro Ala Pro Glu Leu Ile Ser Thr Ile Ser Lys Asp Met
385                 390                 395                 400 aaa gat aca gca gtt cga aat gat ctt cct gcc gga atc gga atc cct       1248
Lys Asp Thr Ala Val Arg Asn Asp Leu Pro Ala Gly Ile Gly Ile Pro
            405                 410                 415 tct gaa aaa gtc acg gct ttg cct tac cgg aaa agc aag ttg tct gcc       1296
Ser Glu Lys Val Thr Ala Leu Pro Tyr Arg Lys Ser Lys Leu Ser Ala
        420                 425                 430 ttc aaa aaa gaa tcg gtg cct ttt acc gaa gca gcg ggc aga ata agc       1344
Phe Lys Lys Glu Ser Val Pro Phe Thr Glu Ala Ala Gly Arg Ile Ser
    435                 440                 445 gcc gaa tcg gtc aca cct tat cct ccg ggc att ccg ttg atc atg gcg       1392
Ala Glu Ser Val Thr Pro Tyr Pro Pro Gly Ile Pro Leu Ile Met Ala
450                 455                 460 ggt gag aga ata aca aaa gag acg atc agc cgg ctg acg cgg ctc gtc       1440
Gly Glu Arg Ile Thr Lys Glu Thr Ile Ser Arg Leu Thr Arg Leu Val
465                 470                 475                 480 gat ctg aat gta cac att cag ggc agc aat cag ctc aaa caa aag caa       1488
Asp Leu Asn Val His Ile Gln Gly Ser Asn Gln Leu Lys Gln Lys Gln
                485                 490                 495 tta act gta tat ata gaa gag gag aaa tca tga acg                       1524
Leu Thr Val Tyr Ile Glu Glu Glu Lys Ser
            500                 505

<210> SEQ ID NO 40
<211> LENGTH: 506
<212> TYPE: PRT
<213> ORGANISM: Bacillus licheniformis DSM 13

<400> SEQUENCE: 40

Met Gln Asn Val Ile Ser Ala Ser Gly Ser Ala Trp Met Pro Lys Lys
1               5                   10                  15

Ile Glu Lys Met Thr Lys Gly Ser Val Tyr Met Lys Thr Pro Leu Tyr
            20                  25                  30

Thr Ala Leu Val Asn His Ala Glu Gly His His Tyr Ser Phe His Val
        35                  40                  45

Pro Gly His His Asn Gly Asp Val Phe Phe Asp Glu Ala Lys Thr Phe
    50                  55                  60

Phe Glu Thr Ile Leu Lys Val Asp Leu Thr Glu Leu Thr Gly Leu Asp
65                  70                  75                  80

Asp Leu His Glu Pro Ser Gly Val Ile Lys Glu Ala Gln Asp Leu Val
                85                  90                  95

Ser Arg Leu Tyr Gly Ala Glu Glu Ser Phe Phe Leu Val Asn Gly Ser
            100                 105                 110

Thr Val Gly Asn Leu Ala Met Ile Leu Ala Val Cys Gln Pro Gly Asp
        115                 120                 125

Thr Ile Leu Val Gln Arg Asn Cys His Lys Ser Val Phe His Ala Ile
    130                 135                 140

Glu Leu Ser Gly Ala His Pro Val Phe Leu Thr Pro Glu Ile Asp Glu
145                 150                 155                 160

Ala Met Ala Val Pro Thr His Ile Leu Tyr Glu Thr Val Glu Asp Ala
                165                 170                 175

Ile Ser Gln Tyr Pro His Ala Lys Gly Ile Val Leu Thr Tyr Pro Asn
            180                 185                 190

Tyr Tyr Gly His Ala Val Asp Leu Lys Pro Ile Ile Glu Lys Ala His
        195                 200                 205
```

```
Gln His Asp Ile Ser Val Leu Val Asp Glu Ala His Gly Ala His Phe
    210                 215                 220

Val Leu Gly His Pro Phe Pro Gln Ser Ser Leu Lys Ala Gly Ala Asp
225                 230                 235                 240

Ala Val Val Gln Ser Ala His Lys Thr Leu Pro Ala Met Thr Met Gly
                245                 250                 255

Ser Tyr Leu His Leu Asn Ser Gly Arg Ile Asn Arg Asp Arg Leu Ala
            260                 265                 270

Tyr Tyr Leu Ser Val Leu Gln Ser Ser Ser Pro Ser Tyr Pro Ile Met
        275                 280                 285

Ala Ser Leu Asp Ile Ala Arg Ala Tyr Ala Glu Asp Ile Leu Lys Thr
    290                 295                 300

Asn Arg Thr Ala Asp Ile Glu Lys Glu Leu Ile Asn Met Arg Glu Val
305                 310                 315                 320

Phe Ser Gln Ile Asn Gly Ala Asp Ile Val Glu Pro Ala Asp Ala Arg
                325                 330                 335

Ile Arg Gln Asp Pro Leu Lys Leu Cys Ile Arg Ser Ala Tyr Gly His
            340                 345                 350

Ser Gly Phe Glu Leu Lys Ser Ile Phe Glu Ala Asn Gly Ile His Pro
        355                 360                 365

Glu Leu Ala Asp Glu Arg Gln Val Leu Leu Ile Leu Pro Leu Glu Gly
    370                 375                 380

Lys Asn Met Pro Ala Pro Glu Leu Ile Ser Thr Ile Ser Lys Asp Met
385                 390                 395                 400

Lys Asp Thr Ala Val Arg Asn Asp Leu Pro Ala Gly Ile Gly Ile Pro
                405                 410                 415

Ser Glu Lys Val Thr Ala Leu Pro Tyr Arg Lys Ser Lys Leu Ser Ala
            420                 425                 430

Phe Lys Lys Glu Ser Val Pro Phe Thr Glu Ala Ala Gly Arg Ile Ser
        435                 440                 445

Ala Glu Ser Val Thr Pro Tyr Pro Pro Gly Ile Pro Leu Ile Met Ala
    450                 455                 460

Gly Glu Arg Ile Thr Lys Glu Thr Ile Ser Arg Leu Thr Arg Leu Val
465                 470                 475                 480

Asp Leu Asn Val His Ile Gln Gly Ser Asn Gln Leu Lys Gln Lys Gln
                485                 490                 495

Leu Thr Val Tyr Ile Glu Glu Glu Lys Ser
            500                 505

<210> SEQ ID NO 41
<211> LENGTH: 780
<212> TYPE: DNA
<213> ORGANISM: Bacillus licheniformis DSM 13
<220> FEATURE:
<221> NAME/KEY: gene
<222> LOCATION: (1)..(780)
<223> OTHER INFORMATION: probable enoyl-CoA hydratase (E.C. 4.2.1.17),
      ysiB
<220> FEATURE:
<221> NAME/KEY: CDS
<222> LOCATION: (1)..(777)

<400> SEQUENCE: 41 atg gca gca tta tca tac gcc gta gac ggc cat gtt gcg acg att acg      48
Met Ala Ala Leu Ser Tyr Ala Val Asp Gly His Val Ala Thr Ile Thr
1               5                   10                  15 att cag cac ccg ccg gca aat gcg cta tcg acg caa gtg ctt gaa gat      96
```

```
                Ile Gln His Pro Pro Ala Asn Ala Leu Ser Thr Gln Val Leu Glu Asp
                                20                  25                  30 ctt tcg gca tgc ctt gat gaa ctt tca gaa cgt cag gat gtc aga agc         144
Leu Ser Ala Cys Leu Asp Glu Leu Ser Glu Arg Gln Asp Val Arg Ser
             35                  40                  45 gtc gtt att cac ggg gaa gga aga ttt ttc tcg gca ggc gct gat att         192
Val Val Ile His Gly Glu Gly Arg Phe Phe Ser Ala Gly Ala Asp Ile
 50                  55                  60 aaa gag ttt aca tca ttg atg gac ggg tct gat tat gca aat ttg gct         240
Lys Glu Phe Thr Ser Leu Met Asp Gly Ser Asp Tyr Ala Asn Leu Ala
 65                  70                  75                  80 gat aag ggc cag cag att ttc gaa aaa gta gaa tct ttt cca aaa ccg         288
Asp Lys Gly Gln Gln Ile Phe Glu Lys Val Glu Ser Phe Pro Lys Pro
                 85                  90                  95 gtg atc gcc gcg att cac ggg gcc gct ctt gga ggc ggt ctt gag cta         336
Val Ile Ala Ala Ile His Gly Ala Ala Leu Gly Gly Gly Leu Glu Leu
             100                 105                 110 gcg atg gca tgc cac atc cgg att gcc gag gaa agc gca aag ctc ggc         384
Ala Met Ala Cys His Ile Arg Ile Ala Glu Glu Ser Ala Lys Leu Gly
         115                 120                 125 ctt ccc gaa ctg aat ctc gga atc att ccc ggc ttt gcg gga acg cag         432
Leu Pro Glu Leu Asn Leu Gly Ile Ile Pro Gly Phe Ala Gly Thr Gln
130                 135                 140 cgc ctt ccc aag tat gtg ggc acc gcc aaa gcg ctt gaa atg atc ggg         480
Arg Leu Pro Lys Tyr Val Gly Thr Ala Lys Ala Leu Glu Met Ile Gly
145                 150                 155                 160 aca tca gag ccg ata tcc ggc aag gaa gct ttt gaa tac ggt ctt gtc         528
Thr Ser Glu Pro Ile Ser Gly Lys Glu Ala Phe Glu Tyr Gly Leu Val
                 165                 170                 175 acg att ttg gcg gcg aat gaa gaa gaa gtg ctg caa aag gca aaa gag         576
Thr Ile Leu Ala Ala Asn Glu Glu Glu Val Leu Gln Lys Ala Lys Glu
             180                 185                 190 ctc gca caa aaa ttc gct gaa aaa agt ccg cag acg atg gct tat gtc         624
Leu Ala Gln Lys Phe Ala Glu Lys Ser Pro Gln Thr Met Ala Tyr Val
         195                 200                 205 att gaa ctc ctg aat tcg agc aaa gtg tat tcg tat gaa gga ggc ctc         672
Ile Glu Leu Leu Asn Ser Ser Lys Val Tyr Ser Tyr Glu Gly Gly Leu
210                 215                 220 aag cta gaa ggg aaa tac ttc ggc gaa gtg ttc caa tcc gag gat gcg         720
Lys Leu Glu Gly Lys Tyr Phe Gly Glu Val Phe Gln Ser Glu Asp Ala
225                 230                 235                 240 aag gaa ggg att cag gca ttt ctt gaa aag cgg aag ccg cat ttt aaa         768
Lys Glu Gly Ile Gln Ala Phe Leu Glu Lys Arg Lys Pro His Phe Lys
                 245                 250                 255 ggg aaa taa caa                                                         780
Gly Lys <210> SEQ ID NO 42
<211> LENGTH: 258
<212> TYPE: PRT
<213> ORGANISM: Bacillus licheniformis DSM 13

<400> SEQUENCE: 42

Met Ala Ala Leu Ser Tyr Ala Val Asp Gly His Val Ala Thr Ile Thr
 1               5                  10                  15

Ile Gln His Pro Pro Ala Asn Ala Leu Ser Thr Gln Val Leu Glu Asp
                20                  25                  30

Leu Ser Ala Cys Leu Asp Glu Leu Ser Glu Arg Gln Asp Val Arg Ser
             35                  40                  45
```

```
Val Val Ile His Gly Glu Gly Arg Phe Phe Ser Ala Gly Ala Asp Ile
    50              55                  60

Lys Glu Phe Thr Ser Leu Met Asp Gly Ser Asp Tyr Ala Asn Leu Ala
 65              70                  75                  80

Asp Lys Gly Gln Gln Ile Phe Glu Lys Val Glu Ser Phe Pro Lys Pro
                85                  90                  95

Val Ile Ala Ala Ile His Gly Ala Ala Leu Gly Gly Gly Leu Glu Leu
                100                 105                 110

Ala Met Ala Cys His Ile Arg Ile Ala Glu Gly Ser Lys Leu Gly
                115                 120                 125

Leu Pro Glu Leu Asn Leu Gly Ile Ile Pro Gly Phe Ala Gly Thr Gln
    130                 135                 140

Arg Leu Pro Lys Tyr Val Gly Thr Ala Lys Ala Leu Glu Met Ile Gly
145                 150                 155                 160

Thr Ser Glu Pro Ile Ser Gly Lys Glu Ala Phe Glu Tyr Gly Leu Val
                165                 170                 175

Thr Ile Leu Ala Ala Asn Glu Glu Val Leu Gln Lys Ala Lys Glu
                180                 185                 190

Leu Ala Gln Lys Phe Ala Glu Lys Ser Pro Gln Thr Met Ala Tyr Val
        195                 200                 205

Ile Glu Leu Leu Asn Ser Ser Lys Val Tyr Ser Tyr Glu Gly Gly Leu
    210                 215                 220

Lys Leu Glu Gly Lys Tyr Phe Gly Glu Val Phe Gln Ser Glu Asp Ala
225                 230                 235                 240

Lys Glu Gly Ile Gln Ala Phe Leu Glu Lys Arg Lys Pro His Phe Lys
                245                 250                 255

Gly Lys

<210> SEQ ID NO 43
<211> LENGTH: 2394
<212> TYPE: DNA
<213> ORGANISM: Bacillus licheniformis DSM 13
<220> FEATURE:
<221> NAME/KEY: gene
<222> LOCATION: (1)..(2394)
<223> OTHER INFORMATION: similar to 3-hydroxyacyl-CoA dehydrogenase
      (E.C. 1.1.1.35)
<220> FEATURE:
<221> NAME/KEY: CDS
<222> LOCATION: (1)..(2391)

<400> SEQUENCE: 43 atg gtc aag cat att cga aaa gcc gcc gtt atc ggt tcc ggt gtt atg      48
Met Val Lys His Ile Arg Lys Ala Ala Val Ile Gly Ser Gly Val Met
 1               5                  10                  15 ggt tcc ggc atc gcg gct cac tta gcc aat atc ggg att cct gta tta     96
Gly Ser Gly Ile Ala Ala His Leu Ala Asn Ile Gly Ile Pro Val Leu
                20                  25                  30 ctg ctc gat atg gtg ccg cat gaa tta aca gat gag gaa agg aaa aaa    144
Leu Leu Asp Met Val Pro His Glu Leu Thr Asp Glu Glu Arg Lys Lys
            35                  40                  45 ggc cgc acc ctt gaa gac ccg gat gtg cgc aat cgg ctg gca cgg aca    192
Gly Arg Thr Leu Glu Asp Pro Asp Val Arg Asn Arg Leu Ala Arg Thr
 50                  55                  60 gcc gta caa aag ctg cta aag caa aaa ccg gct ccg ctg act tca aag    240
Ala Val Gln Lys Leu Leu Lys Gln Lys Pro Ala Pro Leu Thr Ser Lys
 65                  70                  75                  80 aag aat atc agc cgt atc agc aca ggg aac atg gaa gac gat ttt gaa    288
Lys Asn Ile Ser Arg Ile Ser Thr Gly Asn Met Glu Asp Asp Phe Glu
```

```
                85                  90                  95
aag att aaa gat gcc gac tgg att att gaa gtt gtt gtc gaa aac ctg      336
Lys Ile Lys Asp Ala Asp Trp Ile Ile Glu Val Val Val Glu Asn Leu
            100                 105                 110 gag atc aaa aag caa gtg ttt tca aag gtc gat caa tac aga aaa caa      384
Glu Ile Lys Lys Gln Val Phe Ser Lys Val Asp Gln Tyr Arg Lys Gln
        115                 120                 125 gga agc atc gtc agc agc aac aca tca ggc atc tcc gtc agg cag atg      432
Gly Ser Ile Val Ser Ser Asn Thr Ser Gly Ile Ser Val Arg Gln Met
130                 135                 140 gct gag gga agg tcc gct gat ttt aaa aag cac ttt tta gga acg cac      480
Ala Glu Gly Arg Ser Ala Asp Phe Lys Lys His Phe Leu Gly Thr His
145                 150                 155                 160 ttc ttc aat ccg gcc cgc tat tta aag ctc ctt gag gtg att ccg att      528
Phe Phe Asn Pro Ala Arg Tyr Leu Lys Leu Leu Glu Val Ile Pro Ile
                165                 170                 175 gac gaa acg gag ccc gaa gtg ctg tcc ttt atg aag aaa ttc ggc gaa      576
Asp Glu Thr Glu Pro Glu Val Leu Ser Phe Met Lys Lys Phe Gly Glu
            180                 185                 190 gac gtt ctt ggc aaa ggg gtt gtt gaa gcg aaa gac acg cca aac ttt      624
Asp Val Leu Gly Lys Gly Val Val Glu Ala Lys Asp Thr Pro Asn Phe
        195                 200                 205 atc gcc aac cgc atc gga acc tac ggc ttg ctt gtg acg gtt cag gaa      672
Ile Ala Asn Arg Ile Gly Thr Tyr Gly Leu Leu Val Thr Val Gln Glu
210                 215                 220 atg ctg aaa ggc ggc tac acg ata ggc gaa gtc gat tcg att aca ggt      720
Met Leu Lys Gly Gly Tyr Thr Ile Gly Glu Val Asp Ser Ile Thr Gly
225                 230                 235                 240 ccg ctg atc gga cgc ccg aaa agc gcg acc ttc aga acg ctc gat gtc      768
Pro Leu Ile Gly Arg Pro Lys Ser Ala Thr Phe Arg Thr Leu Asp Val
                245                 250                 255 gtc ggc ctt gat aca ttt tca cac gtt gcc aaa aat gtc tat aac caa      816
Val Gly Leu Asp Thr Phe Ser His Val Ala Lys Asn Val Tyr Asn Gln
            260                 265                 270 gtc acg ggc gaa gaa aaa aac gtt ttc cgg ctc cct gaa ttt att gaa      864
Val Thr Gly Glu Glu Lys Asn Val Phe Arg Leu Pro Glu Phe Ile Glu
        275                 280                 285 caa atg ctc gaa aaa ggc tgg atc ggg agc aaa gcg aaa caa ggt ttt      912
Gln Met Leu Glu Lys Gly Trp Ile Gly Ser Lys Ala Lys Gln Gly Phe
290                 295                 300 tac aaa aaa gaa gga aaa gac atc ctt gag ctc gat ccg atg acg atg      960
Tyr Lys Lys Glu Gly Lys Asp Ile Leu Glu Leu Asp Pro Met Thr Met
305                 310                 315                 320 acc tac agc gcg cgt caa aca tta aaa aca tcg gga ctg gaa gcg gcc     1008
Thr Tyr Ser Ala Arg Gln Thr Leu Lys Thr Ser Gly Leu Glu Ala Ala
                325                 330                 335 aag caa atg aaa ggc gca gga gcg aga ttg aaa gcg ctt gtt tat tcc     1056
Lys Gln Met Lys Gly Ala Gly Ala Arg Leu Lys Ala Leu Val Tyr Ser
            340                 345                 350 gat gac agg gcg gga agc ctc ctt tgg aag att aca gct ccg acg ctt     1104
Asp Asp Arg Ala Gly Ser Leu Leu Trp Lys Ile Thr Ala Pro Thr Leu
        355                 360                 365 gta tat tcg gcg gag ctg aca ggg gaa atc gcc gac agc ata acg gcg     1152
Val Tyr Ser Ala Glu Leu Thr Gly Glu Ile Ala Asp Ser Ile Thr Ala
370                 375                 380 gtt gat cag gcg atg aaa tgg gga ttc ggc tgg tcg gaa ggg ccg ttt     1200
Val Asp Gln Ala Met Lys Trp Gly Phe Gly Trp Ser Glu Gly Pro Phe
385                 390                 395                 400 gaa atg tgg gac agc atc ggt gtg aaa agc tcg gtg caa aag ctt gaa     1248
Glu Met Trp Asp Ser Ile Gly Val Lys Ser Ser Val Gln Lys Leu Glu
```

```
Glu Met Trp Asp Ser Ile Gly Val Lys Ser Val Gln Lys Leu Glu
            405                 410                 415 gca gag ggc tgg aag gtc gcg gac tgg gtg aag gaa atg ctc gca aaa       1296
Ala Glu Gly Trp Lys Val Ala Asp Trp Val Lys Glu Met Leu Ala Lys
            420                 425                 430 gga cat gaa acc ttc tac ctt aag gaa aac gga aag acg ttc tac tac       1344
Gly His Glu Thr Phe Tyr Leu Lys Glu Asn Gly Lys Thr Phe Tyr Tyr
            435                 440                 445 tgt ttt gaa agc ggc gaa tac agg gcg ctt caa gaa aac aag aaa acg       1392
Cys Phe Glu Ser Gly Glu Tyr Arg Ala Leu Gln Glu Asn Lys Lys Thr
            450                 455                 460 atc cat ttg tcg tca ctc aaa gaa aca aaa ggc gtc atc aag aaa aac       1440
Ile His Leu Ser Ser Leu Lys Glu Thr Lys Gly Val Ile Lys Lys Asn
465                 470                 475                 480 agc ggg gca agt ttg atc gat tta ggc gat gat gtc gca ctg ctc gaa       1488
Ser Gly Ala Ser Leu Ile Asp Leu Gly Asp Asp Val Ala Leu Leu Glu
                    485                 490                 495 ttt cac tcg aaa agc aac gca atc ggc ctg gac atc att caa atg ctg       1536
Phe His Ser Lys Ser Asn Ala Ile Gly Leu Asp Ile Ile Gln Met Leu
                500                 505                 510 aaa ttt gct ctc gag gaa gta gac gcc aac tat aaa ggg ctt gtg atc       1584
Lys Phe Ala Leu Glu Glu Val Asp Ala Asn Tyr Lys Gly Leu Val Ile
            515                 520                 525 ggc aac cag ggc aaa aat ttc tgc gtc gga gcc aat ctc gcg atg atg       1632
Gly Asn Gln Gly Lys Asn Phe Cys Val Gly Ala Asn Leu Ala Met Met
            530                 535                 540 ctg atg gaa gct caa gac gac aac tat atg gaa att gac atg atc atc       1680
Leu Met Glu Ala Gln Asp Asp Asn Tyr Met Glu Ile Asp Met Ile Ile
545                 550                 555                 560 cgt cag ttc caa gag acg atg atg aaa gtg aaa tac agt tcc aag ccg       1728
Arg Gln Phe Gln Glu Thr Met Met Lys Val Lys Tyr Ser Ser Lys Pro
                565                 570                 575 gtc gtc gct gct ccg ttc ggc atg acg ctt ggc ggg ggg act gag cta       1776
Val Val Ala Ala Pro Phe Gly Met Thr Leu Gly Gly Gly Thr Glu Leu
                580                 585                 590 tgc ctg cct gct gcc cgt gtt caa gcc tca agc gaa tca tac atg ggc       1824
Cys Leu Pro Ala Ala Arg Val Gln Ala Ser Ser Glu Ser Tyr Met Gly
            595                 600                 605 ctc gtt gaa aca ggc gtc ggt ctg att ccg ggc ggc gga ggc aat aaa       1872
Leu Val Glu Thr Gly Val Gly Leu Ile Pro Gly Gly Gly Gly Asn Lys
            610                 615                 620 gag ctt tat tta aat tac ttg aaa ggg ctg cct gaa ggc gtt aaa ccg       1920
Glu Leu Tyr Leu Asn Tyr Leu Lys Gly Leu Pro Glu Gly Val Lys Pro
625                 630                 635                 640 gat atc cag gag gcc gcc atc aag acg ttt gag aca att gcc ctt gca       1968
Asp Ile Gln Glu Ala Ala Ile Lys Thr Phe Glu Thr Ile Ala Leu Ala
                645                 650                 655 aaa acg tcg act tcg gct caa gaa gcg aaa gaa ctg aac atc tta acc       2016
Lys Thr Ser Thr Ser Ala Gln Glu Ala Lys Glu Leu Asn Ile Leu Thr
            660                 665                 670 gca gag gat caa atc agc atc aat cag gat cac ttg tta tac gat gcc       2064
Ala Glu Asp Gln Ile Ser Ile Asn Gln Asp His Leu Leu Tyr Asp Ala
            675                 680                 685 aaa aaa ctc gtc ctg aca ctt tcc gaa agc ggc tac cgt ccg ccg gtg       2112
Lys Lys Leu Val Leu Thr Leu Ser Glu Ser Gly Tyr Arg Pro Pro Val
            690                 695                 700 aaa gag aaa gtt ccg gtg acg ggc gaa acc ggc tat gcg gcg ctc ctg       2160
Lys Glu Lys Val Pro Val Thr Gly Glu Thr Gly Tyr Ala Ala Leu Leu
705                 710                 715                 720
```

```
ctc ggt gct gaa tcg tta aaa ctt tcc ggc gcc atc tct gaa cac gac      2208
Leu Gly Ala Glu Ser Leu Lys Leu Ser Gly Ala Ile Ser Glu His Asp
            725                 730                 735 atg aag att gcg aaa aaa ctg gcg ttt gtc atc gcg ggc ggc cga gtt      2256
Met Lys Ile Ala Lys Lys Leu Ala Phe Val Ile Ala Gly Gly Arg Val
        740                 745                 750 cca ttc ggc gcc gaa gta acg gaa gaa tac ttg ctc aat ttg gaa aga      2304
Pro Phe Gly Ala Glu Val Thr Glu Glu Tyr Leu Leu Asn Leu Glu Arg
    755                 760                 765 gaa gcg ttt ctg agc ctt gtg agc gaa ccg aaa tcg cag gcg aga atg      2352
Glu Ala Phe Leu Ser Leu Val Ser Glu Pro Lys Ser Gln Ala Arg Met
770                 775                 780 cag cat atg ctt gtg aaa ggc aaa cct ttg cgt aat tag gag              2394
Gln His Met Leu Val Lys Gly Lys Pro Leu Arg Asn
785                 790                 795

<210> SEQ ID NO 44
<211> LENGTH: 796
<212> TYPE: PRT
<213> ORGANISM: Bacillus licheniformis DSM 13

<400> SEQUENCE: 44

Met Val Lys His Ile Arg Lys Ala Ala Val Ile Gly Ser Gly Val Met
1               5                   10                  15

Gly Ser Gly Ile Ala Ala His Leu Ala Asn Ile Gly Ile Pro Val Leu
            20                  25                  30

Leu Leu Asp Met Val Pro His Glu Leu Thr Asp Glu Glu Arg Lys Lys
        35                  40                  45

Gly Arg Thr Leu Glu Asp Pro Asp Val Arg Asn Arg Leu Ala Arg Thr
    50                  55                  60

Ala Val Gln Lys Leu Leu Lys Gln Lys Pro Ala Pro Leu Thr Ser Lys
65                  70                  75                  80

Lys Asn Ile Ser Arg Ile Ser Thr Gly Asn Met Glu Asp Asp Phe Glu
                85                  90                  95

Lys Ile Lys Asp Ala Asp Trp Ile Ile Glu Val Val Glu Asn Leu
            100                 105                 110

Glu Ile Lys Lys Gln Val Phe Ser Lys Val Asp Gln Tyr Arg Lys Gln
        115                 120                 125

Gly Ser Ile Val Ser Ser Asn Thr Ser Gly Ile Ser Val Arg Gln Met
    130                 135                 140

Ala Glu Gly Arg Ser Ala Asp Phe Lys Lys His Phe Leu Gly Thr His
145                 150                 155                 160

Phe Phe Asn Pro Ala Arg Tyr Leu Lys Leu Leu Glu Val Ile Pro Ile
                165                 170                 175

Asp Glu Thr Glu Pro Glu Val Leu Ser Phe Met Lys Lys Phe Gly Glu
            180                 185                 190

Asp Val Leu Gly Lys Gly Val Val Glu Ala Lys Asp Thr Pro Asn Phe
        195                 200                 205

Ile Ala Asn Arg Ile Gly Thr Tyr Gly Leu Leu Val Thr Val Gln Glu
    210                 215                 220

Met Leu Lys Gly Gly Tyr Thr Ile Gly Glu Val Asp Ser Ile Thr Gly
225                 230                 235                 240

Pro Leu Ile Gly Arg Pro Lys Ser Ala Thr Phe Arg Thr Leu Asp Val
                245                 250                 255

Val Gly Leu Asp Thr Phe Ser His Val Ala Lys Asn Val Tyr Asn Gln
            260                 265                 270
```

```
Val Thr Gly Glu Glu Lys Asn Val Phe Arg Leu Pro Glu Phe Ile Glu
            275                 280                 285

Gln Met Leu Glu Lys Gly Trp Ile Gly Ser Lys Ala Lys Gln Gly Phe
        290                 295                 300

Tyr Lys Lys Glu Gly Lys Asp Ile Leu Glu Leu Asp Pro Met Thr Met
305                 310                 315                 320

Thr Tyr Ser Ala Arg Gln Thr Leu Lys Thr Ser Gly Leu Glu Ala Ala
                325                 330                 335

Lys Gln Met Lys Gly Ala Gly Ala Arg Leu Lys Ala Leu Val Tyr Ser
            340                 345                 350

Asp Asp Arg Ala Gly Ser Leu Leu Trp Lys Ile Thr Ala Pro Thr Leu
        355                 360                 365

Val Tyr Ser Ala Glu Leu Thr Gly Glu Ile Ala Asp Ser Ile Thr Ala
    370                 375                 380

Val Asp Gln Ala Met Lys Trp Gly Phe Gly Trp Ser Glu Gly Pro Phe
385                 390                 395                 400

Glu Met Trp Asp Ser Ile Gly Val Lys Ser Val Gln Lys Leu Glu
                405                 410                 415

Ala Glu Gly Trp Lys Val Ala Asp Trp Val Lys Glu Met Leu Ala Lys
            420                 425                 430

Gly His Glu Thr Phe Tyr Leu Lys Glu Asn Gly Lys Thr Phe Tyr Tyr
        435                 440                 445

Cys Phe Glu Ser Gly Glu Tyr Arg Ala Leu Gln Glu Asn Lys Lys Thr
    450                 455                 460

Ile His Leu Ser Ser Leu Lys Glu Thr Lys Gly Val Ile Lys Lys Asn
465                 470                 475                 480

Ser Gly Ala Ser Leu Ile Asp Leu Gly Asp Asp Val Ala Leu Leu Glu
                485                 490                 495

Phe His Ser Lys Ser Asn Ala Ile Gly Leu Asp Ile Ile Gln Met Leu
            500                 505                 510

Lys Phe Ala Leu Glu Glu Val Asp Ala Asn Tyr Lys Gly Leu Val Ile
        515                 520                 525

Gly Asn Gln Gly Lys Asn Phe Cys Val Gly Ala Asn Leu Ala Met Met
    530                 535                 540

Leu Met Glu Ala Gln Asp Asp Asn Tyr Met Glu Ile Asp Met Ile Ile
545                 550                 555                 560

Arg Gln Phe Gln Glu Thr Met Met Lys Val Lys Tyr Ser Ser Lys Pro
                565                 570                 575

Val Val Ala Ala Pro Phe Gly Met Thr Leu Gly Gly Gly Thr Glu Leu
            580                 585                 590

Cys Leu Pro Ala Ala Arg Val Gln Ala Ser Ser Glu Ser Tyr Met Gly
        595                 600                 605

Leu Val Glu Thr Gly Val Gly Leu Ile Pro Gly Gly Gly Asn Lys
    610                 615                 620

Glu Leu Tyr Leu Asn Tyr Leu Lys Gly Leu Pro Glu Gly Val Lys Pro
625                 630                 635                 640

Asp Ile Gln Glu Ala Ala Ile Lys Thr Phe Glu Thr Ile Ala Leu Ala
                645                 650                 655

Lys Thr Ser Thr Ser Ala Gln Glu Ala Lys Glu Leu Asn Ile Leu Thr
            660                 665                 670

Ala Glu Asp Gln Ile Ser Ile Asn Gln Asp His Leu Leu Tyr Asp Ala
        675                 680                 685

Lys Lys Leu Val Leu Thr Leu Ser Glu Ser Gly Tyr Arg Pro Pro Val
```

```
                  690                 695                 700
Lys Glu Lys Val Pro Val Thr Gly Glu Thr Gly Tyr Ala Ala Leu Leu
705                     710                 715                 720

Leu Gly Ala Glu Ser Leu Lys Leu Ser Gly Ala Ile Ser Glu His Asp
                725                 730                 735

Met Lys Ile Ala Lys Lys Leu Ala Phe Val Ile Ala Gly Gly Arg Val
                740                 745                 750

Pro Phe Gly Ala Glu Val Thr Glu Glu Tyr Leu Leu Asn Leu Glu Arg
            755                 760                 765

Glu Ala Phe Leu Ser Leu Val Ser Glu Pro Lys Ser Gln Ala Arg Met
        770                 775                 780

Gln His Met Leu Val Lys Gly Lys Pro Leu Arg Asn
785                 790                 795

<210> SEQ ID NO 45
<211> LENGTH: 2838
<212> TYPE: DNA
<213> ORGANISM: Bacillus licheniformis DSM 13
<220> FEATURE:
<221> NAME/KEY: gene
<222> LOCATION: (1)..(2838)
<223> OTHER INFORMATION: 2-oxoglutarate dehydrogenase E1 component
      (E.C. 1.2.4.2)
<220> FEATURE:
<221> NAME/KEY: CDS
<222> LOCATION: (1)..(2835)

<400> SEQUENCE: 45 atg ttt caa aat agt atg aaa caa aga atg act tgg gaa gaa ttt cac       48
Met Phe Gln Asn Ser Met Lys Gln Arg Met Thr Trp Glu Glu Phe His
1               5                   10                  15 ggt ccg aac ctc ggc tat gtg ctg gag ctt tac gat cag tac gtc aag       96
Gly Pro Asn Leu Gly Tyr Val Leu Glu Leu Tyr Asp Gln Tyr Val Lys
            20                  25                  30 gat cca gaa agc ttg gat gct gat tta aaa gag atg ttt gac gaa ctt      144
Asp Pro Glu Ser Leu Asp Ala Asp Leu Lys Glu Met Phe Asp Glu Leu
        35                  40                  45 gga gct ccc ccg ggc gat att agg gcc gcc tct caa aaa aac gaa gag      192
Gly Ala Pro Pro Gly Asp Ile Arg Ala Ala Ser Gln Lys Asn Glu Glu
    50                  55                  60 gca gat ttc acg gct gga tct att caa aaa atc gca tca gcg gta aaa      240
Ala Asp Phe Thr Ala Gly Ser Ile Gln Lys Ile Ala Ser Ala Val Lys
65                  70                  75                  80 ctt gca gaa gat att aga acc tat ggc cat tta aac gct tcc gtc aat      288
Leu Ala Glu Asp Ile Arg Thr Tyr Gly His Leu Asn Ala Ser Val Asn
                85                  90                  95 cca ctg aga aaa aca caa gag aaa cag gag ctt ttt cct ctt gct gag      336
Pro Leu Arg Lys Thr Gln Glu Lys Gln Glu Leu Phe Pro Leu Ala Glu
            100                 105                 110 tac ggg tta act gag cag gat gtg aaa aaa atc ccg gcg tct gtc ata      384
Tyr Gly Leu Thr Glu Gln Asp Val Lys Lys Ile Pro Ala Ser Val Ile
        115                 120                 125 tgc aaa gat gcc cct aaa gaa gta acg aac ggt tta gaa gcc atc cag      432
Cys Lys Asp Ala Pro Lys Glu Val Thr Asn Gly Leu Glu Ala Ile Gln
    130                 135                 140 tac tta aga aac aca tac aaa aaa tcg att tct ttt gaa ttt gac cat      480
Tyr Leu Arg Asn Thr Tyr Lys Lys Ser Ile Ser Phe Glu Phe Asp His
145                 150                 155                 160 gtg cac att ttt gaa gag cgc aac tgg ctg atg aaa aag atc gaa tcc      528
Val His Ile Phe Glu Glu Arg Asn Trp Leu Met Lys Lys Ile Glu Ser
                165                 170                 175
```

| | | |
|---|---|---|
| ggg gaa tta ttc acc ccg aaa tcg aaa gaa aaa ctg gta gaa gtt tta<br>Gly Glu Leu Phe Thr Pro Lys Ser Lys Glu Lys Leu Val Glu Val Leu<br>180 185 190 | | 576 |
| aga agg ctt aca gaa gtg gaa agc ctt gaa cag ttt ctc cac aaa acc<br>Arg Arg Leu Thr Glu Val Glu Ser Leu Glu Gln Phe Leu His Lys Thr<br>195 200 205 | | 624 |
| ttt gtc ggg caa aaa cgc ttt tca ata gaa gga ctt gat gcg ctt gtg<br>Phe Val Gly Gln Lys Arg Phe Ser Ile Glu Gly Leu Asp Ala Leu Val<br>210 215 220 | | 672 |
| ccc atg ctg gat gat att atc gcc aag tcc gtt tcg gca ggt acg aca<br>Pro Met Leu Asp Asp Ile Ile Ala Lys Ser Val Ser Ala Gly Thr Thr<br>225 230 235 240 | | 720 |
| aac gtc aat atc gga atg gcg cac agg ggc cgc ctg aat gtt ctt gcg<br>Asn Val Asn Ile Gly Met Ala His Arg Gly Arg Leu Asn Val Leu Ala<br>245 250 255 | | 768 |
| cat gtg ctc gga aaa cct tat gaa atc att ttt tct gaa ttc cag cat<br>His Val Leu Gly Lys Pro Tyr Glu Ile Ile Phe Ser Glu Phe Gln His<br>260 265 270 | | 816 |
| gcg ccg aac aaa gat ctc gtt ccg tcg gaa ggt tcg acc ggg atc aat<br>Ala Pro Asn Lys Asp Leu Val Pro Ser Glu Gly Ser Thr Gly Ile Asn<br>275 280 285 | | 864 |
| tac ggc tgg acg ggc gac gta aaa tac cac ctc ggc gcc aac cgc cag<br>Tyr Gly Trp Thr Gly Asp Val Lys Tyr His Leu Gly Ala Asn Arg Gln<br>290 295 300 | | 912 |
| att cag gat gag cat acg aaa acg gcg cgc att gcg ctc gcg aac aat<br>Ile Gln Asp Glu His Thr Lys Thr Ala Arg Ile Ala Leu Ala Asn Asn<br>305 310 315 320 | | 960 |
| ccg agc cac ctt gag ttc atc gat ccg atc gtt gag gga tcg aca aga<br>Pro Ser His Leu Glu Phe Ile Asp Pro Ile Val Glu Gly Ser Thr Arg<br>325 330 335 | | 1008 |
| gcc gcc cag gaa acg aga acg gag agc ggc tat ccg gtt caa gac gtc<br>Ala Ala Gln Glu Thr Arg Thr Glu Ser Gly Tyr Pro Val Gln Asp Val<br>340 345 350 | | 1056 |
| aaa aaa tcg atg gcg att ctg att cac ggc gat gcg gca ttc cca ggg<br>Lys Lys Ser Met Ala Ile Leu Ile His Gly Asp Ala Ala Phe Pro Gly<br>355 360 365 | | 1104 |
| gaa ggc att gtc gcg gaa acg ctg aat tta agc cag ctt aaa ggg tat<br>Glu Gly Ile Val Ala Glu Thr Leu Asn Leu Ser Gln Leu Lys Gly Tyr<br>370 375 380 | | 1152 |
| caa gtg ggc gga gcg att cac att atc gcc aat aac atg atc ggc ttt<br>Gln Val Gly Gly Ala Ile His Ile Ile Ala Asn Asn Met Ile Gly Phe<br>385 390 395 400 | | 1200 |
| acg acg gaa agc aat gag tca aga tcg acg aaa tat gca agc gac ctt<br>Thr Thr Glu Ser Asn Glu Ser Arg Ser Thr Lys Tyr Ala Ser Asp Leu<br>405 410 415 | | 1248 |
| gcg aaa ggt ttt gaa att ccg atc gtc cac gtc aat gct gat gat ccc<br>Ala Lys Gly Phe Glu Ile Pro Ile Val His Val Asn Ala Asp Asp Pro<br>420 425 430 | | 1296 |
| gaa gca tgt ctt tca gcg gtt cag ctc gct gtt gaa tac cgc atg act<br>Glu Ala Cys Leu Ser Ala Val Gln Leu Ala Val Glu Tyr Arg Met Thr<br>435 440 445 | | 1344 |
| ttc aac aaa gac ttt ttg atc gat ctg atc ggc tac cgc cgt ttt ggc<br>Phe Asn Lys Asp Phe Leu Ile Asp Leu Ile Gly Tyr Arg Arg Phe Gly<br>450 455 460 | | 1392 |
| cac aat gaa atg gat gag ccg tcc gca acg cag ccg atg ctg tat gat<br>His Asn Glu Met Asp Glu Pro Ser Ala Thr Gln Pro Met Leu Tyr Asp<br>465 470 475 480 | | 1440 |
| gcg gtc aga aag cat ccg acc gtc aaa aac atc ttt gct gaa aag ctg<br>Ala Val Arg Lys His Pro Thr Val Lys Asn Ile Phe Ala Glu Lys Leu | | 1488 |

-continued

```
                    485                 490                 495
att cat aaa ggg atc gtc gat aaa gaa acc gtc ggc aaa atc aag gac      1536
Ile His Lys Gly Ile Val Asp Lys Glu Thr Val Gly Lys Ile Lys Asp
            500                 505                 510 gct gtc cag aag cgt tta gaa gaa gcc tat cgc aaa gtg ccg gcc aaa      1584
Ala Val Gln Lys Arg Leu Glu Glu Ala Tyr Arg Lys Val Pro Ala Lys
        515                 520                 525 aag gaa gac atg acg cat gaa atc gta ctt cca gag ccg gtc tcc aac      1632
Lys Glu Asp Met Thr His Glu Ile Val Leu Pro Glu Pro Val Ser Asn
    530                 535                 540 ggt ttt cct gat gtt gac aca tcg gtt gat ttt gaa act ttg cgc aaa      1680
Gly Phe Pro Asp Val Asp Thr Ser Val Asp Phe Glu Thr Leu Arg Lys
545                 550                 555                 560 atc aat cag gag ctt gtt tca tgg ccg gaa aac ttc aac gtt ttc gat      1728
Ile Asn Gln Glu Leu Val Ser Trp Pro Glu Asn Phe Asn Val Phe Asp
                565                 570                 575 aag cta aaa cga atc ctt gaa agg cgc gcc aaa gct ttc gaa gat gac      1776
Lys Leu Lys Arg Ile Leu Glu Arg Arg Ala Lys Ala Phe Glu Asp Asp
            580                 585                 590 cga aaa gtc gac tgg tcg ctt gca gag gcg atg gcg ttt gcg tcg att      1824
Arg Lys Val Asp Trp Ser Leu Ala Glu Ala Met Ala Phe Ala Ser Ile
        595                 600                 605 ttg aaa gac ggt acg ccg cta agg ctg acc ggg cag gat tca gaa cgc      1872
Leu Lys Asp Gly Thr Pro Leu Arg Leu Thr Gly Gln Asp Ser Glu Arg
    610                 615                 620 ggc aca ttc gca cac cgc aac ctt gtc ctt cac gac agc aag aca ggg      1920
Gly Thr Phe Ala His Arg Asn Leu Val Leu His Asp Ser Lys Thr Gly
625                 630                 635                 640 gac gaa ttc atc gcg ctg cat cac ctt gcc gat acg aaa gcg tca ttt      1968
Asp Glu Phe Ile Ala Leu His His Leu Ala Asp Thr Lys Ala Ser Phe
                645                 650                 655 gcg gtt cac aac agc ccg ctt tct gaa ggg tcc gtc ctc ggc ttc gaa      2016
Ala Val His Asn Ser Pro Leu Ser Glu Gly Ser Val Leu Gly Phe Glu
            660                 665                 670 tac ggc tat aac gtg tct tcg ccg gaa acg atg gtg atc tgg gaa gcg      2064
Tyr Gly Tyr Asn Val Ser Ser Pro Glu Thr Met Val Ile Trp Glu Ala
        675                 680                 685 cag ttt gga gat ttt gca aat gcg gcg caa gtt tac ttt gac cag ttc      2112
Gln Phe Gly Asp Phe Ala Asn Ala Ala Gln Val Tyr Phe Asp Gln Phe
    690                 695                 700 att tct gca gga aga gcg aag tgg ggt caa aaa tca ggg ctg gtt gtt      2160
Ile Ser Ala Gly Arg Ala Lys Trp Gly Gln Lys Ser Gly Leu Val Val
705                 710                 715                 720 ctc ttg ccg cac ggc tat gaa ggg cag ggg cct gag cat tca agc gga      2208
Leu Leu Pro His Gly Tyr Glu Gly Gln Gly Pro Glu His Ser Ser Gly
                725                 730                 735 aga aca gag cga ttc ctt caa ttg gcg gcg gaa aac aac tgg act gtc      2256
Arg Thr Glu Arg Phe Leu Gln Leu Ala Ala Glu Asn Asn Trp Thr Val
            740                 745                 750 gcc aac ctg acg agc gct gcc caa tac ttt cat att tta aga agg cag      2304
Ala Asn Leu Thr Ser Ala Ala Gln Tyr Phe His Ile Leu Arg Arg Gln
        755                 760                 765 gcg aag atg ctc ctt cgc gag gag atc cgc ccg ctg atc atc atg acg      2352
Ala Lys Met Leu Leu Arg Glu Glu Ile Arg Pro Leu Ile Ile Met Thr
    770                 775                 780 ccg aaa agc ctg ctg aga aat ccg aat acc gtg tca gaa gtg cag gag      2400
Pro Lys Ser Leu Leu Arg Asn Pro Asn Thr Val Ser Glu Val Gln Glu
785                 790                 795                 800 ctc agt aac agc agc ttt aag ccg gtc tat gaa atg tca gga ctt tcc      2448
```

```
Leu Ser Asn Ser Ser Phe Lys Pro Val Tyr Glu Met Ser Gly Leu Ser
            805                 810                 815 cat caa tat gac aaa gtg acg cgc ctc gtc ctt tca agc ggg aaa gtt    2496
His Gln Tyr Asp Lys Val Thr Arg Leu Val Leu Ser Ser Gly Lys Val
        820                 825                 830 tcg att gac atc agc gac cat ttc aat aaa atg gaa ggt gaa aag gat    2544
Ser Ile Asp Ile Ser Asp His Phe Asn Lys Met Glu Gly Glu Lys Asp
835                 840                 845 tgg ctg cac att gca cgg gtt gaa gag ctg tat cct ttc cct gca aag    2592
Trp Leu His Ile Ala Arg Val Glu Glu Leu Tyr Pro Phe Pro Ala Lys
    850                 855                 860 cat att aaa gcg atc ttc agc aaa ctt ccg aat ttg gag gag atc gtc    2640
His Ile Lys Ala Ile Phe Ser Lys Leu Pro Asn Leu Glu Glu Ile Val
865                 870                 875                 880 tgg gta cag gaa gaa ccg caa aat atg ggc gca tgg aac tat atc gag    2688
Trp Val Gln Glu Glu Pro Gln Asn Met Gly Ala Trp Asn Tyr Ile Glu
            885                 890                 895 cct tat tta aga gag gta gct cca aag gac gtg aag gtc cgc tat att    2736
Pro Tyr Leu Arg Glu Val Ala Pro Lys Asp Val Lys Val Arg Tyr Ile
        900                 905                 910 ggc aga aga aga cgt tca agt ccg gca gaa ggg gat ccg acg gtt cat    2784
Gly Arg Arg Arg Arg Ser Ser Pro Ala Glu Gly Asp Pro Thr Val His
    915                 920                 925 aaa aag gaa cag gaa cgc att gta tct gat agc ttg act cgc aaa aat    2832
Lys Lys Glu Gln Glu Arg Ile Val Ser Asp Ser Leu Thr Arg Lys Asn
930                 935                 940 taa ggg                                                            2838

<210> SEQ ID NO 46
<211> LENGTH: 944
<212> TYPE: PRT
<213> ORGANISM: Bacillus licheniformis DSM 13

<400> SEQUENCE: 46

Met Phe Gln Asn Ser Met Lys Gln Arg Met Thr Trp Glu Glu Phe His
1               5                   10                  15

Gly Pro Asn Leu Gly Tyr Val Leu Glu Leu Tyr Asp Gln Tyr Val Lys
            20                  25                  30

Asp Pro Glu Ser Leu Asp Ala Asp Leu Lys Glu Met Phe Asp Glu Leu
        35                  40                  45

Gly Ala Pro Pro Gly Asp Ile Arg Ala Ala Ser Gln Lys Asn Glu Glu
    50                  55                  60

Ala Asp Phe Thr Ala Gly Ser Ile Gln Lys Ile Ala Ser Ala Val Lys
65                  70                  75                  80

Leu Ala Glu Asp Ile Arg Thr Tyr Gly His Leu Asn Ala Ser Val Asn
                85                  90                  95

Pro Leu Arg Lys Thr Gln Glu Lys Gln Glu Leu Phe Pro Leu Ala Glu
            100                 105                 110

Tyr Gly Leu Thr Glu Gln Asp Val Lys Lys Ile Pro Ala Ser Val Ile
        115                 120                 125

Cys Lys Asp Ala Pro Lys Glu Val Thr Asn Gly Leu Glu Ala Ile Gln
    130                 135                 140

Tyr Leu Arg Asn Thr Tyr Lys Lys Ser Ile Ser Phe Glu Phe Asp His
145                 150                 155                 160

Val His Ile Phe Glu Glu Arg Asn Trp Leu Met Lys Lys Ile Glu Ser
                165                 170                 175

Gly Glu Leu Phe Thr Pro Lys Ser Lys Glu Lys Leu Val Glu Val Leu
```

-continued

```
            180                 185                 190
Arg Arg Leu Thr Glu Val Glu Ser Leu Glu Gln Phe Leu His Lys Thr
            195                 200                 205
Phe Val Gly Gln Lys Arg Phe Ser Ile Glu Gly Leu Asp Ala Leu Val
            210                 215                 220
Pro Met Leu Asp Asp Ile Ile Ala Lys Ser Val Ser Ala Gly Thr Thr
225                 230                 235                 240
Asn Val Asn Ile Gly Met Ala His Arg Gly Arg Leu Asn Val Leu Ala
                    245                 250                 255
His Val Leu Gly Lys Pro Tyr Glu Ile Ile Phe Ser Glu Phe Gln His
                    260                 265                 270
Ala Pro Asn Lys Asp Leu Val Pro Ser Glu Gly Ser Thr Gly Ile Asn
                    275                 280                 285
Tyr Gly Trp Thr Gly Asp Val Lys Tyr His Leu Gly Ala Asn Arg Gln
                    290                 295                 300
Ile Gln Asp Glu His Thr Lys Thr Ala Arg Ile Ala Leu Ala Asn Asn
305                 310                 315                 320
Pro Ser His Leu Glu Phe Ile Asp Pro Ile Val Glu Gly Ser Thr Arg
                    325                 330                 335
Ala Ala Gln Glu Thr Arg Thr Glu Ser Gly Tyr Pro Val Gln Asp Val
                    340                 345                 350
Lys Lys Ser Met Ala Ile Leu Ile His Gly Asp Ala Ala Phe Pro Gly
                    355                 360                 365
Glu Gly Ile Val Ala Glu Thr Leu Asn Leu Ser Gln Leu Lys Gly Tyr
                    370                 375                 380
Gln Val Gly Gly Ala Ile His Ile Ile Ala Asn Asn Met Ile Gly Phe
385                 390                 395                 400
Thr Thr Glu Ser Asn Glu Ser Arg Ser Thr Lys Tyr Ala Ser Asp Leu
                    405                 410                 415
Ala Lys Gly Phe Glu Ile Pro Ile Val His Val Asn Ala Asp Asp Pro
                    420                 425                 430
Glu Ala Cys Leu Ser Ala Val Gln Leu Ala Val Glu Tyr Arg Met Thr
                    435                 440                 445
Phe Asn Lys Asp Phe Leu Ile Asp Leu Ile Gly Tyr Arg Arg Phe Gly
450                 455                 460
His Asn Glu Met Asp Glu Pro Ser Ala Thr Gln Pro Met Leu Tyr Asp
465                 470                 475                 480
Ala Val Arg Lys His Pro Thr Val Lys Asn Ile Phe Ala Glu Lys Leu
                    485                 490                 495
Ile His Lys Gly Ile Val Asp Lys Glu Thr Val Gly Lys Ile Lys Asp
                    500                 505                 510
Ala Val Gln Lys Arg Leu Glu Ala Tyr Arg Lys Val Pro Ala Lys
                    515                 520                 525
Lys Glu Asp Met Thr His Glu Ile Val Leu Pro Glu Pro Val Ser Asn
530                 535                 540
Gly Phe Pro Asp Val Asp Thr Ser Val Asp Phe Glu Thr Leu Arg Lys
545                 550                 555                 560
Ile Asn Gln Glu Leu Val Ser Trp Pro Glu Asn Phe Asn Val Phe Asp
                    565                 570                 575
Lys Leu Lys Arg Ile Leu Glu Arg Arg Ala Lys Ala Phe Glu Asp Asp
                    580                 585                 590
Arg Lys Val Asp Trp Ser Leu Ala Glu Ala Met Ala Phe Ala Ser Ile
                    595                 600                 605
```

Leu Lys Asp Gly Thr Pro Leu Arg Leu Thr Gly Gln Asp Ser Glu Arg
610                 615                 620

Gly Thr Phe Ala His Arg Asn Leu Val Leu His Asp Ser Lys Thr Gly
625                 630                 635                 640

Asp Glu Phe Ile Ala Leu His His Leu Ala Asp Thr Lys Ala Ser Phe
            645                 650                 655

Ala Val His Asn Ser Pro Leu Ser Glu Gly Ser Val Leu Gly Phe Glu
        660                 665                 670

Tyr Gly Tyr Asn Val Ser Ser Pro Glu Thr Met Val Ile Trp Glu Ala
    675                 680                 685

Gln Phe Gly Asp Phe Ala Asn Ala Ala Gln Val Tyr Phe Asp Gln Phe
690                 695                 700

Ile Ser Ala Gly Arg Ala Lys Trp Gly Gln Lys Ser Gly Leu Val Val
705                 710                 715                 720

Leu Leu Pro His Gly Tyr Glu Gly Gln Gly Pro Glu His Ser Ser Gly
            725                 730                 735

Arg Thr Glu Arg Phe Leu Gln Leu Ala Ala Glu Asn Asn Trp Thr Val
        740                 745                 750

Ala Asn Leu Thr Ser Ala Ala Gln Tyr Phe His Ile Leu Arg Arg Gln
    755                 760                 765

Ala Lys Met Leu Leu Arg Glu Glu Ile Arg Pro Leu Ile Ile Met Thr
770                 775                 780

Pro Lys Ser Leu Leu Arg Asn Pro Asn Thr Val Ser Glu Val Gln Glu
785                 790                 795                 800

Leu Ser Asn Ser Ser Phe Lys Pro Val Tyr Glu Met Ser Gly Leu Ser
            805                 810                 815

His Gln Tyr Asp Lys Val Thr Arg Leu Val Leu Ser Ser Gly Lys Val
        820                 825                 830

Ser Ile Asp Ile Ser Asp His Phe Asn Lys Met Glu Gly Gly Lys Asp
    835                 840                 845

Trp Leu His Ile Ala Arg Val Glu Glu Leu Tyr Pro Phe Pro Ala Lys
850                 855                 860

His Ile Lys Ala Ile Phe Ser Lys Leu Pro Asn Leu Glu Glu Ile Val
865                 870                 875                 880

Trp Val Gln Glu Glu Pro Gln Asn Met Gly Ala Trp Asn Tyr Ile Glu
            885                 890                 895

Pro Tyr Leu Arg Glu Val Ala Pro Lys Asp Val Lys Val Arg Tyr Ile
        900                 905                 910

Gly Arg Arg Arg Ser Ser Pro Ala Glu Gly Asp Pro Thr Val His
    915                 920                 925

Lys Lys Glu Gln Glu Arg Ile Val Ser Asp Ser Leu Thr Arg Lys Asn
930                 935                 940

<210> SEQ ID NO 47
<211> LENGTH: 1545
<212> TYPE: DNA
<213> ORGANISM: Bacillus licheniformis DSM 13
<220> FEATURE:
<221> NAME/KEY: gene
<222> LOCATION: (1)..(1545)
<223> OTHER INFORMATION: probable acid-CoA ligase (E.C. 6.2.1.-), yhfL
<220> FEATURE:
<221> NAME/KEY: CDS
<222> LOCATION: (1)..(1542)

<400> SEQUENCE: 47

-continued

| | |
|---|---|
| atg aat tta gtt tca aaa tta ggg gaa aca gct caa tca aag cct gac<br>Met Asn Leu Val Ser Lys Leu Gly Glu Thr Ala Gln Ser Lys Pro Asp<br>1              5                    10               15 | 48 |
| aga acc gct tat att ttt gga gag caa acg gaa aca tac ggg gga ttg<br>Arg Thr Ala Tyr Ile Phe Gly Glu Gln Thr Glu Thr Tyr Gly Gly Leu<br>               20                   25                   30 | 96 |
| cag cag aaa att gat tgc ttt gcc gaa ggg ctg cgc gaa atc ggg gtg<br>Gln Gln Lys Ile Asp Cys Phe Ala Glu Gly Leu Arg Glu Ile Gly Val<br>          35                   40                   45 | 144 |
| gaa aag gga gat cat gtc gct ttg cta ctc ggc aat aca ccg cat ttt<br>Glu Lys Gly Asp His Val Ala Leu Leu Leu Gly Asn Thr Pro His Phe<br>50                   55                   60 | 192 |
| gtg att gcg ttt tac ggc gcg ctg aag gcc ggg gct gtc gtc ata ccg<br>Val Ile Ala Phe Tyr Gly Ala Leu Lys Ala Gly Ala Val Val Ile Pro<br>65                   70                   75                   80 | 240 |
| atc aat ccg gcc tat acg ccg act gag atc ggc tat atg ctg aca aat<br>Ile Asn Pro Ala Tyr Thr Pro Thr Glu Ile Gly Tyr Met Leu Thr Asn<br>               85                   90                   95 | 288 |
| ggc gat gca aaa gtg atc gtg gct ctg gga cag ctg ctt ccg ctt tac<br>Gly Asp Ala Lys Val Ile Val Ala Leu Gly Gln Leu Leu Pro Leu Tyr<br>               100                 105               110 | 336 |
| gaa aag gtg cat gaa tcc ctt ccg aaa gtc ggc tgc gtc gtg ctt tgc<br>Glu Lys Val His Glu Ser Leu Pro Lys Val Gly Cys Val Val Leu Cys<br>          115                 120               125 | 384 |
| gaa act gga gag ccg ctt cag gaa ccg gaa aac aca gag gtt aag atg<br>Glu Thr Gly Glu Pro Leu Gln Glu Pro Glu Asn Thr Glu Val Lys Met<br>130                  135                 140 | 432 |
| aaa ttg aaa tcg ttt aca agc att atg aaa cct cct gtc cgg ccg ttt<br>Lys Leu Lys Ser Phe Thr Ser Ile Met Lys Pro Pro Val Arg Pro Phe<br>145                   150               155              160 | 480 |
| cct gaa atc gat gac gaa gat acg gcc gcc atc ctc tat acg tca ggc<br>Pro Glu Ile Asp Asp Glu Asp Thr Ala Ala Ile Leu Tyr Thr Ser Gly<br>               165                 170               175 | 528 |
| acc acg gga aga cca aaa ggg gcg atg ctc aca cat caa aat cta ttt<br>Thr Thr Gly Arg Pro Lys Gly Ala Met Leu Thr His Gln Asn Leu Phe<br>          180                 185               190 | 576 |
| tcg aat gca aat gat aca gcc cgc tat ctg aca atg aat gaa tct gac<br>Ser Asn Ala Asn Asp Thr Ala Arg Tyr Leu Thr Met Asn Glu Ser Asp<br>          195                 200               205 | 624 |
| ctt gtc gtc gcc gcc ctg ccg atg ttc cac gtt ttt tgt tta acg gtc<br>Leu Val Val Ala Ala Leu Pro Met Phe His Val Phe Cys Leu Thr Val<br>210                  215                 220 | 672 |
| tgc atg aat gca ccg ctc atg aac ggc gca gcg att ttg atc gtg ccg<br>Cys Met Asn Ala Pro Leu Met Asn Gly Ala Ala Ile Leu Ile Val Pro<br>225                   230               235              240 | 720 |
| aaa ttc agt ccc gcc gag gtt ttc aag ctg att aaa aag cat cag gcg<br>Lys Phe Ser Pro Ala Glu Val Phe Lys Leu Ile Lys Lys His Gln Ala<br>               245                 250               255 | 768 |
| acg atc ttc tca ggc gtt ccg aca atg tac aat tac ctg tac cag tat<br>Thr Ile Phe Ser Gly Val Pro Thr Met Tyr Asn Tyr Leu Tyr Gln Tyr<br>          260                 265               270 | 816 |
| gaa gga gcg gat gaa aca ggc ttt cgg tcc atc agg ctt tgc atc tca<br>Glu Gly Ala Asp Glu Thr Gly Phe Arg Ser Ile Arg Leu Cys Ile Ser<br>          275                 280               285 | 864 |
| ggc gga gcg gcc atg cct gtc gct ctc ctg aaa agc ttt gaa gaa agg<br>Gly Gly Ala Ala Met Pro Val Ala Leu Leu Lys Ser Phe Glu Glu Arg<br>290                  295                 300 | 912 |
| ttc ggc gtc ctc gtt tta gaa ggc tac ggc ttg tcg gag gct tct cct<br>Phe Gly Val Leu Val Leu Glu Gly Tyr Gly Leu Ser Glu Ala Ser Pro<br>305                  310               315              320 | 960 |

```
gtt aca tgc ttt aac ccg ttc agc acc ggc cgc aag cca gga tcg atc    1008
Val Thr Cys Phe Asn Pro Phe Ser Thr Gly Arg Lys Pro Gly Ser Ile
            325                 330                 335 ggc acg aac att ctc aat gtg aaa aac aaa gtc gtc aat gaa ctc ggg    1056
Gly Thr Asn Ile Leu Asn Val Lys Asn Lys Val Val Asn Glu Leu Gly
        340                 345                 350 gaa gag ctg cct gcc ggc caa gtc ggc gag ctg atc gtt aaa ggg cct    1104
Glu Glu Leu Pro Ala Gly Gln Val Gly Glu Leu Ile Val Lys Gly Pro
    355                 360                 365 aat gtc atg aaa ggg tac tac aaa atg ccg gat gag acg gcc cat acg    1152
Asn Val Met Lys Gly Tyr Tyr Lys Met Pro Asp Glu Thr Ala His Thr
370                 375                 380 ata aaa gac gga tgg ctg tat aca ggt gat ttg gca aaa cgg gat gaa    1200
Ile Lys Asp Gly Trp Leu Tyr Thr Gly Asp Leu Ala Lys Arg Asp Glu
385                 390                 395                 400 gac ggt tat ttt tat atc gtc gac aga aaa aaa gat atg att atc gtc    1248
Asp Gly Tyr Phe Tyr Ile Val Asp Arg Lys Lys Asp Met Ile Ile Val
                405                 410                 415 ggc ggc tat aat gtc tat ccg agg gaa atc gaa gag gtg ctc tac ctc    1296
Gly Gly Tyr Asn Val Tyr Pro Arg Glu Ile Glu Glu Val Leu Tyr Leu
            420                 425                 430 cat cca aaa atc gca gaa gcg gtt gtg atc gga gtg ccc gat ccg aat    1344
His Pro Lys Ile Ala Glu Ala Val Val Ile Gly Val Pro Asp Pro Asn
        435                 440                 445 acg gga gaa gcc gtt cat tgc tat gtc gtt ccg aag gat aaa acg ctg    1392
Thr Gly Glu Ala Val His Cys Tyr Val Val Pro Lys Asp Lys Thr Leu
    450                 455                 460 aca gag gag gat gtc ttg tcg cac tgc aaa aag cat ctt gcc aaa tac    1440
Thr Glu Glu Asp Val Leu Ser His Cys Lys Lys His Leu Ala Lys Tyr
465                 470                 475                 480 aag cgc ccg tcg gcg atc gtt ttc atg gat gaa att ccg aaa aac tcg    1488
Lys Arg Pro Ser Ala Ile Val Phe Met Asp Glu Ile Pro Lys Asn Ser
                485                 490                 495 acc ggc aaa att tta agg cgc gct tta aaa gac att ctg aca aac aaa    1536
Thr Gly Lys Ile Leu Arg Arg Ala Leu Lys Asp Ile Leu Thr Asn Lys
            500                 505                 510 tct tga ccc                                                         1545
Ser

<210> SEQ ID NO 48
<211> LENGTH: 513
<212> TYPE: PRT
<213> ORGANISM: Bacillus licheniformis DSM 13

<400> SEQUENCE: 48

Met Asn Leu Val Ser Lys Leu Gly Glu Thr Ala Gln Ser Lys Pro Asp
1               5                   10                  15

Arg Thr Ala Tyr Ile Phe Gly Glu Gln Thr Glu Thr Tyr Gly Gly Leu
            20                  25                  30

Gln Gln Lys Ile Asp Cys Phe Ala Glu Gly Leu Arg Glu Ile Gly Val
        35                  40                  45

Glu Lys Gly Asp His Val Ala Leu Leu Gly Asn Thr Pro His Phe
    50                  55                  60

Val Ile Ala Phe Tyr Gly Ala Leu Lys Ala Gly Ala Val Val Ile Pro
65                  70                  75                  80

Ile Asn Pro Ala Tyr Thr Pro Thr Glu Ile Gly Tyr Met Leu Thr Asn
                85                  90                  95

Gly Asp Ala Lys Val Ile Val Ala Leu Gly Gln Leu Leu Pro Leu Tyr
```

```
            100                 105                 110
Glu Lys Val His Glu Ser Leu Pro Lys Val Gly Cys Val Val Leu Cys
            115                 120                 125
Glu Thr Gly Glu Pro Leu Gln Glu Pro Glu Asn Thr Glu Val Lys Met
            130                 135                 140
Lys Leu Lys Ser Phe Thr Ser Ile Met Lys Pro Pro Val Arg Pro Phe
145                 150                 155                 160
Pro Glu Ile Asp Asp Glu Asp Thr Ala Ala Ile Leu Tyr Thr Ser Gly
                165                 170                 175
Thr Thr Gly Arg Pro Lys Gly Ala Met Leu Thr His Gln Asn Leu Phe
                180                 185                 190
Ser Asn Ala Asn Asp Thr Ala Arg Tyr Leu Thr Met Asn Glu Ser Asp
            195                 200                 205
Leu Val Val Ala Ala Leu Pro Met Phe His Val Phe Cys Leu Thr Val
            210                 215                 220
Cys Met Asn Ala Pro Leu Met Asn Gly Ala Ala Ile Leu Ile Val Pro
225                 230                 235                 240
Lys Phe Ser Pro Ala Glu Val Phe Lys Leu Ile Lys Lys His Gln Ala
                245                 250                 255
Thr Ile Phe Ser Gly Val Pro Thr Met Tyr Asn Tyr Leu Tyr Gln Tyr
                260                 265                 270
Glu Gly Ala Asp Glu Thr Gly Phe Arg Ser Ile Arg Leu Cys Ile Ser
                275                 280                 285
Gly Gly Ala Ala Met Pro Val Ala Leu Leu Lys Ser Phe Glu Glu Arg
            290                 295                 300
Phe Gly Val Leu Val Leu Glu Gly Tyr Gly Leu Ser Glu Ala Ser Pro
305                 310                 315                 320
Val Thr Cys Phe Asn Pro Phe Ser Thr Gly Arg Lys Pro Gly Ser Ile
                325                 330                 335
Gly Thr Asn Ile Leu Asn Val Lys Asn Lys Val Val Asn Glu Leu Gly
                340                 345                 350
Glu Glu Leu Pro Ala Gly Gln Val Gly Glu Leu Ile Val Lys Gly Pro
            355                 360                 365
Asn Val Met Lys Gly Tyr Tyr Lys Met Pro Asp Glu Thr Ala His Thr
            370                 375                 380
Ile Lys Asp Gly Trp Leu Tyr Thr Gly Asp Leu Ala Lys Arg Asp Glu
385                 390                 395                 400
Asp Gly Tyr Phe Tyr Ile Val Asp Arg Lys Lys Asp Met Ile Ile Val
                405                 410                 415
Gly Gly Tyr Asn Val Tyr Pro Arg Glu Ile Glu Glu Val Leu Tyr Leu
                420                 425                 430
His Pro Lys Ile Ala Glu Ala Val Val Ile Gly Val Pro Asp Pro Asn
            435                 440                 445
Thr Gly Glu Ala Val His Cys Tyr Val Val Pro Lys Asp Lys Thr Leu
            450                 455                 460
Thr Glu Glu Asp Val Leu Ser His Cys Lys Lys His Leu Ala Lys Tyr
465                 470                 475                 480
Lys Arg Pro Ser Ala Ile Val Phe Met Asp Glu Ile Pro Lys Asn Ser
                485                 490                 495
Thr Gly Lys Ile Leu Arg Arg Ala Leu Lys Asp Ile Leu Thr Asn Lys
                500                 505                 510
Ser
```

```
<210> SEQ ID NO 49
<211> LENGTH: 876
<212> TYPE: DNA
<213> ORGANISM: Bacillus licheniformis DSM 13
<220> FEATURE:
<221> NAME/KEY: gene
<222> LOCATION: (1)..(876)
<223> OTHER INFORMATION: Agmatinase (E.C. 3.5.1.11), ywhG
<220> FEATURE:
<221> NAME/KEY: CDS
<222> LOCATION: (1)..(873)

<400> SEQUENCE: 49 atg aga ttt gat gaa gca tat tcc ggc aag gtg ttt atc gca agc cgc     48
Met Arg Phe Asp Glu Ala Tyr Ser Gly Lys Val Phe Ile Ala Ser Arg
1               5                   10                  15 ccc gat tgg gaa gag gcg gac gcc atc ctt tac ggc atg ccg atg gat     96
Pro Asp Trp Glu Glu Ala Asp Ala Ile Leu Tyr Gly Met Pro Met Asp
            20                  25                  30 tgg acg gtc agc tac cgt ccc ggc tcc cgc ttc ggt ccg gcg aga atc    144
Trp Thr Val Ser Tyr Arg Pro Gly Ser Arg Phe Gly Pro Ala Arg Ile
        35                  40                  45 cgc gag gtg tcc atc gga ctt gaa gaa tac agc cct tat ttg gac agg    192
Arg Glu Val Ser Ile Gly Leu Glu Glu Tyr Ser Pro Tyr Leu Asp Arg
50                  55                  60 gag ctg gaa gag gtt cat ttc ttt gac gcc ggc gac atc ccg ctg cct    240
Glu Leu Glu Glu Val His Phe Phe Asp Ala Gly Asp Ile Pro Leu Pro
65                  70                  75                  80 ttc ggg aac ccg cag aag agc ctc gac atg att gaa gaa tat gtc gac    288
Phe Gly Asn Pro Gln Lys Ser Leu Asp Met Ile Glu Glu Tyr Val Asp
                85                  90                  95 agc att tta gat aaa gga aaa ttc ccg ctc ggt atg ggg gga gag cat    336
Ser Ile Leu Asp Lys Gly Lys Phe Pro Leu Gly Met Gly Gly Glu His
            100                 105                 110 ctc gtt tca tgg ccg gtc att aaa gcg atg tac aaa aaa tat ccc gat    384
Leu Val Ser Trp Pro Val Ile Lys Ala Met Tyr Lys Lys Tyr Pro Asp
        115                 120                 125 ctt gcc atc atc cat atg gat gcg cac aca gat ctc cgc gtc gac tat    432
Leu Ala Ile Ile His Met Asp Ala His Thr Asp Leu Arg Val Asp Tyr
    130                 135                 140 gaa gga gag ccg ctc tcg cat tcg acg ccg atc cgt aaa gcc gcg gaa    480
Glu Gly Glu Pro Leu Ser His Ser Thr Pro Ile Arg Lys Ala Ala Glu
145                 150                 155                 160 ctg atc gga ccc ggc aat gtc tat tca ttc ggc atc cgc tcc ggc atg    528
Leu Ile Gly Pro Gly Asn Val Tyr Ser Phe Gly Ile Arg Ser Gly Met
                165                 170                 175 aaa gaa gaa ttt gaa tgg gca aaa gaa aac ggc atg cac att tct aaa    576
Lys Glu Glu Phe Glu Trp Ala Lys Glu Asn Gly Met His Ile Ser Lys
            180                 185                 190 ttt gaa gtg ctt gag ccg ctt aaa gcc gtc ctg ccg aaa ctc gcg ggg    624
Phe Glu Val Leu Glu Pro Leu Lys Ala Val Leu Pro Lys Leu Ala Gly
        195                 200                 205 cgt ccg gtt tat gtg acg atc gac atc gat gtc tta gat ccc gcg cat    672
Arg Pro Val Tyr Val Thr Ile Asp Ile Asp Val Leu Asp Pro Ala His
    210                 215                 220 gcg ccg gga acc ggt acg gtt gac gcc gga ggc atc aca tcc aaa gag    720
Ala Pro Gly Thr Gly Thr Val Asp Ala Gly Gly Ile Thr Ser Lys Glu
225                 230                 235                 240 ctg ctc gct tcg att cac gaa atc gcc cgc tca gac gtc aat gtc gtt    768
Leu Leu Ala Ser Ile His Glu Ile Ala Arg Ser Asp Val Asn Val Val
                245                 250                 255
```

```
gga gga gac ctt gtc gaa gtc gct cct gtc tat gac cat tcg gaa caa    816
Gly Gly Asp Leu Val Glu Val Ala Pro Val Tyr Asp His Ser Glu Gln
            260                 265                 270 acc gca aat acg gca agc aag ctg att cgc gaa atg ctg ctc ggc tgg    864
Thr Ala Asn Thr Ala Ser Lys Leu Ile Arg Glu Met Leu Leu Gly Trp
            275                 280                 285 gtg aaa taa aac                                                    876
Val Lys
290

<210> SEQ ID NO 50
<211> LENGTH: 290
<212> TYPE: PRT
<213> ORGANISM: Bacillus licheniformis DSM 13

<400> SEQUENCE: 50

Met Arg Phe Asp Glu Ala Tyr Ser Gly Lys Val Phe Ile Ala Ser Arg
1               5                   10                  15

Pro Asp Trp Glu Glu Ala Asp Ala Ile Leu Tyr Gly Met Pro Met Asp
            20                  25                  30

Trp Thr Val Ser Tyr Arg Pro Gly Ser Arg Phe Gly Pro Ala Arg Ile
        35                  40                  45

Arg Glu Val Ser Ile Gly Leu Glu Glu Tyr Ser Pro Tyr Leu Asp Arg
    50                  55                  60

Glu Leu Glu Glu Val His Phe Phe Asp Ala Gly Asp Ile Pro Leu Pro
65                  70                  75                  80

Phe Gly Asn Pro Gln Lys Ser Leu Asp Met Ile Glu Glu Tyr Val Asp
                85                  90                  95

Ser Ile Leu Asp Lys Gly Lys Phe Pro Leu Gly Met Gly Gly Glu His
            100                 105                 110

Leu Val Ser Trp Pro Val Ile Lys Ala Met Tyr Lys Lys Tyr Pro Asp
        115                 120                 125

Leu Ala Ile Ile His Met Asp Ala His Thr Asp Leu Arg Val Asp Tyr
    130                 135                 140

Glu Gly Glu Pro Leu Ser His Ser Thr Pro Ile Arg Lys Ala Ala Glu
145                 150                 155                 160

Leu Ile Gly Pro Gly Asn Val Tyr Ser Phe Gly Ile Arg Ser Gly Met
                165                 170                 175

Lys Glu Glu Phe Glu Trp Ala Lys Glu Asn Gly Met His Ile Ser Lys
            180                 185                 190

Phe Glu Val Leu Glu Pro Leu Lys Ala Val Leu Pro Lys Leu Ala Gly
        195                 200                 205

Arg Pro Val Tyr Val Thr Ile Asp Ile Asp Val Leu Asp Pro Ala His
    210                 215                 220

Ala Pro Gly Thr Gly Thr Val Asp Ala Gly Gly Ile Thr Ser Lys Glu
225                 230                 235                 240

Leu Leu Ala Ser Ile His Glu Ile Ala Arg Ser Asp Val Asn Val Val
                245                 250                 255

Gly Gly Asp Leu Val Glu Val Ala Pro Val Tyr Asp His Ser Glu Gln
            260                 265                 270

Thr Ala Asn Thr Ala Ser Lys Leu Ile Arg Glu Met Leu Leu Gly Trp
        275                 280                 285

Val Lys
290
```